United States Patent
Ko et al.

(10) Patent No.: US 9,714,234 B2
(45) Date of Patent: Jul. 25, 2017

(54) CARBAZOLE CARBOXAMIDE COMPOUNDS

(71) Applicant: Bristol-Myers Squibb Company, Princeton, NJ (US)

(72) Inventors: Soo Sung Ko, Hockessin, DE (US); Douglas G Batt, Wilmington, DE (US); Myra Beaudoin Bertrand, Lambertville, NJ (US); George Delucca, Pennington, NJ (US); Charles M. Langevine, Brooklyn, NY (US); Qingjie Liu, Newtown, PA (US); Anurag S. Srivastava, Belle Mead, NJ (US); Scott Hunter Watterson, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/392,355

(22) PCT Filed: Jun. 25, 2014

(86) PCT No.: PCT/US2014/043980
§ 371 (c)(1),
(2) Date: Dec. 24, 2015

(87) PCT Pub. No.: WO2014/210087
PCT Pub. Date: Dec. 31, 2014

(65) Prior Publication Data
US 2016/0200710 A1    Jul. 14, 2016

Related U.S. Application Data

(60) Provisional application No. 61/839,130, filed on Jun. 25, 2013.

(51) Int. Cl.
*C07D 209/88* (2006.01)
*C07D 209/86* (2006.01)
(Continued)

(52) U.S. Cl.
CPC ......... *C07D 403/10* (2013.01); *C07D 471/04* (2013.01); *C07D 513/04* (2013.01)

(58) Field of Classification Search
USPC ............... 548/441, 445, 448; 544/284, 285; 514/266.23, 411
See application file for complete search history.

(56) References Cited

U.S. PATENT DOCUMENTS 5,604,236 A    2/1997    Jakubowski et al.
8,084,620 B2*  12/2011   Liu .................. C07D 209/88
                                                544/284

(Continued)

FOREIGN PATENT DOCUMENTS

CN    101475571    6/2011
WO    WO 2005/005429    1/2005
(Continued)

OTHER PUBLICATIONS

Eisenberg et al (Journal of Autoimmunity vol. 32 pp. 223-230 published 2009).*
(Continued)

*Primary Examiner* — Timothy Thomas
*Assistant Examiner* — George W Kosturko
(74) *Attorney, Agent, or Firm* — Gary D. Greenblatt

(57) ABSTRACT

Disclosed are compounds of Formula (I); and salts thereof, wherein: Formula (II); Q is: $R_1$ is —C(CH$_3$)2OH, —NHC(=O)C(CH$_3$)$_3$, —N(CH3)2, or —CH$_2$R$_d$; $R_2$ is Cl or —CH$_3$; $R_3$ is H, F, or —CH$_3$; $R_a$ is H or —CH$_3$; $R_b$ is H, F, Cl, or —OCH3 $R_c$ is H or F; and Rd is —OH, —OCH3, —NHC(=O)CH3, or fORMULA (III), Also disclosed are methods of using such compounds as inhibitors of Bruton's tyrosine kinase (Btk), and pharmaceutical compositions comprising such compounds. These compounds are useful in treating, preventing, or slowing the progression of diseases or disorders in a variety of therapeutic areas, such as autoimmune diseases and vascular disease.

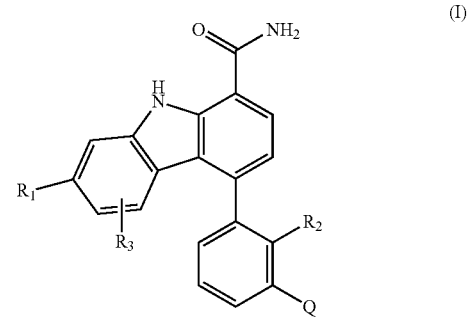

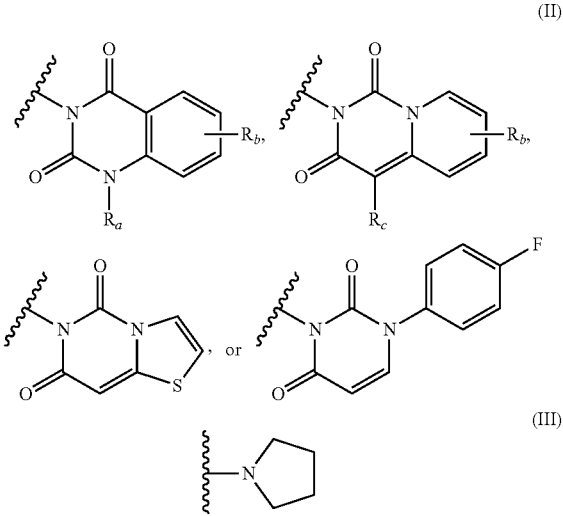

9 Claims, 3 Drawing Sheets

(51) Int. Cl.
*C07D 239/91* (2006.01)
*C07D 239/96* (2006.01)
*A61K 31/505* (2006.01)
*A61K 31/407* (2006.01)
*C07D 403/10* (2006.01)
*C07D 471/04* (2006.01)
*C07D 513/04* (2006.01)

(56) References Cited

U.S. PATENT DOCUMENTS

| | | | |
|---|---|---|---|
| 8,362,065 B2 | 1/2013 | Liu et al. | |
| 8,685,969 B2 | 4/2014 | Liu et al. | |
| 2006/0084650 A1 | 4/2006 | Dong et al. | |
| 2008/0045536 A1 | 2/2008 | Vaccaro et al. | |
| 2009/0281131 A1 | 11/2009 | Gopalan et al. | |
| 2010/0016302 A1* | 1/2010 | Kondru | C07D 487/04 514/233.2 |
| 2010/0160303 A1* | 6/2010 | Liu | C07D 209/88 514/228.2 |
| 2012/0136023 A1 | 5/2012 | Bell et al. | |
| 2014/0378475 A1 | 12/2014 | Batt et al. | |

FOREIGN PATENT DOCUMENTS

| WO | WO 2005/014599 | 2/2005 |
|---|---|---|
| WO | WO 2005/047290 | 5/2005 |
| WO | WO 2006/053121 | 5/2006 |
| WO | WO 2006/064355 | 6/2006 |
| WO | WO 2006/099075 | 9/2006 |
| WO | WO 2007/038314 | 4/2007 |
| WO | WO 2007/061764 | 5/2007 |
| WO | WO 2008/032171 | 3/2008 |
| WO | WO 2008/033858 | 3/2008 |
| WO | WO 2009/024819 | 2/2009 |
| WO | WO 2009/075830 | 6/2009 |
| WO | WO 2009/102498 | 8/2009 |
| WO | WO 2009/141627 | 11/2009 |
| WO | WO 2010/015636 | 2/2010 |
| WO | WO 2012/059232 | 5/2012 |
| WO | WO 2012/156334 | 11/2012 |

OTHER PUBLICATIONS

Honigberg et al., (PNAS vol. 107 pp. 13075-13080 published 2010).*
Yoshida et al., (Biochemical and Biophysical Research Communications vol. 418, pp. 234-240 published Jan. 2012).*
Wright et al (J. Med. Chem vol. 30 pp. 2277-2283 published 1987).*
Lou, Y., et al., "Bruton's Tyrosine Kinase Inhibitors: Approaches to Potent and Selective Inhibition, Preclinical and Clinical Evaluation for Inflammatory Diseases and B Cell Malignancies," Journal of Medicinal Chemistry, vol. 55, pp. 4539-4550 (2012).
IPER for PCT/US2014/043980 dated Jan. 7, 2016.
Leplante, S.R., "Assessing Atropisomer Axial Chirality in Drug Discovery and Development," J. Med. Chem. 54(20), pp. 7005-7022 (2011).
Clayden, J., "The Challenge of Atropisomerism in Drug Discovery," Angew. Chem. Int. Ed., vol. 48, pp. 6398-6401 (2009).

* cited by examiner

CARBAZOLE CARBOXAMIDE COMPOUNDS

CROSS-REFERENCE TO RELATED APPLICATIONS

This application is a national phase application under 35 U.S.C. §371 of International Patent Application No. PCT/US2014/043980, filed Jun. 25, 2014, which claims priority to U.S. Provisional Application 61/839,130, filed Jun. 25, 2013, which are expressly incorporated fully herein by reference.

DESCRIPTION

The present invention generally relates to carbazole carboxamide compounds useful as kinase inhibitors, including the modulation of Bruton's tyrosine kinase (Btk) and other Tec family kinases such as Itk. Provided herein are carbazole carboxamide compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk and other Tec family kinases such as Itk, in a mammal.

Protein kinases, the largest family of human enzymes, encompass well over 500 proteins. Btk is a member of the Tec family of tyrosine kinases, and is a regulator of early B-cell development, as well as mature B-cell activation, signaling, and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium signal upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to *Staphylococcus*-induced arthritis.

A large body of evidence supports the role of B-cells and the humoral immune system in the pathogenesis of autoimmune and/or inflammatory diseases. Protein-based therapeutics (such as RITUXAN®) developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

In view of the numerous conditions that are contemplated to benefit by treatment involving modulation of protein kinases, it is immediately apparent that new compounds capable of modulating protein kinases such as Btk and methods of using these compounds should provide substantial therapeutic benefits to a wide variety of patients.

U.S. Pat. No. 8,084,620 and WO 2011/159857 disclose tricyclic carboxamide compounds useful as kinase inhibitors, including the modulation of Btk and other Tec family kinases.

There still remains a need for compounds useful as Btk inhibitors and yet having selectivity over Jak2 tyrosine kinase. Further, there still remains a need for compounds useful as Btk inhibitors that have selectivity over Jak2 tyrosine kinase and also have improved potency in the whole blood BCR-stimulated CD69 expression assay.

Applicants have found potent compounds that have activity as Btk inhibitors. Further, applicants have found compounds that have activity as Btk inhibitors and are selective over Jak2 tyrosine kinase. Further still, applicants have found compounds that have activity as Btk inhibitors, are selective over Jak2 tyrosine kinase, and have improved potency in the whole blood BCR-stimulated CD69 expression assay. These compounds are provided to be useful as pharmaceuticals with desirable stability, bioavailability, therapeutic index, and toxicity values that are important to their drugability.

SUMMARY OF THE INVENTION

The present invention provides carbazole compounds, which are useful as inhibitors of Btk, and are useful for the treatment of proliferative diseases, allergic diseases, autoimmune diseases and inflammatory diseases, including salts and prodrugs thereof.

The present invention also provides pharmaceutical compositions comprising at least one compound of Formula (I) or a pharmaceutically acceptable salt thereof; and a pharmaceutically acceptable carrier.

The present invention also provides a method of inhibiting Btk activity comprising administering to a mammal in need thereof at least one compound of Formula (I) or a pharmaceutically acceptable salt thereof.

The present invention also provides a method for treating allergic disorders and/or autoimmune and/or inflammatory diseases, comprising administering to a mammal in need thereof at least one compound of Formula (I), or a pharmaceutically acceptable salt thereof.

The present invention also provides a method for treating proliferative diseases, such as cancer, comprising administering to a mammal in need thereof at least one compound of Formula (I) or a pharmaceutically acceptable salt thereof.

The present invention also provides a method of treating a disease or disorder associated with Btk activity, the method comprising administering to a mammal in need thereof, at least one compound of Formula (I) or a pharmaceutically acceptable salt thereof.

The present invention also provides processes and intermediates for making the compounds of Formula (I) and/or salts thereof.

The present invention also provides a compound of Formula (I) or a pharmaceutically acceptable salt thereof, for use in therapy.

The present invention also provides the use of the compounds of Formula (I) or pharmaceutically acceptable salts thereof, for the manufacture of a medicament for the treatment or prophylaxis of Btk related conditions, such as proliferative diseases, allergic diseases, autoimmune diseases and inflammatory diseases.

The present invention also provides the use of the compounds of Formula (I) or pharmaceutically acceptable salts thereof, for the manufacture of a medicament for treatment of cancer.

The compounds of Formula (I) and compositions comprising the compounds of Formula (I) may be used in treating, preventing, or curing various Btk related conditions. Pharmaceutical compositions comprising these compounds are useful in treating, preventing, or slowing the progression of diseases or disorders in a variety of therapeutic areas, such as proliferative diseases, allergic diseases, autoimmune diseases and inflammatory diseases.

These and other features of the invention will be set forth in expanded form as the disclosure continues.

BRIEF DESCRIPTION OF THE DRAWINGS

The invention is illustrated by reference to the accompanying drawings described below.

DETAILED DESCRIPTION

Figure 1:
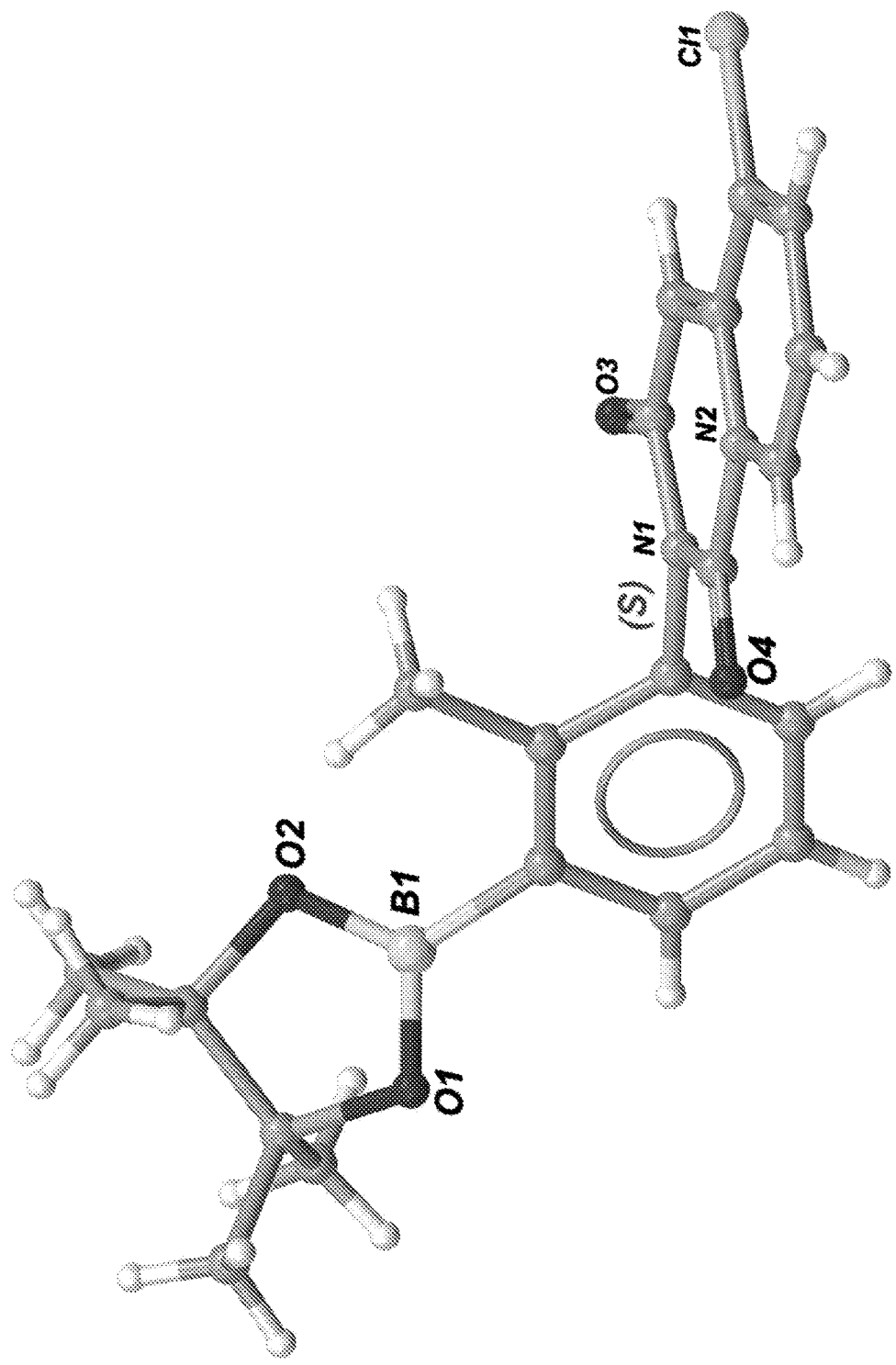
FIG. 1 shows the absolute stereochemistry of Intermediate 15.

The first aspect of the present invention provides at least one compound of Formula (I):

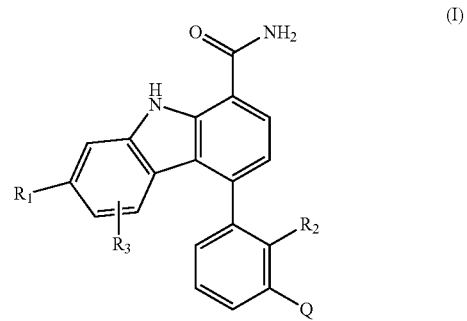

or a salt thereof, wherein:

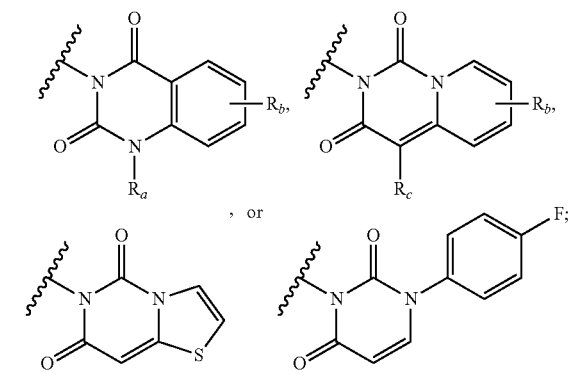

$R_1$ is —C(CH$_3$)$_2$OH, —NHC(=O)C(CH$_3$)$_3$, —N(CH$_3$)$_2$, or —CH$_2$R$_d$;
$R_2$ is Cl or —CH$_3$;
$R_3$ is H, F, or —CH$_3$;
$R_a$ is H or —CH$_3$;
$R_b$ is H, F, Cl, or —OCH$_3$;
$R_c$ is H or F; and
$R_d$ is —OH, —OCH$_3$, —NHC(=O)CH$_3$, or

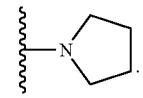

One embodiment provides compounds of Formula (I), wherein $R_1$ is —C(CH$_3$)$_2$OH; and Q, $R_2$, and $R_3$ are defined in the first aspect.

One embodiment provides compounds of Formula (I), wherein $R_1$ is —NHC(=O)C(CH$_3$)$_3$; and Q, $R_2$, and $R_3$ are defined in the first aspect.

One embodiment provides compounds of Formula (I) or a salt thereof, wherein $R_1$ is —N(CH$_3$)$_2$; and Q, $R_2$, and $R_3$ are defined in the first aspect.

One embodiment provides compounds of Formula (I) or a salt thereof, wherein $R_1$ is —CH$_2$R$_d$; and Q, $R_2$, $R_3$, and $R_d$ are defined in the first aspect.

One embodiment provides compounds of Formula (I) or a salt thereof, wherein $R_2$ is Cl; and Q, $R_1$, and $R_3$ are defined in the first aspect.

One embodiment provides compounds of Formula (I) or a salt thereof, wherein $R_2$ is —CH$_3$; and Q, $R_1$, and $R_3$ are defined in the first aspect.

One embodiment provides compounds of Formula (I), wherein $R_1$ is —C(CH$_3$)$_2$OH; $R_2$ is Cl; and Q and $R_3$ are defined in the first aspect.

One embodiment provides compounds of Formula (I), wherein $R_1$ is —C(CH$_3$)$_2$OH; $R_2$ is Cl; $R_3$ is H; and Q is defined in the first aspect.

One embodiment provides compounds of Formula (I), wherein $R_1$ is —C(CH$_3$)$_2$OH; $R_2$ is —CH$_3$; and Q and $R_3$ are defined in the first aspect.

One embodiment provides compounds of Formula (I), wherein $R_1$ is —C(CH$_3$)$_2$OH; $R_2$ is —CH$_3$; $R_3$ is H; and Q is defined in the first aspect.

One embodiment provides compounds of Formula (I), wherein $R_1$ is —C(CH$_3$)$_2$OH; $R_2$ is —CH$_3$; $R_3$ is —CH$_3$; and Q is defined in the first aspect.

One embodiment provides compounds of Formula (I) or a salt thereof, wherein Q is:

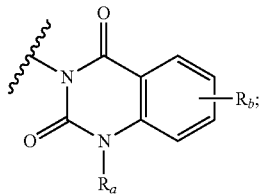

and $R_1$, $R_2$, $R_3$, and $R_a$ are defined in the first aspect. The compounds of this embodiment have the structure of Formula (II):

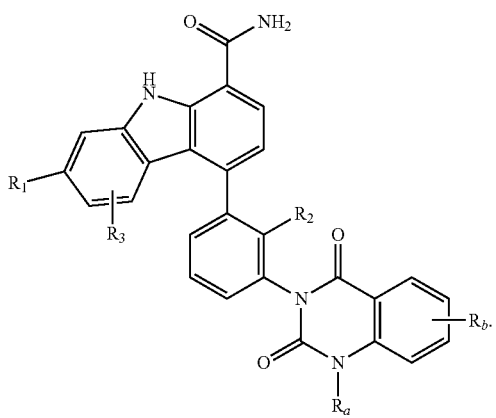

(II)

Included in this embodiment are compounds of Formula (II) in which Q is:

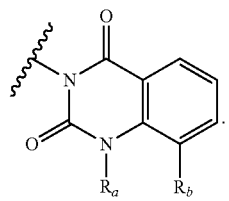

One embodiment provides compounds of Formula (II), wherein $R_1$ is —C(CH$_3$)$_2$OH; and $R_2$, $R_3$, $R_a$, and $R_b$ are defined in the first aspect. The compounds of this embodiment have the structure of Formula (IIA):

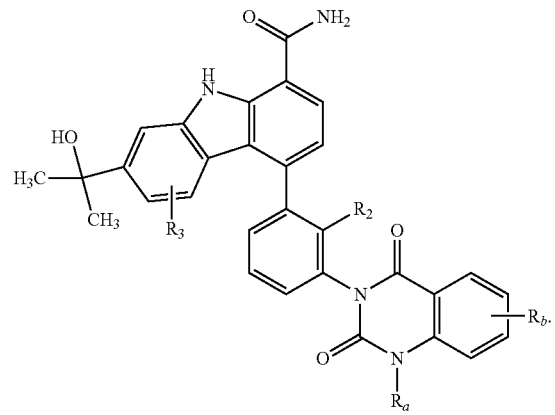

(IIA)

Included in this embodiment are compounds of Formula (IIA) in which $R_2$ is Cl or —CH$_3$; $R_3$ is H; $R_a$ is H or —CH$_3$, including —CD$_3$; and $R_b$ is H, F, or —OCH$_3$. Also, included in this embodiment are compounds of Formula (IIA) in which Q is:

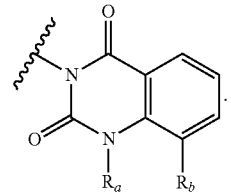

One embodiment provides a compound of Formula (II) or a salt thereof, wherein the compound is selected from: 4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (1 and 2); 4-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (3); 4-(3-(S)-(8-fluoro-1-methyl(d$_3$)-2,4-dioxo-1,2-dihydroquinazolin-3(4H)-yl)-2-methylphenyl)-7-(2-hydroxypropan-2-yl)-9H-carbazole-1-carboxamide (4); 4-(2-chloro-3-(8-fluoro-1-methyl-2,4-dioxo-1,2-dihydroquinazolin-3(4H)-yl)phenyl)-7-(2-hydroxypropan-2-yl)-9H-carbazole-1-carboxamide (5); 4-(2-chloro-3-(1-methyl-2,4-dioxo-1,2-dihydroquinazolin-3(4H)-yl)phenyl)-7-(2-hydroxypropan-2-yl)-9H-carbazole-1-carboxamide (6); 7-(2-hydroxypropan-2-yl)-4-(3-(8-methoxy-1-methyl-2,4-dioxo-1,2-dihydroquinazolin-3(4H)-yl)-2-methylphenyl)-9H-carbazole-1-carboxamide (7); 4-(3-(6-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (8); 4-(3-(S)-(8-fluoro-1-methyl-2,4-dioxo-1,2-dihydroquinazolin-3(4H)-yl)-2-methylphenyl)-7-(2-hydroxypropan-2-yl)-5-methyl-9H-carbazole-1-carboxamide (24); 4-(3-(8-fluoro-1-methyl-2,4-dioxo-1,2-dihydroquinazolin-3(4H)-yl)-2-methylphenyl)-7-(2-hydroxypropan-2-yl)-5-methyl-9H-carbazole-1-carboxamide (25); 4-(3-(S)-(8-fluoro-1-methyl-2,4-dioxo-1,2-dihydroquinazolin-3(4H)-yl)-2-methylphenyl)-7-(2-hydroxypropan-2-yl)-8-methyl-9H-carbazole-1-carboxamide (26); 4-(3-(S)-(8-fluoro-1-methyl(d$_3$)-2,4-dioxo-1,2-dihydroquinazolin-3(4H)-yl)-2-methylphenyl)-7-(2-hydroxypropan-2-yl)-5-methyl-9H- carbazole-1-carboxamide (27); and 8-fluoro-4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (33).

One embodiment provides compounds of Formula (I) or a salt thereof, wherein Q is:

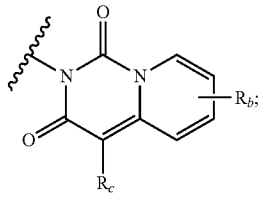

and $R_1$, $R_2$, $R_3$, $R_b$, and $R_c$ are defined in the first aspect. The compounds of this embodiment have the structure of Formula (III):

(III)

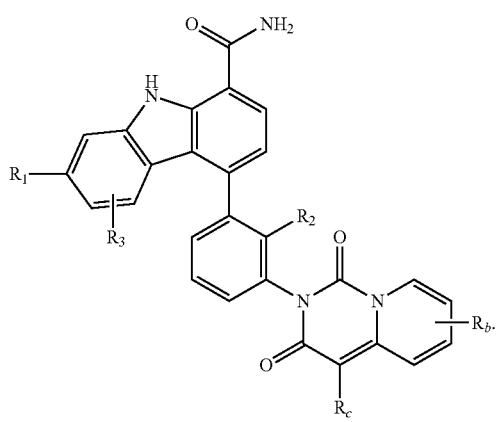

Included in this embodiment are compounds of Formula (III) in which Q is:

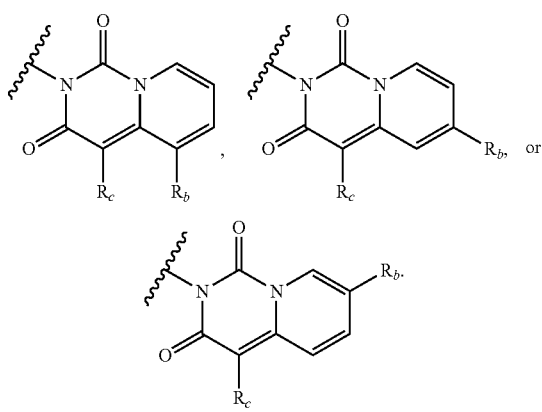

One embodiment provides compounds of Formula (III) or a salt thereof, wherein $R_2$ is —$CH_3$; and $R_1$, $R_3$, $R_b$, and $R_c$ are defined in the first aspect. The compounds of this embodiment have the structure of Formula (IIIA):

(IIIA)

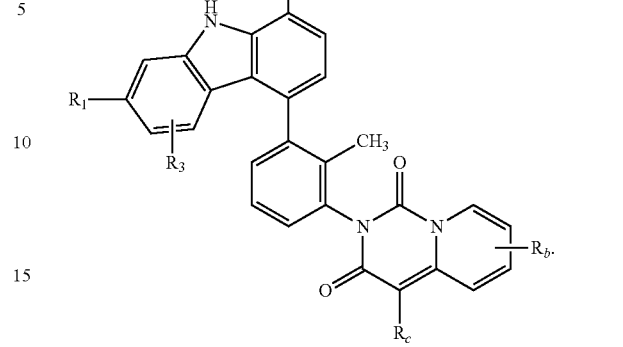

Included in this embodiment are compounds of Formula (IIIA) in which $R_1$ is —$C(CH_3)_2OH$, —$NHC(=O)C(CH_3)_3$, —$N(CH_3)_2$, or —$CH_2R_d$; $R_3$ is H, F, or —$CH_3$; $R_b$ is H, F, Cl, or —$OCH_3$; $R_c$ is H or F; and $R_d$ is —OH, —$OCH_3$, —$NHC(=O)CH_3$, or

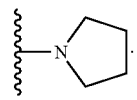

Also included in this embodiment are compounds in which $R_3$ is H.

One embodiment provides a compound of Formula (III) or a salt thereof, wherein the compound is selected from: 7-(2-hydroxypropan-2-yl)-4-(3-(7-methoxy-1,3-dioxo-1H-pyrido[1,2-c]pyrimidin-2(3H)-yl)-2-methylphenyl)-9H-carbazole-1-carboxamide (10); 7-(2-hydroxypropan-2-yl)-4-(3-(6-methoxy-1,3-dioxo-1H-pyrido[1,2-c]pyrimidin-2(3H)-yl)-2-methylphenyl)-9H-carbazole-1-carboxamide (11); 7-(2-hydroxypropan-2-yl)-4-(3-(5-methoxy-1,3-dioxo-1H-pyrido[1,2-c]pyrimidin-2(3H)-yl)-2-methylphenyl)-9H-carbazole-1-carboxamide (12); 4-(3-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (13); 4-(3-(R)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (14); 4-(3-(S)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (15); 4-(3-(5-chloro-1,3-dioxo-1H-pyrido[1,2-c]pyrimidin-2(3H)-yl)-2-methylphenyl)-7-pivalamido-9H-carbazole-1-carboxamide (16); 4-(3-(5-chloro-1,3-dioxo-1H-pyrido[1,2-c]pyrimidin-2(3H)-yl)-2-methylphenyl)-7-(methoxymethyl)-9H-carbazole-1-carboxamide (17); 4-(3-(5-fluoro-1,3-dioxo-1H-pyrido[1,2-c]pyrimidin-2(3H)-yl)-2-methylphenyl)-7-(methoxymethyl)-9H-carbazole-1-carboxamide (18); 4-(3-(4-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (19); 4-(3-5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (21); 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (22 and 23); 4-(3-(5-fluoro-1,3-dioxo-1H-pyrido[1,2-c]pyrimidin-2(3H)-yl)-2-methylphenyl)-7-(hydroxymethyl)-9H-carbazole-1-carboxamide (28); 7-(dimethylamino)-4-(3-(5-fluoro-1,3-dioxo-1H-pyrido[1,2-c]pyrimidin-2(3H)-yl)-2-methylphenyl)-9H-carbazole-1-carboxamide (29); 7-(acetamidomethyl)-4-(3-(5-fluoro-1,3-dioxo-1H-pyrido[1,2-c]pyrimidin-2(3H)-yl)-2-methylphenyl)-9H-carbazole-1-carboxamide (30); and 4-(3-(5-chloro-1,3-dioxo-1H-pyrido[1,2-c]pyrimidin-2(3H)-yl)-2-methylphenyl)-7-(pyrrolidin-1-ylmethyl)-9H-carbazole-1-carboxamide (31).

One embodiment provides compounds of Formula (I) or a salt thereof, wherein Q is:

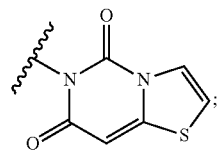 [SMILES: *n1c(=O)cc2sccn2c1=O]

and $R_1$, $R_2$, and $R_3$ are defined in the first aspect. The compounds of this embodiment have the structure of Formula (IV):

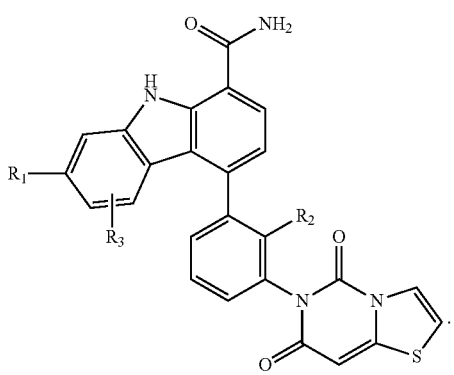

(IV)

One embodiment provides compounds of Formula (IV), wherein $R_1$ is —C(CH$_3$)$_2$OH; and $R_2$, and $R_3$ are defined in the first aspect. The compounds of this embodiment have the structure of Formula (IVA):

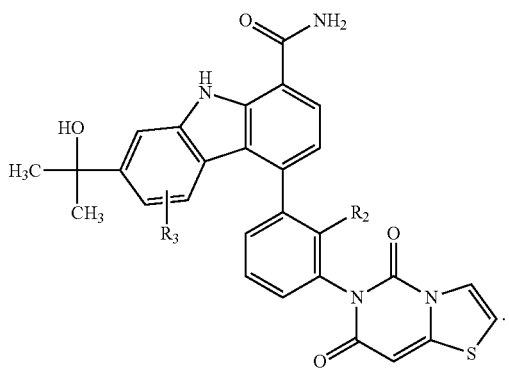

(IVA)

Included in this embodiment are compounds of Formula (IVA) in which $R_2$ is —CH$_3$. Also included in this embodiment are compounds of Formula (IVA) in which $R_3$ is H.

One embodiment provides compounds of Formula (I) or a salt thereof, wherein Q is:

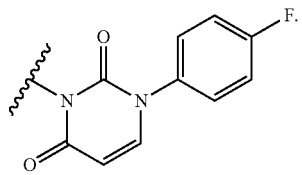 [SMILES: *n1c(=O)ccn(-c2ccc(F)cc2)c1=O]

The compounds of this embodiment have the structure of Formula (V):

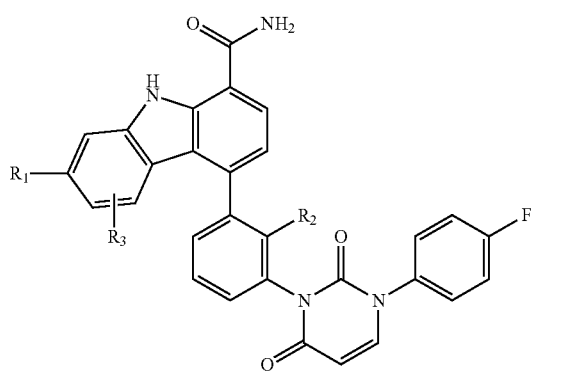

(V)

wherein $R_1$, $R_2$, and $R_3$ are defined in the first aspect.

One embodiment provides compounds of Formula (V), wherein $R_1$ is —C(CH$_3$)$_2$OH. The compounds of this embodiment have the structure of Formula (Va):

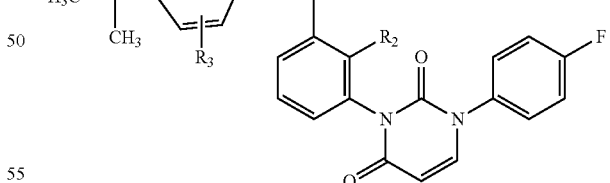

(VA)

wherein $R_2$ and $R_3$ are defined in the first aspect. Included in this embodiment are compounds of Formula (Va) in which $R_2$ is —CH$_3$. Also included in this embodiment are compounds of Formula (Va) in which $R_3$ is H.

One embodiment provides compounds of Formula (I) or a salt thereof, wherein $R_3$ is —CH$_3$; and $R_1$, $R_2$, and Q are defined in the first aspect. Included in this embodiment are compounds having the structure of Formula (IA):

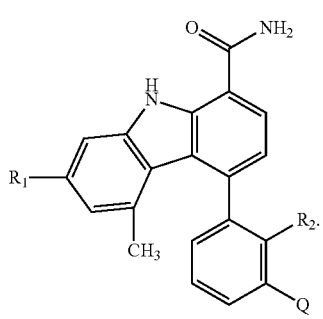

(IA)

Also included in this embodiment are compounds of Formula (I) and compounds of Formula (VI) in which $R_1$ is —C(CH$_3$)$_2$OH.

One embodiment provides a compound of Formula (I) or a salt thereof, wherein the compound is selected from: 4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (1 and 2); 4-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (3); 4-(3-(S)-(8-fluoro-1-methyl(d$_3$)-2,4-dioxo-1,2-dihydroquinazolin-3(4H)-yl)-2-methylphenyl)-7-(2-hydroxypropan-2-yl)-9H-carbazole-1-carboxamide (4); 4-(2-chloro-3-(8-fluoro-1-methyl-2,4-dioxo-1,2-dihydroquinazolin-3(4H)-yl)phenyl)-7-(2-hydroxypropan-2-yl)-9H-carbazole-1-carboxamide (5); 4-(2-chloro-3-(1-methyl-2,4-dioxo-1,2-dihydroquinazolin-3(4H)-yl)phenyl)-7-(2-hydroxypropan-2-yl)-9H-carbazole-1-carboxamide (6); 7-(2-hydroxypropan-2-yl)-4-(3-(8-methoxy-1-methyl-2,4-dioxo-1,2-dihydroquinazolin-3(4H)-yl)-2-methylphenyl)-9H-carbazole-1-carboxamide (7); 4-(3-(6-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (8); 4-(3-(3-(4-fluorophenyl)-2,6-dioxo-2,3-dihydropyrimidin-1(6H)-yl)-2-methylphenyl)-7-(2-hydroxypropan-2-yl)-9H-carbazole-1-carboxamide (9); 7-(2-hydroxypropan-2-yl)-4-(3-(7-methoxy-1,3-dioxo-1H-pyrido[1,2-c]pyrimidin-2(3H)-yl)-2-methylphenyl)-9H-carbazole-1-carboxamide (10); 7-(2-hydroxypropan-2-yl)-4-(3-(6-methoxy-1,3-dioxo-1H-pyrido[1,2-c]pyrimidin-2(3H)-yl)-2-methylphenyl)-9H-carbazole-1-carboxamide (11); 7-(2-hydroxypropan-2-yl)-4-(3-(5-methoxy-1,3-dioxo-1H-pyrido[1,2-c]pyrimidin-2(3H)-yl)-2-methylphenyl)-9H-carbazole-1-carboxamide (12); 4-(3-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (13); 4-(3-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (14 and 15); 4-(3-(5-chloro-1,3-dioxo-1H-pyrido[1,2-c]pyrimidin-2(3H)-yl)-2-methylphenyl)-7-pivalamido-9H-carbazole-1-carboxamide (16); 4-(3-(5-chloro-1,3-dioxo-1H-pyrido[1,2-c]pyrimidin-2(3H)-yl)-2-methylphenyl)-7-pivalamido-9H-carbazole-1-carboxamide (17); 4-(3-(5-fluoro-1,3-dioxo-1H-pyrido[1,2-c]pyrimidin-2(3H)-yl)-2-methylphenyl)-7-(methoxymethyl)-9H-carbazole-1-carboxamide (18); 4-(3-(4-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (19); 4-(3-(5,7-dioxo-5H-thiazolo[3,2-c]pyrimidin-6(7H)-yl)-2-methylphenyl)-7-(2-hydroxypropan-2-yl)-9H-carbazole-1-carboxamide (20); 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (21); 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (22 and 23); 4-(3-(S)-(8-fluoro-1-methyl-2,4-dioxo-1,2-dihydroquinazolin-3(4H)-yl)-2-methylphenyl)-7-(2-hydroxypropan-2-yl)-5-methyl-9H-carbazole-1-carboxamide (24); 4-(3-(8-fluoro-1-methyl-2,4-dioxo-1,2-dihydroquinazolin-3(4H)-yl)-2-methylphenyl)-7-(2-hydroxypropan-2-yl)-5-methyl-9H-carbazole-1-carboxamide (25); 4-(3-(S)-(8-fluoro-1-methyl-2,4-dioxo-1,2-dihydroquinazolin-3(4H)-yl)-2-methylphenyl)-7-(2-hydroxypropan-2-yl)-8-methyl-9H-carbazole-1-carboxamide (26); 4-(3-(S)-(8-fluoro-1-methyl(d$_3$)-2,4-dioxo-1,2-dihydroquinazolin-3(4H)-yl)-2-methylphenyl)-7-(2-hydroxypropan-2-yl)-5-methyl-9H-carbazole-1-carboxamide (27); 4-(3-(5-fluoro-1,3-dioxo-1H-pyrido[1,2-c]pyrimidin-2(3H)-yl)-2-methylphenyl)-7-(hydroxymethyl)-9H-carbazole-1-carboxamide (28); 7-(dimethylamino)-4-(3-(5-fluoro-1,3-dioxo-1H-pyrido[1,2-c]pyrimidin-2(3H)-yl)-2-methylphenyl)-9H-carbazole-1-carboxamide (29); 7-(acetamidomethyl)-4-(3-(5-fluoro-1,3-dioxo-1H-pyrido[1,2-c]pyrimidin-2(3H)-yl)-2-methylphenyl)-9H-carbazole-1-carboxamide (30); 4-(3-(5-chloro-1,3-dioxo-1H-pyrido[1,2-c]pyrimidin-2(3H)-yl)-2-methylphenyl)-7-(pyrrolidin-1-ylmethyl)-9H-carbazole-1-carboxamide (31); and 4-(3-(5-fluoro-1,3-dioxo-1H-pyrido[1,2-c]pyrimidin-2(3H)-yl)-2-methylphenyl)-7-(methoxymethyl)-9H-carbazole-1-carboxamide (32).

Atropisomers are stereoisomers resulting from hindered rotation about a single bond axis where the rotational barrier is high enough to allow for the isolation of the individual rotational isomers. (LaPlante et al., *J. Med. Chem.*, 54:7005-7022 (2011)).

The compounds of Formula (I) have two stereogenic axes: bond (a) between the tricyclic carbazole group and the phenyl group; and bond (b) between the asymmetric heterocyclic dione group Q and the phenyl group.

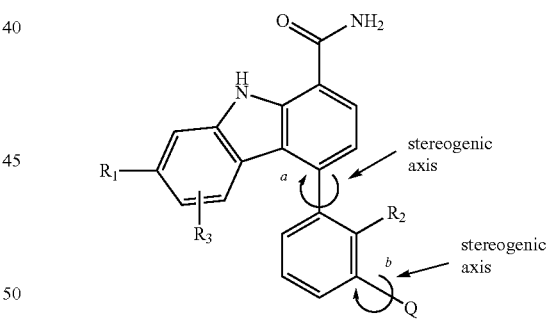

Due to the non-symmetric nature of the substitutions to the rings connected by the single bonds labeled a and b, and due to limited rotation about these bonds caused by steric hindrance, the compounds of Formula (I) can form rotational isomers. If the rotational energy barriers are sufficiently high, hindered rotations about bond (a) and/or bond (b) occur at rates that are slow enough to allow isolation of the separated atropisomers as different compounds. Thus, the compounds of Formula (I) can form four rotational isomers, which under certain conditions, such as chromatography on a chiral stationary phase, can be separated into individual atropisomers. In solution, the compounds of Formula (I) can be provided as a mixture of four diastereomers, or separated into mixtures of two pairs of diastereomers or single atropisomers.

For the compounds of Formula (I), the pair of rotational isomers formed by hindered rotation about stereogenic axis (a), represented by the structures:

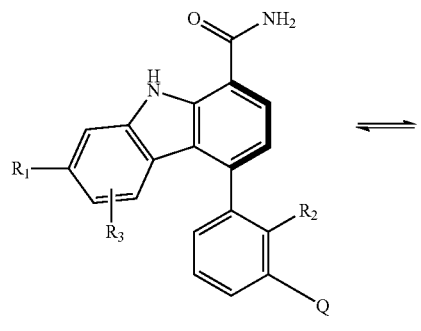

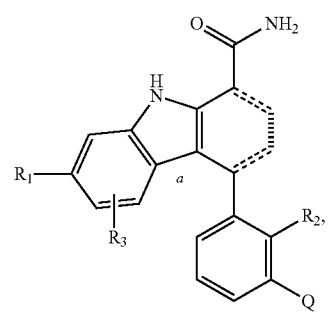

were found to be separable. However, at ambient temperatures and above, a solution containing one of the individual rotational isomers was found to undergo racemization around the stereogenic axis (a) to form a mixture of atropisomers, for example, over a period of hours. Stable rotational isomers formed by hindered rotation about stereogenic axis (b) were isolated and found to be stable in solution at ambient and physiological temperatures.

The two rotational isomers of the compound of Formula (II) that are formed by the hindered rotation about stereogenic axis (b) can be represented as follows:

(II-1)

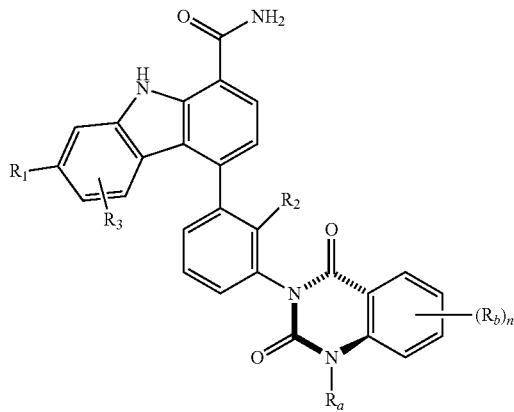

(II-2)

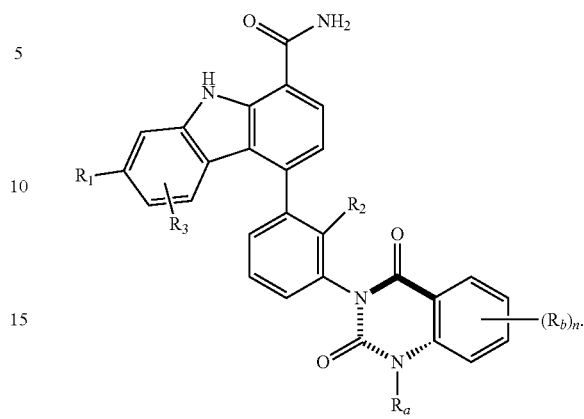

The two rotational isomers of the compound of Formula (III) that are formed by the hindered rotation about stereogenic axis (b) can be represented as follows:

(III-1)

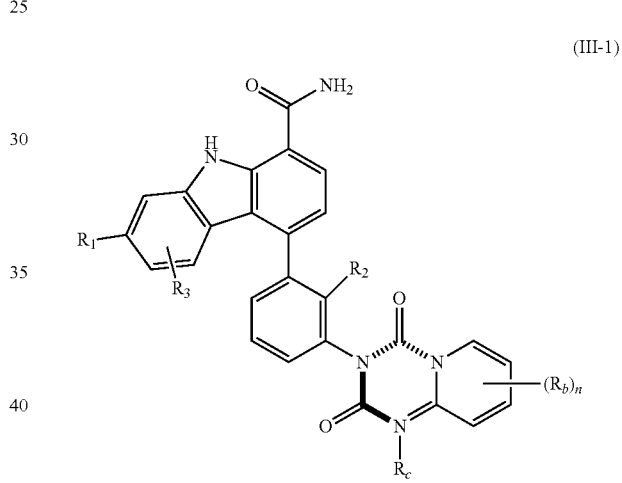

(III-2)

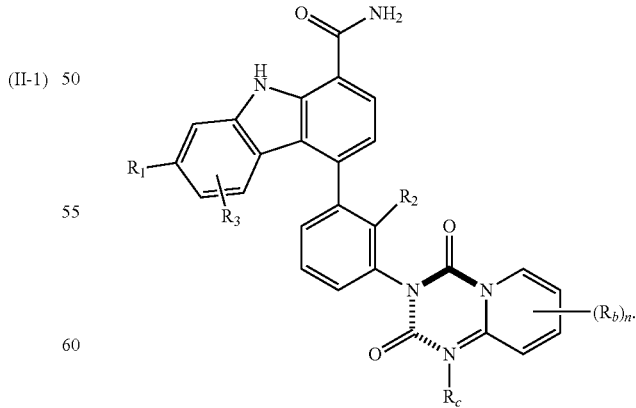

The two rotational isomers of the compound of Formula (IV) that are formed by the hindered rotation about stereogenic axis (b) can be represented as follows:

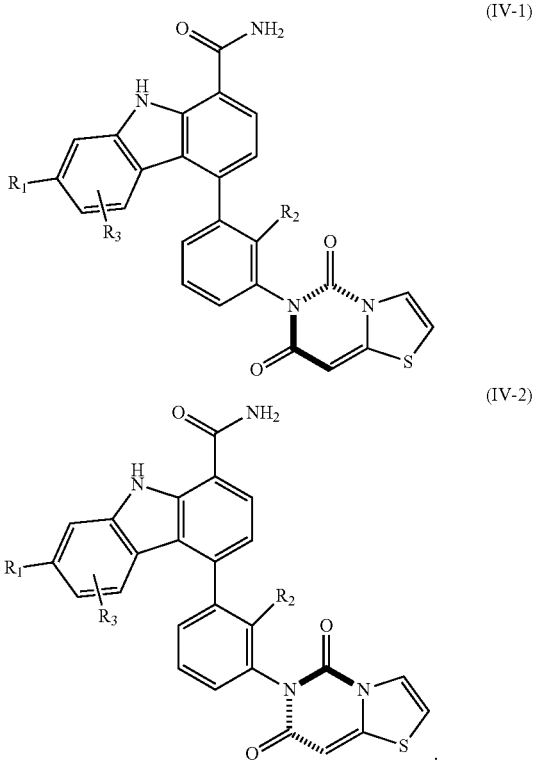

The two rotational isomers of the compound of Formula (V) that are formed by the hindered rotation about stereogenic axis (b) can be represented as follows:

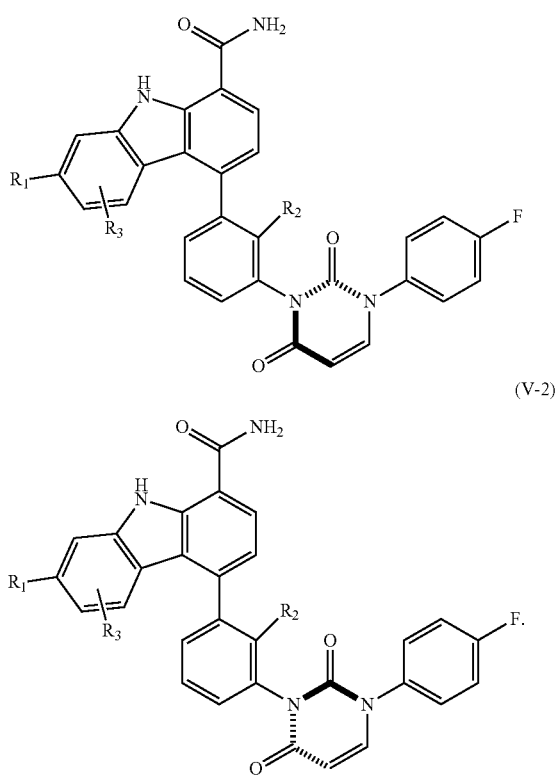

The absolute spacial configurations of the atropisomers can be determined by single crystal x-ray crystallography.

Thus, compounds of Formula (I) can be isolated as individual atropisomers, as mixtures comprising the two atropisomers, or as stable pairs of diastereomers, wherein one pair has the (R) configuration about bond (b) but is a mixture of the (R) and (S) configurations about bond (a), and the other pair has the (S) configuration about bond (b) but is a mixture of the (R) and (S) configurations about bond (a).

Compounds of Formula (I) can be separated into pairs of diastereomers with a single absolute configuration about bond (b) but a mixture of two interconverting absolute configurations about bond (a); or alternatively, pairs of diastereomers with a single absolute configuration about bond (a) but a mixture of two interconverting absolute configurations about bond (b). Such separation can be achieved using methods known in the art, such as preparative chromatography on a chiral stationary phase.

Compounds of this invention can exist as a mixture of four atropisomers that can preferably be separated by various techniques, including Supercritical Fluid Chromatography (SFC), to give individual atropisomers or mixtures of two atropisomers. SFC, which is a form of normal phase HPLC, is a separation technique that uses super/subcritical fluid $CO_2$ and polar organic modifiers such as alcohols as mobile phases. (White et al., *J. Chromatography A* 1074: 175-185 (2005)).

One embodiment provides a compound of Formula (II-1) or a salt thereof, wherein $R_2$, $R_3$, $R_a$, and $R_b$ are defined in the first aspect. Included in this embodiment are compounds of Formula (II-1) in which $R_2$ is Cl or —$CH_3$; $R_3$ is H, F, or —$CH_3$; $R_a$ is H or —$CH_3$, including —$CD_3$; and $R_b$ is H, F, or —$OCH_3$.

One embodiment provides a compound of Formula (III-2) or a salt thereof, wherein $R_1$, $R_3$, $R_b$, and $R_c$ are defined in the first aspect. Included in this embodiment are compounds of Formula (III-2) in which $R_1$ is —$C(CH_3)_2OH$, —NHC(=O)C(CH_3)_3, —N(CH_3)_2, or —$CH_2R_d$; $R_3$ is H, F, or —$CH_3$; $R_b$ is H, F, Cl, or —$OCH_3$; $R_c$ is H or F; and $R_d$ is —OH, —$OCH_3$, —NHC(=O)$CH_3$, or

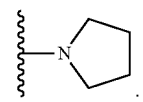 [SMILES: *N1CCCC1]

Also included in this embodiment are compounds in which $R_3$ is H.

One embodiment provides a compound selected from the exemplified examples within the scope of the first aspect or a salt thereof.

One embodiment provides a compound selected from any subset list of compounds within the scope of the first aspect or of any of the above embodiments, or a salt thereof.

In one embodiment, a composition is provided comprising a compound of Formula (II) or a salt thereof. Included in this embodiment is a composition comprising a mixture in any proportion of (i) a compound of Formula (II-1) and (ii) a compound of Formula (II-2), or salts thereof. Compositions of this embodiment include pharmaceutical compositions.

In one embodiment, a composition is provided comprising at least 98 equivalent weight % of a compound selected from the compound of Formula (II-1) and the compound of Formula (II-2), based on the total equivalent weight of the compounds of Formula (II-1) and Formula (II-2). Included in this embodiment, are compositions comprising at 99 equivalent weight %, 99.5 equivalent weight %, 99.8 equivalent weight %, and 99.9 equivalent weight % of a selected compound based on the total equivalent weight of the compounds of Formula (II-1) and Formula (II-2). Compositions of this embodiment include pharmaceutical compositions.

In one embodiment, a composition is provided comprising a compound of Formula (III) or a salt thereof. Included in this embodiment is a composition comprising a mixture in any proportion of (i) a compound of Formula (III-1) and (ii) a compound of Formula (III-2), or salts thereof. Compositions of this embodiment include pharmaceutical compositions.

In one embodiment, a composition is provided comprising at least 98 equivalent weight % of a compound selected from the compound of Formula (III-1) and the compound of Formula (III-2), based on the total equivalent weight of the compounds of Formula (III-1) and Formula (III-2). Included in this embodiment, are compositions comprising at 99 equivalent weight %, 99.5 equivalent weight %, 99.8 equivalent weight %, and 99.9 equivalent weight % of a selected compound based on the total equivalent weight of the compounds of Formula (III-1) and Formula (III-2). Compositions of this embodiment include pharmaceutical compositions.

In one embodiment, a composition is provided comprising a compound of Formula (IV) or a salt thereof. Included in this embodiment is a composition comprising a mixture in any proportion of (i) a compound of Formula (IV-1) and (ii) a compound of Formula (IV-2), or salts thereof. Compositions of this embodiment include pharmaceutical compositions.

In one embodiment, a composition is provided comprising at least 98 equivalent weight % of a compound selected from the compound of Formula (IV-1) and the compound of Formula (IV-2), based on the total equivalent weight of the compounds of Formula (IV-1) and Formula (IV-2). Included in this embodiment, are compositions comprising at 99 equivalent weight %, 99.5 equivalent weight %, 99.8 equivalent weight %, and 99.9 equivalent weight % of a selected compound based on the total equivalent weight of the compounds of Formula (IV-1) and Formula (IV-2). Compositions of this embodiment include pharmaceutical compositions.

In one embodiment, a composition is provided comprising a compound of Formula (V) or a salt thereof. Included in this embodiment is a composition comprising a mixture in any proportion of (i) a compound of Formula (V-1) and (ii) a compound of Formula (V-2), or salts thereof. Compositions of this embodiment include pharmaceutical compositions.

In one embodiment, a composition is provided comprising at least 98 equivalent weight % of a compound selected from the compound of Formula (V-1) and the compound of Formula (V-2), based on the total equivalent weight of the compounds of Formula (V-1) and Formula (V-2). Included in this embodiment, are compositions comprising at 99 equivalent weight %, 99.5 equivalent weight %, 99.8 equivalent weight %, and 99.9 equivalent weight % of a selected compound based on the total equivalent weight of the compounds of Formula (V-1) and Formula (V-2). Compositions of this embodiment include pharmaceutical compositions.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds or a salt thereof" refers to at least one compound, at least one salt of the compounds, or a combination thereof. For example, a compound of Formula (I) or a salt thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Compounds of Formula (I) can form salts which are also within the scope of this invention. Unless otherwise indicated, reference to an inventive compound is understood to include reference to one or more salts thereof. Pharmaceutically acceptable (i.e., non-toxic, physiologically acceptable) salts are preferred, in which the anion does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to Btk, or effective to treat or prevent autoimmune and/or inflammatory disease states, such as systemic lupus erythematosis, multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with Formula (I) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrastemally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, anti-oxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers, etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlledrelease formulation as may be provided in a dispersion of active compound in hydroxypropylmethyl cellulose.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

UTILITY

The compounds of the invention modulate kinase activity, including the modulation of Btk. Other types of kinase activity that may be modulated by the compounds of the instant invention include, but are not limited to, the Tec family of compounds, such as BMX, Btk, ITK, TXK and Tec, and mutants thereof.

Accordingly, compounds of Formula (I) have utility in treating conditions associated with the modulation of kinase activity, and particularly the selective inhibition of Btk activity. Such conditions include B-cell mediated diseases in which cytokine levels are modulated as a consequence of intracellular signaling.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of Btk, compounds of Formula (I) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, Kawasaki disease, chronic inflammatory demyelinating polyneuropathy (CIDP), dermatomyositis, uveitis, anti-factor-VIII disease, ankylosing spondylitis, myasthenia gravis, Goodpasture's disease, antiphospholipid syndrome, ANCA-associated vasculitis, dermatomyositis/polymyositis, cerebral malaria, chronic pulmonary inflammatory disease, silicosis, pulmonary sarcoidosis, bone resorption disease, allograft rejections, fever and myalgias due to infection, cachexia secondary to infection, myeloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, systemic lupus erythematosis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusion injury arising from stroke and cardiac ischemia reperfusion injury arising from myocardial infarction. Another preferred method of treatment is one in which the condition is multiple myeloma.

In addition, the Btk inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified above as if repeated at length, as well as any other condition that is affected by Btk kinase activity.

"Therapeutically effective amount" is intended to include an amount of a compound of the present invention that is effective when administered alone or in combination to inhibit Btk.

One embodiment provides methods for treating such Btk kinase-associated conditions, comprising administering to a subject in need thereof at least one compound of Formula (I) or a pharmaceutically acceptable salt thereof. A therapeutically-effective amount for treating such conditions may be administered. The methods of the present embodiment may be employed to treat Btk kinase-associated conditions such as treatment of allergic disorders and/or autoimmune and/or inflammatory diseases including, but not limited to, SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

The methods of treating Btk kinase-associated conditions may comprise administering at least one compound of Formula (I) alone or in combination with each other and/or other suitable therapeutic agents useful in treating such conditions. Therapeutically-effective amounts of at least one compound of Formula (I) and other suitable therapeutic agents for treating such conditions may be administered. Accordingly, "therapeutically effective amount" is also intended to include an amount of the combination of compounds claimed that is effective to inhibit Btk. The combination of compounds is preferably a synergistic combination. Synergy, as described, for example, by Chou et al., *Adv. Enzyme Regul.*, 22:27-55 (1984), occurs when the effect (in this case, inhibition of Btk) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-Btk effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Another embodiment provides the compounds of Formula (I) or pharmaceutically acceptable salts thereof, for use in therapy. In the present embodiment, the use in therapy may include the administration of a therapeutically-effective amount of a compound of Formula (I) pharmaceutically acceptable salts thereof.

The present invention also provides the use of the compounds of Formula (I) or pharmaceutically acceptable salts thereof, for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I) or pharmaceutically acceptable salts thereof for the treatment of prophylaxis of an allergic disorder and/or autoimmune and/or inflammatory disease.

The present invention also provides the use of the compounds of Formula (I) or pharmaceutically acceptable salts thereof, for the manufacture of a medicament for treatment of cancer. The present embodiment may include the use for the manufacture of a medicament includes the administration of a therapeutically-effective amount of a compound of Formula (I) or pharmaceutically acceptable salts thereof for the treatment of prophylaxis of an allergic disorder and/or autoimmune and/or inflammatory disease.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Examples of compounds of Formula (I) as specified in the "Examples" section below, have been tested in one or more of the assays described below.

Preferred compounds of Formula (I) inhibit Btk enzymes with $IC_{50}$ values of 6 nM or less, for example, from 0.001 to 6 nM, as measured by the Human Recombinant Btk enzyme assay. More preferably, the compounds of Formula (I) inhibit Btk enzymes with $IC_{50}$ values of 2 nM and less, for example, from 0.001 to 2 nM. Other preferred compounds inhibit Btk enzymes with $IC_{50}$ values of 1.0 nM and less, for example, from 0.001 to 1.0 nM.

Preferred compounds of Formula (I) have reduced inhibition of the Jak2 kinase with $IC_{50}$ values above 50 nM, for example, greater than 250 nM, as measured by the Jak2 tyrosine kinase assay. More preferably, the compounds of Formula (I) inhibit Jak2 enzymes with $IC_{50}$ values of greater than 400 nM, for example, with $IC_{50}$ values of greater than 700 nM.

Preferred compounds of Formula (I) have ratios of Jak2 $IC_{50}$ inhibition values, as measured by the Jak2 tyrosine kinase assay, to Btk $IC_{50}$ inhibition values, as measured by the Human Recombinant Btk enzyme assay, of 150 and greater, for example, ratios of 300 and greater. More preferably, the compounds of Formula (I) have ratios of Jak2 $IC_{50}$ inhibition values to Btk $IC_{50}$ inhibition values of 400 and greater, for example, ratios of 500 and greater.

Preferred compounds of Formula (I) have improved potency in the whole blood BCR-stimulated CD69 expression assay with $IC_{50}$ values of 250 nM or less, for example, from 0.1 to 250 nM. More preferably, the compounds of Formula (I) have potency in the whole blood BCR-stimulated CD69 expression assay with $IC_{50}$ values of 160 nM or less, for example, from 0.1 to 160 nM; and with $IC_{50}$ values of 100 nM or less, for example, from 0.1 to 100 nM.

Methods of Preparation

Compounds of Formula (I) can be prepared using methods shown in Scheme 1. Substituted carbazolecarboxamides 1 (wherein Y is an appropriate group such as Br, Cl or trifluoromethanesulfonyloxy; preferably Br) can be converted to the corresponding boronate esters 2 (R'=alkyl, or both R' groups taken together form a ring such as 4,4,5,5-tetramethyl-1,3,2-dioxaborolane or 5,5-dimethyl-1,3,2-dioxaborinane) using methods well known in the chemical literature (see, for example, Ishiyama, T. et al., *Tetrahedron*, 57:9813 (2001), and references cited therein). Examples of such methods are the reaction of 1 with 4,4,4',4',5,5,5',5'-octamethyl-2,2'-bi(1,3,2-dioxaborolane) or 5,5,5',5'-tetramethyl-2,2'-bi(1,3,2-dioxaborinane) in the presence of a base such as potassium acetate and a suitable catalyst such as 1,1'-bis(diphenylphosphino)ferrocene palladium(II) chloride in a suitable solvent.

Compounds 2 can be converted into compounds 4 of Formula (I), wherein Z represents a substituted monocyclic or fused bicyclic heterocyclic ring (substituent Q in compounds of Formula (I)) by reaction with an appropriate compound 3 (wherein Y' is an appropriate group such as Br or trifluoromethanesulfonyloxy, preferably Br). This conversion may be achieved by using a suitable base such as potassium carbonate, cesium carbonate or tripotassium phosphate, and a suitable catalyst such as tetrakis (triphenylphosphine)palladium, 1,1'-bis(diphenylphosphino)ferrocene palladium(II) chloride, or 1,1'-bis(di-tert-butylphosphino)ferrocene palladium(II) chloride, in a suitable solvent such as dioxane or tetrahydrofuran, optionally with a suitable cosolvent such as water. Such coupling reactions are commonly known as Suzuki-Miyaura coupling reactions, and are well known in the chemical literature (see, for example, Heravi, M. M., *Tetrahedron*, 68:9145 (2012), and references cited therein).

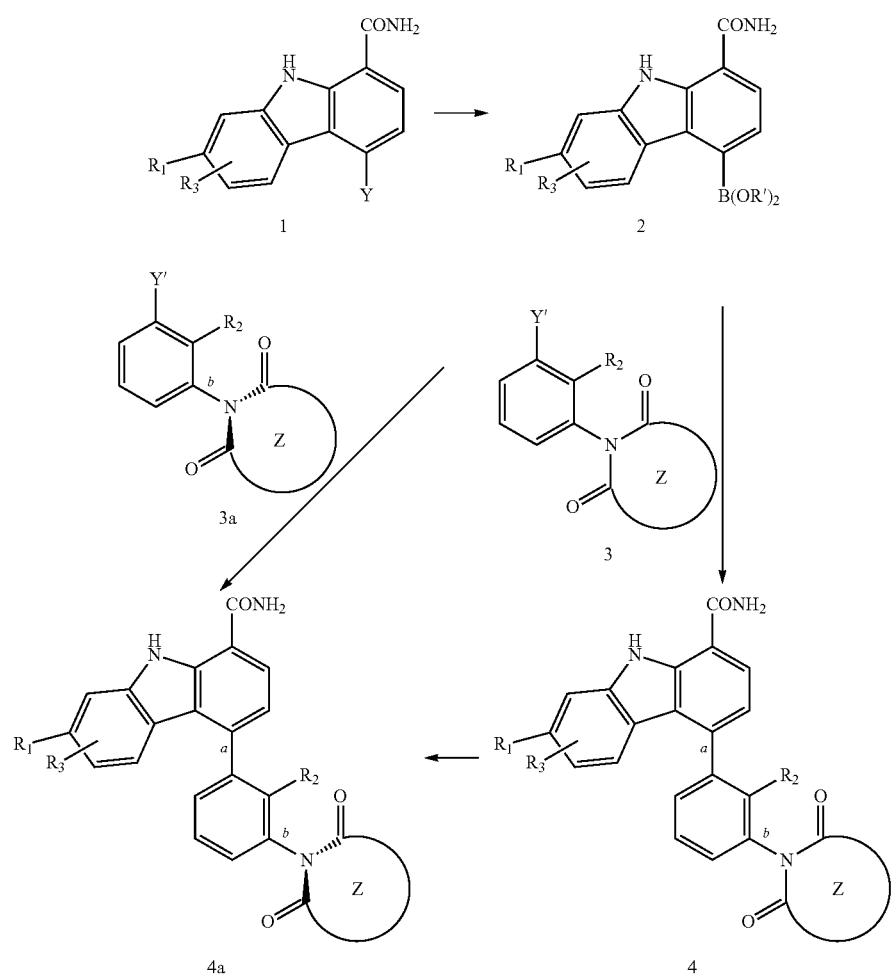

Scheme 1

Due to the non-symmetric nature of the aromatic rings connected by the single bonds labeled a and b in Scheme 1, and due to limited rotation about these bonds caused by steric hindrance, compounds of Formula (I) display chirality, known as atropisomerism. Thus, under certain conditions, such as chromatography on a chiral stationary phase, the four diastereomers due to the two chiral bonds can be observed as four separate peaks in the chromatogram. Hindered rotation about bond b occurs at a rate which is slow enough to allow isolation of separated atropisomers as different compounds which are stable at normal room temperature. However, hindered rotation about bond a can occur at a rate such that, if separated, these atropisomers will quickly interconvert at room temperature, and the separated atropisomers about bond a may not be capable of storage as separate stable compounds. Thus, compounds of Formula (I) can be isolated either as mixtures of four diastereomers, or as stable pairs of diastereomers, wherein one pair has the (R) configuration about bond b but is a mixture of the (R) and (S) configurations about bond a, and the other pair has the (S) configuration about bond b but is a mixture of the (R) and (S) configurations about bond a.

Compounds 4 of Formula (I) can be separated into pairs of diastereomers 4a, with a single absolute configuration about bond b (either that shown, or the opposite absolute configuration) but a mixture of two interconverting absolute configurations about bond a. Such separation can be achieved using methods known in the art, such as preparative chromatography on a chiral stationary phase. Alternatively, compounds 4a of Formula (I), which are configurationally stable pairs of diastereomers as described above, may be prepared from compounds 2 via the same Suzuki-Miyaura coupling reaction described above but using a single enantiomer 3a (of the absolute configuration shown, or of the opposite absolute configuration), as long as the conditions of the Suzuki-Miyaura coupling are such that racemization of 3a or 4a does not occur.

Compounds 4 of Formula (I) can also be prepared using methods shown in Scheme 2. Substituted boronic esters 5, wherein Z represents a substituted monocyclic or fused bicyclic heterocyclic ring (substituent Q in compounds of Formula (I)), can be reacted with substituted carbazolecarboxamides 1 (wherein Y is an appropriate group such as Br, Cl or trifluoromethanesulfonyloxy, preferably Br) under conditions of the Suzuki-Miyaura coupling reaction as described above, to provide compounds 4 of Formula (I) as mixtures of four diastereomers. Optionally, as described above, such compounds can be separated into pairs of interconverting diastereomers 4a with a single absolute configuration about bond b (either that shown, or the opposite absolute configuration) and a mixture of absolute configurations about bond a. Alternatively, compounds 5 can be separated into single enantiomers 5a, and reacted with compounds 1 in Suzuki-Miyaura coupling reactions, under conditions which will not cause racemization of 5a, to give compounds 4a of Formula (I).

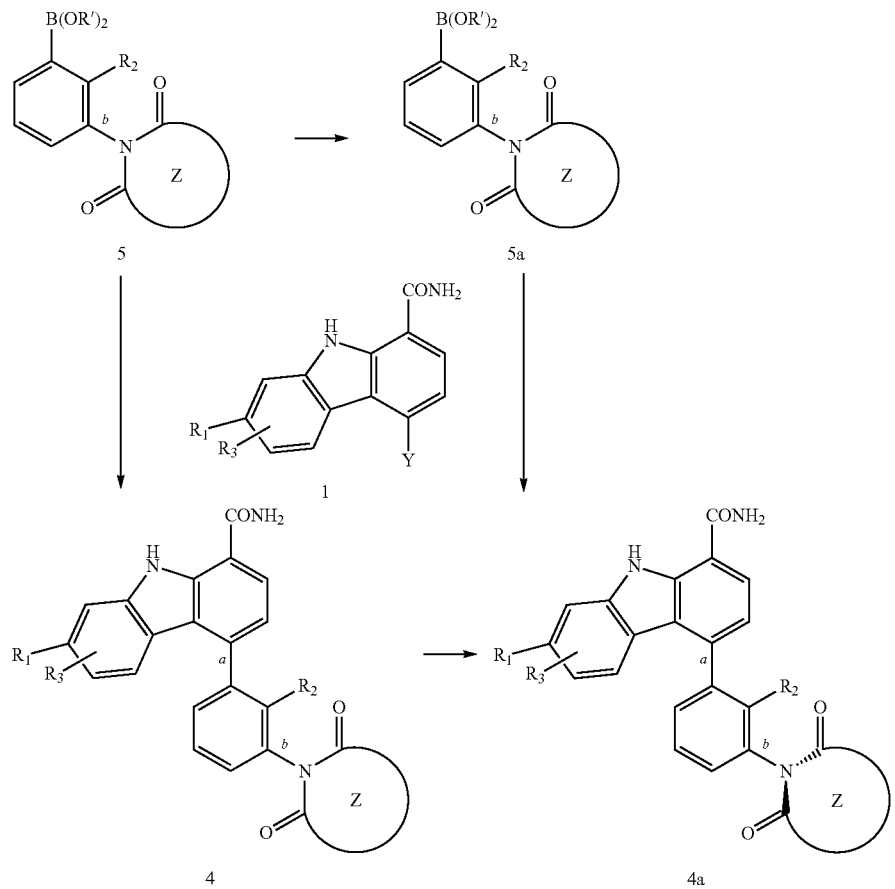

An alternative method for the synthesis of certain compounds 7 of Formula (I) is shown in Scheme 3. A suitably substituted 4-arylimino-1H-benzo[d][1,3]oxazin-2(4H)-one 6 can react with boronic esters 2 under conditions of the Suzuki-Miyaura coupling reaction as described above, to provide compounds 7 of Formula (I) as mixtures of four diastereomers. During the course of the reaction, the 4-arylimino-1H-benzo[d][1,3]oxazin-2(4H)-one moiety present in 6 rearranges to the 3-arylquinazoline-2,4(1H,3H)-dione moiety present in the reaction product 7.

Scheme 3

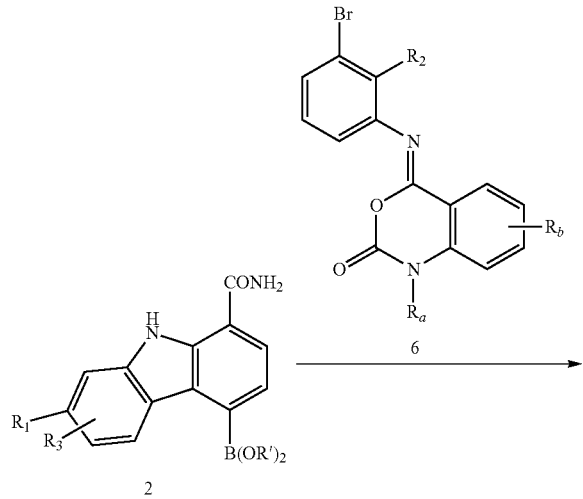

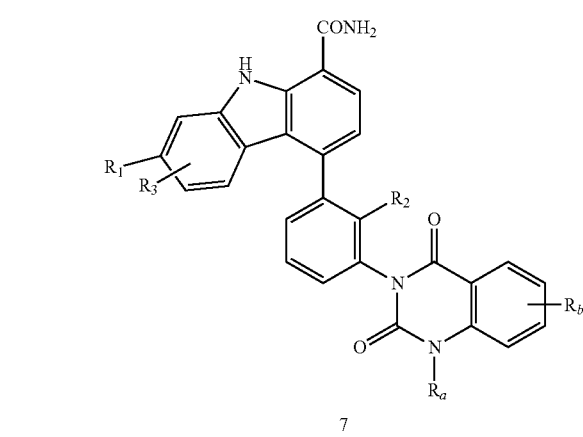

An alternative method for the synthesis of certain compounds 9 of Formula (I) is shown in Scheme 4. A compound 8 of Formula (I), either as a mixture of four diastereomers or a mixture of two interconverting diastereomers, can be treated with an alkylating agent such as iodomethane or trideuteroiodomethane, in the presence of a suitable base such as cesium carbonate or potassium carbonate, in a suitable solvent such as DMF or THF, to give a compound 9 of Formula (I), wherein $R_a$ is the alkyl group derived from the alkylating agent used.

Scheme 4

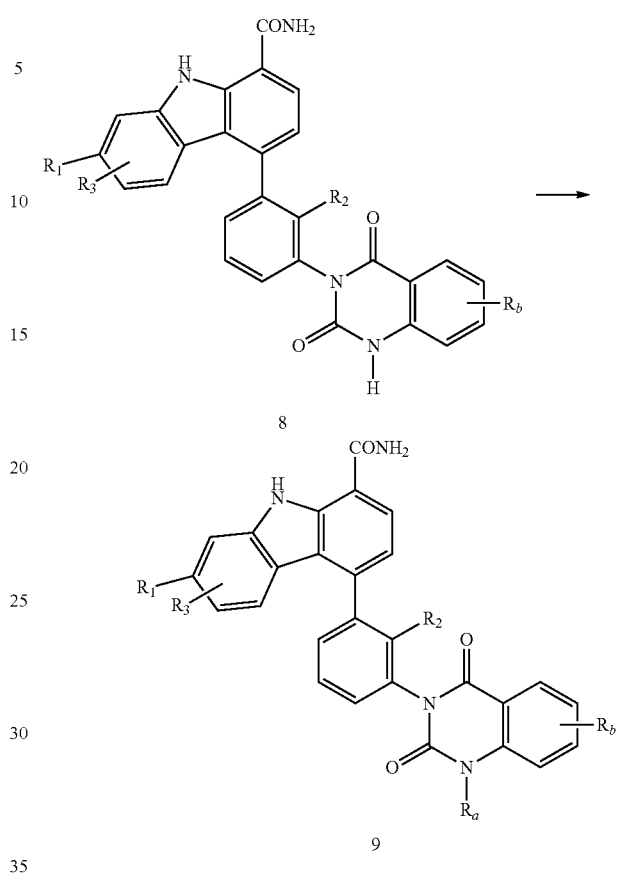

Intermediate compounds 1, used in the preparation of compounds of Formula (I), can be prepared using methods known in the chemical literature, for example in U.S. Pat. No. 8,084,620, and shown in Scheme 5. An appropriately substituted cyclohexanone 10 and a 2-hydrazinylbenzoic acid 11 or a suitable salt of 11 such as a hydrochloric acid salt (wherein Y is a suitable group such as Br, Cl or trifluoromethanesulfonyloxy, preferably Br), both readily prepared by methods well known in the chemical literature, can react in a suitable solvent with an appropriate catalyst, for example ethanol with hydrochloric acid, toluene with p-toluenesulfonic acid or trifluoroacetic acid, or acetic acid (in which case the solvent also can serve as the catalyst), at a suitable temperature to provide the corresponding tetrahydrocarbazole derivative 12. This reaction is commonly known as the Fischer indole synthesis, and is well known in the chemical literature (for example, see Kamata, J. et al., *Chem. Pharm. Bull.*, 52:1071 (2004)). Alternatively, the Fischer indole synthesis can be carried out in two consecutive steps: 10 can react with 11 under suitable conditions (such as in an appropriate solvent such as ethanol or toluene, optionally with a suitable catalyst such as p-toluenesulfonic acid) to form an intermediate hydrazone, which can be isolated and then reacted further under suitable conditions (for example, ethanol with hydrochloric acid, acetic acid with zinc chloride, or toluene with trifluoroacetic acid) to form 12.

Scheme 5

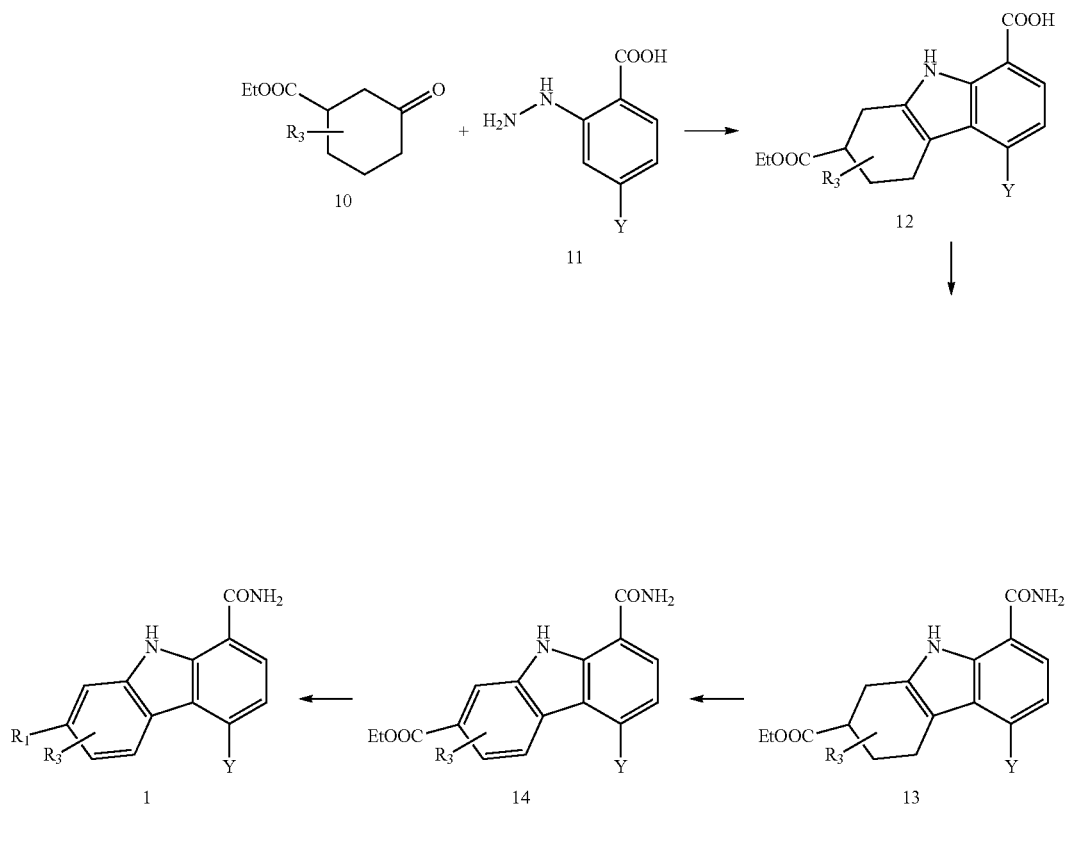

The carboxylic acid 12 can be converted to the carboxamide 13 using methods well known in the chemical literature, for example by conversion of 12 to the acid chloride by treatment with oxalyl chloride or thionyl chloride, followed by treatment with ammonia; or by treatment of 12 with ammonia in the presence of a coupling reagent such as carbodiimide or N-(3-dimethylaminopropyl)-N'-ethylcarbodiimide hydrochloride and 1-hydroxybenzotriazole or 1-hydroxy-7-azabenzotriazole. Conversion of the tetrahydrocarbazole 13 to the carbazole 14 can be performed using methods well known in the chemical literature, for example by treatment of 13 with an oxidizing agent such as 2,3-dichloro-5,6-dicyanobenzoquinone in a suitable solvent.

Conversion of the ethoxycarbonyl group of 14 to the substituent $R_1$ of compound 1 can be performed using methods well known in the chemical literature. For example, treatment of 14 with a reagent such as methyllithium or methylmagnesium chloride can provide compound 1 wherein $R_1$ is a 2-hydroxy-2-methylethyl group. Alternatively, treatment of 14 with a reducing agent such as lithium aluminum hydride can provide compound 1 wherein $R_1$ is hydroxymethyl. These and other $R_1$ groups can also be further manipulated to provide still other $R_1$ groups. For example, a compound 1 wherein $R_1$ is hydroxymethyl can be converted to a compound 1 wherein $R_1$ is methoxymethyl by treatment with thionyl chloride followed by treatment of the intermediate compound 1 wherein $R_1$ is chloromethyl with methanol. Additional examples are known in the chemical literature, for example as reported in U.S. Pat. No. 8,084,620.

Intermediate compounds 3 and 5, used in the preparation of compounds 4 of Formula (I), can be prepared by a variety of methods. Some of these methods are shown in Scheme 6. An isatoic anhydride 15 can react with a substituted aniline 16 to produce an amide 17. Such reactions can be carried out under a variety of conditions, for example by heating in a suitable solvent, or by heating in the presence of an auxiliary reagent such as trimethylaluminum. A compound 17 can be converted into a substituted quinazolinedione 18 (which is an example of a compound 3 of Scheme 1), for example by treatment in a suitable solvent with phosgene or triphosgene. Optionally, a compound 18 can be converted to the corresponding boronate ester 19 (which is an example of a compound 5 of Scheme 2) using methods previously described for the conversion of 1 into 2 (see the discussion of Scheme 1 above). Alternatively, a compound 18 can optionally be converted into a compound 20 where $R_a$ is an alkyl group (an example of a compound 3 of Scheme 1) using methods known well known in the chemical literature, for example by treatment with an alkylating agent such as iodomethane in the presence of a suitable base such as cesium carbonate.

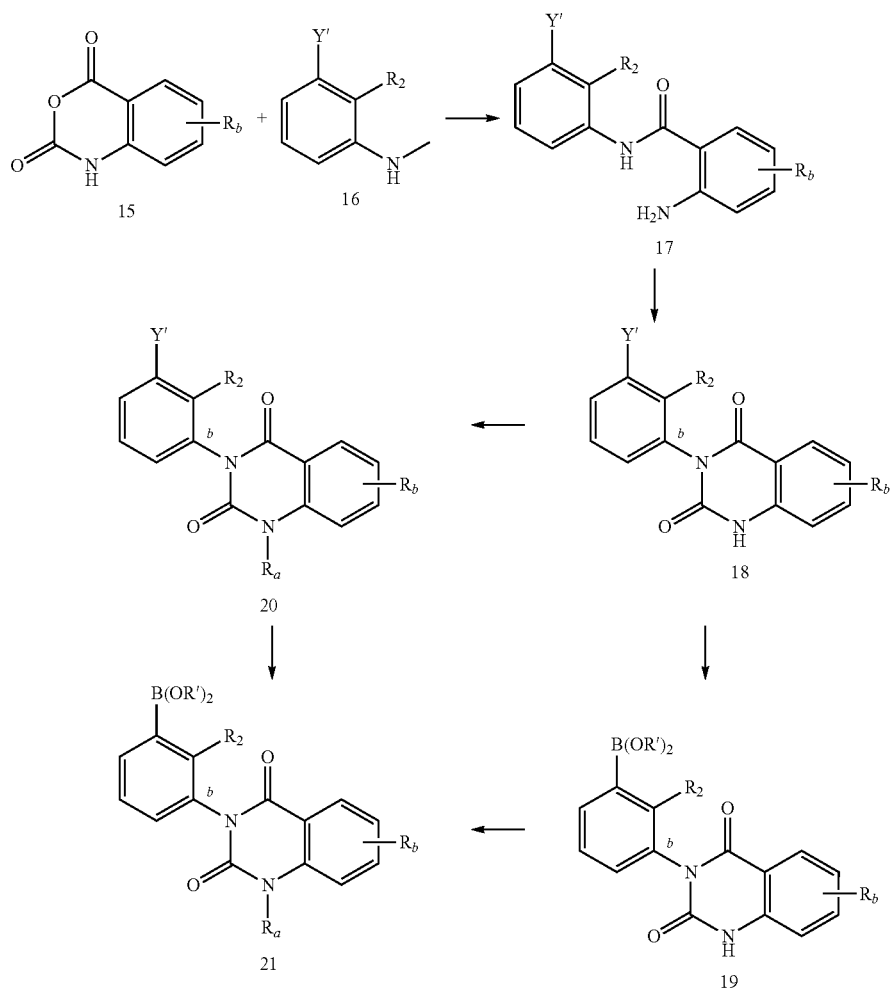

Scheme 6

A compound 20 can be optionally converted into a corresponding boronate ester 21 (which is an example of a compound 5 of Scheme 2) using the same methods described above. A compound 19 can also be optionally converted into the corresponding compound 21 by methods similar to those described for the conversion of 18 into 20.

As discussed above, the quinazolinedione intermediates 18, 19, 20, and 21 display chirality due to hindered rotation about the bond labeled b. If desired, these intermediates can be resolved into separate enantiomeric atropisomers, for example by chromatography on a chiral stationary phase. The separated enantiomers can then optionally be subjected to the conversions described above (18 to 19, 18 to 20, 19 to 21, or 20 to 21) to provide certain examples of the compounds 3a of Scheme 1 or 5a of Scheme 2.

Intermediate compounds 6 of Scheme 3 can be prepared using the method shown in Scheme 7. An N-substituted isatoic anhydride 22, wherein $R_a$ is an alkyl group, can react with a substituted aniline 16 to produce an amide 23. Such reactions can be carried out under a variety of conditions, for example by heating in a suitable solvent, or by heating in the presence of an auxiliary reagent such as trimethylaluminum. A compound 23 can be converted into a substituted aryliminobenzoxazinone 6, for example by treatment in a suitable solvent with phosgene or triphosgene.

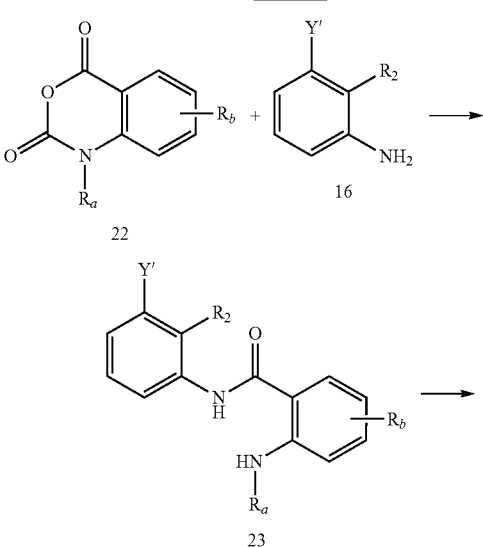

Scheme 7

-continued

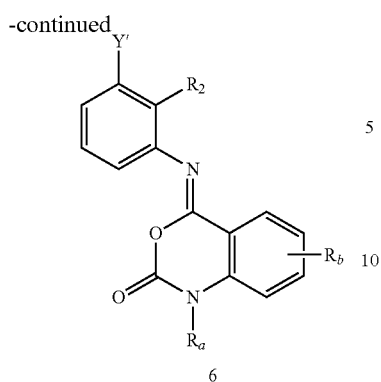

Some additional methods which can be used to prepare compounds 3 and 5, used in the preparation of compounds 4 of the current invention, are shown in Scheme 8. A substituted pyridyl-2-acetic acid 24 or a salt of a substituted pyridyl-2-acetic acid such as a sodium salt (which are either commercially available or can be prepared by methods well known in the literature) can be reacted with an aniline 16 under a variety of methods well known in the chemical literature to provide an amide 25. For example, the reaction can be performed in the presence of a coupling reagent such as O-(7-azabenzotriazol-1-yl)-1,1,3,3-tetramethyluronium hexafluorophosphate (HATU), or a mixture of 1-[3-(dimethylamino)propyl]-3-ethyl-carbodiimide hydrochloride (EDC) and 1-hydroxybenzotriazole hydrate (HOBT). An amide 25 can be converted into the corresponding substituted 1H-pyrido[1,2-c]pyrimidine-1,3(2H)-dione 26 (which is an example of an intermediate compound 3 of Scheme 1) by heating with a reagent such as carbonyldiimidazole in an appropriate solvent such as toluene.

Scheme 8

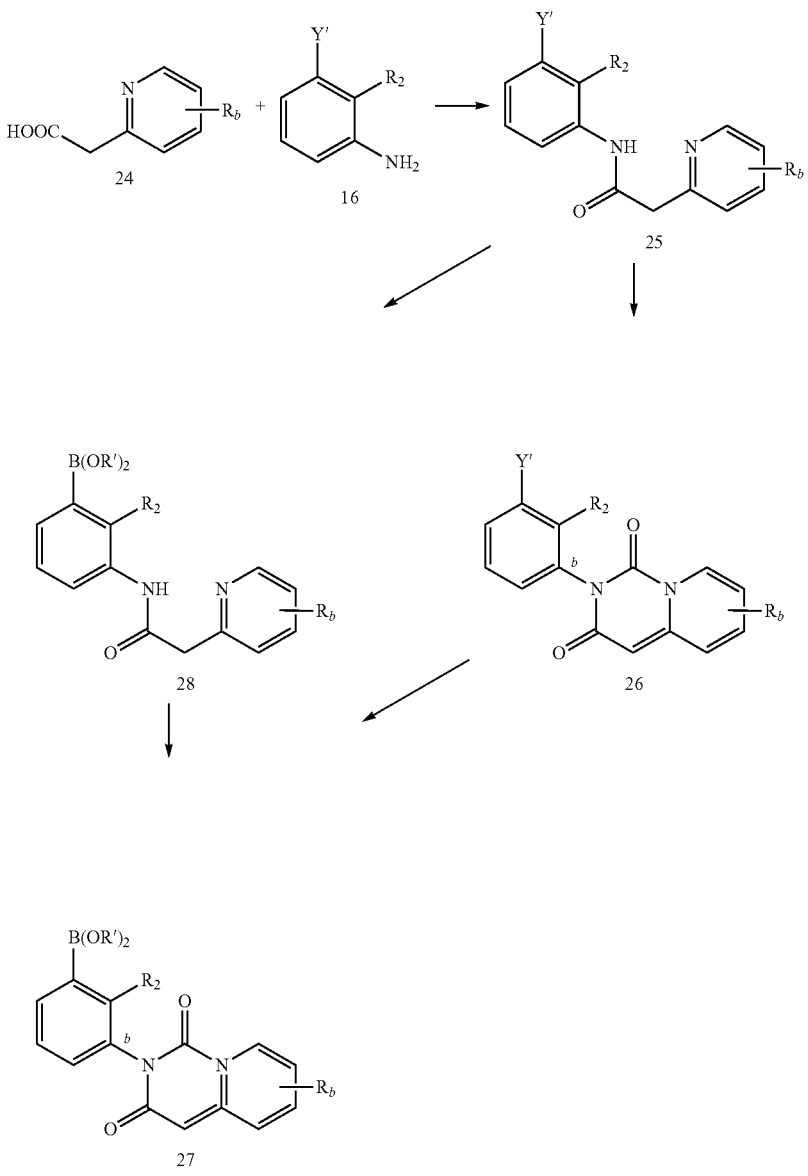

Intermediate 26 can optionally be converted into the corresponding boronate ester 27 (which is an example of an intermediate compound 5 of Scheme 2) using methods previously described for the conversion of 1 into 2 (see the discussion of Scheme 1 above). Alternatively, compound 25 can be converted into the corresponding boronate ester 28 using methods previously described, followed by conversion of 28 to 27 by heating with a reagent such as carbonyldiimidazole.

In Scheme 8, the pyridyl ring in the structures shown can also be replaced with another nitrogen heterocycle, such as a thiazole. In this case, the corresponding compounds of structures 26 and 28 will contain a 5H-thiazolo[3,2-c]pyrimidine-5,7(6H)-dione moiety in place of the 1H-pyrido[1,2-c]pyrimidine-1,3(2H)-dione moiety shown.

As discussed above, the 1H-pyrido[1,2-c]pyrimidine-1,3(2H)-dione compounds 26 and 27 display chirality due to hindered rotation about the bond labeled b. If desired, these intermediates can be resolved into separate enantiomers, for example by chromatography on a chiral stationary phase, to provide certain examples of the intermediate compounds 3a of Scheme 1 or 5a of Scheme 2.

Scheme 9

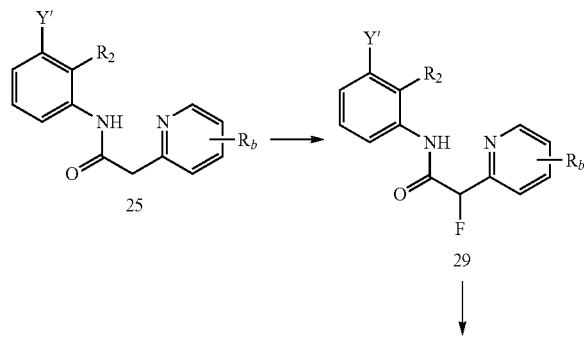

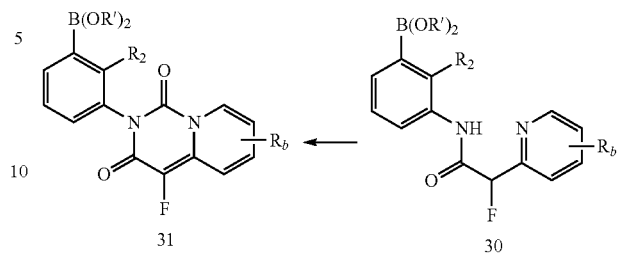

Scheme 9 illustrates another method for preparing certain intermediate compounds 5 of Scheme 2. The amide 25, prepared as shown in Scheme 8, can be treated with a fluorinating agent such as 1-(chloromethyl)-4-fluoro-1,4-diazoniabicyclo[2.2.2]octane bis(tetrafluoroborate) [SELECTFLUOR®] in a suitable solvent to prepare the fluoro-substituted amide 29. This compound can then be converted into the fluorinated boronate ester 30, and subsequently into the intermediate 31 (which is an example of an intermediate compound 5 of Scheme 2) using methods described in Scheme 8.

Scheme 10

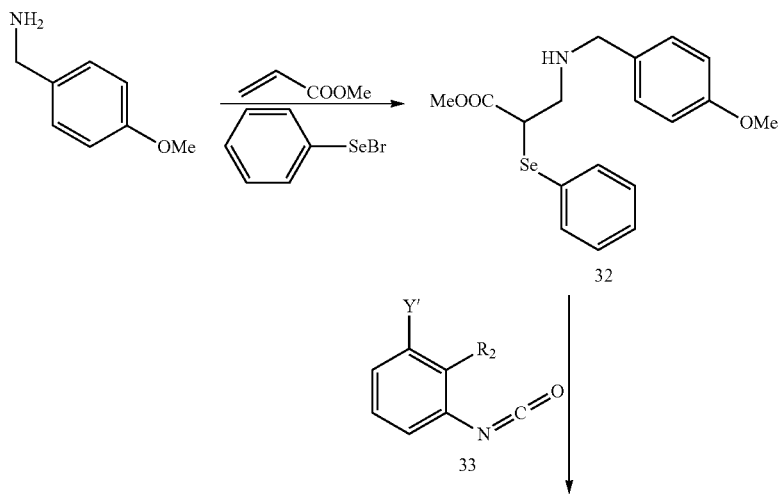

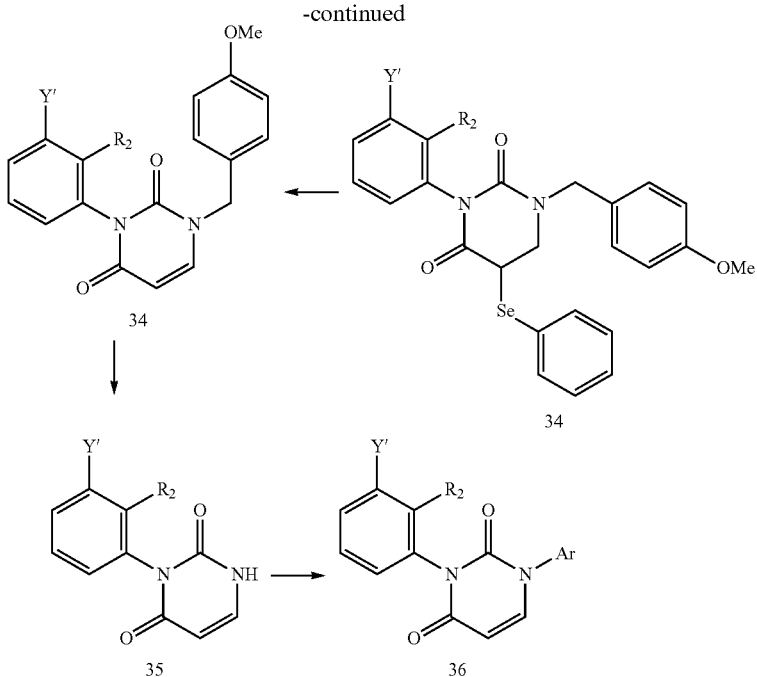

Preparation of a compound 3 of Scheme 1, wherein Z represents a substituted pyrimidine-1,3-dione moiety, can be achieved using the method shown in Scheme 10, following a general procedure reported by Cao, J. et al. (*Synthetic Commun.*, 39:205 (2009)). Compound 32 can be prepared by combining p-methoxybenzylamine, methyl acrylate and phenyl hypobromoselenoite. This material can be reacted with an appropriate aryl isocyanate 33 (which can be prepared using methods well known in the chemical literature) from the aniline 16 (see Scheme 6) to provide the substituted dihydropyrimidine-1,3-dione 34. Treatment of this compound with an oxidizing agent such as hydrogen peroxide can provide the substituted pyrimidine-1,3-dione 34. Removal of the p-methoxybenzyl group can be achieved using a number of methods reported in the chemical literature, for example by treatment with a mixture of trifluoromethanesulfonic acid and trifluoroacetic acid (as reported by Wu, F. et al., *J. Org. Chem.*, 69:9307 (2004)). The resulting pyrimidine-1,3-dione 35 can be reacted with an aryl boronic acid using conditions described by Jacobsen, M. F. et al. (*J. Org. Chem.*, 71:9183 (2006)) to provide 36, which is an example of an intermediate compound 3 of Scheme 1.

EXAMPLES

Preparation of compounds of the current invention, and intermediates used in the preparation of compounds of the current invention, can be prepared using procedures shown in the following examples and related procedures. The methods and conditions used in these examples, and the actual compounds prepared in these examples, are not meant to be limiting, but are meant to demonstrate how the compounds of the current invention can be prepared. Starting materials and reagents used in these examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared).

Column chromatography was generally performed using the flash chromatography technique (Still, W. C. et al., *J. Org. Chem.*, 43:2923 (1978)), or with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters SunFire $C_{18}$, Waters XBridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chiral super-critical fluid chromatographic separation of enantiomers or pairs of diastereomers was performed using conditions described for the individual cases. Mass spectral data were obtained by liquid chromatography mass spectroscopy using electrospray ionization.

Single crystal x-ray diffraction data were collected on a Bruker-AXS APEX2 CCD system using Cu Kα radiation (λ=1.5418 Å). Indexing and processing of the measured intensity data were carried out with the APEX2 software package/program suite (see the APEX2 User Manual, v1.27; Bruker AXS, Inc., WI 53711 USA). When indicated, crystals were cooled in the cold stream of an Oxford Cryosystems cryostream cooler (Cosier, J. et al., *J. Appl. Cryst.*, 19:105 (1986)) during data collection. The structures were solved by direct methods and refined on the basis of observed reflections using the crystallographic package SHELXTL (see the APEX2 User Manual, v1.27; Bruker AXS, Inc., WI 53711 USA). The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied. Unit cell parameters were obtained according to the procedure described in Stout et al., *X-Ray Structure Determination: A Practical Guide*, MacMillan (1968).

Chemical names were determined using CHEMDRAW® Ultra, version 9.0.5 (CambridgeSoft). The following abbreviations are used:

ABBREVIATIONS

CDI carbonyldiimidazole
DCM dichloromethane
DIEA diisopropylethylamine
DMF N,N-dimethylformamide
DMSO dimethyl sulfoxide
dppf 1,1'-bis(diphenylphosphino)ferrocene
DSC differential scanning calorimetry
DTT dithiothreitol
EDC 1-[3-(dimethylamino)propyl]-3-ethyl-carbodiimide hydrochloride
EDTA ethylenediamine tetraacetate
EtOAc ethyl acetate
EtOH ethanol
g gram(s)
h hour(s)
HATU O-(7-azabenzotriazol-1-yl)-1,1,3,3-tetramethyluronium hexafluorophosphate
HOBT 1-hydroxybenzotriazole hydrate
HPLC High Pressure Liquid Chromatography
IPA isopropanol
Me methyl
MeCN acetonitrile
MeOH methanol
min minute(s)
mmol millimole(s)
t-butyl tertiary butyl
TFA trifluoroacetic acid
THF tetrahydrofuran Intermediate 1

3-(3-Bromo-2-methylphenyl)-8-fluoroquinazoline-2,4(1H,3H)-dione

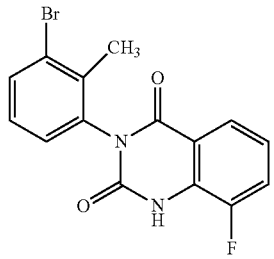

(I-1)

Intermediate 1A: 2-Amino-N-(3-bromo-2-methylphenyl)-3-fluorobenzamide

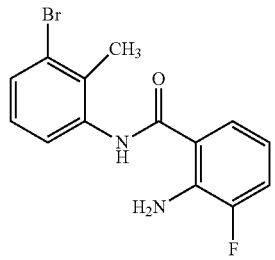

(I-1A)

A solution of 8-fluoro-1H-benzo[d][1,3]oxazine-2,4-dione (2.00 g, 11.0 mmol) and 3-bromo-2-methylaniline (4.11 g, 22.1 mmol) in dioxane (20 mL) in sealed reaction vials was heated at 110° C. for 4 days. The cooled mixture was treated with 10% aqueous $K_2CO_3$ and stirred at room temperature for 30 min. The mixture was extracted 3 times with DCM, and the combined organic phases were washed with water, dried and concentrated. The residue was triturated with ether to give a gray solid (2.50 g). The mother liquor was concentrated and the residue was again triturated with ether to give a gray solid (230 mg). The two solids were combined to provide 2-amino-N-(3-bromo-2-methylphenyl)-3-fluorobenzamide as a gray solid (2.73 g, 78% yield). Mass spectrum m/z 323, 325 $(M+H)^+$.

Alternative Method:

A suspension of 8-fluoro-1H-benzo[d][1,3]oxazine-2,4-dione (3.00 g, 16.6 mmol) in xylenes (50 mL) was treated with 3-bromo-2-methylaniline (3.08 g, 16.6 mmol) and heated to reflux. After 6 hours, the mixture was allowed to cool to room temperature overnight. The resulting suspension was diluted with hexanes and the precipitate was collected by filtration, rinsed with hexanes and air-dried to provide 2-amino-N-(3-bromo-2-methylphenyl)-3-fluorobenzamide as a white solid (4.50 g, 84% yield). Mass spectrum m/z 323, 325 $(M+H)^+$. $^1H$ NMR (400 MHz, chloroform-d) δ 7.69 (d, J=7.9 Hz, 1H), 7.65 (br. s., 1H), 7.50-7.46 (m, 1H), 7.32 (d, J=8.1 Hz, 1H), 7.19-7.11 (m, 2H), 6.73-6.64 (m, 1H), 5.69 (br. s., 2H), 2.44 (s, 3H).

Intermediate 1:

A solution of 2-amino-N-(3-bromo-2-methylphenyl)-3-fluorobenzamide (5.70 g, 17.6 mmol) in THF (100 mL) was treated with bis(trichloromethyl)carbonate (triphosgene) (6.28 g, 21.2 mmol) at room temperature and stirred for 15 min. The mixture was diluted with EtOAc, carefully treated with saturated aqueous NaHCO$_3$ and stirred at room temperature until gas evolved stopped. The separated organic phase was washed sequentially with saturated aqueous NaHCO$_3$, water and brine, and was dried and concentrated. The residue was triturated with ether to provide 3-(3-bromo-2-methylphenyl)-8-fluoroquinazoline-2,4(1H,3H)-dione as an off-white solid (6 g, 97% yield). Mass spectrum m/z 349, 351 (M+H)$^+$.

Intermediate 2

8-Fluoro-1-methyl-3-(2-methyl-3-(4,4,5,5-tetramethyl-1,3,2-dioxaborolan-2-yl)phenyl)quinazoline-2,4(1H,3H)-dione

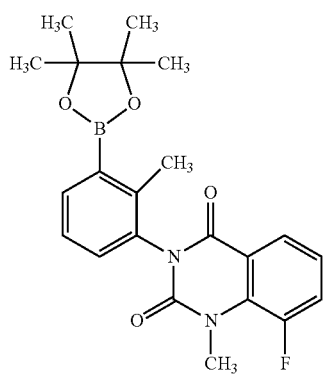

Intermediate 2A: 3-(3-Bromo-2-methylphenyl)-8-fluoro-1-methylquinazoline-2,4(1H,3H)-dione

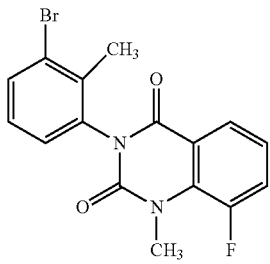

A solution of 3-(3-bromo-2-methylphenyl)-8-fluoroquinazoline-2,4(1H,3H)-dione (4.80 g, 13.8 mmol) in DMF (25 mL) was treated with Cs$_2$CO$_3$ (13.44 g, 41.2 mmol). The suspension was stirred at room temperature and treated dropwise (but quickly) with iodomethane (4.30 mL, 68.7 mmol) and stirred rapidly at room temperature for 1 h. The mixture was diluted with EtOAc and water (200 mL). The organic phase was separated and washed sequentially with water and brine, then was dried and concentrated to provide 3-(3-bromo-2-methylphenyl)-8-fluoro-1-methylquinazoline-2,4(1H,3H)-dione as a tan glassy solid (4.80 g, 96% yield). Mass spectrum m/z 363, 365 (M+H)$^+$.

Intermediate 2:

A mixture of 3-(3-bromo-2-methylphenyl)-8-fluoro-1-methylquinazoline-2,4(1H,3H)-dione (4.8 g, 13.2 mmol), 4,4,4',4',5,5,5',5'-octamethyl-2,2'-bi(1,3,2-dioxaborolane) (4.36 g, 17.2 mmol), potassium acetate (3.89 g, 39.6 mmol) and PdCl$_2$(dppf) DCM adduct (0.540 g, 0.661 mmol) in dioxane (65 mL) was heated to reflux for 2 h. After cooling to room temperature, the mixture was filtered through CELITE® and the solids were rinsed with EtOAc. The filtrate was diluted with EtOAc, washed with water, and dried and concentrated. The residue was subjected to column chromatography on silica gel (80 g), eluting with EtOAc-hexanes (gradient from 20-50%), to provide 8-fluoro-1-methyl-3-(2-methyl-3-(4,4,5,5-tetramethyl-1,3,2-dioxaborolan-2-yl)phenyl)quinazoline-2,4(1H,3H)-dione as a white solid (4.61 g, 85% yield). Mass spectrum m/z 411 (M+H)$^+$. $^1$H NMR (400 MHz, chloroform-d) δ 8.14-8.08 (m, 1H), 7.93 (dd, J=7.5, 1.3 Hz, 1H), 7.48 (ddd, J=14.0, 8.0, 1.5 Hz, 1H), 7.34 (t, J=7.6 Hz, 1H), 7.27-7.20 (m, 2H), 3.88 (d, J=7.9 Hz, 3H), 2.36 (s, 3H), 1.36 (s, 12H).

Intermediates 3 and 3A

8-Fluoro-1-methyl-3-(S)-(2-methyl-3-(4,4,5,5-tetramethyl-1,3,2-dioxaborolan-2-yl)phenyl)quinazoline-2,4(1H,3H)-dione, and 8-Fluoro-1-methyl-3-(R)-(2-methyl-3-(4,4,5,5-tetramethyl-1,3,2-dioxaborolan-2-yl)phenyl)quinazoline-2,4(1H,3H)-dione

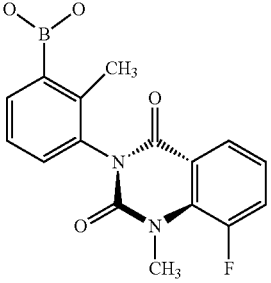

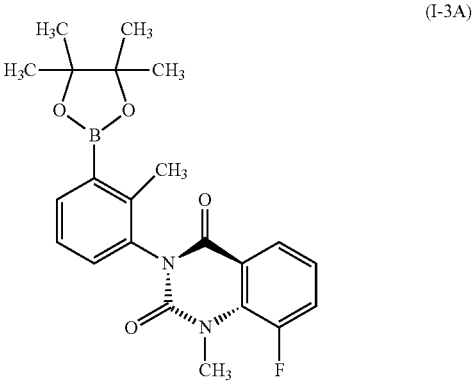

A sample of racemic 8-fluoro-1-methyl-3-(2-methyl-3-(4,4,5,5-tetramethyl-1,3,2-dioxaborolan-2-yl)phenyl)quinazoline-2,4(1H,3H)-dione [Intermediate 2] was separated by chiral super-critical fluid chromatography as follows: column: (R,R)-WHELK-O® 1 (5×50 cm, 10 µm); Mobile Phase: CO$_2$-MeOH (76:24) at 290 mL/min, 100 bar, 40° C.; sample preparation: 100 mg/mL in DCM-IPA (6:4); injection: 10.0 mL. The first peak eluting from the column provided the (S) isomer, 8-fluoro-1-methyl-3-(S)-(2-methyl-3-(4,4,5,5-tetramethyl-1,3,2-dioxaborolan-2-yl)phenyl)quinazoline-2,4(1H,3H)-dione [Intermediate 3] as a white solid. Mass spectrum m/z 411 (M+H)$^+$. $^1$H NMR (400 MHz, chloroform-d) δ 8.14-8.08 (m, 1H), 7.93 (dd, J=7.5, 1.3 Hz, 1H), 7.48 (ddd, J=14.0, 8.0, 1.5 Hz, 1H), 7.34 (t, J=7.6 Hz, 1H), 7.27-7.20 (m, 2H), 3.88 (d, J=7.9 Hz, 3H), 2.36 (s, 3H), 1.36 (s, 12H).

The second peak eluting from the column provided the (R) isomer, 8-fluoro-1-methyl-3-(R)-(2-methyl-3-(4,4,5,5-tetramethyl-1,3,2-dioxaborolan-2-yl)phenyl)quinazoline-2,4(1H,3H)-dione [Intermediate 3A] as a white solid. Mass spectrum m/z 411 (M+H)$^+$. $^1$H NMR (400 MHz, chloroform-d) δ 8.13-8.08 (m, 1H), 7.93 (dd, J=7.5, 1.3 Hz, 1H), 7.48 (ddd, J=13.9, 8.1, 1.5 Hz, 1H), 7.37-7.31 (m, 1H), 7.27-7.20 (m, 2H), 3.88 (d, J=7.9 Hz, 3H), 2.36 (s, 3H), 1.36 (s, 12H).

Intermediate 4

7-(2-Hydroxypropan-2-yl)-4-(4,4,5,5-tetramethyl-1,3,2-dioxaborolan-2-yl)-9H-carbazole-1-carboxamide

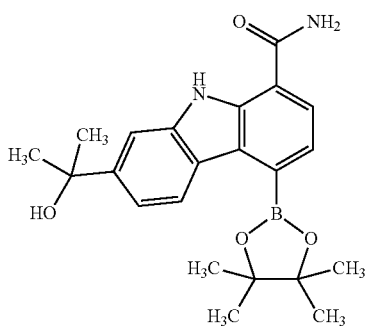

(I-4)

A mixture 4-bromo-7-(2-hydroxypropan-2-yl)-9H-carbazole-1-carboxamide [synthesized according to the procedure described in U.S. Pat. No. 8,084,620, Intermediate 73-2] (3.00 g, 8.64 mmol), 4,4,4',4',5,5,5',5'-octamethyl-2,2'-bi(1,3,2-dioxaborolane) (2.19 g, 8.64 mmol) and potassium acetate (2.12 g, 21.6 mmol) in dioxane (30 mL) was bubbled with nitrogen for 5 min. PdCl$_2$(dppf) DCM adduct (0.353 g, 0.432 mmol) was added and the mixture was bubbled with nitrogen for another 5 min. The reaction vessel was sealed and heated at 90° C. overnight. The cooled mixture was diluted with DCM, washed twice with water, dried and concentrated. The residue was purified by column chromatography on silica gel (40 g+12 g stacked columns), eluting with EtOAc-hexanes, to provide 7-(2-hydroxypropan-2-yl)-4-(4,4,5,5-tetramethyl-1,3,2-dioxaborolan-2-yl)-9H-carbazole-1-carboxamide as a light yellow solid (2.79 g, 82% yield). Mass spectrum m/z 377 (M+H–H$_2$O)$^+$.

Intermediate 5

3-(3-Bromo-2-methylphenyl)-8-fluoro-1-methyl(d$_3$)quinazoline-2,4(1H,3H)-dione

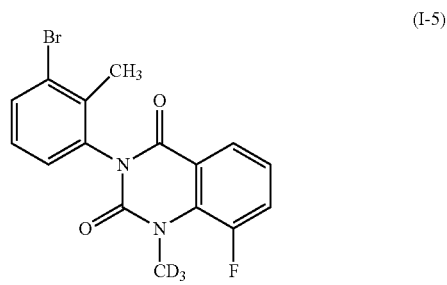 [SMILES: [2H]C([2H])([2H])n1c(=O)n(-c2cccc(Br)c2C)c(=O)c2cccc(F)c21]

(I-5)

A mixture of 3-(3-bromo-2-methylphenyl)-8-fluoroquinazoline-2,4(1H,3H)-dione [Intermediate 1] (203 mg, 0.581 mmol) and Cs$_2$CO$_3$ (379 mg, 1.16 mmol) in DMF (2.25 mL) was treated with iodomethane-d$_3$ (0.054 mL, 0.872 mmol) and the mixture was stirred at room temperature for 1.5 h. The mixture was diluted with water (ca. 20 mL), and the resulting material was triturated and stirred at room temperature, forming a suspended solid. The precipitate was collected by filtration, washed with water and dried under vacuum to provide 3-(3-bromo-2-methylphenyl)-8-fluoro-1-methyl(d$_3$)quinazoline-2,4(1H,3H)-dione as an off-white solid (189.5 mg, 90% yield). Mass spectrum m/z 366, 368 (M+H)$^+$. $^1$H NMR (400 MHz, DMSO-d$_3$) δ 7.93 (d, J=7.0 Hz, 1H), 7.79-7.69 (m, 2H), 7.39-7.25 (m, 3H), 2.12 (s, 3H).

Intermediate 6

3-(3-Bromo-2-methylphenyl)-8-methoxy-1-methylquinazoline-2,4(1H,3H)-dione

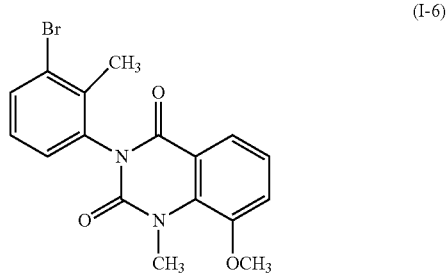

(I-6)

Intermediate 6A: 2-Amino-N-(3-bromo-2-methylphenyl)-3-methoxybenzamide

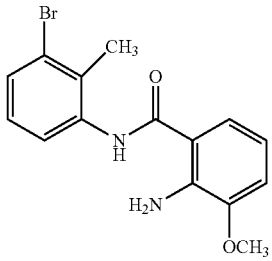

(I-6A)

A mixture of 3-bromo-2-methylaniline (482 mg, 2.59 mmol) and 8-methoxy-1H-benzo[d][1,3]oxazine-2,4-dione (500 mg, 2.59 mmol) in toluene (20 mL) was treated with 2 M trimethylaluminum in toluene (3.24 mL, 6.47 mmol) at 0° C. The mixture was stirred at room temperature for 10 minutes, then heated at 70° C. overnight. The mixture was cooled to room temperature, treated with 1 M aqueous HCl and extracted 3 times with EtOAc. The combined organic phases were washed sequentially with saturated aqueous NaHCO$_3$ and water, dried and concentrated. The residue was subjected to column chromatography on silica gel (40 g), eluting with EtOAc-hexanes (gradient from 0-100%), to provide 2-amino-N-(3-bromo-2-methylphenyl)-3-methoxybenzamide as a white solid (302 mg, 35% yield). Mass spectrum m/z 335, 337 (M+H)$^+$. $^1$H NMR (400 MHz, chloroform-d) δ 7.72 (d, J=7.3 Hz, 2H), 7.46 (dd, J=8.0, 0.8 Hz, 1H), 7.17-7.10 (m, 2H), 6.90 (dd, J=7.9, 0.9 Hz, 1H), 6.72-6.66 (m, 1H), 5.88 (br. s., 2H), 3.92 (s, 3H), 2.43 (s, 3H).

Intermediate 6B: 3-(3-Bromo-2-methylphenyl)-8-methoxyquinazoline-2,4(1H,3H)-dione

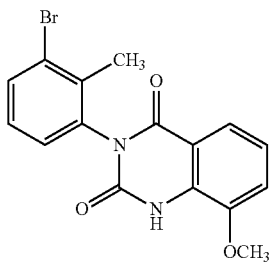

(I-6B)

A solution of 2-amino-N-(3-bromo-2-methylphenyl)-3-methoxybenzamide (302 mg, 0.901 mmol) and triphosgene (321 mg, 1.08 mmol) in THF (20 mL) was stirred at room temperature for 2 h. The mixture was treated carefully with saturated aqueous NaHCO$_3$ and stirred until gas evolution ceased. The mixture was extracted twice with DCM, and the combined organic phases were washed with water, dried and concentrated to provide 3-(3-bromo-2-methylphenyl)-8-methoxyquinazoline-2,4(1H,3H)-dione (339 mg). Mass spectrum m/z 361, 363 (M+H)$^+$.

Intermediate 6: 3-(3-Bromo-2-methylphenyl)-8-methoxy-1-methylquinazoline-2,4(1H,3H)-dione A mixture of 3-(3-bromo-2-methylphenyl)-8-methoxyquinazoline-2,4(1H,3H)-dione (535 mg, 1.48 mmol), iodomethane (0.185 mL, 2.96 mmol) and Cs$_2$CO$_3$ (965 mg, 2.96 mmol) in THF (20 mL) was stirred at room temperature overnight. The mixture was filtered and concentrated. The residue was dissolved in DCM, washed sequentially with saturated aqueous NaHCO$_3$ and water, dried and concentrated. The residue was subjected to column chromatography on silica gel (40 g), eluting with EtOAc-hexanes (gradient from 0-100%), to provide 3-(3-bromo-2-methylphenyl)-8-methoxy-1-methylquinazoline-2,4(1H, 3H)-dione (442 mg). Mass spectrum m/z 375, 377 (M+H)$^+$. $^1$H NMR (400 MHz, chloroform-d) δ 7.90 (dd, J=7.2, 2.3 Hz, 1H), 7.66 (dd, J=8.0, 1.2 Hz, 1H), 7.31-7.22 (m, 2H), 7.22-7.19 (m, 1H), 7.17-7.13 (m, 1H), 3.97 (s, 3H), 3.89 (s, 3H), 2.23 (s, 3H).

Intermediate 7

3-(3-Bromo-2-methylphenyl)-6-fluoro-1-methylquinazoline-2,4(1H,3H)-dione

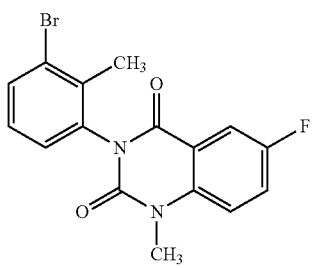

(I-7)

Intermediate 7A: 2-Amino-N-(3-bromo-2-methylphenyl)-5-fluorobenzamide

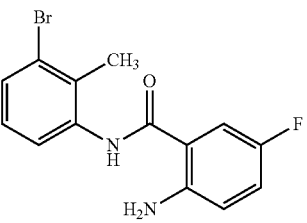

(I-7A)

A mixture of 3-bromo-2-methylaniline (1.50 g, 8.06 mmol) and 6-fluoro-1H-benzo[d][1,3]oxazine-2,4-dione (1.46 g, 8.06 mmol) in toluene (40 mL) was cooled on an ice-water bath and treated portionwise with 2 M trimethylaluminum in toluene (10.1 mL, 20.2 mmol). The mixture was stirred at room temperature for 30 min, then was heated at 70° C. overnight. The mixture was cooled to 0° C., carefully treated with 1 M aqueous HCl, and extracted 3 times with EtOAc. The combined organic phases were washed sequentially with saturated aqueous NaHCO$_3$ and water, dried and concentrated. The residue was subjected to column chromatography on silica gel (120 g), eluting with EtOAc-hexanes (gradient from 5-40%), to provide 2-amino-N-(3-bromo-2-methylphenyl)-5-fluorobenzamide (0.893 g, 87% purity, 30% yield). Mass spectrum m/z 323, 325 (M+H)$^+$. $^1$H NMR (400 MHz, MeOH-d$_4$) δ 7.54 (1H, dd, J=8.03, 0.99 Hz), 7.48 (1H, dd, J=9.68, 3.08 Hz), 7.33 (1H, d, J=7.26 Hz), 7.16 (1H, t, J=7.92 Hz), 7.04-7.12 (1H, m), 6.83 (1H, dd, J=9.02, 4.62 Hz), 2.39 (3H, s).

Intermediate 7B: 3-(3-Bromo-2-methylphenyl)-6-fluoroquinazoline-2,4(1H,3H)-dione

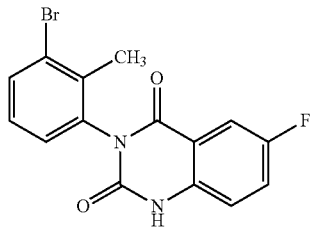

(I-7B)

A solution of 2-amino-N-(3-bromo-2-methylphenyl)-5-fluorobenzamide (0.893 g, 2.76 mmol) and triphosgene (0.984 g, 3.32 mmol) in THF (30 mL) was stirred at room temperature for 2 h. The mixture was carefully treated with saturated aqueous NaHCO₃ and stirred until gas evolution ceased. The mixture was extracted twice with DCM. The combined organic phases were washed with water, dried and concentrated. The residue was triturated with DCM to give a white solid, isolated by filtration. The filtrate was concentrated and subjected to column chromatography on silica gel (40 g), eluting with EtOAc-hexanes (gradient from 0-80%), to provide additional solid. The two solids were combined to provide 3-(3-bromo-2-methylphenyl)-6-fluoroquinazoline-2,4(1H,3H)-dione as a white solid (845 mg, 87% yield). Mass spectrum m/z 349, 351 (M+H)⁺.

Intermediate 7:

A mixture of 3-(3-bromo-2-methylphenyl)-6-fluoroquinazoline-2,4(1H,3H)-dione (742 mg, 2.13 mmol), iodomethane (0.159 mL, 2.55 mmol) and Cs₂CO₃ (1.04 g, 3.19 mmol) in THF (20 mL) was stirred at room temperature overnight. The mixture was filtered and concentrated. The residue was dissolved in DCM and washed sequentially with saturated aqueous NaHCO₃ and water, dried and concentrated to provide 3-(3-bromo-2-methylphenyl)-6-fluoro-1-methylquinazoline-2,4(1H,3H)-dione (742 mg, 96% yield). Mass spectrum m/z 363, 365 (M+H)⁺.

Intermediate 8

(Z)-4-((3-Bromo-2-chlorophenyl)imino)-1-methyl-1H-benzo[d][1,3]oxazin-2(4H)-one

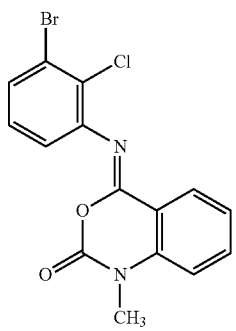

(I-8)

Intermediate 8A: N-(3-Bromo-2-chlorophenyl)-2-(methylamino)benzamide

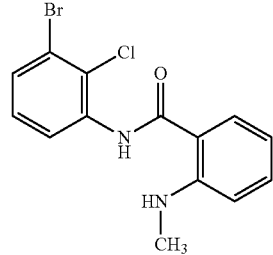

(I-8A)

A mixture of 3-bromo-2-chloroaniline [prepared according to the procedure described in U.S. Pat. No. 8,242,260] (240 mg, 1.16 mmol) and toluene (10 mL) at 0° C. was slowly treated with 2 M trimethylaluminum in toluene (0.99 mL, 1.98 mmol). The mixture was allowed to warm to room temperature and stirred for 15 min. A partial suspension of 1-methyl-1H-benzo[d][1,3]oxazine-2,4-dione (300 mg, 1.52 mmol) in toluene (4 mL) was added slowly. The resulting mixture was heated at 50° C. for 4 h, cooled to 0° C., and treated dropwise with 1 M aqueous HCl until no more gas evolution was observed. The mixture was stirred for 2 h while warming to room temperature, then was extracted with EtOAc. The organic phase was washed sequentially with NaHCO₃ and brine, dried and concentrated. The residue was purified by column chromatography on silica gel (80 g), eluting with EtOAc-hexanes (gradient from 0-30%), to provide N-(3-bromo-2-chlorophenyl)-2-(methylamino)benzamide as a yellow solid (110 mg, 28% yield). Mass spectrum m/z 339 (M+H)⁺. ¹H NMR (400 MHz, DMSO-d₆) δ 10.00 (s, 1H), 7.78 (dd, J=7.9, 1.5 Hz, 1H), 7.67 (dd, J=8.1, 1.5 Hz, 1H), 7.57 (dd, J=8.0, 1.4 Hz, 1H), 7.53 (d, J=1.3 Hz, 1H), 7.38 (ddd, J=8.4, 7.1, 1.4 Hz, 1H), 7.32 (t, J=8.0 Hz, 1H), 6.70 (d, J=8.4 Hz, 1H), 6.68-6.61 (m, 1H), 2.79 (d, J=5.1 Hz, 3H).

Intermediate 8: (Z)-4-((3-Bromo-2-chlorophenyl)imino)-1-methyl-1H-benzo[d][1,3]oxazin-2(4H)-one A solution of N-(3-bromo-2-chlorophenyl)-2-(methylamino)benzamide (150 mg, 0.442 mmol) in THF (15 mL) was cooled to 0° C. and treated with triphosgene (197 mg, 0.663 mmol). The mixture was stirred at room temperature for 1 h, then was cooled to 0° C. and treated with water until gas evolution ceased. The mixture was concentrated, and the residue was dissolved in EtOAc and washed sequentially with saturated aqueous NaHCO₃, water and brine, and dried and concentrated. The residue was purified by column chromatography on silica gel, eluting with EtOAc-hexanes (gradient from 0-50%), to provide (Z)-4-((3-bromo-2-chlorophenyl)imino)-1-methyl-1H-benzo[d][1,3]oxazin-2(4H)-one as a beige solid (130 mg, 81% yield). ¹H NMR (400 MHz, chloroform-d) δ 8.33 (dd, J=7.8, 1.4 Hz, 1H), 7.72-

7.61 (m, 1H), 7.41 (dd, J=7.9, 1.5 Hz, 1H), 7.36-7.28 (m, 1H), 7.16-7.08 (m, 2H), 7.07-7.01 (m, 1H), 3.55 (s, 3H).

J=8.1 Hz, 1H), 7.22 (t, J=8.3 Hz, 1H), 7.15 (ddd, J=11.0, 8.0, 1.2 Hz, 1H), 6.69 (td, J=8.0, 5.1 Hz, 1H), 5.72 (br. s., 2H).

Intermediate 9

3-(3-Bromo-2-chlorophenyl)-8-fluoro-1-methylquinazoline-2,4(1H,3H)-dione

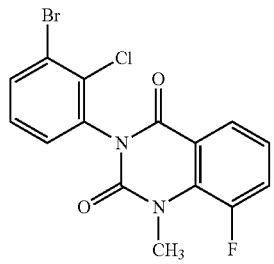

(I-9)

Intermediate 9B: 3-(3-Bromo-2-chlorophenyl)-8-fluoroquinazoline-2,4(1H,3H)-dione

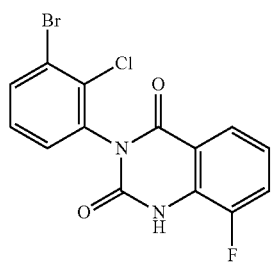

(I-9B)

Intermediate 9A: 2-Amino-N-(3-bromo-2-chlorophenyl)-3-fluorobenzamide

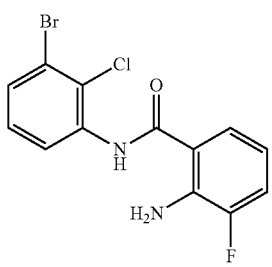

(I-9A)

A mixture of 3-bromo-2-chloroaniline [prepared according to the procedure described in U.S. Pat. No. 8,242,260] (600 mg, 2.91 mmol) and toluene (10 mL) was cooled to 0° C. and slowly treated with 2 M trimethylaluminum in toluene (2.47 mL, 4.94 mmol). The mixture was allowed to warm to room temperature and stirred for 15 min. Next, 8-fluoro-1H-benzo[d][1,3]oxazine-2,4-dione (684 mg, 3.78 mmol) was added in one portion and the mixture was heated to 50° C. for 16 h. The mixture was cooled to 0° C. and treated dropwise with 1 M aqueous HCl until gas evolution stopped, and stirred for 2 h while allowing to warm to room temperature. The mixture was extracted 3 times with EtOAc. The combined organic phases were washed sequentially with saturated aqueous NaHCO$_3$ and brine, dried and concentrated. The residue was purified by column chromatography on silica gel (24 g), eluting with EtOAc-hexanes (gradient from 0-30%), to provide 2-amino-N-(3-bromo-2-chlorophenyl)-3-fluorobenzamide as a pale yellow solid (350 mg, 35% yield). Mass spectrum m/z 343 (M+H)$^+$. $^1$H NMR (400 MHz, chloroform-d) δ 8.46 (dd, J=8.4, 1.3 Hz, 1H), 8.42 (br. s., 1H), 7.43 (dd, J=8.0, 1.4 Hz, 1H), 7.34 (d, Triphosgene (453 mg, 1.53 mmol) was added in one portion to a solution of amino-N-(3-bromo-2-chlorophenyl)-3-fluorobenzamide (350 mg, 1.02 mmol) in THF (10 mL) at 0° C. The mixture was stirred at room temperature for 1 h, then cooled to 0° C. and treated with water until no gas evolution was observed. The mixture was concentrated and the residue was dissolved in EtOAc, washed sequentially with saturated aqueous NaHCO$_3$, water and brine, and dried and concentrated. The residue was purified by column chromatography on silica gel (24 g), eluting with EtOAc-hexanes (gradient from 0-50%), to provide 3-(3-bromo-2-chlorophenyl)-8-fluoroquinazoline-2,4(1H,3H)-dione as a yellow solid (320 mg, 85% yield). Mass spectrum m/z 369 (M+H)$^+$. $^1$H NMR (400 MHz, chloroform-d) δ 8.54 (br. s., 1H), 7.97 (d, J=8.1 Hz, 1H), 7.77 (dd, J=6.8, 2.6 Hz, 1H), 7.46 (ddd, J=9.8, 8.3, 1.2 Hz, 1H), 7.36-7.29 (m, 2H), 7.24 (td, J=8.0, 4.8 Hz, 1H).

Intermediate 9:

Iodomethane (0.102 mL, 1.623 mmol) was added slowly to a mixture of 3-(3-bromo-2-chlorophenyl)-8-fluoroquinazoline-2,4(1H,3H)-dione (300 mg, 0.812 mmol), DMF (5 mL) and Cs$_2$CO$_3$ (529 mg, 1.62 mmol). The mixture was stirred at room temperature for 2 h, then was diluted with EtOAc, washed sequentially with water and brine, and dried and concentrated. The residue was purified by column chromatography on silica gel (24 g), eluting with EtOAc-hexanes (gradient from 0-30%), to provide 3-(3-bromo-2-chlorophenyl)-8-fluoro-1-methylquinazoline-2,4(1H,3H)-dione as a yellow solid (280 mg, 90% yield). Mass spectrum m/z 383 (M+H)$^+$. $^1$H NMR (400 MHz, chloroform-d) δ 8.09 (dq, J=7.8, 0.8 Hz, 1H), 7.79-7.71 (m, 1H), 7.49 (ddd, J=13.9, 8.1, 1.5 Hz, 1H), 7.32-7.29 (m, 2H), 7.29-7.22 (m, 2H), 3.88 (s, 1.5H, 3.86 (s, 1.5H).

Intermediate 10

2-(3-Bromo-2-methylphenyl)-5-methoxy-1H-pyrido[1,2-c]pyrimidine-1,3(2H)-dione

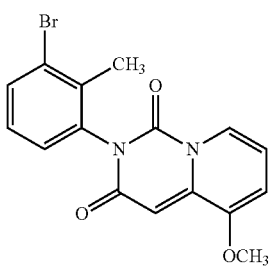
(I-10)

Intermediate 10A: Ethyl 2-(3-methoxypyridin-2-yl)acetate

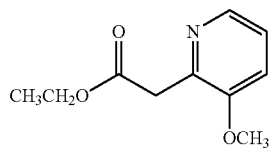
(I-10A)

A stirred solution of diisopropylamine (0.385 mL, 2.70 mmol) in THF (2 mL) at 0° C. was treated slowly with 1.6 M n-butyllithium in hexanes (1.69 mL, 2.70 mmol). The mixture was stirred for 15 min, then was added via syringe over 5 min to a stirred solution of 3-methoxy-2-picoline (0.133 g, 1.08 mmol) and diethyl carbonate (0.262 mL, 2.16 mmol) in THF (5 mL) at −78° C. After stirring for 45 min more, the cooling bath was removed and stirring was continued overnight at room temperature. The mixture was treated with saturated aqueous NH$_4$Cl and diluted with EtOAc. The organic phase was separated, washed sequentially with saturated aqueous NaHCO$_3$ and brine, and dried and concentrated. The residue was purified by column chromatography on silica gel (12 g), eluting with 50% EtOAc-hexanes, to provide ethyl 2-(3-methoxypyridin-2-yl)acetate as an oil (0.17 g, 81% yield). Mass spectrum m/z 196 (M+H)$^+$.

Intermediate 10B: Sodium 2-(3-methoxypyridin-2-yl)acetate

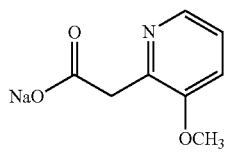
(I-10B)

A stirred solution of ethyl 2-(3-methoxypyridin-2-yl)acetate (0.17 g, 0.871 mmol) in THF (2.5 mL) at room temperature was treated with 3 M aqueous NaOH (0.581 mL, 1.74 mmol). After 7 h, the mixture was concentrated to remove the THF and the aqueous residue was frozen on dry ice and lyophilized to provide sodium 2-(3-methoxypyridin-2-yl)acetate as a white solid. A quantitative yield was assumed and the material was used without further purification. Mass spectrum m/z 168 (M+H)$^+$.

Intermediate 10C: N-(3-Bromo-2-methylphenyl)-2-(3-methoxypyridin-2-yl)acetamide

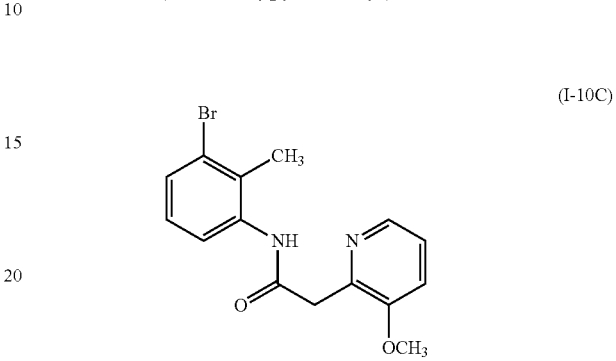
(I-10C)

A mixture of sodium 2-(3-methoxypyridin-2-yl)acetate (0.166 g, 0.871 mmol), 3-bromo-2-methylaniline (0.118 mL, 0.958 mmol), DIEA (0.608 mL, 3.48 mmol) and HATU (0.397 g, 1.045 mmol) in DMF (4.0 mL) was stirred at room temperature. After 1 h, the mixture was diluted with EtOAc and washed twice with 10% aqueous LiCl, then with brine, dried and concentrated. The residue was purified by column chromatography on silica gel to provide N-(3-bromo-2-methylphenyl)-2-(3-methoxypyridin-2-yl)acetamide as a pale yellow solid (0.213 g, 73% yield). Mass spectrum m/z 335, 337 (M+H)$^+$.

Intermediate 10:

A mixture of N-(3-bromo-2-methylphenyl)-2-(3-methoxypyridin-2-yl)acetamide (0.136 g, 0.406 mmol) and CDI (0.263 g, 1.62 mmol) in toluene (2 mL) was heated at 110° C. After 4 h, the mixture was cooled, diluted with EtOAc and washed sequentially with water and brine. The organic phase was dried and concentrated, and the residue was purified by column chromatography on silica gel (24 g), eluting with 40% EtOAc-hexanes, to provide 2-(3-bromo-2-methylphenyl)-5-methoxy-1H-pyrido[1,2-c]pyrimidine-1,3(2H)-dione as a yellow solid (0.0729 g, 50% yield). Mass spectrum m/z 361, 363 (M+H)$^+$.

Intermediate 11

2-(3-Bromo-2-methylphenyl)-6-methoxy-1H-pyrido[1,2-c]pyrimidine-1,3(2H)-dione

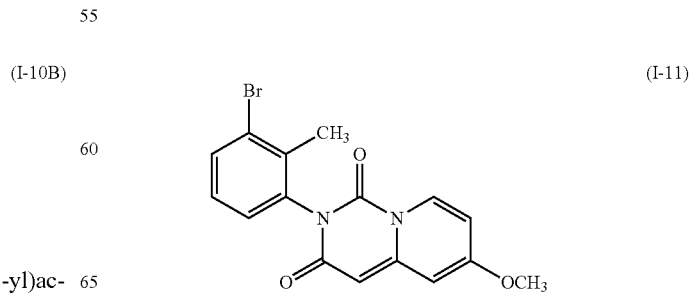
(I-11)

This intermediate was synthesized from 4-methoxy-2-methylpyridine following the general synthetic route described for Intermediate 10. Mass spectrum m/z 361, 363 (M+H)+.

Intermediate 12

2-(3-Bromo-2-methylphenyl)-7-methoxy-1H-pyrido[1,2-c]pyrimidine-1,3(2H)-dione

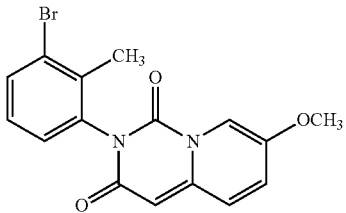
(I-12)

This intermediate was synthesized from 3-methoxy-6-picoline following the general synthetic route described for Intermediate 10. Mass spectrum m/z 361, 363 (M+H)+.

Intermediate 13

5-Chloro-2-(2-methyl-3-(4,4,5,5-tetramethyl-1,3,2-dioxaborolan-2-yl)phenyl)-1H-pyrido[1,2-c]pyrimidine-1,3(2H)-dione(racemic)

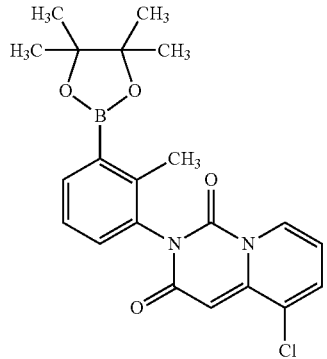
(I-13)

Intermediate 13A: Diethyl 2-(3-chloropyridin-2-yl)malonate

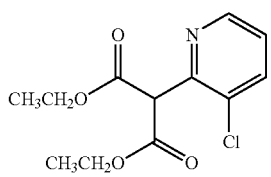
(I-13A)

A mixture of 3-chloro-2-fluoropyridine (5.00 g, 38.0 mmol), diethyl malonate (14.61 g, 91 mmol) and Cs₂CO₃ (29.7 g, 91 mmol) in DMSO (42 mL) was heated at 100° C. for 7 h. After stirring overnight at room temperature, the mixture was diluted with EtOAc and washed twice with water, then with brine. The combined aqueous layers were extracted with EtOAc, and the combined organic phases were dried and concentrated to give crude diethyl 2-(3-chloropyridin-2-yl)malonate as a colorless oil, used without further purification. Mass spectrum m/z 272 (M+H)+.

Intermediate 13B: Ethyl 2-(3-chloropyridin-2-yl)acetate

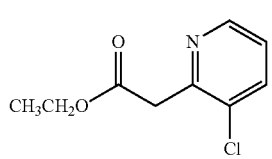
(I-13B)

A mixture of diethyl 2-(3-chloropyridin-2-yl)malonate (10.32 g, 38 mmol), sodium chloride (5.55 g, 95 mmol) and water (3.4 mL, 190 mmol) in DMSO (40 mL) was heated at 145° C. for 8 h. The mixture was cooled to room temperature, diluted with EtOAc and washed twice with water, then with brine. The organic phase was dried and concentrated to provide crude ethyl 2-(3-chloropyridin-2-yl)acetate, used without further purification. Mass spectrum m/z 200 (M+H)+.

Intermediate 13C: Sodium 2-(3-chloropyridin-2-yl)acetate

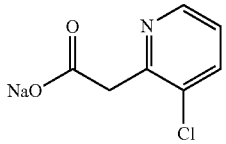
(I-13C)

A solution of ethyl 2-(3-chloropyridin-2-yl)acetate (7.59 g, 38 mmol) in THF (76 mL) was treated at room temperature with 3 M aqueous NaOH (25.3 mL, 76 mmol). The mixture was stirred at room temperature overnight and concentrated to remove the THF. The aqueous residue was frozen on dry ice and lyophilized to give sodium 2-(3-chloropyridin-2-yl)acetate as an off-white solid, used without further purification. Mass spectrum m/z 172, (M+H)+.

Intermediate 13D: N-(3-Bromo-2-methylphenyl)-2-(3-chloropyridin-2-yl)acetamide

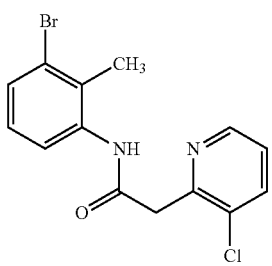
(I-13D)

A mixture of sodium 2-(3-chloropyridin-2-yl)acetate (7.39 g, 38 mmol), 3-bromo-2-methylaniline (4.7 mL, 38.4 mmol), DIEA (13.3 mL, 76 mmol) and HATU (14.59 g, 38.4 mmol) in DMF (127 mL) was stirred at room temperature. After 90 min the mixture was diluted with EtOAc and washed twice with 10% LiCl, then with brine. The combined aqueous layers were extracted with EtOAc, and the combined organic phases were dried and concentrated to a small volume. The solution was seeded with a crystal from an earlier batch and allowed to stand overnight to provide a precipitate which was collected by filtration and washed with 50% EtOAc-hexanes to provide a white solid. The filtrate was concentrated and recrystallized similarly three times to provide additional solid. The solids were combined to give N-(3-bromo-2-methylphenyl)-2-(3-chloropyridin-2-yl)acetamide as a white solid (11.43 g, 89% yield). Mass spectrum m/z 339, 341 (M+H)$^+$. $^1$H NMR (400 MHz, chloroform-d) δ 9.76 (br. s., 1H), 8.52 (d, j=3.5 Hz, 1H), 7.92 (d, J=7.9 Hz, 1H), 7.80 (dd, J=8.1, 1.1 Hz, 1H), 7.36 (d, J=7.9 Hz, 1H), 7.32-7.23 (m, 1H), 7.06 (t, J=8.0 Hz, 1H), 4.16 (s, 2H), 2.39 (s, 3H).

Intermediate 13E: 2-(3-Chloropyridin-2-yl)-N-(2-methyl-3-(4,4,5,5-tetramethyl-1,3,2-dioxaborolan-2-yl)phenyl)acetamide

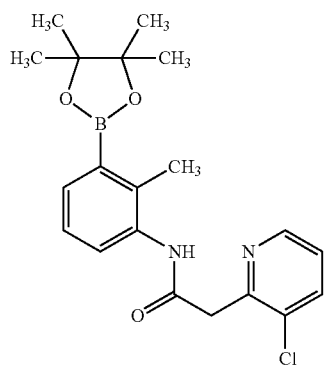

(I-13E)

A mixture of N-(3-bromo-2-methylphenyl)-2-(3-chloropyridin-2-yl)acetamide (4.0 g, 11.8 mmol) and 4,4,4',4',5,5,5',5'-octamethyl-2,2'-bi(1,3,2-dioxaborolane) (3.29 g, 13.0 mmol) in DMSO (5 mL) and dioxane (25 mL) was bubbled with argon for 7 min, followed by addition of potassium acetate (2.89 g, 29.4 mmol). Argon bubbling was continued for 7 min after which PdCl$_2$(dppf) DCM adduct (0.481 g, 0.589 mmol) was added. The mixture was heated at 90° C. for 7 h. The cooled mixture was diluted with EtOAc and filtered through CELITE®. The filtrate was washed sequentially with water and brine. The combined aqueous layers were extracted with EtOAc, and the combined organic phases were dried and concentrated. The residue was recrystallized from EtOAc to provide a white solid. The mother liquor was concentrated and the residue was recrystallized from EtOAc. The two solids were combined to provide 2-(3-chloropyridin-2-yl)-N-(2-methyl-3-(4,4,5,5-tetramethyl-1,3,2-dioxaborolan-2-yl)phenyl)acetamide as a white solid (3.88 g, 85% yield). Mass spectrum m/z 387, 389 (M+H)$^+$.

Intermediate 13:

A mixture of 2-(3-chloropyridin-2-yl)-N-(2-methyl-3-(4,4,5,5-tetramethyl-1,3,2-dioxaborolan-2-yl)phenyl)acetamide (0.192 g, 0.497 mmol) and CDI (0.322 g, 1.99 mmol) in toluene (2 mL) was heated at 110° C. After 5 h, the cooled mixture was diluted with EtOAc and washed sequentially with water and brine. The combined aqueous layers were extracted with EtOAc, and the combined organic phases were dried and concentrated. The residue was purified by column chromatography on silica gel, eluting with EtOAc-hexanes, to provide racemic 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione as a bright yellow solid (0.133 g, 65% yield). Mass spectrum m/z 413 (M+H)$^+$.

Intermediates 14 and 15

5-Chloro-2-(R)-(2-methyl-3-(4,4,5,5-tetramethyl-1,3,2-dioxaborolan-2-yl)phenyl)-1H-pyrido[1,2-c]pyrimidine-1,3(2H)-dione (I-14), and 5-Chloro-2-(S)-(2-methyl-3-(4,4,5,5-tetramethyl-1,3,2-dioxaborolan-2-yl)phenyl)-1H-pyrido[1,2-c]pyrimidine-1,3(2H)-dione (I-15)

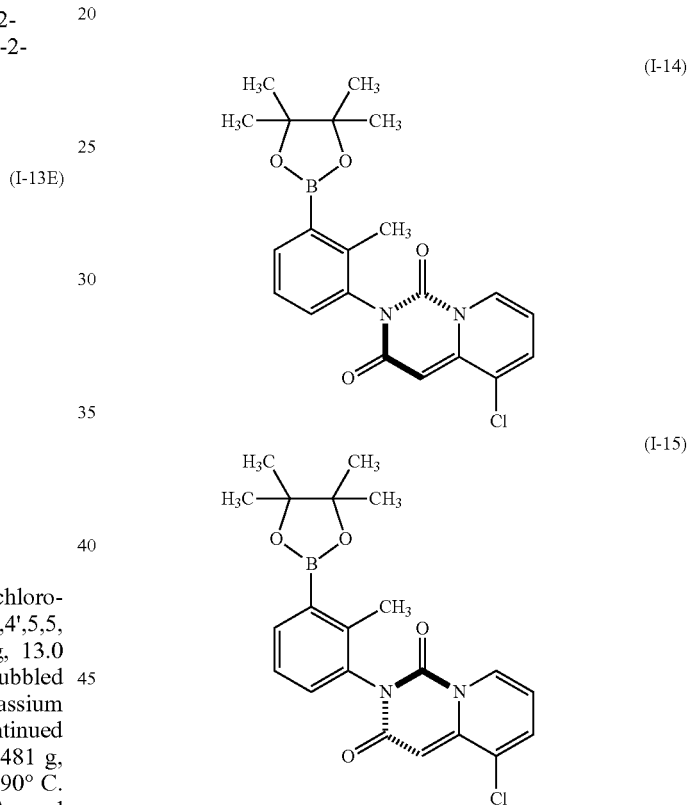

A sample of racemic 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 13] was separated by chiral super-critical fluid chromatography as follows: column: WHELK-O® RR (3×25 cm, 5 μm); Mobile Phase: CO$_2$-MeOH (55:45) at 200 mL/min, 100 bar, 35° C.; sample preparation: 96 mg/mL in MeCN-DCM (1:4); injection: 5 mL. The first peak eluting from the column provided 5-chloro-2-(R)-(2-methyl-3-(4,4,5,5-tetramethyl-1,3,2-dioxaborolan-2-yl)phenyl)-1H-pyrido[1,2-c]pyrimidine-1,3(2H)-dione [Intermediate 14]. The second peak eluting from the column provided 5-chloro-2-(S)-(2-methyl-3-(4,4,5,5-tetramethyl-1,3,2-dioxaborolan-2-yl)phenyl)-1H-pyrido[1,2-c]pyrimidine-1,3(2H)-dione [Intermediate 15]. The mass spectrum and $^1$H NMR for both enantiomers were the same as those for Intermediate 13.

The absolute configuration of Intermediate 15 was confirmed by single crystal x-ray analysis of crystals prepared by dissolving the compound in excess acetone and slowly evaporating the solvent at room temperature. Unit cell dimensions: a=19.6161(8) Å, b=9.1411(4) Å, c=12.7541(6) Å, α=90°, β=113.165(2)°, γ=90°; Space group: C2; Molecules of Intermediate 35/asymmetric unit (Z'): 1; Density, calc g-cm$^{-3}$: 1.304. Fractional atomic coordinates at room temperature are given in Table 1, and a depiction of the structure is given in FIG. 1.

TABLE 1

Fractional Atomic Coordinates for Intermediate 15 at Room Temperature

| Atom | X | Y | Z | Atom | X | Y | Z |
|---|---|---|---|---|---|---|---|
| C11 | −0.1755 | −0.1003 | 0.3365 | C21 | 0.0166 | −0.2724 | 0.3622 |
| O1 | 0.2261 | 0.6937 | 0.2037 | O3 | −0.0487 | 0.3988 | 0.3318 |
| C1 | 0.2132 | 0.8050 | 0.1156 | O4 | 0.1356 | 0.0809 | 0.3596 |
| C2 | 0.1347 | 0.7655 | 0.0313 | H1 | 0.1356 | 0.3551 | 0.5384 |
| O2 | 0.1028 | 0.6968 | 0.1045 | H2 | 0.2203 | 0.5422 | 0.5706 |
| B1 | 0.1597 | 0.6467 | 0.1980 | H3 | 0.2313 | 0.6587 | 0.4179 |
| C3 | 0.1403 | 0.4028 | 0.4772 | H4 | 0.0388 | 0.8624 | −0.0807 |
| C4 | 0.1906 | 0.5142 | 0.4966 | H5 | 0.1101 | 0.9509 | −0.0687 |
| C5 | 0.1012 | 0.4308 | 0.2727 | H6 | 0.0796 | 0.9586 | 0.0279 |
| C6 | 0.1966 | 0.5843 | 0.4048 | H7 | 0.0613 | 0.2788 | 0.1461 |
| C7 | 0.0966 | 0.3615 | 0.3668 | H8 | 0.0655 | 0.4356 | 0.0994 |
| C8 | 0.1517 | 0.5466 | 0.2926 | H9 | 0.0019 | 0.3967 | 0.1400 |
| C9 | 0.0863 | 0.8966 | −0.0281 | H10 | 0.1556 | 0.5689 | −0.0231 |
| C10 | 0.0532 | 0.3809 | 0.1539 | H11 | 0.1519 | 0.6967 | −0.1073 |
| C11 | 0.1298 | 0.6565 | −0.0585 | H12 | 0.0787 | 0.6339 | −0.1029 |
| C12 | 0.2226 | 0.9474 | 0.1724 | H13 | 0.1871 | 0.9571 | 0.2066 |
| C13 | 0.2710 | 0.7829 | 0.0643 | H14 | 0.2151 | 1.0241 | 0.1175 |
| N1 | 0.0457 | 0.2404 | 0.3528 | H15 | 0.2718 | 0.9545 | 0.2304 |
| C14 | 0.0746 | 0.1035 | 0.3564 | H16 | 0.3176 | 0.8231 | 0.1147 |
| N2 | 0.0270 | −0.0148 | 0.3551 | H17 | 0.2550 | 0.8312 | −0.0083 |
| C15 | −0.0287 | 0.2712 | 0.3397 | H18 | 0.2769 | 0.6801 | 0.0543 |
| C16 | −0.0453 | 0.0086 | 0.3467 | H19 | −0.1208 | 0.1615 | 0.3296 |
| C17 | −0.0720 | 0.1477 | 0.3375 | H20 | 0.1039 | −0.1652 | 0.3637 |
| C18 | 0.0561 | −0.1540 | 0.3608 | H21 | −0.0838 | −0.3378 | 0.3584 |
| C19 | −0.0563 | −0.2557 | 0.3562 | H22 | 0.0370 | −0.3652 | 0.3671 |
| C20 | −0.0863 | −0.1218 | 0.3472 | — | — | — | — |

Alternatively, a sample of racemic 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 13] was separated by chiral super-critical fluid chromatography as follows: column: WHELK-O® RR (3×25 cm, 5 μm); Mobile Phase: CO$_2$—CH$_3$CN (55:45) at 200 mL/min, 100 bar, 35° C.; sample preparation: 96 mg/mL in MeCN-DCM (1:4); injection: 5 mL. The first peak eluting from the column provided one atropisomer of 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 15]. The material could be further purified by dissolving in THF/hexanes and collecting the resulting yellow solid.

Intermediate 16

4-Fluoro-2-(2-methyl-3-(4,4,5,5-tetramethyl-1,3,2-dioxaborolan-2-yl)phenyl)-1H-pyrido[1,2-c]pyrimidine-1,3(2H)-dione

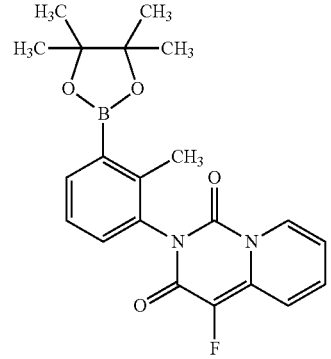

(I-16)

Intermediate 16A: N-(3-Bromo-2-methylphenyl)-2-(pyridin-2-yl)acetamide

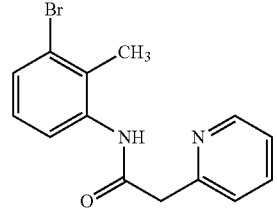

(I-16A)

A mixture of 3-bromo-2-methylaniline (2.36 mL, 19.1 mmol), pyridin-2-yl-acetic acid hydrochloride (3.32 g, 19.1 mmol), EDC (5.50 g, 28.7 mmol), HOBT (0.146 g, 0.956 mmol) and DIEA (13.4 mL, 76 mmol) in 1,2-dichloroethane (70 mL) was stirred at room temperature for 3 h. The mixture was diluted with DCM and washed twice with water. The combined aqueous layers were extracted with DCM. The combined organic phases were dried and concentrated to a reduced volume, then diluted with hexane. The precipitated crystals were collected by filtration. The filtrate was concentrated and recrystallized from DCM-hexane to provide additional solid. The two batches of solid were combined to provide N-(3-bromo-2-methylphenyl)-2-(pyridin-2-yl)acetamide as a tan solid (4.78 g. 82% yield). Mass spectrum m/z 305, 307 (M+H)$^+$.

Intermediate 16B: N-(3-Bromo-2-methylphenyl)-2-fluoro-2-(pyridin-2-yl)acetamide

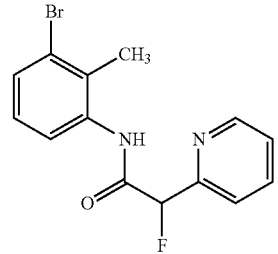

(I-16B)

A mixture of N-(3-bromo-2-methylphenyl)-2-(pyridin-2-yl)acetamide (0.5 g, 1.64 mmol) and 1-(chloromethyl)-4-fluoro-1,4-diazoniabicyclo[2.2.2]octanebis-(tetrafluoroborate) [SELECTFLUOR®] (0.871 g, 2.46 mmol) in 1,2-dichloroethane (8.0 mL) was heated at 90° C. overnight. Additional SELECTFLUOR® (300 mg) was added and the mixture was heated overnight at 60° C. A third portion of SELECTFLUOR® (150 mg) was added and heating was continued for another 3 h. The cooled mixture was partitioned between EtOAc and water. The organic phase was washed with brine, dried and concentrated. The residue was purified by column chromatography on silica gel (80 g), eluting with EtOAc-hexanes (35%, then 50%), to provide N-(3-bromo-2-methylphenyl)-2-fluoro-2-(pyridin-2-yl)acetamide as a light brown solid (0.177 g, 33% yield). ¹H NMR (400 MHz, chloroform-d) δ 8.84 (br. s., 1H), 8.67 (dt, J=4.8, 0.9 Hz, 1H), 7.91-7.79 (m, 2H), 7.60 (d, J=7.7 Hz, 1H), 7.44-7.35 (m, 2H), 7.08 (t, J=8.1 Hz, 1H), 6.08-5.93 (m, 1H), 2.41 (s, 3H).

Intermediate 16C: 2-Fluoro-N-(2-methyl-3-(4,4,5,5-tetramethyl-1,3,2-dioxaborolan-2-yl)phenyl)-2-(pyridin-2-yl)acetamide

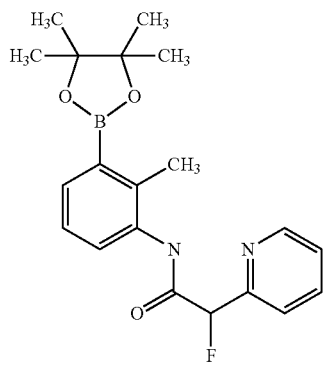

(I-16C)

A mixture N-(3-bromo-2-methylphenyl)-2-fluoro-2-(pyridin-2-yl)acetamide (0.122 g, 0.378 mmol), 4,4,4',4',5,5,5',5'-octamethyl-2,2'-bi(1,3,2-dioxaborolane) (0.105 g, 0.415 mmol) and potassium acetate (0.093 g, 0.944 mmol) in DMSO (0.6 mL) and dioxane (3.0 mL) was bubbled with nitrogen for 5 min, followed by the addition of PdCl₂(dppf) DCM adduct (0.015 g, 0.019 mmol). After bubbling with nitrogen for another 5 min, the mixture was heated at 90° C. overnight. The cooled mixture was diluted with EtOAc, washed twice with water, dried and concentrated. The residue was subjected to column chromatography on silica gel (40 g), eluting with EtOAc-hexanes (30%, then 50%), to provide 2-fluoro-N-(2-methyl-3-(4,4,5,5-tetramethyl-1,3,2-dioxaborolan-2-yl)phenyl)-2-(pyridin-2-yl)acetamide as a pale-colored oil (0.11 g, 79% yield). Mass spectrum m/z 371 (M+H)⁺.

Intermediate 16:

A mixture of 2-fluoro-N-(2-methyl-3-(4,4,5,5-tetramethyl-1,3,2-dioxaborolan-2-yl)phenyl)-2-(pyridin-2-yl)acetamide (0.155 g, 0.419 mmol) and CDI (0.272 g, 1.675 mmol) in toluene (3.0 mL) was stirred at 110° C. for 6 h. The cooled mixture was partitioned between EtOAc and water, and the aqueous layer was extracted with EtOAc. The combined organic layers were washed with brine, dried and concentrated, and the residue was purified by column chromatograph on silica gel, eluting with EtOAc-hexanes, to provide 4-fluoro-2-(2-methyl-3-(4,4,5,5-tetramethyl-1,3,2-dioxaborolan-2-yl)phenyl)-1H-pyrido[1,2-c]pyrimidine-1,3(2H)-dione as a yellow solid (43.1 mg, 26% yield). Mass spectrum m/z 397 (M+H)⁺.

Intermediate 17

6-(2-Methyl-3-(4,4,5,5-tetramethyl-1,3,2-dioxaborolan-2-yl)phenyl)-5H-thiazolo[3,2-c]pyrimidine-5,7(6H)-dione

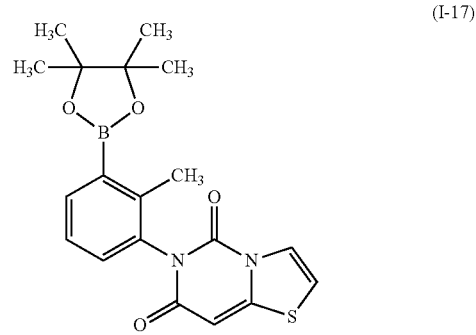 [SMILES: Cc1c(B2OC(C)(C)C(C)(C)O2)cccc1-n1c(=O)cc2sccn2c1=O]

(I-17)

Intermediate 17A: N-(3-Bromo-2-methylphenyl)-2-(thiazol-2-yl)acetamide

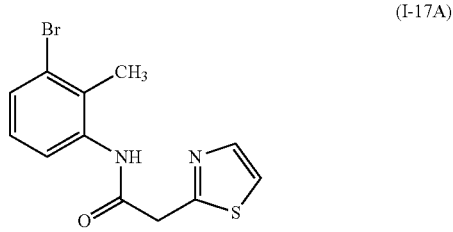 [SMILES: Cc1c(Br)cccc1NC(=O)Cc1nccs1]

(I-17A)

A mixture of 3-bromo-2-methylaniline (0.764 mL, 6.20 mmol), 1,3-thiazol-2-ylacetic acid (0.74 g, 5.17 mmol) and DIEA (1.63 mL, 9.30 mmol) in DMF (15 mL) was treated with HATU (2.36 g, 6.20 mmol). After stirring overnight, the mixture was diluted with EtOAc, washed twice with 10% aqueous LiCl followed by brine, and the combined aqueous layers were extracted with EtOAc. The combined organic layers were dried and concentrated, and the residue was purified by column chromatography on silica gel, eluting with EtOAc-hexanes, to give N-(3-bromo-2-methylphenyl)-2-(thiazol-2-yl)acetamide as a white solid (0.681 g, 42% yield). ¹H NMR (400 MHz, chloroform-d) δ 9.84-9.65 (m, 1H), 7.91 (d, J=7.9 Hz, 1H), 7.84 (d, J=3.3 Hz, 1H), 7.42-7.35 (m, 2H), 7.07 (t, J=8.0 Hz, 1H), 4.18 (s, 2H), 2.38 (s, 3H).

Intermediate 17B: N-(2-Methyl-3-(4,4,5,5-tetramethyl-1,3,2-dioxaborolan-2-yl)phenyl)-2-(thiazol-2-yl)acetamide

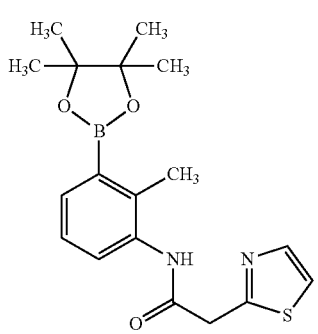

(I-17B)

A mixture N-(3-bromo-2-methylphenyl)-2-(thiazol-2-yl)acetamide (0.53 g, 1.70 mmol) 4,4,4',4',5,5,5',5'-octamethyl-2,2'-bi(1,3,2-dioxaborolane) (0.476 g, 1.87 mmol) and potassium acetate (0.418 g, 4.26 mmol) in DMSO (1.6 mL) and dioxane (8 mL) was bubbled with nitrogen for 5 min, followed by the addition of PdCl$_2$(dppf) DCM adduct (0.070 g, 0.085 mmol). After bubbling with nitrogen for another 5 min, the mixture was heated at 90° C. for 7 h. The cooled mixture was diluted with EtOAc and filtered through CELITE®. The filtrate was washed sequentially with water and brine, and dried and concentrated. The residue was purified by column chromatography on silica gel (40 g), eluting with 50% EtOAc-hexanes, to give N-(2-methyl-3-(4,4,5,5-tetramethyl-1,3,2-dioxaborolan-2-yl)phenyl)-2-(thiazol-2-yl)acetamide as an off-white solid (0.45 g, 74% yield). Mass spectrum m/z 359 (M+H)$^+$.

Intermediate 17:

A mixture of N-(2-methyl-3-(4,4,5,5-tetramethyl-1,3,2-dioxaborolan-2-yl)phenyl)-2-(thiazol-2-yl)acetamide (0.45 g, 1.26 mmol) and CDI (0.815 g, 5.02 mmol) in toluene (6.5 mL) was heated at 110° C. for 2 h. The cooled mixture was partitioned between EtOAc and water. The organic layer was washed with brine, and the combined aqueous layers were extracted with EtOAc. The combined organic layers were dried and concentrated. The residue was purified by column chromatography on silica gel (40 g), eluting with 70% EtOAc-hexanes, to give 6-(2-methyl-3-(4,4,5,5-tetramethyl-1,3,2-dioxaborolan-2-yl)phenyl)-5H-thiazolo[3,2-c]pyrimidine-5,7(6H)-dione as a tan solid (34% yield). Mass spectrum m/z 385 (M+H)$^+$.

Intermediate 18

5-Fluoro-2-(2-methyl-3-(4,4,5,5-tetramethyl-1,3,2-dioxaborolan-2-yl)phenyl)-1H-pyrido[1,2-c]pyrimidine-1,3(2H)-dione(racemic)

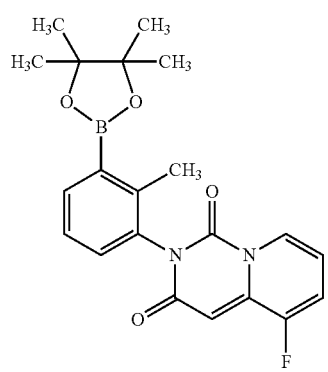

(I-18)

Intermediate 18A: Diethyl 2-(3-fluoropyridin-2-yl)malonate

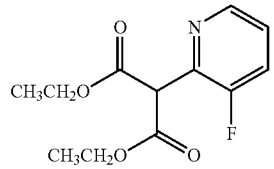

(I-18A)

A mixture of 2,3-difluoropyridine (2.00 g, 17.4 mmol), Cs$_2$CO$_3$ (13.59 g, 41.7 mmol) and diethyl malonate (6.68 g, 41.7 mmol) in DMSO (19 mL) was heated at 100° C. for 4.5 h. The mixture was poured onto ice, diluted with EtOAc, and the organic phase was separated, washed sequentially with water and brine, and dried and concentrated. The residue was purified by column chromatography on silica gel (80 g), eluting with EtOAc-hexanes (sequentially 10%, 20% and 30%), to provide diethyl 2-(3-fluoropyridin-2-yl)malonate as a pale colored oil (2.68 g, 60% yield). $^1$H NMR (400 MHz, chloroform-d) δ 8.42 (dt, J=4.6, 1.3 Hz, 1H), 7.43 (ddd, J=9.4, 8.3, 1.4 Hz, 1H), 7.30 (dt, J=8.5, 4.3 Hz, 1H), 5.09 (d, J=1.1 Hz, 1H), 4.30 (q, J=7.0 Hz, 4H), 1.33-1.26 (m, 6H).

Intermediate 18B: Ethyl 2-(3-fluoropyridin-2-yl)acetate

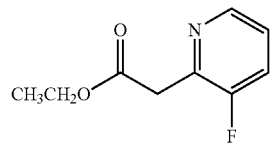

(I-18B)

A mixture of diethyl 2-(3-fluoropyridin-2-yl)malonate (2.68 g, 10.5 mmol), sodium chloride (0.675 g, 11.6 mmol) and water (0.378 mL, 21.0 mmol) in DMSO (15 mL) was heated at 145° C. for 4.5 h. The mixture was cooled, diluted with EtOAc and washed sequentially with water and brine. The organic phase was dried and concentrated to provide ethyl 2-(3-fluoropyridin-2-yl)acetate as a pale colored oil (1.9 g, 99% yield). Mass spectrum m/z 184 (M+H)$^+$.

Intermediate 18C: Sodium 2-(3-fluoropyridin-2-yl)acetate

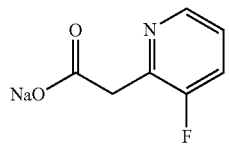

(I-18C)

A stirred solution of ethyl 2-(3-fluoropyridin-2-yl)acetate (1.90 g, 10.4 mmol) in THF (26 mL) was treated with 3 M aqueous NaOH (6.9 mL, 20.7 mmol) and stirred at room temperature overnight. The mixture was concentrated to remove the THF, and the residual aqueous solution was frozen and lyophilized to provide sodium 2-(3-fluoropyridin-2-yl)acetate as a white solid, used without further purification. Mass spectrum m/z 156 (M+H)⁺.

Intermediate 18D: N-(3-Bromo-2-methylphenyl)-2-(3-fluoropyridin-2-yl)acetamide

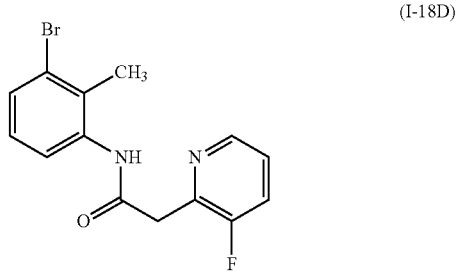 [SMILES: Cc1c(Br)cccc1NC(=O)Cc1ncccc1F]

(I-18D)

A mixture of sodium 2-(3-fluoropyridin-2-yl)acetate (1.85 g, 10.4 mmol), 3-bromo-2-methylaniline (1.4 mL, 11.4 mmol), DIEA (5.4 mL, 31.1 mmol) and HATU (4.73 g, 12.4 mmol) in DMF (30 mL) was stirred at room temperature for 1.25 h. The mixture was diluted with EtOAc and washed twice with 10% aqueous LiCl, then with brine. The combined aqueous layers were extracted with EtOAc, and the combined organic phases were dried and concentrated. The residue was dissolved in hot EtOAc, allowed to cool, and the resulting white solid collected by filtration and washed with 60% EtOAc-hexanes. The combined filtrates were concentrated and the residue was recrystallized twice using the same procedure. The residue from concentration of the final filtrate was purified by column chromatography on silica gel, eluting with EtOAc-hexanes, to provide a solid which was combined with the recrystallized batches to provide N-(3-bromo-2-methylphenyl)-2-(3-fluoropyridin-2-yl)acetamide as a white solid (2.029 g, 61% yield). Mass spectrum m/z 323, 325 (M+H)⁺.

Intermediate 18E: 2-(3-Fluoropyridin-2-yl)-N-(2-methyl-3-(4,4,5,5-tetramethyl-1,3,2-dioxaborolan-2-yl)phenyl)acetamide

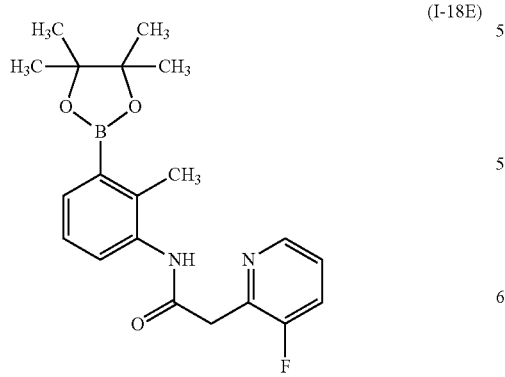

(I-18E)

A mixture of N-(3-bromo-2-methylphenyl)-2-(3-fluoropyridin-2-yl)acetamide (4.2 g, 13.6 mmol) and 4,4,4',4',5,5,5',5'-octamethyl-2,2'-bi(1,3,2-dioxaborolane) (3.80 g, 14.9 mmol) in dioxane (40 mL) was bubbled with nitrogen for 10 min. Potassium acetate (3.33 g, 34.0 mmol) was added to the mixture, bubbling was continued for another 5 min, and PdCl₂(dppf) DCM adduct (0.555 g, 0.679 mmol) was added. The mixture was heated at 100° C. overnight. The cooled mixture was diluted with EtOAc, washed sequentially with water and brine, dried and concentrated. The residue was purified by column chromatography on silica gel, eluting with DCM-methyl t-butyl ether, to provide 2-(3-fluoropyridin-2-yl)-N-(2-methyl-3-(4,4,5,5-tetramethyl-1,3,2-dioxaborolan-2-yl)phenyl)acetamide as a white solid (3.80 g, 76% yield). Mass spectrum m/z 370 (M+H)⁺.

Intermediate 18:

A mixture of 2-(3-fluoropyridin-2-yl)-N-(2-methyl-3-(4,4,5,5-tetramethyl-1,3,2-dioxaborolan-2-yl)phenyl)acetamide (9.01 g, 24.3 mmol) and CDI (15.78 g, 97 mmol) in toluene (97 mL) was heated at 120° C. for 7 h. The cooled mixture was diluted with EtOAc and washed sequentially with water and brine. The combined aqueous layers were extracted with EtOAc, and the combined organic phases were dried and concentrated. The residue was purified by column chromatography on silica gel (220 g), eluting with EtOAc-hexanes (gradient from 20-100%), to provide 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione as a yellow solid (6.26 g, 65% yield). Mass spectrum m/z 397 (M+H)⁺. ¹H NMR (400 MHz, chloroform-d) δ 8.11 (dd, J=7.6, 0.8 Hz, 1H), 7.94 (dd, J=7.5, 1.3 Hz, 1H), 7.35 (t, J=7.5 Hz, 1H), 7.23 (dd, J=7.8, 1.4 Hz, 1H), 6.85-6.76 (m, 1H), 6.35 (td, J=7.4, 5.0 Hz, 1H), 6.09 (s, 1H), 2.36 (s, 3H), 1.36 (s, 12H).

Intermediates 19 and 20

5-Fluoro-2-(2-methyl-3-(4,4,5,5-tetramethyl-1,3,2-dioxaborolan-2-yl)phenyl)-1H-pyrido[1,2-c]pyrimidine-1,3(2H)-dione (single enantiomers)

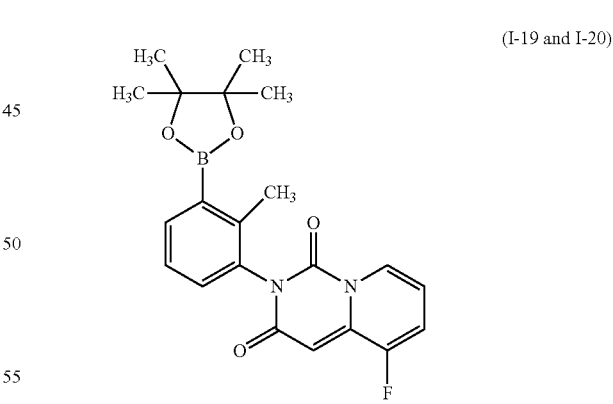

(I-19 and I-20)

Racemic 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 18] (7.50 g) was separated by chiral super-critical fluid chromatography as follows: column: CHIRALCEL® OD-H (5×25 cm, 5 μm); Mobile Phase: CO₂-MeOH (76:24) at 280 mL/min, 100 bar, 40° C.; sample preparation: 62.5 mg/mL in DCM-MeOH (1:1); injection: 0.83 mL.

The first peak eluting from the column provided one enantiomer of 5-fluoro-2-(2-methyl-3-(4,4,5,5-tetramethyl- 1,3,2-dioxaborolan-2-yl)phenyl)-1H-pyrido[1,2-c]pyrimidine-1,3(2H)-dione [Intermediate 19] as a yellow solid (3.20 g, chiral purity 99.3%).

The second peak eluting from the column provided the other enantiomer of 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 20] as a yellow solid (2.98 g, chiral purity 98.6%).

The mass spectrum and $^1$H NMR for both enantiomers were the same as those for Intermediate 18.

Intermediate 21

3-(3-Bromo-2-methylphenyl)-1-(4-fluorophenyl)pyrimidine-2,4(1H,3H)-dione

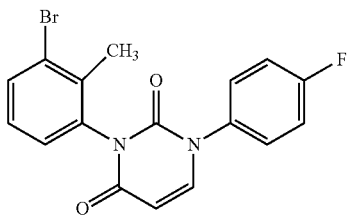

(I-21)

Intermediate 21A: Methyl 3-(4-methoxybenzylamino)-2-(phenylselanyl)propanoate

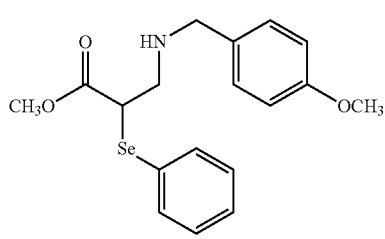

(I-21A)

A suspension of phenyl hypobromoselenoite (5.54 g, 23.5 mmol) and zinc(II) chloride (1.27 g, 9.29 mmol) in DCM (116 mL) was treated with methyl acrylate (2.1 mL, 23.2 mmol). The mixture was stirred at room temperature for 30 min, then was treated with (4-methoxyphenyl)methanamine (6.4 mL, 48.8 mmol), forming a thick suspension. After being stirred for 16 h, the precipitate was removed by filtration, washed with EtOAc, and the combined filtrates were concentrated. The residue was purified by column chromatography on silica gel (120 g), eluting with EtOAc-hexanes (gradient from 0-50%), to provide methyl 3-(4-methoxybenzylamino)-2-(phenylselanyl)propanoate as a light brown oil (3.68 g, 42% yield). Mass spectrum m/z 380 (M+H)$^+$. $^1$H NMR (400 MHz, DMSO-d$_6$) δ 7.53-7.49 (m, 2H), 7.39-7.28 (m, 3H), 7.18 (d, J=8.6 Hz, 2H), 6.88-6.82 (m, 2H), 3.89 (dd, J=8.8, 5.9 Hz, 1H), 3.73 (s, 3H), 3.61 (s, 2H), 3.55 (s, 3H), 2.93-2.78 (m, 2H).

Intermediate 21B:
1-Bromo-3-isocyanato-2-methylbenzene

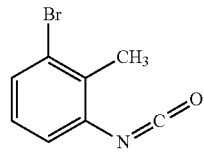

(I-21B)

A solution of triphosgene (2.25 g, 7.58 mmol) in toluene (27 mL), cooled in an ice-water bath, was treated slowly with a solution of 3-bromo-2-methylaniline (3.00 g, 16.1 mmol) and DIEA (5.6 mL, 32.2 mmol) in toluene (5.4 mL). The resulting suspension was stirred at room temperature for 2 h. The precipitate was removed by filtration and washed with EtOAc. The combined filtrates were diluted with EtOAc, washed with brine, dried and concentrated to provide 1-bromo-3-isocyanato-2-methylbenzene as a brown oil (3.68 g, 98%). $^1$H NMR (400 MHz, DMSO-d$_6$) δ 7.49 (dd, J=8.1, 0.9 Hz, 1H), 7.31 (dd, J=7.9, 0.7 Hz, 1H), 7.15 (td, J=8.0, 0.7 Hz, 1H), 2.38 (s, 3H).

Intermediate 21C: 3-(3-Bromo-2-methylphenyl)-1-(4-methoxybenzyl)-5-(phenylselanyl)dihydropyrimidine-2,4(1H,3H)-dione

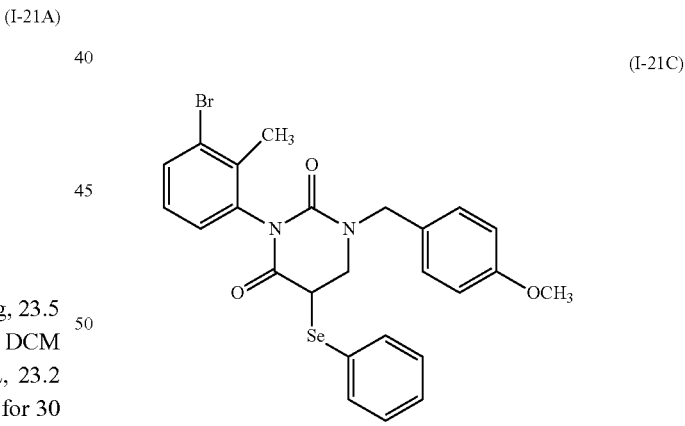

(I-21C)

A mixture of methyl 3-((4-methoxybenzyl)amino)-2-(phenylselanyl)propanoate (3.68 g, 9.73 mmol), 1-bromo-3-isocyanato-2-methylbenzene (2.27 g, 10.7 mmol), and K$_2$CO$_3$ (0.672 g, 4.86 mmol) in DMF (49 mL) was heated at 65° C. for 5 h. The cooled mixture was partitioned between water and EtOAc. The organic phase was washed with brine, dried and concentrated to provide 3-(3-bromo-2-methylphenyl)-1-(4-methoxybenzyl)-5-(phenylselanyl)dihydropyrimidine-2,4(1H,3H)-dione as a light brown solid (5.43 g). Mass spectrum m/z 557, 559, 561 (M+H)$^+$.

Intermediate 21D: 3-(3-Bromo-2-methylphenyl)-1-(4-methoxybenzyl)pyrimidine-2,4(1H,3H)-dione

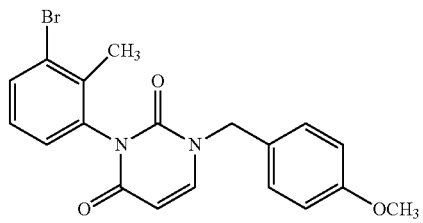
(I-21D)

A solution of 3-(3-bromo-2-methylphenyl)-1-(4-methoxybenzyl)-5-(phenylselanyl)dihydropyrimidine-2,4(1H,3H)-dione (5.43 g, 9.73 mmol) in THF (97 mL) was treated with 30% aqueous hydrogen peroxide (5.0 mL, 48.6 mmol) and the mixture was stirred at room temperature for 30 min. Water was added and the mixture was extracted with EtOAc. The organic phase was washed with brine, dried and concentrated. The residue was purified by column chromatography on silica gel (220 g), eluting with EtOAc-hexanes (gradient from 25-70%), to provide 3-(3-bromo-2-methylphenyl)-1-(4-methoxybenzyl)pyrimidine-2,4(1H,3H)-dione as a white solid (2.10 g, 54% yield). Mass spectrum m/z 401, 403 (M+H)$^+$. $^1$H NMR (400 MHz, DMSO-d$_6$) δ 7.95 (d, J=7.9 Hz, 1H), 7.70-7.65 (m, 1H), 7.32-7.28 (m, 2H), 7.25-7.22 (m, 2H), 6.96-6.91 (m, 2H), 5.86 (d, J=7.9 Hz, 1H), 4.89 (d, J=2.4 Hz, 2H), 3.74 (s, 3H), 2.02 (s, 3H).

Intermediate 21E: 3-(3-Bromo-2-methylphenyl)pyrimidine-2,4(1H,3H)-dione

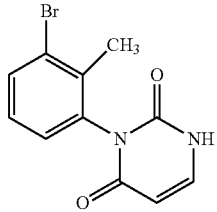
(I-21E)

A solution of 3-(3-bromo-2-methylphenyl)-1-(4-methoxybenzyl)pyrimidine-2,4(1H,3H)-dione (0.87 g, 2.17 mmol) in TFA (5.5 mL) was treated with trifluoromethanesulfonic acid (0.55 mL) and the mixture was stirred at room temperature overnight. The mixture was slowly poured onto ice and stirred while warming to room temperature. The precipitate was collected by filtration, washed with water and dried to provide 3-(3-bromo-2-methylphenyl)pyrimidine-2,4(1H,3H)-dione as a purple solid (0.62 g, 96% yield). Mass spectrum m/z 281, 283 (M+H)$^+$. $^1$H NMR (400 MHz, DMSO-d$_6$) δ 11.36 (d, J=4.4 Hz, 1H), 7.67 (dd, J=6.5, 2.8 Hz, 1H), 7.60 (dd, J=7.7, 5.9 Hz, 1H), 7.27-7.21 (m, 2H), 5.72 (dd, J=7.7, 1.3 Hz, 1H), 2.07 (s, 3H).

Intermediate 21:

A stirred suspension of copper(II) acetate (0.543 g, 2.99 mmol), 3-(3-bromo-2-methylphenyl)pyrimidine-2,4(1H,3H)-dione (0.42 g, 1.49 mmol), (4-fluorophenyl)boronic acid (0.418 g, 2.99 mmol), and activated molecular sieves (750 mg) in dry DCM (25 mL) was treated with pyridine (0.363 mL, 4.48 mmol) and stirred at room temperature overnight. The mixture was diluted with DCM, filtered through CELITE®, and the solids were washed with DCM and THF. The combined filtrates were washed with water, dried and concentrated. The residue was purified by column chromatography on silica gel (40 g), eluting with EtOAc-hexanes (gradient from 20-40%), to give 3-(3-bromo-2-methylphenyl)-1-(4-fluorophenyl)pyrimidine-2,4(1H,3H)-dione as a yellow glassy solid (0.36 g, 43% yield). Mass spectrum m/z 375, 377 (M+H)$^+$. $^1$H NMR (400 MHz, DMSO-d$_6$) δ 7.91 (d, J=7.9 Hz, 1H), 7.68 (dd, J=7.9, 1.3 Hz, 1H), 7.60-7.51 (m, 2H), 7.40-7.22 (m, 4H), 5.95 (d, J=7.9 Hz, 1H), 2.21-2.12 (m, 3H).

Intermediate 22

4-Bromo-7-(2-hydroxypropan-2-yl)-5-methyl-9H-carbazole-1-carboxamide

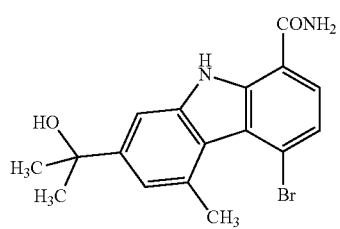
(I-22)

Intermediate 22A: Ethyl 3-hydroxy-5-methylbenzoate

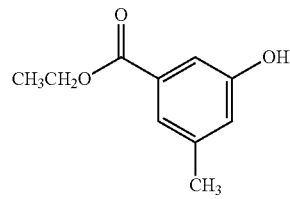
(I-22A)

A solution of 3-hydroxy-5-methylbenzoic acid (prepared according to the procedure of Turner et al., *J. Org. Chem.*, 24:1952 (1959); 2.50 g, 16.4 mmol) in EtOH (100 mL) was treated with sulfuric acid (5 mL, 94 mmol) and heated to reflux on an oil bath. After 18 h the solution was cooled to room temperature. The solution was concentrated to a reduced volume (20-30 mL) and diluted with water (100-150 mL). A gum deposited which became a solid on stirring and trituration. The precipitate was collected by filtration, washed with water and dried under vacuum to provide ethyl 3-hydroxy-5-methylbenzoate as an off-white solid (2.63 g, 89% yield). Mass spectrum m/z 181 (M+H)$^+$. $^1$H NMR (400 MHz, chloroform-d) δ 7.46 (d, J=0.7 Hz, 1H), 7.40 (s, 1H), 6.90 (s, 1H), 4.39 (q, J=7.0 Hz, 2H), 2.37 (s, 3H), 1.41 (t, J=7.2 Hz, 3H).

Intermediate 22B: Ethyl 3-hydroxy-5-methylcyclohexancarboxylate

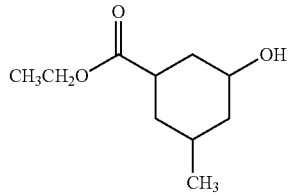

(I-22B)

A solution of ethyl 3-hydroxy-5-methylbenzoate (2.63 g, 14.6 mmol) in EtOH (50 mL) was combined with 5% rhodium on alumina (0.5 g) in a Parr pressure bottle and shaken under a hydrogen atmosphere (60 psig) at room temperature. After 21.5 h, the vessel was vented and purged with nitrogen. The mixture was filtered through CELITE® and the solids were washed with EtOH. The combined filtrates were concentrated under vacuum to provide ethyl 3-hydroxy-5-methylcyclohexanecarboxylate as a colorless oily liquid (2.64 g, 97% yield). Mass spectrum m/z 187 (M+H)$^+$, 169 (M+H−H$_2$O)$^+$.

Intermediate 22C: Ethyl 3-methyl-5-oxocyclohexancarboxylate

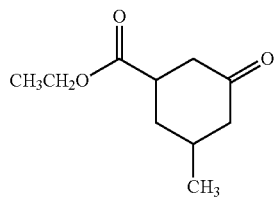

(I-22C)

A solution of ethyl 3-hydroxy-5-methylcyclohexanecarboxylate (2.64 g, 14.2 mmol) in acetone (45 mL) was stirred on an ice-water bath and treated dropwise with Jones reagent (4.25 mL, 14.9 mmol) until the yellow color persisted for more than 30 min. The mixture was then treated with isopropanol (ca. 2 mL) and stirred on ice until the yellow color was discharged and the mixture was a blue-green slurry. The supernatant was decanted through CELITE®. The sludge was stirred and triturated several times with fresh acetone until it was mostly a powdery solid, with the acetone washes were also filtered through CELITE®. The combined filtrates and washes were concentrated. The residue was dissolved in ether, washed with saturated brine, dried and concentrated to provide ethyl 3-methyl-5-oxocyclohexanecarboxylate as a nearly colorless oily liquid (2.275 g, 87% yield; mixture of diastereomers, ratio about 95:5). $^1$H NMR (major isomer) (400 MHz, chloroform-d) δ 4.18 (q, J=7.3 Hz, 2H), 2.72 (tt, J=12.7, 4.0 Hz, 1H), 2.62-2.53 (m, 1H), 2.50 (dd, J=13.1, 1.0 Hz, 1H), 2.45-2.36 (m, 1H), 2.16 (dtt, J=13.3, 3.5, 1.8 Hz, 1H), 2.07-1.97 (m, 1H), 1.97-1.82 (m, 1H), 1.57-1.42 (m, 1H), 1.29 (t, J=7.2 Hz, 3H), 1.09 (d, J=6.4 Hz, 3H).

Intermediate 22D: 5-Bromo-2-ethoxycarbonyl-4-methyl-2,3,4,9-tetrahydro-1H-carbazole-8-carboxylic acid

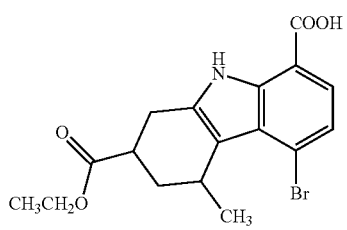

(I-22D)

A suspension of 4-bromo-2-hydrazinylbenzoic acid hydrochloride [prepared according to the procedure described in U.S. Pat. No. 8,084,620, Intermediate 46-1] (605 mg, 2.26 mmol) in acetic acid (10 mL) was treated with ethyl 3-methyl-5-oxocyclohexanecarboxylate (500 mg, 2.71 mmol) and the mixture was heated at 100-105° C. After 6 h the temperature was reduced to 95° C. and stirring was continued overnight. After 22 h total the mixture was cooled to room temperature and most of the solvent was removed under vacuum. The residue was stirred in EtOAc and the mixture was filtered to remove a small amount of precipitate. The filtrate was washed with water, dried over sodium sulfate and concentrated under vacuum to give crude 5-bromo-2-(ethoxycarbonyl)-4-methyl-2,3,4,9-tetrahydro-1H-carbazole-8-carboxylic acid (mixture of diastereomers) as a dark brown gum (860 mg). Mass spectrum m/z 380, 382 (M+H)$^+$.

Intermediate 22E: Ethyl 5-bromo-8-carbamoyl-4-methyl-2,3,4,9-tetrahydro-1H-carbazole-2-carboxylate

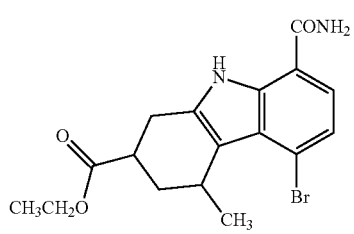

(I-22E)

A solution of crude 5-bromo-2-(ethoxycarbonyl)-4-methyl-2,3,4,9-tetrahydro-1H-carbazole-8-carboxylic acid (860 mg) in THF (15 mL) was treated with 1-hydroxy-7-azabenzotriazole (369 mg, 2.71 mmol) and EDC (520 mg, 2.71 mmol) and the suspension was stirred at room temperature. After 2 h, the mixture was bubbled with anhydrous ammonia for about 2 min, forming a thick orange slurry. After 2.5 h more the mixture was diluted with water and EtOAc and the layers were separated. The aqueous phase was extracted again with EtOAc and the combined organic layers were washed sequentially with 1 M aqueous NaOH and brine, and dried and concentrated. The residue was subjected to column chromatography on silica gel (80 g), eluting with EtOAc-hexanes (gradient from 25-100%), to provide impure ethyl 5-bromo-8-carbamoyl-4-methyl-2,3,4,9-tetrahydro-1H-carbazole-2-carboxylate (mixture of diastereomers) as a yellow-tan solid (265 mg, 31% yield). Mass spectrum m/z 379, 381 (M+H)⁺.

Intermediate 22F: Ethyl 5-bromo-8-carbamoyl-4-methyl-9H-carbazole-2-carboxylate

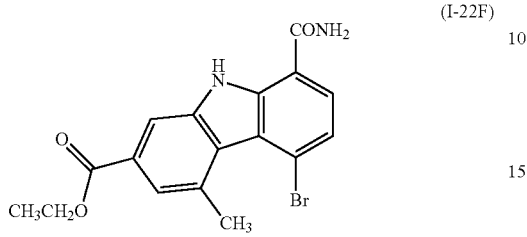

(I-22F)

A solution of impure ethyl 5-bromo-8-carbamoyl-4-methyl-2,3,4,9-tetrahydro-1H-carbazole-2-carboxylate (250 mg, 0.659 mmol) in THF (7 mL) was treated with 2,3-dichloro-5,6-dicyanobenzoquinone (329 mg, 1.45 mmol) and heated on an oil bath at 60° C. After 2.4 h the mixture was cooled to room temperature and diluted with EtOAc. The mixture was filtered and the precipitate was rinsed with EtOAc and dried under vacuum to provide a very fine white solid (71.6 mg). The filtrate was washed four times with saturated aqueous NaHCO₃, then with brine. The organic phase was dried and concentrated, and the residue was sonicated in a mixture of EtOAc and MeOH. The precipitate was collected by filtration, washed with EtOAc and dried to provide a pale yellow solid (50.5 mg). This filtrate was subjected to column chromatography on silica gel (12 g), eluting with EtOAc-hexanes (gradient from 25-100%), to provide a solid which was sonicated in a minimal amount of EtOAc. The precipitate was collected by filtration, rinsed with minimal EtOAc and dried to provide a pale yellow solid (5.2 mg). The three isolated solids were combined to provide ethyl 5-bromo-8-carbamoyl-4-methyl-9H-carbazole-2-carboxylate as a pale yellow solid (127 mg, 51% yield). Mass spectrum m/z 375, 377 (M+H)⁺. ¹H NMR (400 MHz, DMSO-d₆) δ 12.17 (s, 1H), 8.42 (d, J=1.1 Hz, 1H), 8.25 (br. s., 1H), 7.88 (d, J=8.1 Hz, 1H), 7.62 (br. s., 1H), 7.59 (d, J=0.7 Hz, 1H), 7.56 (d, J=8.1 Hz, 1H), 4.36 (q, J=7.0 Hz, 2H), 3.20 (s, 3H), 1.38 (t, J=7.0 Hz, 3H).

Intermediate 22: Ethyl 4-bromo-7-(2-hydroxypropan-2-yl)-5-methyl-9H-carbazole-1-carboxylate A suspension of ethyl 5-bromo-8-carbamoyl-4-methyl-9H-carbazole-2-carboxylate (120 mg, 0.320 mmol) in THF (2.5 mL) was stirred at −78° C. and treated dropwise with 1.6 M methyllithium in ether (0.800 mL, 1.28 mmol) over about 2.5 min. Within 0.5 h the mixture was a solid yellow mass. After 45 min from the completion of addition, THF (1 mL) was added and the mixture warmed sufficiently (still below 0° C.) to allow partial mixing, then was cooled again to −78° C. After 90 min from the completion of addition, the mixture was treated with saturated aqueous NH₄Cl (2 mL) and a small amount of water, and allowed to warm to room temperature with vigorous stirring. The mixture was extracted twice with EtOAc. The combined organic phases were washed with saturated brine, dried and concentrated. The residue was subjected to column chromatography on silica gel (12 g), eluting with EtOAc-hexanes (gradient from 40-100%), to provide 4-bromo-7-(2-hydroxypropan-2-yl)-5-methyl-9H-carbazole-1-carboxamide as an off-white solid (96.3 mg, 83% yield). Mass spectrum m/z 343, 345 (M+H–H₂O)⁺. ¹H NMR (400 MHz, DMSO-d₆) δ 11.73 (s, 1H), 8.19 (br. s., 1H), 7.82-7.73 (m, 2H), 7.54 (br. s., 1H), 7.45 (d, J=8.1 Hz, 1H), 7.14 (d, J=0.9 Hz, 1H), 5.03 (s, 1H), 3.14 (s, 3H), 1.50 (s, 6H).

Intermediate 23

4-Bromo-7-(2-hydroxypropan-2-yl)-8-methyl-9H-carbazole-1-carboxamide

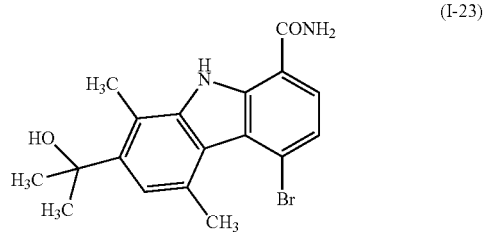 [SMILES: Cc1c(C(C)(C)O)cc(C)c2c1[nH]c1c(C(N)=O)ccc(Br)c12]

(I-23)

Following the procedures used to prepare Intermediate 22, 3-hydroxy-2-methylbenzoic acid was converted into 4-bromo-7-(2-hydroxypropan-2-yl)-8-methyl-9H-carbazole-1-carboxamide. Mass spectrum m/z 343, 345 (M+H–H₂O)⁺. ¹H NMR (400 MHz, DMSO-d₆) δ 10.86 (s, 1H), 8.38-8.26 (m, 2H), 7.89 (d, J=8.1 Hz, 1H), 7.67 (br. s., 1H), 7.44 (d, J=8.1 Hz, 2H), 5.09 (s, 1H), 2.81 (s, 3H), 1.63 (s, 6H).

Intermediates 24 and 24A

8-Fluoro-1-methyl(d₃)-3-(S)-(2-methyl-3-(4,4,5,5-tetramethyl-1,3,2-dioxaborolan-2-yl)phenyl)quinazoline-2,4(1H,3H)-dione (I-24), and 8-Fluoro-1-methyl(d₃)-3-(R)-(2-methyl-3-(4,4,5,5-tetramethyl-1,3,2-dioxaborolan-2-yl)phenyl)quinazoline-2,4(1H,3H)-dione (I-24A)

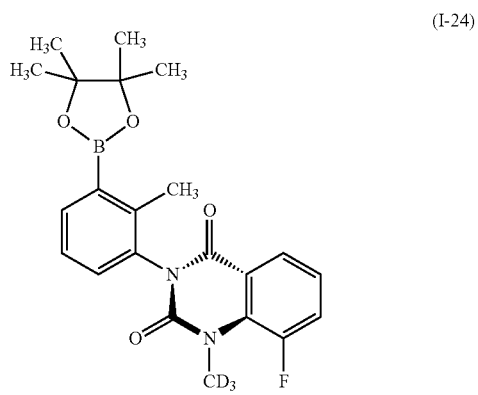

(I-24)

-continued

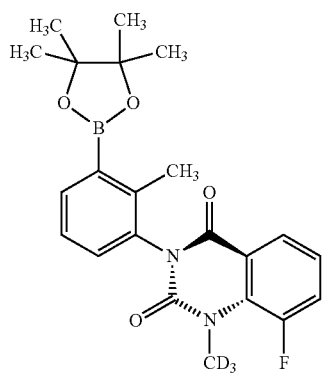

Intermediate 24B: 8-Fluoro-1-methyl(d₃)-3-(RS)-(2-methyl-3-(4,4,5,5-tetramethyl-1,3,2-dioxaborolan-2-yl)phenyl)quinazoline-2,4(1H,3H)-dione

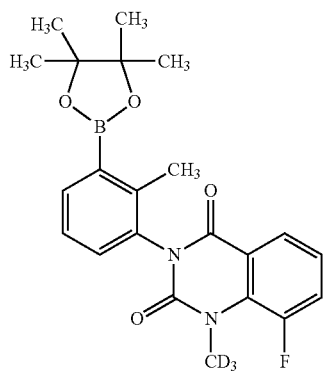

A mixture of 3-(3-bromo-2-methylphenyl)-8-fluoro-1-methyl(d₃)quinazoline-2,4(1H,3H)-dione [Intermediate 5] (3.00 g, 8.19 mmol), 4,4,4',4',5,5,5',5'-octamethyl-2,2'-bi(1,3,2-dioxaborolane) (2.70 g, 10.7 mmol) and potassium acetate (2.41 g, 24.6 mmol) in dioxane (40 mL) was bubbled with argon with sonication for ca. 2 min, then was treated with PdCl₂(dppf) DCM adduct (0.335 g, 0.410 mmol). The mixture was heated at 90° C. for 15.75 h. The cooled mixture was diluted with EtOAc, filtered through CELITE®, and the solids were rinsed with EtOAc. The combined filtrates were concentrated, and the residue was purified by column chromatography on silica gel (330 g), eluting with EtOAc-hexanes (gradient from 0-40%), to give 8-fluoro-1-methyl (d₃)-3-(RS)-(2-methyl-3-(4,4,5,5-tetramethyl-1,3,2-dioxaborolan-2-yl)phenyl)quinazoline-2,4(1H,3H)-dione as an off-white solid (3.23 g, 95% yield). Mass spectrum m/z 414 (M+H)⁺. ¹H NMR (400 MHz, chloroform-d) δ 8.14-8.07 (m, 1H), 7.93 (dd, J=7.4, 1.4 Hz, 1H), 7.48 (ddd, J=13.9, 8.1, 1.5 Hz, 1H), 7.37-7.31 (m, 1H), 7.27-7.19 (m, 2H), 2.36 (s, 3H), 1.36 (s, 12H).

Intermediates 24 and 24A:

A sample of 8-fluoro-1-methyl(d₃)-3-(RS)-(2-methyl-3-(4,4,5,5-tetramethyl-1,3,2-dioxaborolan-2-yl)phenyl)quinazoline-2,4(1H,3H)-dione [Intermediate 24B] was separated by super-critical fluid chromatography as follows: column: WHELK-O® R,R (3×25 cm, 5 μm); Mobile Phase: CO₂-MeOH (70:30) at 200 mL/min, 100 bar, 30° C.; sample preparation: 3.7 mg/mL in MeOH; injection: 4.17 mL. The first peak eluting from the column provided the S enantiomer, 8-fluoro-1-methyl(d₃)-3-(S)-(2-methyl-3-(4,4,5,5-tetramethyl-1,3,2-dioxaborolan-2-yl)phenyl)quinazoline-2,4(1H,3H)-dione [Intermediate 24] as a white solid. The second peak eluting from the column provided the R enantiomer, 8-fluoro-1-methyl(d₃)-3-(R)-(2-methyl-3-(4,4,5,5-tetramethyl-1,3,2-dioxaborolan-2-yl)phenyl)quinazoline-2,4(1H,3H)-dione [Intermediate 24A] as a white solid. The mass spectrum and ¹H NMR for both enantiomers were the same as those for Intermediate 24B.

Alternative Synthesis of 8-Fluoro-1-methyl(d₃)-3-(S)-(2-methyl-3-(4,4,5,5-tetramethyl-1,3,2-dioxaborolan-2-yl)phenyl)quinazoline-2,4(1H,3H)-dione [Intermediate 24]:

Intermediate 24C: 8-Fluoro-3-(2-methyl-3-(4,4,5,5-tetramethyl-1,3,2-dioxaborolan-2-yl)phenyl)quinazoline-2,4(1H,3H)-dione

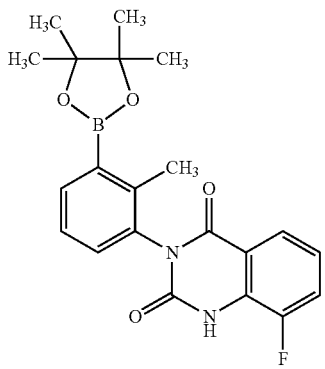

A stirred mixture of 3-(3-bromo-2-methylphenyl)-8-fluoroquinazoline-2,4(1H,3H)-dione [Intermediate 1] (0.349 g, 1.00 mmol), 4,4,4',4',5,5,5',5'-octamethyl-2,2'-bi(1,3,2-dioxaborolane) (0.305 g, 1.20 mmol), PdCl₂(dppf) DCM adduct (0.041 g, 0.050 mmol) and potassium acetate (0.245 g, 2.50 mmol) in dioxane (20 mL) and DMSO (4 mL) was bubbled with nitrogen for 5 min, then heated at 90° C. overnight. The mixture was cooled to room temperature and partitioned between EtOAc and water. The organic phase was washed sequentially with saturated aqueous NaHCO₃ and brine, dried and concentrated. The residue was purified by column chromatography on silica gel, eluting with 20% EtOAc-hexane, to give 8-fluoro-3-(2-methyl-3-(4,4,5,5-tetramethyl-1,3,2-dioxaborolan-2-yl)phenyl)quinazoline-2,4(1H,3H)-dione as a white solid (0.326 g, 82% yield). Mass Spectrum m/z 397 (M+H)⁺. ¹H NMR (500 MHz, DMSO-d₆) δ 11.78 (s, 1H), 7.80 (d, J=7.2 Hz, 1H), 7.72 (dd, J=7.4, 1.5 Hz, 1H), 7.71-7.56 (m, 1H), 7.45-7.35 (m, 1H), 7.35-7.29 (m, 1H), 7.29-7.16 (m, 1H), 2.22 (s, 3H), 1.33 (s, 12H).

83

Intermediate 24D: 8-Fluoro-3-(S)-(2-methyl-3-(4,4,5,5-tetramethyl-1,3,2-dioxaborolan-2-yl)phenyl)quinazoline-2,4(1H,3H)-dione

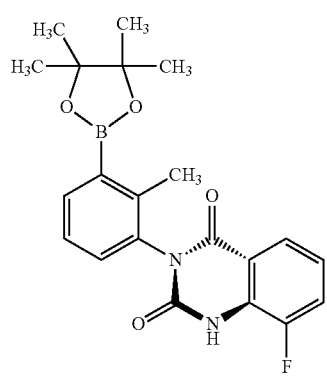

(I-24D)

A sample of 8-fluoro-3-(2-methyl-3-(4,4,5,5-tetramethyl-1,3,2-dioxaborolan-2-yl)phenyl)quinazoline-2,4(1H,3H)-dione [Intermediate 24C] was separated by chiral supercritical fluid chromatography as follows: column: CHIRALCEL® OD-H (5×25 cm, 5 μm); Mobile Phase: $CO_2$-MeOH (70:30) at 300 mL/min, 100 bar, 40° C.; sample preparation: 103 mg/mL in DCM-MeOH (44:56); injection: 5.0 mL. The second peak eluting from the column gave the S enantiomer, 8-fluoro-3-(S)-(2-methyl-3-(4,4,5,5-tetramethyl-1,3,2-dioxaborolan-2-yl)phenyl)quinazoline-2,4(1H,3H)-dione, as a white solid. Mass spectrum m/z 397 $(M+H)^+$. $^1$H NMR (400 MHz, chloroform-d) δ 8.19 (s, 1H), 7.99 (d, J=8.1 Hz, 1H), 7.95 (dd, J=7.3, 1.3 Hz, 1H), 7.46 (ddd, J=9.8, 8.3, 1.2 Hz, 1H), 7.39-7.32 (m, 1H), 7.28-7.18 (m, 2H), 2.39 (s, 3H), 1.36 (s, 12H).

Intermediate 24:

A solution of 8-fluoro-3-(S)-(2-methyl-3-(4,4,5,5-tetramethyl-1,3,2-dioxaborolan-2-yl)phenyl)quinazoline-2,4(1H,3H)-dione [Intermediate 24D] (5.42 g, 13.7 mmol) in THF (100 mL) was stirred on an ice-water bath and treated with $Cs_2CO_3$ (6.24 g, 19.2 mmol), then with iodomethane-$d_3$ (1.02 mL, 16.4 mmol) and the mixture was stirred at room temperature for 16.25 h. The mixture was filtered, the solid was rinsed with EtOAc, and the combined filtrates were concentrated. The residue was dissolved in EtOAc and washed sequentially with water and brine, dried and concentrated to provide 8-fluoro-1-methyl($d_3$)-3-(S)-(2-methyl-3-(4,4,5,5-tetramethyl-1,3,2-dioxaborolan-2-yl)phenyl)quinazoline-2,4(1H,3H)-dione as a white solid (5.538 g, 98% yield). Mass spectrum m/z 414 $(M+H)^+$. $^1$H NMR (400 MHz, chloroform-d) δ 8.11 (dq, J=7.8, 0.8 Hz, 1H), 7.93 (dd, J=7.5, 1.3 Hz, 1H), 7.48 (ddd, J=13.9, 8.1, 1.5 Hz, 1H), 7.38-7.30 (m, 1H), 7.27-7.20 (m, 2H), 2.36 (s, 3H), 1.36 (s, 12H).

84

Intermediate 25

4-Bromo-7-(methoxymethyl)-9H-carbazole-1-carboxamide

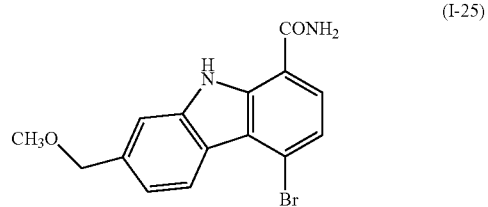

(I-25)

A stirred suspension of 4-bromo-7-(hydroxymethyl)-9H-carbazole-1-carboxamide [prepared according to the procedure described in U.S. Pat. No. 8,084,620, Example 30-02] (0.5 g, 1.57 mmol) in THF (10 mL) was treated dropwise with thionyl chloride (0.252 mL, 3.45 mmol) and the mixture was stirred at room temperature for 1 h. The mixture was treated with MeOH (0.2 mL), and the solvent and excess thionyl chloride were removed under vacuum. The residue was dissolved in MeOH (10 mL), and sodium methoxide (0.423 g, 7.83 mmol) was added. The mixture was stirred overnight at room temperature. The mixture was diluted with EtOAc and washed sequentially with water and brine. The combined aqueous layers were extracted with EtOAc, and the combined organic phases were dried and concentrated. The residue was purified by column chromatography on silica gel (40 g), eluting with EtOAc-hexanes (gradient from 0-100%), to give 4-bromo-7-(methoxymethyl)-9H-carbazole-1-carboxamide as a white solid (119 mg, 23% yield). Mass spectrum m/z 333, 335 $(M+H)^+$.

Examples 1 and 2

4-(3-(8-Fluoro-2,4-dioxo-1,2-dihydroquinazolin-3(4H)-yl)-2-methylphenyl)-7-(2-hydroxypropan-2-yl)-9H-carbazole-1-carboxamide (Mixtures of Two Interconverting diastereomers)

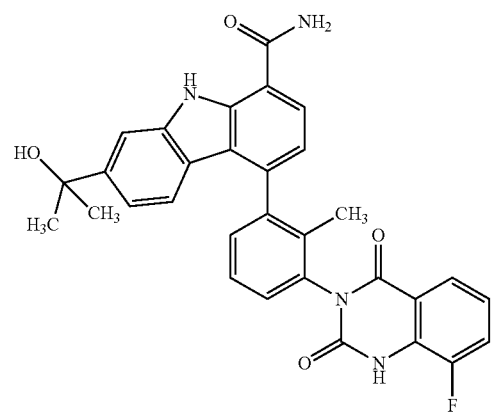

(1 and 2)

Preparation 1A: 4-(3-(8-Fluoro-2,4-dioxo-1,2-dihydroquinazolin-3(4H)-yl)-2-methylphenyl)-7-(2-hydroxypropan-2-yl)-9H-carbazole-1-carboxamide (Mixture of Four diastereomers)

A mixture of 7-(2-hydroxypropan-2-yl)-4-(4,4,5,5-tetramethyl-1,3,2-dioxaborolan-2-yl)-9H-carbazole-1-carboxamide (43.4 mg, 0.110 mmol) [Intermediate 4], 3-(3-bromo-2-methylphenyl)-8-fluoroquinazoline-2,4(1H,3H)-dione (32 mg, 0.092 mmol) [Intermediate 1], tetrakis(triphenylphosphine)palladium (5.3 mg, 4.58 µmol), and potassium carbonate (38.0 mg, 0.275 mmol) in THF (3 mL) was sealed in a vial and heated at 90° C. overnight. The cooled mixture was purified by column chromatography on silica gel (40 g), eluting with DCM-MeOH—NH$_4$OH (gradient from 90:9:1 to 97:2.7:0.3), to give 4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (mixture of four diastereomers) as a white solid (6 mg, 13% yield. Mass spectrum m/z 519 (M+H–H$_2$O)$^+$.

$^1$H NMR (500 MHz, chloroform-d/MeOH-d$_4$) δ 7.70 (d, J=1.5 Hz, 1H), 7.62-7.58 (m, 1H), 7.55-7.47 (m, 2H), 7.46-7.42 (m, 1H), 7.38 (d, J=7.9 Hz, 1H), 7.28-7.19 (m, 3H), 7.14 (dd, J=8.4, 1.5 Hz, 1H), 7.10 (dd, J=10.9, 7.9 Hz, 1H), 1.89 (s, 3H), 1.61 (dd, J=10.2, 3.2 Hz, 6H).

$^1$H NMR (400 MHz, DMSO-d$_6$) δ 11.85 (s, 0.5H), 11.79 (s, 0.5H), 11.39 (s, 1H), 8.16 (br. s., 1H), 7.99 (d, J=7.7 Hz, 1H), 7.90-7.79 (m, 2H), 7.69-7.61 (m, 1H), 7.53-7.42 (m, 3H), 7.35 (dt, J=6.0, 3.3 Hz, 1H), 7.28-7.20 (m, 1H), 7.11-7.06 (m, 1H), 7.03 (t, J=7.5 Hz, 2H), 4.98 (s, 0.5H), 4.96 (s, 0.5H), 1.76 (s, 3H), 1.48-1.42 (m, 6H).

$^{19}$F NMR (376 MHz, DMSO-d$_6$) δ –129.97 (s, 1F), –130.02 (s, 1F).

Examples 1 and 2

A sample of 4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (mixture of four diastereomers) (1.2 g) was separated by chiral super-critical fluid chromatography as follows: column: CHIRALCEL® OD-H (3×25 cm, 5 µm); Mobile Phase: CO$_2$-(1:1 MeOH-acetonitrile) (45:55) at 145 mL/min, 100 bar, 40° C.; sample preparation: 50 mg/mL in DMSO-MeOH (1:1); injection: 3.5 mL.

The first peak eluting from the column provided one pair of interconverting diastereomers of 4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide [Example 1] as a white solid (603 mg).

The second peak eluting from the column provided the other pair of interconverting diastereomers 4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide [Example 2] as a white solid (584 mg).

The mass spectra and NMR spectra for both were the same as those for the mixture of four diastereomers shown above. The absolute stereochemistry of Examples 1 and 2 has not been assigned.

Example 3

4-(3-(S)-(8-Fluoro-1-methyl-2,4-dioxo-1,2-dihydroquinazolin-3(4H)-yl)-2-methylphenyl)-7-(2-hydroxypropan-2-yl)-9H-carbazole-1-carboxamide (Mixture of Two Interconverting diastereomers)

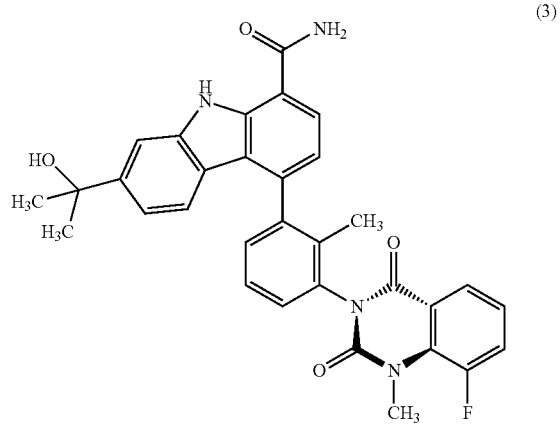

(3)

Preparation 3A: 4-(3-(8-Fluoro-1-methyl-2,4-dioxo-1,2-dihydroquinazolin-3(4H)-yl)-2-methylphenyl)-7-(2-hydroxypropan-2-yl)-9H-carbazole-1-carboxamide (Mixture of Four diastereomers)

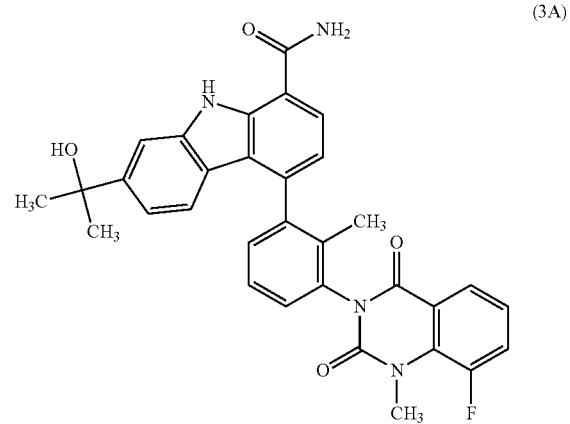 [SMILES: Cc1c(-c2ccc(C(N)=O)c3[nH]c4cc(C(C)(C)O)ccc4c23)cccc1-n1c(=O)c2cccc(F)c2n(C)c1=O]

(3A)

A mixture of 4-bromo-7-(2-hydroxypropan-2-yl)-9H-carbazole-1-carboxamide [synthesized according to the procedure described in U.S. Pat. No. 8,084,620, Intermediate 73-2] (827 mg, 2.38 mmol), 8-fluoro-1-methyl-3-(2-methyl-3-(4,4,5,5-tetramethyl-1,3,2-dioxaborolan-2-yl)phenyl)quinazoline-2,4(1H,3H)-dione [Intermediate 2] (850 mg, 2.07 mmol), 2 M aqueous tripotassium phosphate (3.11 mL, 6.22 mmol), and tetrakis(triphenylphosphine)palladium (120 mg, 0.104 mmol) in a mixture of toluene (27 mL) and EtOH (9 mL) was heated at reflux under nitrogen overnight. The mixture was cooled to room temperature, diluted with EtOAc, washed with water, dried and concentrated. The residue was subjected to column chromatography on silica gel (330 g), eluting with DCM-MeOH—NH$_4$OH (gradient from 90:9:1 to 97:2.7:0.3), to give 4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of four diastereomers) as a white solid (860 mg, 74% yield). Mass spectrum m/z 533 (M+H−H$_2$O)$^+$. $^1$H NMR (400 MHz, chloroform-d) δ 10.56 (s, 1H), 8.15 (dd, J=9.8, 8.7 Hz, 1H), 7.71-7.64 (m, 2H), 7.54-7.42 (m, 3H), 7.36 (dd, J=7.7, 1.3 Hz, 1H), 7.28-7.24 (m, 3H), 7.18-7.11 (m, 1H), 6.02 (br. s., 2H), 3.91 (dd, J=7.9, 2.9 Hz, 3H), 1.90 (s, 3H), 1.85 (d, J=4.0 Hz, 1H), 1.67 (d, J=1.3 Hz, 6H). $^1$H NMR (400 MHz, DMSO-d$_6$) δ 11.40 (s, 1H), 8.17 (br. s., 1H), 8.04-7.93 (m, 2H), 7.84 (d, J=1.1 Hz, 1H), 7.74 (ddd, J=14.4, 8.0, 1.3 Hz, 1H), 7.54-7.42 (m, 3H), 7.38-7.30 (m, 2H), 7.12-7.05 (m, 1H), 7.04-6.99 (m, 2H), 4.99 (d, J=1.3 Hz, 1H), 3.75 (t, J=8.4 Hz, 3H), 1.76 (s, 3H), 1.50-1.45 (m, 6H).

Alternative Preparation 3A:

A mixture of 4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (mixture of four diastereomers) [Preparation 1A] (20 mg, 0.037 mmol), iodomethane (0.15 mL of a 35 mg/mL solution in DMF; 5.29 mg, 0.037 mmol) and Cs$_2$CO$_3$ (12.1 mg, 0.037 mmol) in DMF (2 mL) was stirred at room temperature for 17 h. The mixture was diluted with EtOAc, the organics were washed sequentially with water and 10% aqueous LiCl, and dried and concentrated. The residue was purified by column chromatography on silica gel (12 g), eluting with DCM:MeOH:NH$_4$OH (gradient from 90:9:1 to 97:2.7:0.3) to give 4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of four diastereomers) as a white solid (19 mg, 93% yield). Mass spectrum m/z 533 (M+H−H$_2$O)$^+$. $^1$H NMR (400 MHz, chloroform-d) δ 10.56 (s, 1H), 8.14 (dd, J=9.6, 8.5 Hz, 1H), 8.04 (s, 1H), 7.70-7.63 (m, 2H), 7.54-7.41 (m, 3H), 7.35 (dd, J=7.8, 1.2 Hz, 1H), 7.28-7.22 (m, 3H), 7.14 (dd, J=7.8, 1.7 Hz, 1H), 3.90 (dd, J=7.9, 2.9 Hz, 3H), 1.90 (s, 3H), 1.66 (d, J=1.3 Hz, 6H).

Example 3

A sample of 4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of four diastereomers) (532 mg, 0.966 mmol) was separated by chiral super-critical fluid chromatography as follows: column: Lux Cel-4 (3×25 cm, 5 μm); Mobile Phase: CO$_2$-MeOH (60:40) at 85 mL/min; sample preparation: 6.7 mg/mL in MeOH-acetone (9:1); injection: 3 mL.

Peaks 3 and 4 eluting from the column were collected together and concentrated to give 4-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of two interconverting diastereomers) as a light yellow solid (230 mg).

Mass spectrum m/z 533 (M+H−H$_2$O)$^+$. $^1$H NMR (400 MHz, DMSO-d$_6$) δ 11.40 (s, 1H), 8.16 (br. s., 1H), 8.04-7.93 (m, 2H), 7.84 (s, 1H), 7.78-7.69 (m, 1H), 7.55-7.43 (m, 3H), 7.39-7.30 (m, 2H), 7.13-6.98 (m, 3H), 4.99 (d, J=1.1 Hz, 1H), 3.75 (t, J=8.4 Hz, 3H), 1.75 (s, 3H), 1.47 (d, J=4.4 Hz, 6H).

Alternative Synthesis of Example 3:

A suspension of 8-fluoro-1-methyl-3-(S)(2-methyl-3-(4,4,5,5-tetramethyl-1,3,2-dioxaborolan-2-yl)phenyl)quinazoline-2,4(1H,3H)-dione [Intermediate 3] (13.00 g, 31.7 mmol), 4-bromo-7-(2-hydroxypropan-2-yl)-9H-carbazole-1-carboxamide [synthesized according to the procedure described in U.S. Pat. No. 8,084,620, Intermediate 73-2, and recrystallized from MeOH] (10.00 g, 28.8 mmol), Cs$_2$CO$_3$ (18.77 g, 57.6 mmol), THF (120 mL) and water (30 mL) was bubbled with nitrogen for 5 min, then was treated with PdCl$_2$(dppf) DCM adduct (1.11 g, 1.44 mmol). The mixture was heated at 40° C. for 24 h, then cooled to room temperature. The mixture was filtered through a pad of CELITE® and the solids were washed with EtOAc. The combined filtrates were washed with brine, dried and concentrated. The residue was purified by column chromatography on silica gel (330 g), eluting with a gradient from DCM to EtOAc, to give a solid. Recrystallization from acetone provided 4-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of two interconverting diastereomers) as a crystalline solid (6.80 g, 86% yield). $^1$H NMR (500 MHz, DMSO-d$_6$) δ 11.40 (s, 1H), 8.17 (br. s., 1H), 8.00 (d, J=7.7 Hz, 2H), 7.95 (d, J=7.7 Hz, 1H), 7.84 (s, 1H), 7.72 (dd, J=14.3, 8.1 Hz, 1H), 7.52-7.47 (m, 1H), 7.50-7.44 (m, 1H), 7.47-7.42 (m, 1H), 7.38-7.34 (m, 1H), 7.35-7.29 (m, 1H), 7.12-7.05 (m, 1H), 7.04-7.00 (m, 1H), 7.04-6.98 (m, 1H), 4.99 (s, 1H), 3.74 (dd, J=11.9, 8.1 Hz, 3H), 1.75 (s, 3H), 1.47 (s, 3H), 1.46 (s, 3H).

Figure 2:
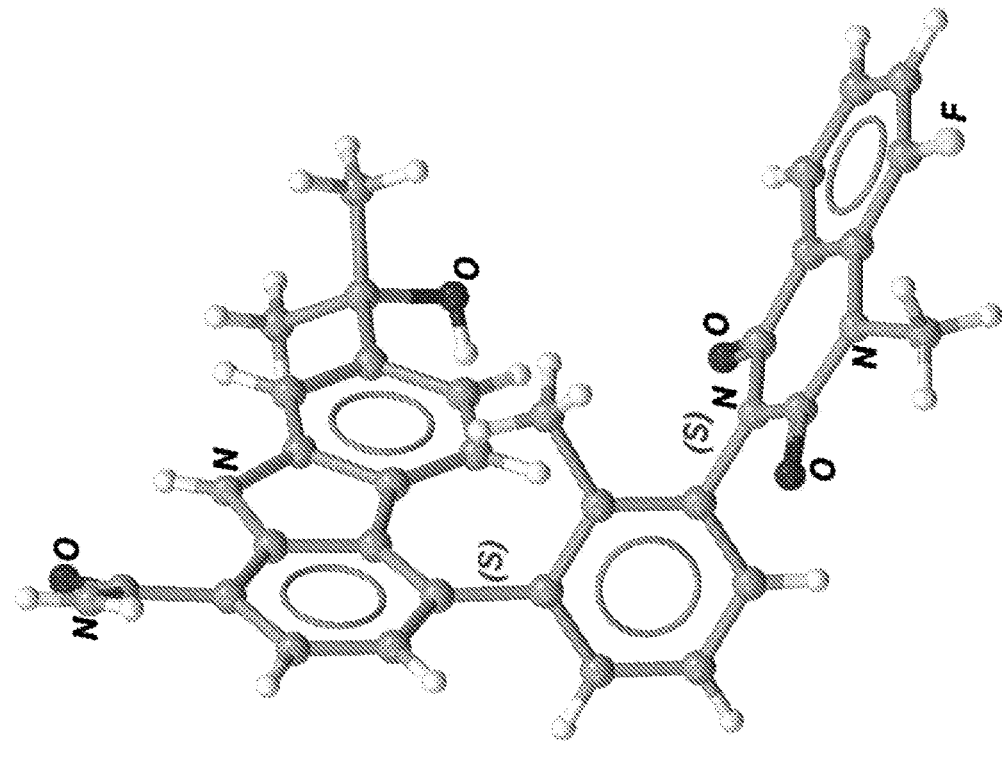
FIG. 2 shows the absolute stereochemistry of the two interconverting diastereomers of Example 3.
Figure 2:
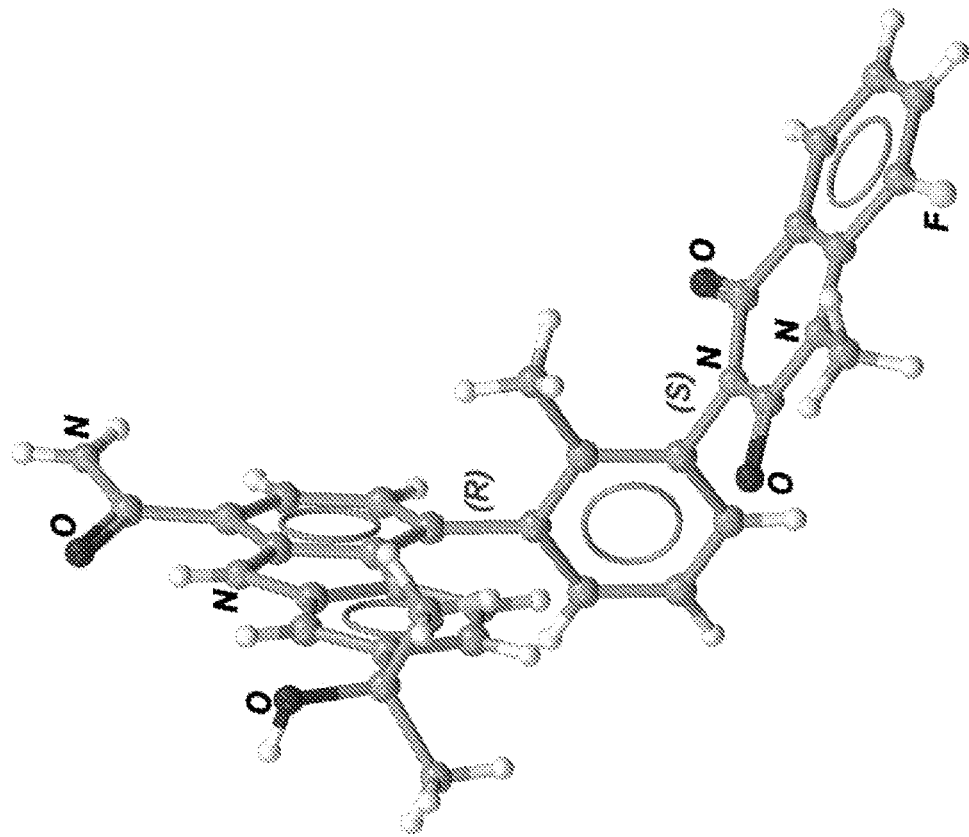
Figure 3:
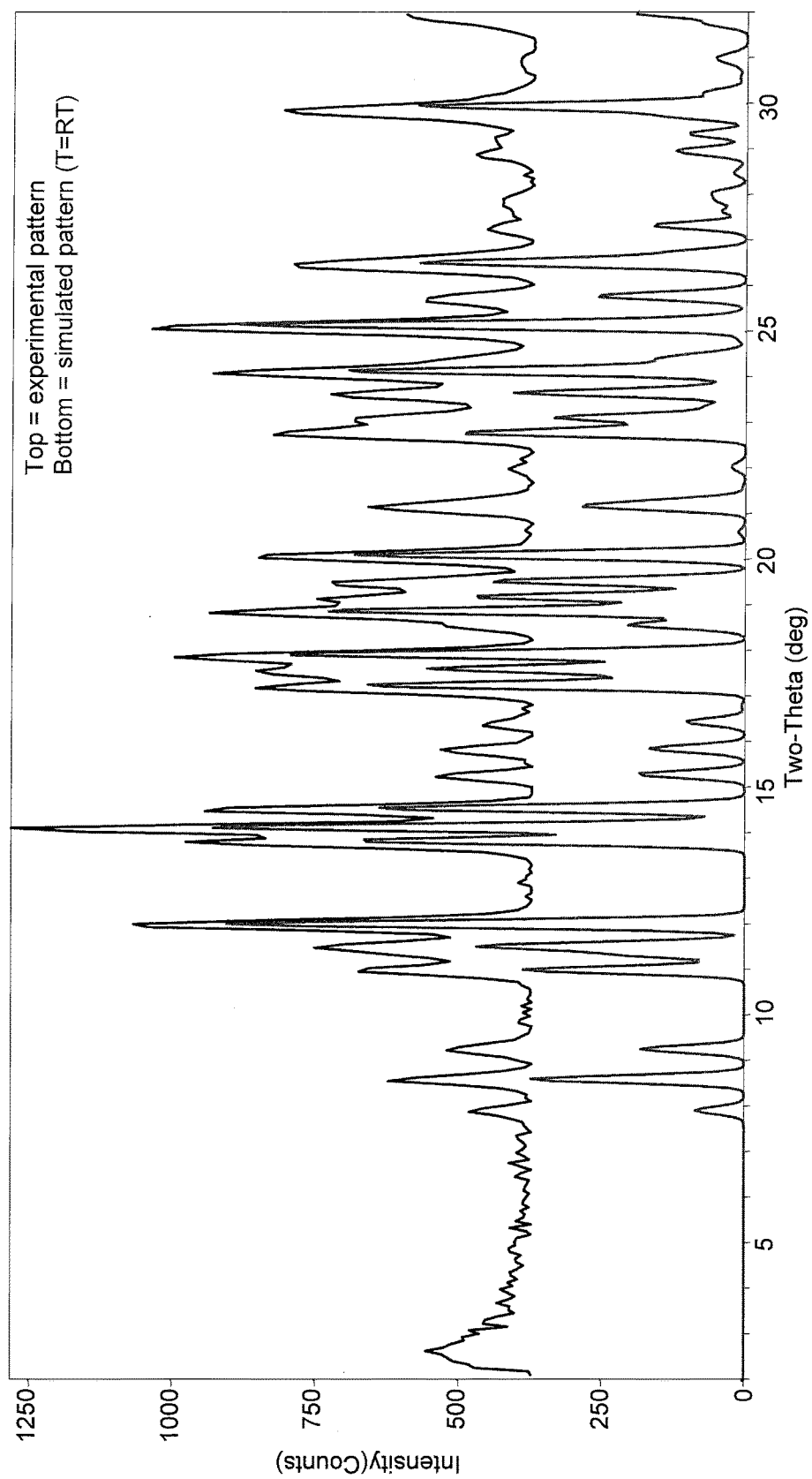
FIG. 3 shows the experimental and the simulated PXRD patterns (Cu Kα radiation λ=1.5418 Å) of Example 3 monohydrate, crystal Form H1-6.

The absolute stereochemistries of the two interconverting diastereomers of Example 3 are shown in FIG. 2. The stereochemistry of Example 3 was confirmed by small crystal x-ray analysis. Several crystal forms were obtained.

Crystal Form SA-1 was prepared by the slow evaporation of an aqueous methanol solution at room temperature. Form SA-1 is a mixed solvate crystal having a stoichiometry of one molecule of methanol and one molecule of water for each molecule of Example 3.

Crystal Form SB-2 was prepared from a solution of EtOH/racemic propylene glycol. Form SB-2 is a mixed solvate crystal having a stoichiometry of one molecule of 1-(S)-propylene glycol and 0.5 molecule of water for each molecule of Example 3.

Crystal Form SC-3 was prepared by the slow evaporation of an acetone solution at room temperature. Form SC-3 is a mixed solvate crystal having a stoichiometry of one molecule of acetone and one molecule of water for each molecule of Example 3.

Crystal Form SD-3 was prepared a THF slurry. Form SD-3 is a mixed solvate crystal having a stoichiometry of 1.5 molecule of THF and one molecule of water for each molecule of Example 3.

Crystal Form SE-2 was prepared by the slow evaporation of an EtOH/THF solution at room temperature. Form SE-2 is a mixed solvate crystal having a stoichiometry of one molecule of ethanol and 0.5 molecule of water for each molecule of Example 3.

Crystal Form M2-4 was prepared by the slow evaporation of a methanol solution at room temperature. Form M2-4 is a dimethanolate crystal.

Crystal Form AN-5 was prepared by the slow evaporation of acetonitrile solution at room temperature. Form AN-5 contains acetonitrile.

Crystal Form H1-6 was prepared from a n-BuOAc slurry. Form H1-6 is a monohydrate crystal.

Crystal Form E-7 was prepared by the slow evaporation of an EtOH/THF solution at room temperature. Form E-7 contains ethanol.

Crystal Form SE-8 was prepared by the slow evaporation of an EtOH/THF solution at room temperature. Form SE-8 is a mixed solvate crystal.

Unit cell parameters of these crystal forms are shown in Table 4, and fractional atomic coordinates of these crystal forms are shown in Tables 5 through 14.

Example 4

4-(3-(S)-(8-Fluoro-1-methyl(d$_3$)-2,4-dioxo-1,2-dihydroquinazolin-3(4H)-yl)-2-methylphenyl)-7-(2-hydroxypropan-2-yl)-9H-carbazole-1-carboxamide (Mixture of Two Interconverting diastereomers)

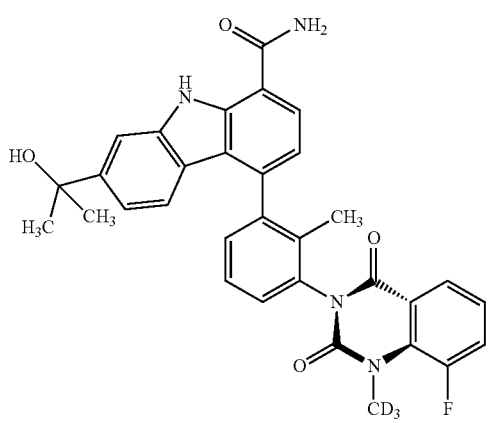

(4)

Preparation 4A: 4-(3-(8-Fluoro-1-methyl(d$_3$)-2,4-dioxo-1,2-dihydroquinazolin-3(4H)-yl)-2-methylphenyl)-7-(2-hydroxypropan-2-yl)-9H-carbazole-1-carboxamide (Mixture of Four diastereomers)

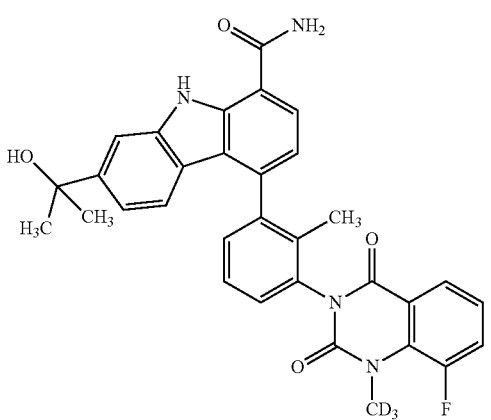

(4A)

A mixture of 7-(2-hydroxypropan-2-yl)-4-(4,4,5,5-tetramethyl-1,3,2-dioxaborolan-2-yl)-9H-carbazole-1-carboxamide [Intermediate 4] (53.8 mg, 0.137 mmol), 3-(3-bromo-2-methylphenyl)-8-fluoro-1-methyl(d$_3$)quinazoline-2,4(1H,3H)-dione [Intermediate 5] (50 mg, 0.137 mmol), and K$_2$CO$_3$ (56.6 mg, 0.410 mmol) in toluene (1.2 mL) and EtOH (0.4 mL) was bubbled with argon for about 5 min (1 min with sonication). The mixture was treated with tetrakis(triphenylphosphine)palladium (7.9 mg, 6.83 µmol), heated at 90° C. for 16.25 h, and cooled to room temperature. The mixture was concentrated, and the residue was sonicated in MeOH, filtered, and purified by preparative HPLC (PHENOMENEX® Axia C18 30×100 mm, 10-100% acetonitrile-water containing 0.1% trifluoroacetic acid, 10 min, 30 mL/min, 254 nm) in 5 injections. The appropriate fractions were combined, treated with saturated aqueous NaHCO$_3$ and concentrated under vacuum to an aqueous suspension. The precipitate was collected by filtration, washed with water and dried under vacuum to provide 4-(3-(8-fluoro-1-methyl(d$_3$)-2,4-dioxo-1,2-dihydroquinazolin-3(4H)-yl)-2-methylphenyl)-7-(2-hydroxypropan-2-yl)-9H-carbazole-1-carboxamide (mixture of four diastereomers) as a white solid (24.3 mg, 31% yield). Mass spectrum m/z 536 (M+H–H$_2$O)$^+$. $^1$H NMR (400 MHz, DMSO-d$_6$) δ 11.40 (s, 1H), 8.17 (br. s., 1H), 8.04-7.92 (m, 2H), 7.84 (s, 1H), 7.79-7.67 (m, 1H), 7.55-7.42 (m, 3H), 7.40-7.29 (m, 2H), 7.13-6.97 (m, 3H), 4.99 (s, 1H), 1.76 (s, 3H), 1.53-1.42 (2s, 6H).

Example 4

4-(3-(8-Fluoro-1-methyl(d$_3$)-2,4-dioxo-1,2-dihydroquinazolin-3(4H)-yl)-2-methylphenyl)-7-(2-hydroxypropan-2-yl)-9H-carbazole-1-carboxamide (mixture of four diastereomers) (86 mg) was separated by chiral super-critical fluid chromatography as follows: column: Lux Cel-4 (3×25 cm, 5 µm); Mobile Phase: CO$_2$-MeOH (60:40) at 85 mL/min; sample preparation: 1.3 mg/mL in MeOH-MeCN; injection: 3 mL. Peaks 3 and 4 eluting from the column were collected together and concentrated to give 4-(3-(S)-(8-fluoro-1-methyl(d$_3$)-2,4-dioxo-1,2-dihydroquinazolin-3(4H)-yl)-2-methylphenyl)-7-(2-hydroxypropan-2-yl)-9H-carbazole-1-carboxamide (mixture of two interconverting diastereomers) (27 mg) as a white solid. Mass spectrum and NMR were identical to those of the mixture of four diastereomers.

Example 5

4-(2-Chloro-3-(8-fluoro-1-methyl-2,4-dioxo-1,2-dihydroquinazolin-3(4H)-yl)phenyl)-7-(2-hydroxypropan-2-yl)-9H-carbazole-1-carboxamide (Mixture of Four diastereomers)

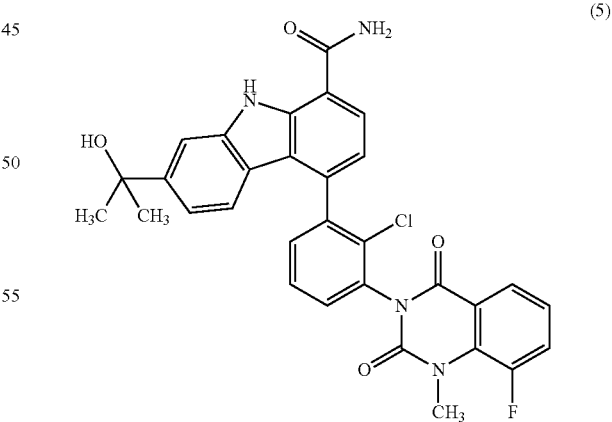

(5)

A mixture of 7-(2-hydroxypropan-2-yl)-4-(4,4,5,5-tetramethyl-1,3,2-dioxaborolan-2-yl)-9H-carbazole-1-carboxamide [Intermediate 4] (50 mg, 0.127 mmol), 3-(3-bromo-2-chlorophenyl)-8-fluoro-1-methylquinazoline-2,4(1H,3H)-dione [Intermediate 9] (48.6 mg, 0.127 mmol), EtOH (1 mL), toluene (1 mL) and 2 M aqueous Na$_2$CO$_3$ (0.21 mL, 0.418 mmol) was bubbled with nitrogen for 5 min and treated with tetrakis(triphenylphosphine)palladium (11.7 mg, 10.2 μmol). The mixture was heated at 90° C. for 16 h, cooled to room temperature and partitioned between EtOAc and water. The organic phase was dried and concentrated, and the residue was purified by column chromatography on silica gel (12 g), eluting with MeOH-DCM containing 1% triethylamine (gradient from 0-5%). The resulting material was further purified using preparative HPLC (PHENOMENEX® Axia $C_{18}$ 30×100 mm), eluting with MeCN-water containing 0.1% trifluoroacetic acid (gradient from 20-100%, 10 min, 30 mL/min). The appropriate fractions were combined, treated with saturated aqueous $NaHCO_3$ and concentrated. The residue was dissolved in EtOAc, washed sequentially with water and brine, dried and concentrated to provide 4-(2-chloro-3-(8-fluoro-1-methyl-2,4-dioxo-1,2-dihydroquinazolin-3(4H)-yl)phenyl)-7-(2-hydroxypropan-2-yl)-9H-carbazole-1-carboxamide (mixture of four diastereomers) as a white solid (6 mg, 8% yield). Mass spectrum m/z 571 (M+H)$^+$. $^1$H NMR (400 MHz, chloroform-d) δ 0.55 (s, 1H), 8.13 (t, J=7.5 Hz, 1H), 7.78-7.38 (m, 6H), 7.20-7.08 (m, 1H), 3.90 (s, 1.5H), 3.88 (s, 1.5H), 1.65 (s, 6H). $^{19}$F NMR (400 MHz, chloroform-d) δ 121.34 ppm.

Example 6

4-(2-Chloro-3-(1-methyl-2,4-dioxo-1,2-dihydroquinazolin-3(4H)-yl)phenyl)-7-(2-hydroxypropan-2-yl)-9H-carbazole-1-carboxamide (Mixture of Four diastereomers)

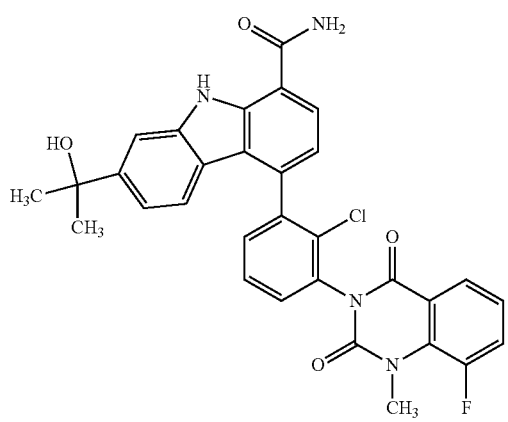

(6)

A mixture of 7-(2-hydroxypropan-2-yl)-4-(4,4,5,5-tetramethyl-1,3,2-dioxaborolan-2-yl)-9H-carbazole-1-carboxamide [Intermediate 4] (140 mg, 0.356 mmol), (Z)-4-((3-bromo-2-chlorophenyl)imino)-1-methyl-1H-benzo[d][1,3]oxazin-2(4H)-one [Intermediate 8] (100 mg, 0.274 mmol), $K_2CO_3$ (151 mg, 1.09 mmol), toluene (3 mL) and EtOH (3 mL) was bubbled with nitrogen for 5 min, and treated with tetrakis(triphenylphosphine)palladium (32 mg, 0.027 mmol). The mixture was heated at 90° C., then was cooled to room temperature and concentrated. The residue was partitioned between water and EtOAc, and the aqueous phase was extracted three times with EtOAc. The combined organic phases were washed with brine, dried and concentrated. The residue was purified by column chromatography on silica gel (80 g), eluting with MeOH-DCM containing 0.5% $NH_4OH$ (gradient from 0-10%), to provide a white solid. This was further purified by preparative HPLC, eluting with MeCN-water containing TFA (gradient from 30-100%). The combined fractions containing the product were treated with saturated aqueous $NaHCO_3$ and concentrated. The aqueous residue was extracted 3 times with EtOAc, and the combined organic phases were washed with brine, dried and concentrated to provide 4-(2-chloro-3-(1-methyl-2,4-dioxo-1,2-dihydroquinazolin-3(4H)-yl)phenyl)-7-(2-hydroxypropan-2-yl)-9H-carbazole-1-carboxamide (mixture of four diastereomers) as an off-white solid (50 mg, 32% yield). Mass spectrum m/z 535, 537 (M+H–$H_2O$)$^+$. $^1$H NMR (400 MHz, DMSO-$d_6$) δ 11.40 (s, 1H), 8.20-8.16 (m, 1H), 8.16 (d, J=1.3 Hz, 0.5H), 8.12-8.08 (m, 0.5H), 7.98 (d, J=7.9 Hz, 1H), 7.90-7.86 (m, 0.5H), 7.85-7.82 (m, 1.5H), 7.74-7.70 (m, 1H), 7.69-7.63 (m, 1H), 7.58-7.53 (m, 2H), 7.48 (br. s., 1H), 7.41-7.34 (m, 1H), 7.13-6.99 (m, 3H), 4.99 (s, 0.5H), 4.99 (s, 0.5H), 3.61 (s, 1.5H), 3.59 (s, 1.5H), 1.47 (m, 6H).

Example 7

7-(2-Hydroxypropan-2-yl)-4-(3-(8-methoxy-1-methyl-2,4-dioxo-1,2-dihydroquinazolin-3(4H)-yl)-2-methylphenyl)-9H-carbazole-1-carboxamide (Mixture of Four diastereomers)

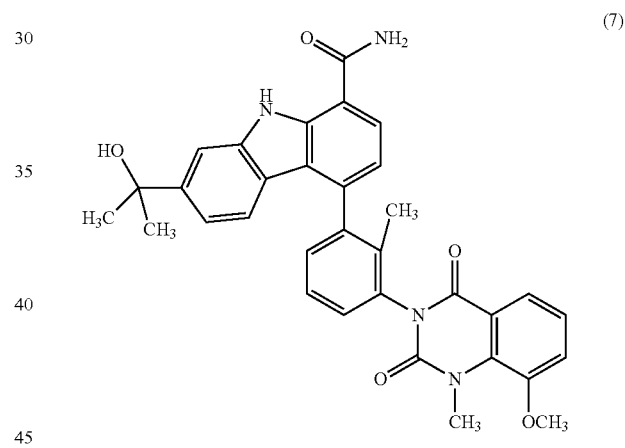

(7)

A mixture of 7-(2-hydroxypropan-2-yl)-4-(4,4,5,5-tetramethyl-1,3,2-dioxaborolan-2-yl)-9H-carbazole-1-carboxamide [Intermediate 4] (42 mg, 0.107 mmol), 3-(3-bromo-2-methylphenyl)-8-methoxy-1-methylquinazoline-2,4(1H,3H)-dione [Intermediate 6] (40 mg, 0.107 mmol), $PdCl_2$(dppf) DCM adduct (8.7 mg, 10.7 μmol) and $Cs_2CO_3$ (70 mg, 0.213 mmol) in THF (2 mL) and water (0.5 mL) in a pressure reaction vial was heated at 70° C. After 2 h, additional 7-(2-hydroxypropan-2-yl)-4-(4,4,5,5-tetramethyl-1,3,2-dioxaborolan-2-yl)-9H-carbazole-1-carboxamide (20 mg, 0.051 mmol) was added, and heating was continued for 6 h more. The mixture was cooled to room temperature, filtered, and the organic phase of the filtrate was separated and concentrated. The residue was purified by column chromatography on silica gel (40 g), eluting with EtOAc, to give 7-(2-hydroxypropan-2-yl)-4-(3-(8-methoxy-1-methyl-2,4-dioxo-1,2-dihydroquinazolin-3(4H)-yl)-2-methylphenyl)-9H-carbazole-1-carboxamide (mixture of four diastereomers) (54 mg, 85% yield). Mass spectrum m/z 545 (M–$H_2O$+H)$^+$, 585 (M+Na)$^+$. $^1$H NMR (400 MHz, chloroform-d) δ 10.55 (s, 1H), 7.95 (ddd, J=10.2, 6.7, 2.6

Hz, 1H), 7.69 (s, 1H), 7.63 (dd, J=7.8, 1.0 Hz, 1H), 7.52-7.46 (m, 1H), 7.38 (dd, J=17.4, 7.7 Hz, 2H), 7.28-7.24 (m, 4H), 7.10 (dd, J=7.7, 2.0 Hz, 1H), 3.96 (d, J=0.9 Hz, 3H), 3.92 (d, J=1.8 Hz, 3H), 1.88 (s, 3H), 1.66 (d, J=1.8 Hz, 6H).

Example 8

4-(3-(6-Fluoro-1-methyl-2,4-dioxo-1,2-dihydroquinazolin-3(4H)-yl)-2-methylphenyl)-7-(2-hydroxypropan-2-yl)-9H-carbazole-1-carboxamide (Mixture of Four diastereomers)

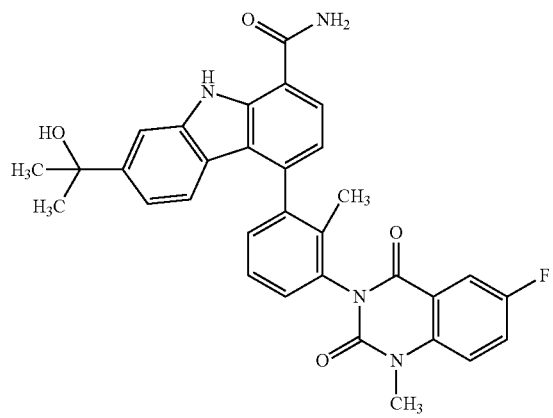

(8)

A mixture of 7-(2-hydroxypropan-2-yl)-4-(4,4,5,5-tetramethyl-1,3,2-dioxaborolan-2-yl)-9H-carbazole-1-carboxamide [Intermediate 4] (40 mg, 0.101 mmol), 3-(3-bromo-2-methylphenyl)-6-fluoro-1-methylquinazoline-2,4(1H, 3H)-dione [Intermediate 7] (37 mg, 0.101 mmol), tetrakis (triphenylphosphine)palladium (5.9 mg, 5.07 μmol) and 2 M aqueous tripotassium phosphate (0.101 mL, 0.203 mmol) in THF (2 mL) was heated at 110° C. for 10 h. The mixture was cooled to room temperature and the organic phase was separated and concentrated. The residue was purified by preparative HPLC (Waters XBridge $C_{18}$, 19×150 mm, 5-μm), eluting with MeOH-water containing 10 mM ammonium acetate (gradient from 5-95%, 20 mL/min). Fractions containing the product were combined and dried via centrifugal evaporation. The material was further purified by preparative HPLC (Waters XBridge $C_{18}$, 19×250 mm, 5-μm), eluting with MeCN-water containing 10 mM ammonium acetate (gradient from 5-95%, 20 mL/min). Fractions containing the desired product were combined and dried via centrifugal evaporation to give 4-(3-(6-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of four diastereomers) (15 mg, 27% yield). Mass spectrum m/z 533 (M−$H_2O$+H)$^+$. $^1$H NMR (500 MHz, DMSO-$d_6$) δ 11.42 (1H, s), 8.19 (1H, br. s.), 8.00 (1H, d, J=7.43 Hz), 7.74-7.90 (3H, m), 7.62 (1H, dd, J=9.41, 4.46 Hz), 7.43-7.53 (3H, m), 7.36 (1H, d, J=5.95 Hz), 6.98-7.11 (3H, m), 3.57-3.64 (3H, m), 1.74 (3H, s), 1.43-1.51 (6H, m).

Example 9

4-(3-(3-(4-Fluorophenyl)-2,6-dioxo-2,3-dihydropyrimidin-1(6H)-yl)-2-methylphenyl)-7-(2-hydroxypropan-2-yl)-9H-carbazole-1-carboxamide (Mixture of Four diastereomers)

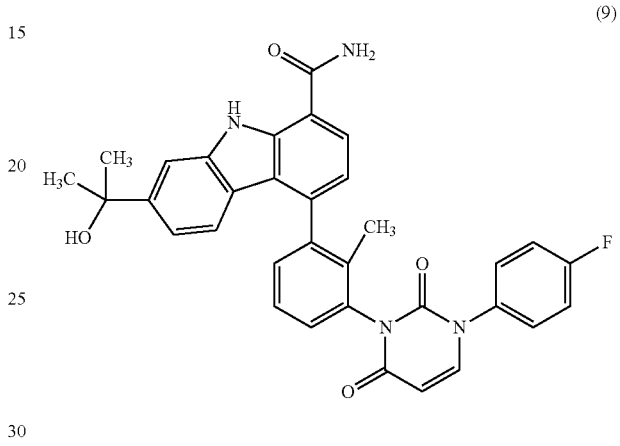

(9)

A mixture of 7-(2-hydroxypropan-2-yl)-4-(4,4,5,5-tetramethyl-1,3,2-dioxaborolan-2-yl)-9H-carbazole-1-carboxamide [Intermediate 4] (100 mg, 0.254 mmol), 3-(3-bromo-2-methylphenyl)-1-(4-fluorophenyl)pyrimidine-2,4(1H, 3H)-dione [Intermediate 21] (100 mg, 0.266 mmol), $Cs_2CO_3$ (165 mg, 0.507 mmol) and $PdCl_2$(dppf) DCM adduct (20.7 mg, 0.025 mmol) in THF (5.0 mL) and water (1.3 mL) was heated at 45° C. for 17 h. Heating was increased to 80° C. for 2 h, then to 85° C. for 18 h. The mixture was cooled, concentrated, dissolved in DMF-MeOH and purified by preparative HPLC. The appropriate fractions were combined, treated with solid $NaHCO_3$, and concentrated to an aqueous suspension. The precipitate was collected by filtration, washed with water and dried. The filtrates were concentrated to provide additional precipitate which was collected by filtration, washed with water and dried. The two precipitates were combined to give 4-(3-(3-(4-fluorophenyl)-2,6-dioxo-2,3-dihydropyrimidin-1(6H)-yl)-2-methylphenyl)-7-(2-hydroxypropan-2-yl)-9H-carbazole-1-carboxamide (mixture of four diastereomers) as a white solid (59 mg, 41% yield). Mass spectrum m/z 545 (M+H−$H_2O$)$^+$. $^1$H NMR (400 MHz, DMSO-$d_6$) δ 11.38 (d, J=4.8 Hz, 1H), 8.16 (br. s., 1H), 7.98 (dd, J=7.7, 2.9 Hz, 1H), 7.91 (dd, J=7.9, 1.1 Hz, 1H), 7.82 (d, J=10.1 Hz, 1H), 7.58 (ddd, J=9.1, 4.9, 2.3 Hz, 2H), 7.51-7.40 (m, 3H), 7.39-7.28 (m, 3H), 7.04 (s, 1H), 6.99 (t, J=7.4 Hz, 1H), 6.92-6.82 (m, 1H), 5.98 (dd, J=16.1, 7.9 Hz, 1H), 4.98-4.90 (m, 1H), 1.79 (d, J=4.0 Hz, 3H), 1.49-1.36 (m, 6H).

Example 10

7-(2-Hydroxypropan-2-yl)-4-(3-(7-methoxy-1,3-dioxo-1H-pyrido[1,2-c]pyrimidin-2(3H)-yl)-2-methylphenyl)-9H-carbazole-1-carboxamide (Mixture of Four diastereomers)

(10)

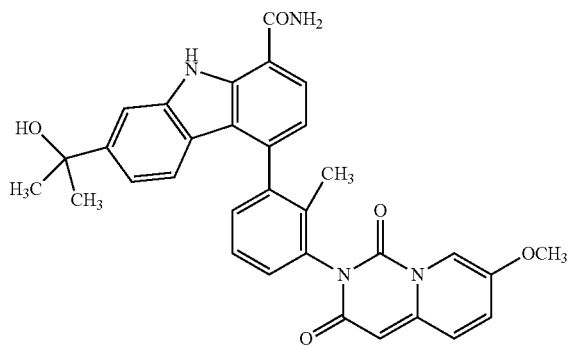

A mixture of 7-(2-hydroxypropan-2-yl)-4-(4,4,5,5-tetramethyl-1,3,2-dioxaborolan-2-yl)-9H-carbazole-1-carboxamide [Intermediate 4] (26.4 mg, 0.067 mmol), 2-(3-bromo-2-methylphenyl)-7-methoxy-1H-pyrido[1,2-c]pyrimidine-1,3(2H)-dione [Intermediate 12] (22 mg, 0.061 mmol) and 2 M aqueous $Na_2CO_3$ (0.076 mL, 0.152 mmol) in DMF (1.5 mL) was bubbled with argon for 5 min, then treated with $PdCl_2$(dppf) DCM adduct (2.5 mg, 3.05 µmol). After bubbling with argon for 30 sec more, the vial was sealed and the mixture was stirred at 90° C. for 4 h. The cooled mixture was partitioned between EtOAc and water, and the organic layer was washed with brine, dried and concentrated. The residue was purified by column chromatography on silica gel (24 g), eluting with EtOAc-hexanes (sequentially 85%, 95% and 100%), to give 7-(2-hydroxypropan-2-yl)-4-(3-(7-methoxy-1,3-dioxo-1H-pyrido[1,2-c]pyrimidin-2(3H)-yl)-2-methylphenyl)-9H-carbazole-1-carboxamide (mixture of four diastereomers) as a yellow solid (11.6 mg, 34% yield). Mass spectrum m/z 531 (M+H–$H_2O$)$^+$. $^1$H NMR (400 MHz, chloroform-d) δ 10.53 (d, J=7.7 Hz, 1H), 7.77 (d, J=16.5 Hz, 1H), 7.69-7.63 (m, 2H), 7.54-7.48 (m, 1H), 7.45-7.33 (m, 2H), 7.26-7.20 (m, 1H), 7.15 (dd, J=13.4, 7.9 Hz, 1H), 6.98-6.92 (m, 1H), 6.91-6.87 (m, 1H), 5.84 (d, J=2.2 Hz, 1H), 3.81 (s, 3H), 1.89 (s, 3H), 1.55 (s, 6H).

Example 11

7-(2-Hydroxypropan-2-yl)-4-(3-(6-methoxy-1,3-dioxo-1H-pyrido[1,2-c]pyrimidin-2(3H)-yl)-2-methylphenyl)-9H-carbazole-1-carboxamide (Mixture of Four diastereomers)

(11)

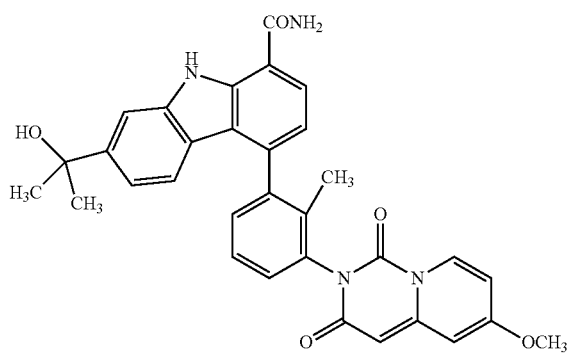

A mixture of 7-(2-hydroxypropan-2-yl)-4-(4,4,5,5-tetramethyl-1,3,2-dioxaborolan-2-yl)-9H-carbazole-1-carboxamide [Intermediate 4] (48 mg, 0.122 mmol), 2-(3-bromo-2-methylphenyl)-6-methoxy-1H-pyrido[1,2-c]pyrimidine-1,3(2H)-dione [Intermediate 11] (40 mg, 0.111 mmol) and $Cs_2CO_3$ (72 mg, 0.221 mmol) in THF (1.5 mL) and water (0.375 mL) was bubbled with argon for 3 min, then treated with $PdCl_2$(dppf) DCM adduct (4.5 mg, 5.54 µmol). Bubbling with argon was continued for 1 min and the mixture was then heated at 45° C. After 3.5 h, the mixture was cooled, diluted with EtOAc, washed sequentially with water and brine, and the combined aqueous layers were extracted with EtOAc. The combined organic phases were dried and concentrated. The residue was purified by column chromatography on silica gel (24 g), eluting with EtOAc, to give an impure material. The residue was purified further by preparative HPLC. The appropriate fractions were treated with saturated aqueous $NaHCO_3$, combined and extracted with EtOAc. The organic phase was washed with brine, dried and concentrated to give 7-(2-hydroxypropan-2-yl)-4-(3-(6-methoxy-1,3-dioxo-1H-pyrido[1,2-c]pyrimidin-2(3H)-yl)-2-methylphenyl)-9H-carbazole-1-carboxamide (mixture of four diastereomers) as a yellow solid (17.7 mg, 28% yield). Mass spectrum 549 (M+H)$^+$. $^1$H NMR (400 MHz, chloroform-d) δ 10.53 (d, J=7.3 Hz, 1H), 8.28 (dd, J=19.4, 8.1 Hz, 1H), 7.69-7.62 (m, 2H), 7.52-7.47 (m, 1H), 7.41 (dd, J=3.7, 1.3 Hz, 1H), 7.37-7.34 (m, 1H), 7.24-7.21 (m, 1H), 7.13 (dd, J=10.3, 7.7 Hz, 1H), 6.19 (ddd, J=8.0, 4.5, 2.6 Hz, 1H), 6.06 (d, J=2.4 Hz, 1H), 5.67 (d, J=2.0 Hz, 1H), 3.90-3.89 (m, 3H), 1.89-1.88 (m, 3H), 1.65-1.62 (m, 6H).

Example 12

7-(2-Hydroxypropan-2-yl)-4-(3-(5-methoxy-1,3-dioxo-1H-pyrido[1,2-c]pyrimidin-2(3H)-yl)-2-methylphenyl)-9H-carbazole-1-carboxamide (Mixture of Four diastereomers)

(12)

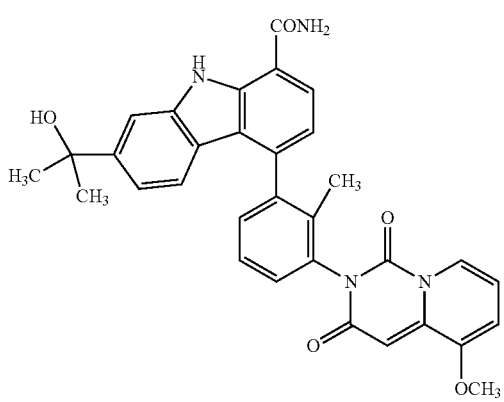

A mixture of 7-(2-hydroxypropan-2-yl)-4-(4,4,5,5-tetramethyl-1,3,2-dioxaborolan-2-yl)-9H-carbazole-1-carboxamide [Intermediate 4] (88 mg, 0.222 mmol), 2-(3-bromo-2-methylphenyl)-5-methoxy-1H-pyrido[1,2-e]pyrimidine-1,3(2H)-dione [Intermediate 10] (73 mg, 0.202 mmol) and 2 M aqueous $Na_2CO_3$ (0.252 mL, 0.505 mmol) in DMF (1.5 mL) at room temperature was bubbled with argon for 5 min. $PdCl_2$(dppf) DCM adduct (8.2 mg, 10.1 µmol) was added, bubbling with nitrogen was continued for another 30 sec, and the mixture was heated at 90° C. After 4 h, the cooled mixture was diluted with EtOAc and washed sequentially with water and brine. The combined aqueous layers were extracted with EtOAc. The combined organic phases were dried and concentrated. The residue was purified by column chromatography on silica gel (40 g), eluting with EtOAc, to give a brownish solid. This was triturated in MeOH with sonication, collected by filtration and dried to provide 7-(2-hydroxypropan-2-yl)-4-(3-(5-methoxy-1,3-dioxo-1H-pyrido[1,2-c]pyrimidin-2(3H)-yl)-2-methylphenyl)-9H-carbazole-1-carboxamide (mixture of four diastereomers) as a light yellow-tan solid (29.7 mg, 25% yield). Mass spectrum 549 (M+H)$^+$. $^1$H NMR (400 MHz, DMSO-d$_6$) δ 11.38 (s, 1H), 8.15 (br. s., 1H), 7.98 (d, J=7.9 Hz, 1H), 7.91 (d, J=7.5 Hz, 1H), 7.82 (s, 1H), 7.53-7.42 (m, 3H), 7.34 (d, J=7.3 Hz, 1H), 7.07-6.98 (m, 3H), 6.71 (d, J=7.5 Hz, 1H), 6.60-6.54 (m, 1H), 5.93 (s, 1H), 4.97 (s, 1H), 3.91 (s, 3H), 1.73 (s, 3H), 1.48-1.43 (m, 6H).

Example 13

4-(3-(5-Chloro-1,3-dioxo-1H-pyrido[1,2-c]pyrimidin-2(3H)-yl)-2-methylphenyl)-7-(2-hydroxypropan-2-yl)-9H-carbazole-1-carboxamide (Mixture of Four diastereomers)

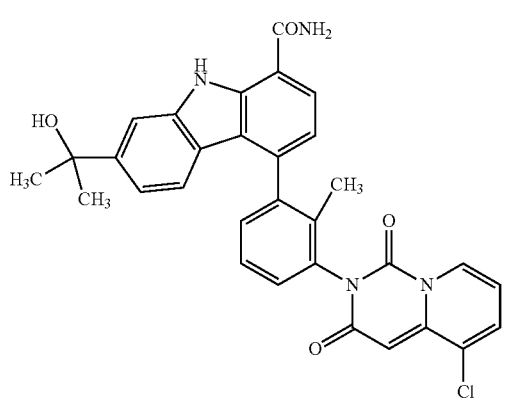

(13)

A mixture of 4-bromo-7-(2-hydroxypropan-2-yl)-9H-carbazole-1-carboxamide [synthesized according to the procedure described in U.S. Pat. No. 8,084,620, Intermediate 73-2] (23.1 mg, 0.067 mmol), 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione (25 mg, 0.061 mmol) [Intermediate 13] and Cs$_2$CO$_3$ (39.5 mg, 0.121 mmol) in THF (1.5 mL) and water (0.375 mL) was bubbled with argon for 3 min. The mixture was treated PdCl$_2$(dppf) DCM adduct (2.5 mg, 3.03 µmol) and bubbling was continued for 1 min. The mixture was heated at 45° C. for 3.5 h. The cooled mixture was diluted with EtOAc, washed sequentially with water and brine, and the combined aqueous layers were extracted with EtOAc. The combined organic phases were dried and concentrated, and purified by preparative HPLC (Luna Axia C$_{18}$ 30×100 mm, 5 µm), eluting with MeCN-water containing 0.1% TFA (gradient from 30-90%, 30 mL/min) to give 4-(3-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of four diastereomers) as a yellow solid (14 mg, 39% yield). Mass spectrum 553 (M+H)$^+$. $^1$H NMR (400 MHz, chloroform-d) δ 10.54 (d, J=5.9 Hz, 1H), 8.30 (ddt, J=19.6, 7.6, 0.9 Hz, 1H), 7.70-7.62 (m, 2H), 7.54-7.49 (m, 1H), 7.45-7.41 (m, 1H), 7.37-7.33 (m, 1H), 7.26-7.20 (m, 2H), 7.13 (dd, J=12.1, 7.7 Hz, 1H), 6.37 (td, J=7.3, 5.1 Hz, 1H), 6.32 (d, J=3.1 Hz, 1H), 1.89 (s, 3H), 1.65-1.63 (m, 6H).

Examples 14 and 15

4-(3-(R)-(5-Chloro-1,3-dioxo-1H-pyrido[1,2-c]pyrimidin-2(3H)-yl)-2-methylphenyl)-7-(2-hydroxypropan-2-yl)-9H-carbazole-1-carboxamide (14), and 4-(3-(S)-(5-Chloro-1,3-dioxo-1H-pyrido[1,2-c]pyrimidin-2(3H)-yl)-2-methylphenyl)-7-(2-hydroxypropan-2-yl)-9H-carbazole-1-carboxamide (15)

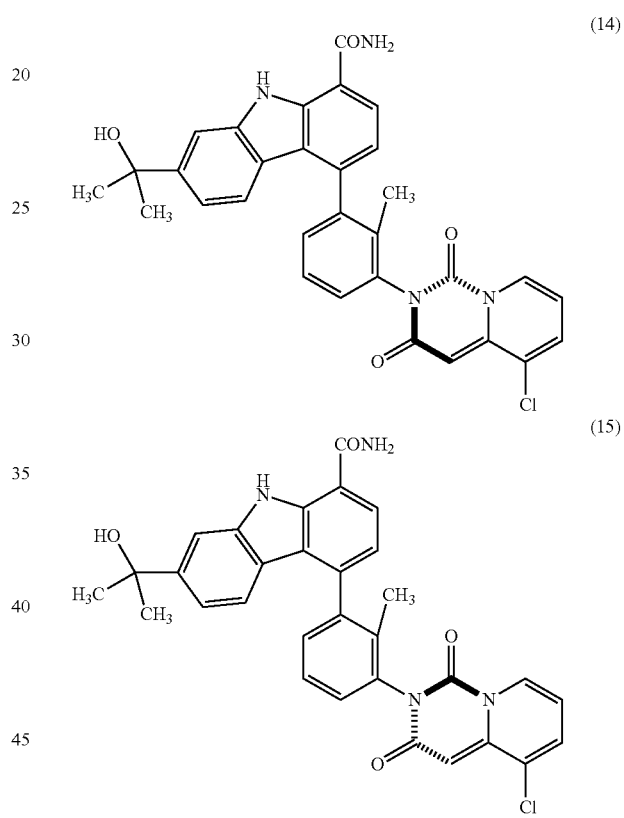

(14)

(15)

A sample of 4-(3-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of four diastereomers) [Example 13] was separated by chiral supercritical fluid chromatography as follows: First pass: column: Lux Cellulose-3 (3×25 cm, 5 µm); Mobile Phase: CO$_2$-MeOH (70:30) at 140 mL/min, 100 bar, 35° C.; sample preparation: 13 mg/mL in MeOH; injection: 4.5 mL; Second pass: column: CHIRALCEL® AS (2×50 cm, 10 µm); Mobile Phase: CO$_2$-MeOH (55:45) at 120 mL/min, 100 bar, 35° C.

The first and third peaks eluting from the column were combined to provide a mixture of two interconverting diastereomers of 4-(3-(R)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide. [Example 14]. Mass spectrum m/z 553 (M+H)$^+$. $^1$H NMR (400 MHz, DMSO-d$_6$) δ 11.39 (d, J=3.7 Hz, 1H), 8.34-8.21 (m, 1H), 8.16 (br. s., 1H), 7.99 (dd, J=7.7, 1.5 Hz, 1H), 7.83 (s, 1H), 7.60 (d, J=7.0 Hz, 1H), 7.53-7.41 (m, 3H), 7.35 (d, J=7.3 Hz, 1H), 7.09-6.94 (m, 3H), 6.57 (td, J=7.3, 3.6 Hz, 1H), 6.00 (d, J=18.9 Hz, 1H), 4.97 (s, 1H), 1.75 (m, 3H), 1.46 (m, 6H).

The second and fourth peaks eluting from the column were combined to provide a mixture of two other interconverting diastereomers of 4-(3-(S)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide.

[Example 15]. Mass spectrum m/z 553 (M+H)+. 1H NMR (400 MHz, DMSO-$d_6$) δ 11.39 (d, J=4.0 Hz, 1H), 8.36-8.21 (m, 1H), 8.16 (br. s., 1H), 7.99 (dd, J=7.7, 1.8 Hz, 1H), 7.83 (s, 1H), 7.60 (d, J=7.0 Hz, 1H), 7.54-7.41 (m, 3H), 7.35 (d, J=7.5 Hz, 1H), 7.08-6.94 (m, 3H), 6.57 (td, J=7.3, 3.6 Hz, 1H), 6.00 (d, J=18.7 Hz, 1H), 4.97 (d, J=0.9 Hz, 1H), 1.75 (m, 3H), 1.46 (m, 6H).

Alternative Synthesis of Example 15

4-(3-(S)-(5-Chloro-1,3-dioxo-1H-pyrido[1,2-c]pyrimidin-2(3H)-yl)-2-methylphenyl)-7-(2-hydroxypropan-2-yl)-9H-carbazole-1-carboxamide (Mixture of Two Interconverting diastereomers)

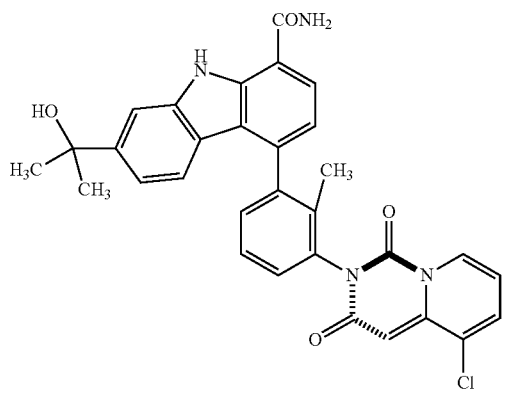

(15)

A solution of 4-bromo-7-(2-hydroxypropan-2-yl)-9H-carbazole-1-carboxamide [synthesized according to the procedure described in U.S. Pat. No. 8,084,620, Intermediate 73-2] (0.16 g, 0.461 mmol), 5-chloro-2-(S)-(2-methyl-3-(4,4,5,5-tetramethyl-1,3,2-dioxaborolan-2-yl)phenyl)-1H-pyrido[1,2-c]pyrimidine-1,3(2H)-dione (single enantiomer) [Intermediate 15] (0.209 g, 0.507 mmol) and 3 M aqueous $K_3PO_4$ (0.384 mL, 1.15 mmol) in THF (3.0 mL) was bubbled with argon for 5 min. The mixture was treated with 1,1'-bis(di-t-butylphosphino)ferrocene palladium dichloride (15 mg, 23 μmol) and bubbling was continued for 30 sec. The reaction vessel was sealed, and subjected to three cycles of evacuation and filling with argon. The mixture was stirred overnight at room temperature, then was diluted with EtOAc, washed sequentially with water and brine, and the combined aqueous layers were extracted with EtOAc. The combined organic phases were dried and concentrated. The residue was combined with that from an identical reaction done on one-quarter of the scale and purified by chromatography to give 4-(3-(S)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of two interconverting diastereomers) as a yellow solid (154 mg, 48% yield).

Example 16

4-(3-(5-Chloro-1,3-dioxo-1H-pyrido[1,2-c]pyrimidin-2(3H)-yl)-2-methylphenyl)-7-pivalamido-9H-carbazole-1-carboxamide (Mixture of Four diastereomers)

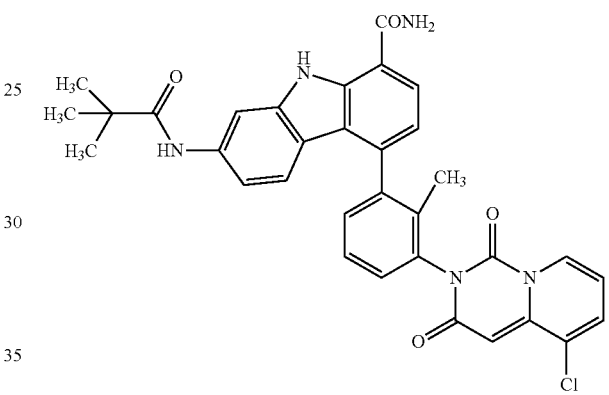

(16)

A mixture of 4-bromo-7-pivalamido-9H-carbazole-1-carboxamide [synthesized according to the procedure described in U.S. Pat. No. 8,084,620, Example 57-51] (0.062 g, 0.160 mmol), 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 13] (0.055 g, 0.133 mmol) and $Cs_2CO_3$ (0.087 g, 0.267 mmol) in THF (2.5 mL) and water (0.625 mL) was bubbled with nitrogen for 2 min, then was treated with $PdCl_2$(dppf) DCM adduct (5.4 mg, 6.66 μmol). Bubbling was continued for 30 sec, then the mixture was heated at 60° C. for 5 h and stirred overnight at room temperature. The mixture was diluted with EtOAc, dried and concentrated. The residue was purified by column chromatography on silica gel, eluting with EtOAc-hexanes, to give 4-(3-(5-chloro-1,3-dioxo-1H-pyrido[1,2-c]pyrimidin-2 (3H)-yl)-2-methylphenyl)-7-pivalamido-9H-carbazole-1-carboxamide (mixture of four diastereomers) as a yellow solid (38 mg, 42% yield). Mass spectrum m/z 594 (M+H)+. 1H NMR (400 MHz, DMSO-$d_6$) δ 11.42 (d, J=9.0 Hz, 1H), 9.23 (s, 1H), 8.29-8.22 (m, 1H), 8.15 (br. s., 1H), 8.09 (dd, J=15.5, 1.7 Hz, 1H), 7.96 (dd, J=7.8, 2.1 Hz, 1H), 7.62-7.58 (m, 1H), 7.54-7.36 (m, 4H), 7.02 (s, 3H), 6.57 (dt, J=9.3, 7.3 Hz, 1H), 5.99 (d, J=6.2 Hz, 1H), 1.73 (d, J=3.1 Hz, 3H), 1.24 (d, J=1.1 Hz, 9H).

Example 17

4-(3-(5-Chloro-1,3-dioxo-1H-pyrido[1,2-c]pyrimidin-2(3H)-yl)-2-methylphenyl)-7-(methoxymethyl)-9H-carbazole-1-carboxamide (Mixture of Four diastereomers)

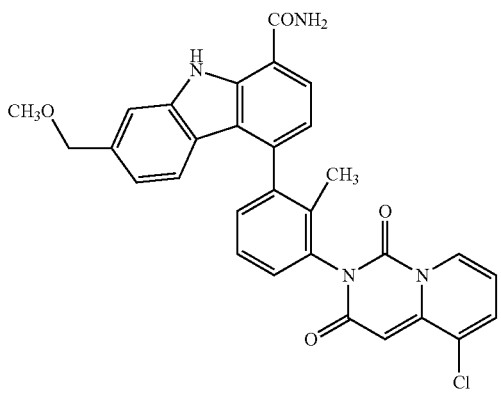

(17)

A mixture of 4-bromo-7-(methoxymethyl)-9H-carbazole-1-carboxamide [Intermediate 25] (31.1 mg, 0.093 mmol), 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 13] (35 mg, 0.085 mmol) and $Cs_2CO_3$ (55.3 mg, 0.170 mmol) in THF (1.5 mL) and water (0.375 mL) was bubbled with argon for 3 min. The mixture was treated with $PdCl_2$(dppf) DCM adduct (3.5 mg, 4.24 μmol) and bubbling was continued for 1 min. The mixture was heated at 45° C. for 5 h and cooled to room temperature. The mixture was partitioned between EtOAc and water, the organic layer was washed with brine and the combined aqueous layers were extracted with EtOAc. The combined organic phases were dried and concentrated, and the residue was purified by preparative HPLC. Product-containing fractions were treated with saturated aqueous $NaHCO_3$, combined and extracted with EtOAc. The organic layer was dried and concentrated, and the residue was purified twice by column chromatography on silica gel (24 g, then 12 g), eluting with EtOAc, to provide 4-(3-(5-chloro-1,3-dioxo-1H-pyrido[1,2-c]pyrimidin-2(3H)-yl)-2-methylphenyl)-7-(methoxymethyl)-9H-carbazole-1-carboxamide (mixture of four diastereomers) as a yellow solid (9.7 mg, 20% yield). Mass spectrum m/z 539 $(M+H)^+$. $^1H$ NMR (400 MHz, DMSO-$d_6$) δ 11.53-11.51 (m, 1H), 8.33-8.28 (m, 1H), 8.19 (br. s., 1H), 8.05-8.00 (m, 1H), 7.67 (s, 1H), 7.60 (d, J=6.6 Hz, 1H), 7.54-7.42 (m, 5H), 7.38 (dd, J=7.5, 1.3 Hz, 1H), 7.07-7.00 (m, 2H), 6.85 (dd, J=8.3, 1.4 Hz, 1H), 6.61-6.53 (m, 2H), 5.97 (s, 1H), 4.49 (s, 2H), 3.29 (s, 3H).

Example 18

4-(3-(5-Fluoro-1,3-dioxo-1H-pyrido[1,2-c]pyrimidin-2(3H)-yl)-2-methylphenyl)-7-(methoxymethyl)-9H-carbazole-1-carboxamide (Mixture of Four diastereomers)

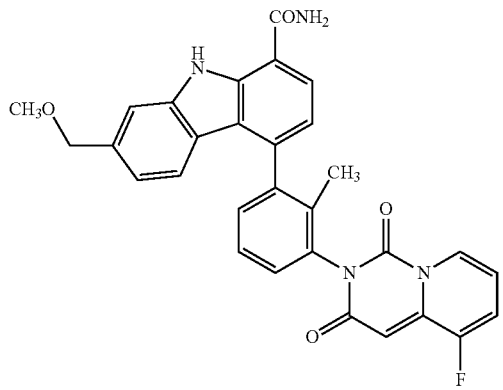

(18)

A mixture of 4-bromo-7-(methoxymethyl)-9H-carbazole-1-carboxamide [Intermediate 25] (0.05 g, 0.150 mmol), 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 18] (0.065 g, 0.165 mmol) and $Cs_2CO_3$ (0.098 g, 0.300 mmol) in dioxane (2.0 mL) and water (0.5 mL) was bubbled with argon for 2 min. The mixture was treated with $PdCl_2$(dppf) DCM adduct (6.1 mg, 7.50 μmol), bubbling with argon for 30 sec more, then heated for 6 h at 50° C. The cooled mixture was diluted with DCM-MeOH, dried and concentrated. The residue was purified by column chromatography on silica gel (40 g), eluting with EtOAc-hexanes (gradient from 80-100%), to give 4-(3-(5-fluoro-1,3-dioxo-1H-pyrido[1,2-c]pyrimidin-2(3H)-yl)-2-methylphenyl)-7-(methoxymethyl)-9H-carbazole-1-carboxamide (mixture of four diastereomers) as a yellow solid (0.0481 g, 57% yield). Mass spectrum m/z 523 $(M+H)^+$. $^1H$ NMR (400 MHz, DMSO-$d_6$) δ 11.51 (d, J=5.7 Hz, 1H), 8.19 (br. s., 1H), 8.16-8.06 (m, 2H), 8.02 (dd, J=7.8, 1.9 Hz, 1H), 7.67 (d, J=3.5 Hz, 1H), 7.55-7.42 (m, 5H), 7.38 (d, J=7.5 Hz, 1H), 7.23 (t, J=8.7 Hz, 1H), 7.05 (d, J=7.7 Hz, 1H), 6.85 (ddd, J=8.2, 3.8, 1.4 Hz, 1H), 6.60-6.52 (m, 1H), 5.86 (d, J=15.0 Hz, 2H), 4.49 (s, 2H), 3.29 (d, J=1.1 Hz, 3H).

Example 19

4-(3-(4-Fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (Mixture of Four diastereomers)

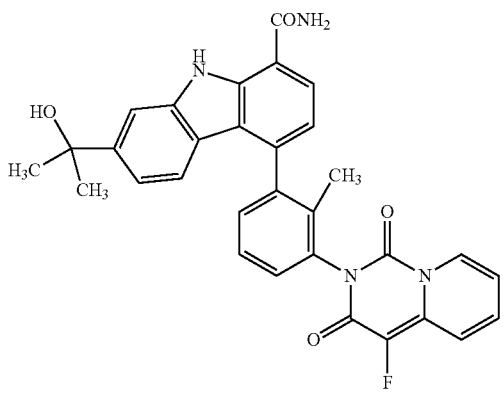

(19)

A mixture of 4-bromo-7-(2-hydroxypropan-2-yl)-9H-carbazole-1-carboxamide [synthesized according to the procedure described in U.S. Pat. No. 8,084,620, Intermediate 73-2] (0.034 g, 0.097 mmol), 4-fluoro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 16] (0.035 g, 0.088 mmol) and $Cs_2CO_3$ (0.058 g, 0.177 mmol) in THF (1.5 mL) and water (0.375 mL) was bubbled with argon for 3 min. The mixture was treated with $PdCl_2$(dppf) DCM adduct (3.6 mg, 4.42 μmol), bubbled with argon for 1 min more, and heated at 45° C. After 5 h, the cooled mixture was diluted with EtOAc and washed sequentially with water and brine. The combined aqueous layers were extracted with EtOAc, and the combined organic phases were dried and concentrated. The residue was purified by preparative HPLC. Fractions containing the product were treated with saturated aqueous $NaHCO_3$, combined and partitioned between EtOAc and saturated aqueous $NaHCO_3$. The organic layer was washed with brine, dried and concentrated to give 4-(3-(4-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of four diastereomers) as a yellow solid (0.0109 g, 22% yield). Mass spectrum m/z 537 $(M+H)^+$. $^1$H NMR (400 MHz, DMSO-$d_6$) δ 11.39 (d, J=2.4 Hz, 1H), 8.27-8.13 (m, 2H), 7.99 (dd, J=7.8, 2.3 Hz, 2H), 7.83 (s, 1H), 7.55-7.43 (m, 3H), 7.40-7.26 (m, 2H), 7.07-6.94 (m, 3H), 6.64-6.55 (m, 1H), 4.97 (d, J=4.8 Hz, 1H), 1.75 (d, J=1.3 Hz, 3H), 1.48-1.43 (m, 6H).

Example 20

4-(3-(5,7-Dioxo-5H-thiazolo[3,2-c]pyrimidin-6(7H)-yl)-2-methylphenyl)-7-(2-hydroxypropan-2-yl)-9H-carbazole-1-carboxamide (Mixture of Four diastereomers)

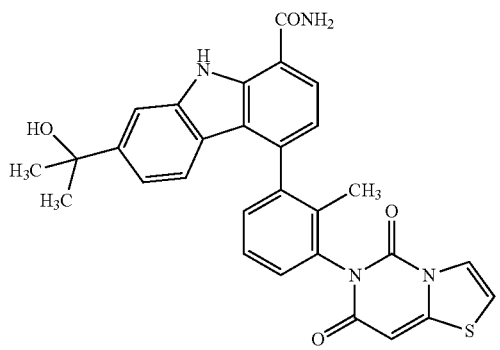

(20)

A mixture of 4-bromo-7-(2-hydroxypropan-2-yl)-9H-carbazole-1-carboxamide [synthesized according to the procedure described in U.S. Pat. No. 8,084,620, Intermediate 73-2] (0.040 g, 0.115 mmol), 6-(2-methyl-3-(4,4,5,5-tetramethyl-1,3,2-dioxaborolan-2-yl)phenyl)-5H-thiazolo[3,2-c]pyrimidine-5,7(6H)-dione [Intermediate 17] (0.04 g, 0.104 mmol) and $Cs_2CO_3$ (0.068 g, 0.208 mmol) in THF (2.0 mL) and water (0.5 mL) was bubbled with argon for 3 min, then was treated with $PdCl_2$(dppf) DCM adduct (4.3 mg, 5.20 μmol). Bubbling was continued for 30 sec more, then the mixture heated at 50° C. for 5 h. The cooled mixture was partitioned between EtOAc and water, and the organic layer was washed with brine. The combined aqueous layers were extracted with EtOAc, and the combined organic phases were dried and concentrated. The residue was purified by column chromatography on silica gel (40 g), eluting with EtOAc, to give 4-(3-(5,7-dioxo-5H-thiazolo[3,2-c]pyrimidin-6(7H)-yl)-2-methylphenyl)-7-(2-hydroxypropan-2-yl)-9H-carbazole-1-carboxamide (mixture of four diastereomers) as a reddish solid (0.032 g, 56% yield). Mass spectrum m/z 525 $(M+H)^+$. $^1$H NMR (400 MHz, DMSO-$d_6$) δ 11.38 (d, J=4.8 Hz, 1H), 8.16 (br. s., 1H), 7.98 (dd, J=7.8, 1.2 Hz, 1H), 7.83 (d, J=1.8 Hz, 1H), 7.75-7.64 (m, 1H), 7.51-7.39 (m, 3H), 7.33 (dd, J=7.4, 1.2 Hz, 1H), 7.07-6.92 (m, 4H), 6.29 (d, J=13.6 Hz, 1H), 4.97 (s, 1H), 1.75-1.73 (m, 3H), 1.47-1.43 (m, 6H).

Example 21

4-(3-(5-Fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (Mixture of Four diastereomers)

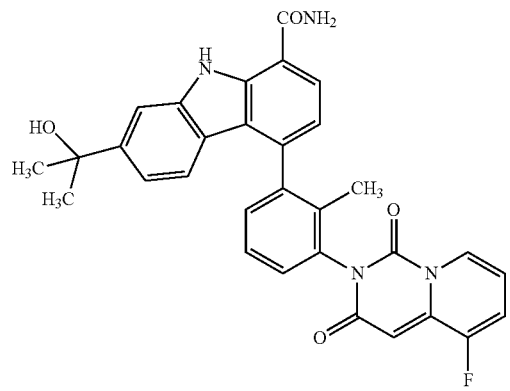

(21)

A mixture of 4-bromo-7-(2-hydroxypropan-2-yl)-9H-carbazole-1-carboxamide [synthesized according to the procedure described in U.S. Pat. No. 8,084,620, Intermediate 73-2] (0.048 g, 0.139 mmol), 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 18] (0.050 g, 0.126 mmol) and $Cs_2CO_3$ (0.082 g, 0.252 mmol) in THF (2.0 mL) and water (0.5 mL) was bubbled with nitrogen for 2 min. The mixture was treated with $PdCl_2$(dppf) DCM adduct (5.2 mg, 6.31 μmol), bubbling was continued for 30 sec and the vial was sealed. The mixture was heated at 50° C. for 5 h. The cooled mixture was diluted with EtOAc and washed sequentially with water and brine. The combined aqueous layers were extracted with DCM. The combined organic layers were dried and concentrated. The residue was purified by column chromatography on silica gel to provide 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of four diastereomers) as a yellow solid (0.0375 g, 54% yield). Mass spectrum m/z 537 $(M+H)^+$. $^1$H NMR (400 MHz, DMSO-$d_6$) δ 11.38 (d, J=4.6 Hz, 1H), 8.21-8.03 (m, 2H), 7.98 (dd, J=7.9, 1.5 Hz, 1H), 7.86-7.78 (m, 1H), 7.54-7.39 (m, 3H), 7.35 (d, J=7.5 Hz, 1H), 7.23 (t, J=8.9 Hz, 1H), 7.09-6.92 (m, 3H), 6.61-6.50 (m, 1H), 5.86 (d, J=19.4 Hz, 1H), 4.96 (d, J=1.8 Hz, 1H), 1.74 (d, J=2.6 Hz, 3H), 1.45 (d, J=4.6 Hz, 6H).

Examples 22 and 23

4-(3-(5-Fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (Mixtures of Two Interconverting diastereomers)

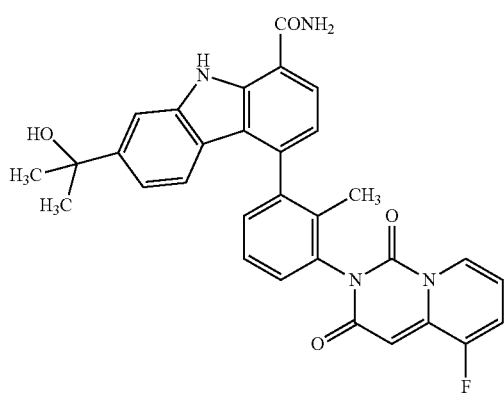

(22 and 23)

A sample of 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of four diastereomers) [Example 21] was separated by chiral supercritical fluid chromatography as follows: First pass: column: CHIRALPAK® IA (3×25 cm, 5 μm); Mobile Phase: $CO_2$-MeOH (50:50) at 150 mL/min, 100 bar, 40° C.; sample preparation: 7 mg/mL in MeOH-DCM (1:1) with added DMSO; injection: 2 mL; Second pass: column: CHIRALCEL® OD-H (3×25 cm, 5 μm); Mobile Phase: $CO_2$-MeOH (50:50) at 120 mL/min, 100 bar, 35° C.; sample preparation: 3.7 mg/mL in MeOH-chloroform (3:1); injection: 4 mL.

The first and second peaks eluting from the column were combined to provide a mixture of two interconverting diastereomers of 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide. [Example 22]. Mass spectrum m/z 519 $(M+H-H_2O)^+$. $^1H$ NMR (400 MHz, DMSO-$d_6$) δ 11.42-11.36 (m, 1H), 8.20-8.06 (m, 2H), 7.99 (d, J=7.0 Hz, 1H), 7.83 (br. s., 1H), 7.54-7.41 (m, 3H), 7.35 (d, J=7.3 Hz, 1H), 7.23 (t, J=8.7 Hz, 1H), 7.09-6.94 (m, 3H), 6.61-6.51 (m, 1H), 5.87 (d, J=19.6 Hz, 1H), 4.97 (s, 1H), 1.75 (s, 3H), 1.48-1.42 (m, 6H).

The third and fourth peaks eluting from the column were combined to provide another mixture of two interconverting diastereomers of 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide as a yellow solid. [Example 23]. Mass spectrum m/z 519 $(M+H-H_2O)^+$. $^1H$ NMR (400 MHz, DMSO-$d_6$) δ 11.41-11.37 (m, 1H), 8.21-8.06 (m, 2H), 8.02-7.96 (m, 1H), 7.83 (br. s., 1H), 7.54-7.41 (m, 3H), 7.35 (d, J=7.3 Hz, 1H), 7.23 (t, J=8.6 Hz, 1H), 7.08-6.95 (m, 3H), 6.60-6.52 (m, 1H), 5.87 (d, J=19.6 Hz, 1H), 4.99-4.95 (m, 1H), 1.78-1.73 (m, 3H), 1.48-1.43 (m, 6H).

Alternative Synthesis of Example 22:

Using the procedure of the Alternative Synthesis of Example 15, 4-bromo-7-(2-hydroxypropan-2-yl)-9H-carbazole-1-carboxamide [synthesized according to the procedure described in U.S. Pat. No. 8,084,620, Intermediate 73-2] and 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione (single enantiomer) [Intermediate 19] were converted to 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of two interconverting diastereomers) as a yellow solid.

Alternative Synthesis of Example 23:

Using the procedure of the Alternative Synthesis of Example 15, 4-bromo-7-(2-hydroxypropan-2-yl)-9H-carbazole-1-carboxamide [synthesized according to the procedure described in U.S. Pat. No. 8,084,620, Intermediate 73-2] and 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione (single enantiomer) [Intermediate 20] were converted to 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of two interconverting diastereomers) as a yellow solid.

Example 24

4-(3-(S)-(8-Fluoro-1-methyl-2,4-dioxo-1,2-dihydroquinazolin-3(4H)-yl)-2-methylphenyl)-7-(2-hydroxypropan-2-yl)-5-methyl-9H-carbazole-1-carboxamide (Mixture of Two diastereomers)

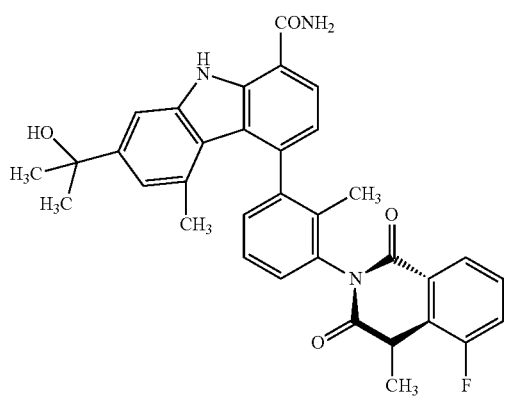

(24)

A mixture of 4-bromo-7-(2-hydroxypropan-2-yl)-5-methyl-9H-carbazole-1-carboxamide [Intermediate 22] (45 mg, 0.125 mmol), 8-fluoro-1-methyl-3-(S)-(2-methyl-3-(4,4,5,5-tetramethyl-1,3,2-dioxaborolan-2-yl)phenyl)quinazoline-2,4(1H,3H)-dione [Intermediate 3] (61 mg, 0.149 mmol), and 2.0 M aqueous $K_3PO_4$ (0.187 mL, 0.374 mmol) in THF (1.25 mL) in a vial was bubbled with argon for 1 min while swirling in an ultrasonic water bath. The mixture was treated with 1,1'-bis(di-t-butylphosphino)ferrocene palladium(II) chloride (5.1 mg, 6.23 μmol) and the vial was sealed and heated at 45° C. After 15.25 h the mixture was cooled to room temperature and concentrated. The residue was sonicated in acetonitrile and the supernatant was filtered and purified by preparative HPLC (PHENOMENEX® Axia C$_{18}$), eluting with MeCN-water containing 0.1% TFA (gradient from 10-100%). The fractions containing the product were treated with saturated aqueous NaHCO$_3$ and concentrated to provide an aqueous suspension. The precipitate was collected by filtration, washed with water and dried to provide 4-(3-(S)-(8-fluoro-1-methyl-2,4-dioxo-1,2-dihydroquinazolin-3(4H)-yl)-2-methylphenyl)-7-(2-hydroxypropan-2-yl)-5-methyl-9H-carbazole-1-carboxamide (mixture of two diastereomers) as a white solid (49.4 mg, 67% yield). Mass spectrum m/z 547 (M+H–H$_2$O)$^+$. $^1$H NMR (400 MHz, MeOH-d$_4$) δ 8.05 (t, J=8.1 Hz, 1H), 7.91 (d, J=7.7 Hz, 1H), 7.61 (ddd, J=14.3, 8.1, 1.4 Hz, 1H), 7.57 (s, 1H), 7.54-7.48 (m, 1H), 7.47-7.42 (m, 1H), 7.37-7.28 (m, 2H), 7.02 (dd, J=7.9, 1.3 Hz, 2H), 3.85 (2d, J=3.7 Hz, 3H), 1.92 (2s, 3H), 1.76 (2s, 3H), 1.61 (s, 6H).

Example 25

4-(3-(S)-(8-Fluoro-1-methyl-2,4-dioxo-1,2-dihydroquinazolin-3(4H)-yl)-2-methylphenyl)-7-(2-hydroxypropan-2-yl)-5-methyl-9H-carbazole-1-carboxamide (Single diastereomer)

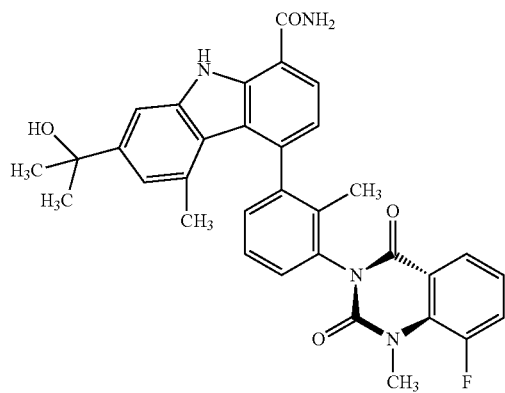

(25)

4-(3-(S)-(8-Fluoro-1-methyl-2,4-dioxo-1,2-dihydroquinazolin-3(4H)-yl)-2-methylphenyl)-7-(2-hydroxypropan-2-yl)-5-methyl-9H-carbazole-1-carboxamide (mixture of two diastereomers) [Example 24] (42.7 mg, 0.076 mmol) was resolved by chiral super-critical fluid chromatography as follows: column: Regis WHELK-O® R,R (3×25, 5 μm); Mobile Phase: CO$_2$-MeOH (60:40) at 85 mL/min, 100 bar; sample preparation: 10.7 mg/mL in MeCN-MeOH (9:1); injection: 0.50 mL. The second peak eluting from the column was concentrated to give a single diastereomer @resumed to be 4-(R)-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide) as an off-white solid (13.0 mg). The chiral purity was found to be 89%. Mass spectrum m/z 547 (M+H–H$_2$O)$^+$. $^1$H NMR (400 MHz, MeOH-d$_4$) δ 8.04 (d, J=7.5 Hz, 1H), 7.90 (d, J=7.7 Hz, 1H), 7.65-7.55 (m, 2H), 7.52-7.48 (m, 1H), 7.47-7.41 (m, 1H), 7.35-7.27 (m, 2H), 7.05-6.97 (m, 2H), 3.85 (d, J=7.9 Hz, 3H), 1.91 (s, 3H), 1.75 (s, 3H), 1.61 (s, 6H).

Example 26

4-(3-(S)-(8-Fluoro-1-methyl-2,4-dioxo-1,2-dihydroquinazolin-3(4H)-yl)-2-methylphenyl)-7-(2-hydroxypropan-2-yl)-8-methyl-9H-carbazole-1-carboxamide (Mixture of Two Interconverting diastereomers)

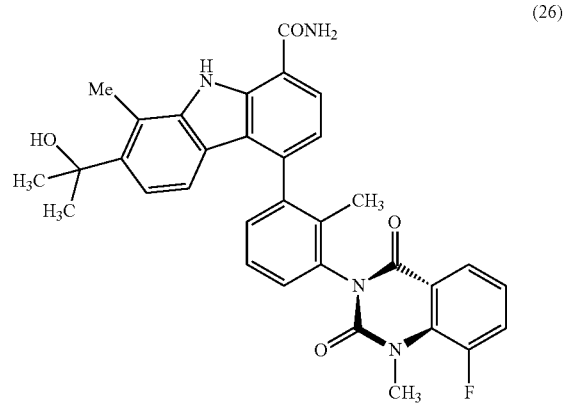

(26)

A mixture of 4-bromo-7-(2-hydroxypropan-2-yl)-8-methyl-9H-carbazole-1-carboxamide [Intermediate 23] (30 mg, 0.083 mmol), 8-fluoro-1-methyl-3-(S)-(2-methyl-3-(4,4,5,5-tetramethyl-1,3,2-dioxaborolan-2-yl)phenyl)quinazoline-2,4(1H,3H)-dione [Intermediate 3] (40.9 mg, 0.100 mmol), and 2.0 M aqueous K$_3$PO$_4$ (125 μL, 0.249 mmol) in THF (1 mL) in a vial was bubbled with argon for 1 min with sonication. The mixture was treated with 1,1'-bis(di-t-butylphosphino)ferrocene palladium(II) chloride (3.4 mg, 4.15 μmol) and the tube was sealed and heated at 45° C. After 15.25 h the mixture was cooled to room temperature and concentrated. The residue was sonicated in MeCN and the supernatant was filtered and purified by preparative HPLC (PHENOMENEX® Axia C$_{18}$ 30×100 mm), eluting with MeCN-water containing 0.1% TFA (gradient from 10-100%). The appropriate fractions were combined, treated with saturated aqueous NaHCO$_3$ and concentrated to provide an aqueous suspension. The precipitate was collected by filtration, washed with water and dried under vacuum to provide 4-(3-(S)-(8-fluoro-1-methyl-2,4-dioxo-1,2-dihydroquinazolin-3(4H)-yl)-2-methylphenyl)-7-(2-hydroxypropan-2-yl)-8-methyl-9H-carbazole-1-carboxamide (mixture of two interconverting diastereomers) as an off-white solid (33 mg, 70% yield). Mass spectrum m/z 547 (M+H–H$_2$O)$^+$. $^1$H NMR (400 MHz, MeOH-d$_4$) δ 8.08 (dd, J=17.3, 7.6 Hz, 1H), 7.98 (d, J=7.7 Hz, 1H), 7.62 (dd, J=14.1, 8.1 Hz, 1H), 7.56-7.50 (m, 1H), 7.46-7.38 (m, 2H), 7.38-7.30 (m, 1H), 7.23 (dd, J=12.5, 8.6 Hz, 1H), 7.11 (dd, J=7.8, 1.4 Hz, 1H), 7.05 (t, J=8.7 Hz, 1H), 3.88 (dd, J=10.5, 7.8 Hz, 3H), 2.85 (s, 3H), 1.83 (s, 3H), 1.71 (d, J=2.0 Hz, 6H).

Example 27

4-(3-(S)-(8-Fluoro-1-methyl(d₃)-2,4-dioxo-1,2-dihydroquinazolin-3(4H)-yl)-2-methylphenyl)-7-(2-hydroxypropan-2-yl)-5-methyl-9H-carbazole-1-carboxamide (Mixture of Two diastereomers)

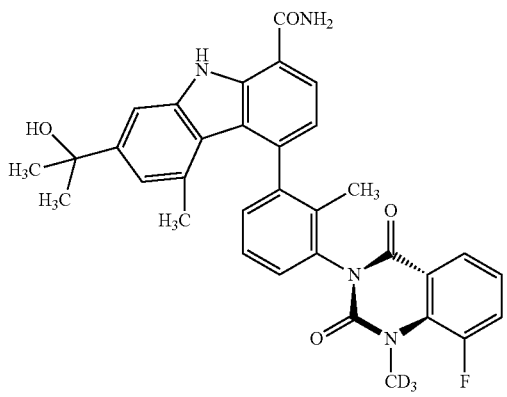

(27)

A mixture of 4-bromo-7-(2-hydroxypropan-2-yl)-5-methyl-9H-carbazole-1-carboxamide [Intermediate 22] (45 mg, 0.125 mmol), 8-fluoro-1-methyl(d₃)-3-(S)-(2-methyl-3-(4,4,5,5-tetramethyl-1,3,2-dioxaborolan-2-yl)phenyl)quinazoline-2,4(1H,3H)-dione [Intermediate 24] (62 mg, 0.149 mmol), and 2.0 M aqueous $K_3PO_4$, (0.187 mL, 0.374 mmol) in THF (1.25 mL) in a vial was bubbled with argon for 1 min with sonication. The mixture was treated with 1,1'-bis(di-t-butylphosphino)ferrocene palladium(II) chloride (5.1 mg, 6.23 μmol) and the tube was sealed and heated at 45° C. After 16.5 h the mixture was cooled to room temperature and concentrated. The residue was sonicated in MeCN, filtered and purified by preparative HPLC (PHENOMENEX® Axia C₁₈ 30×100 mm), eluting with MeCN-water containing 0.1% TFA (gradient from 10-100%). The product-containing fractions were combined, treated with saturated aqueous NaHCO₃ and concentrated to an aqueous suspension. The precipitate was collected by filtration, rinsed with water and dried under vacuum to provide 4-(3-(S)-(8-fluoro-1-methyl(d₃)-2,4-dioxo-1,2-dihydroquinazolin-3(4H)-yl)-2-methylphenyl)-7-(2-hydroxypropan-2-yl)-5-methyl-9H-carbazole-1-carboxamide (mixture of two diastereomers) as an off-white solid (41.0 mg, 57% yield). Mass spectrum m/z 550 (M+H–H₂O)⁺. ¹H NMR (400 MHz, MeOH-d₄) δ 8.05 (t, J=8.1 Hz, 1H), 7.91 (d, J=7.7 Hz, 1H), 7.61 (ddd, J=14.3, 8.1, 1.4 Hz, 1H), 7.57 (s, 1H), 7.54-7.48 (m, 1H), 7.47-7.42 (m, 1H), 7.37-7.28 (m, 2H), 7.02 (dd, J=7.9, 1.3 Hz, 2H), 1.92 (2s, 3H), 1.76 (2s, 3H), 1.61 (s, 6H)

The compounds in Table 2 were prepared by procedures analogous to those described above, using Intermediates described or prepared by methods similar to those described or by methods available to those skilled in the art.

TABLE 2

| Ex | Structure | FW | Obs. m/z (M + H)⁺ |
|---|---|---|---|
| 28 | 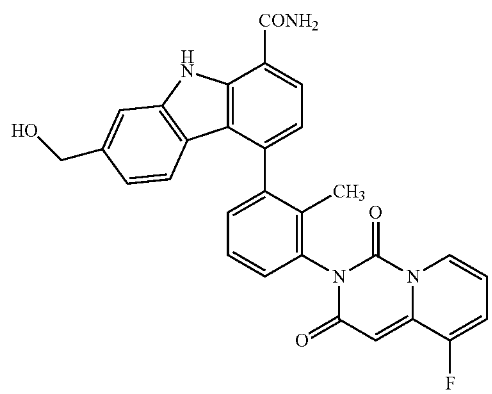 [SMILES: Cc1c(-c2ccc(C(N)=O)c3[nH]c4cc(CO)ccc4c23)cccc1-n1c(=O)cc2c(F)cccn2c1=O] | 508.51 | 509 |
| 29 | 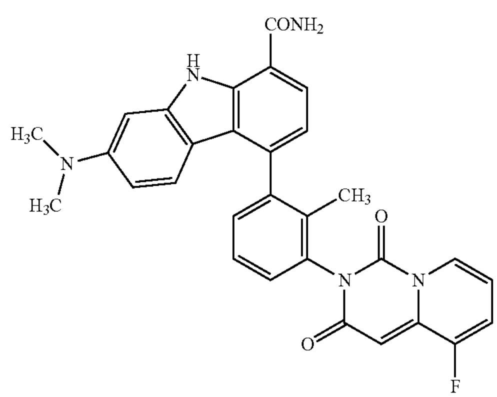 [SMILES: Cc1c(-c2ccc(C(N)=O)c3[nH]c4cc(N(C)C)ccc4c23)cccc1-n1c(=O)cc2c(F)cccn2c1=O] | 535.58 | 536 |

TABLE 2-continued

| Ex | Structure | FW | Obs. m/z (M + H)+ |
|---|---|---|---|
| 30 | 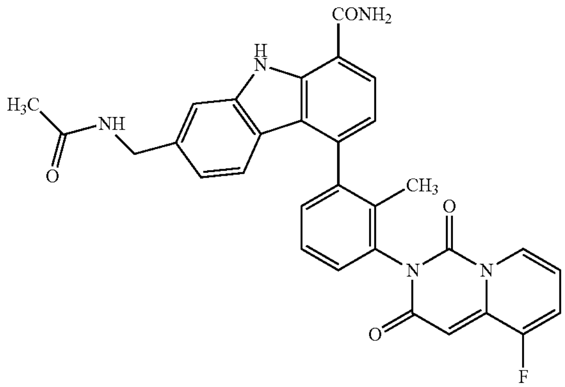 [SMILES: CC(=O)NCc1ccc2c(c1)[nH]c1c(C(N)=O)ccc(-c3cccc(-n4c(=O)cc5c(F)cccn5c4=O)c3C)c12] | 549.56 | 550 |
| 31 | 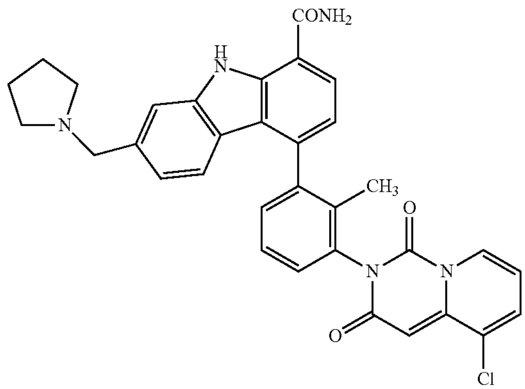 [SMILES: Cc1c(-c2ccc(C(N)=O)c3[nH]c4cc(CN5CCCC5)ccc4c23)cccc1-n1c(=O)cc2c(Cl)cccn2c1=O] | 578.07 | 579 |
| 32 | 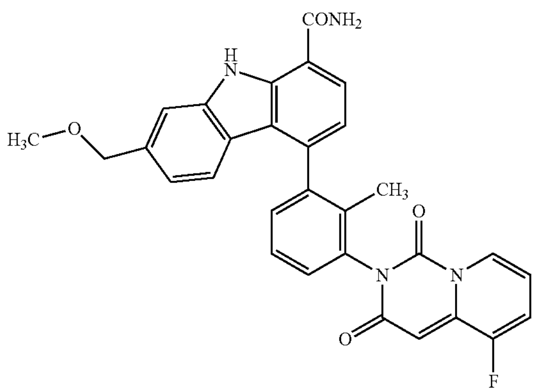 [SMILES: COCc1ccc2c(c1)[nH]c1c(C(N)=O)ccc(-c3cccc(-n4c(=O)cc5c(F)cccn5c4=O)c3C)c12] | 522.53 | 523 |
| 33 | 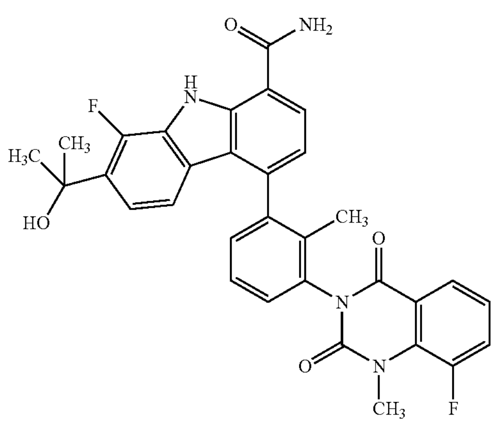 [SMILES: Cc1c(-c2ccc(C(N)=O)c3[nH]c4c(F)c(C(C)(C)O)ccc4c23)cccc1-n1c(=O)c2cccc(F)c2n(C)c1=O] | 568.58 | 569.3 |

Comparative Example 34

7-(2-Hydroxypropan-2-yl)-4-(2-methyl-3-(4-oxoquinazolin-3(4H)-yl)phenyl)-9H-carbazole-1-carboxamide

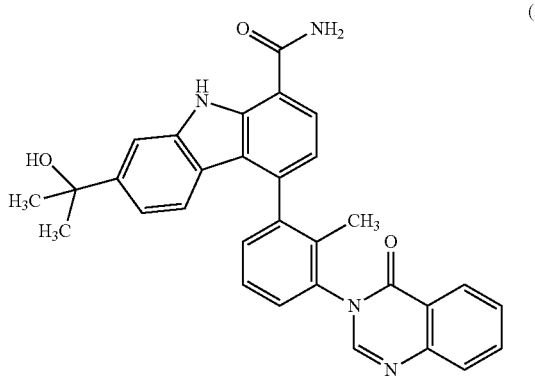

(34)

Comparative Example 34 was disclosed in U.S. Pat. No. 8,084,620 as Example 76-15 and was prepared according to the procedure described therein.

Comparative Example 35

7-(2-Hydroxypropan-2-yl)-3-methyl-4-(2-methyl-3-(4-oxoquinazolin-3(4H)-yl)phenyl)-9H-pyrido[3,4-b]indole-1-carboxamide

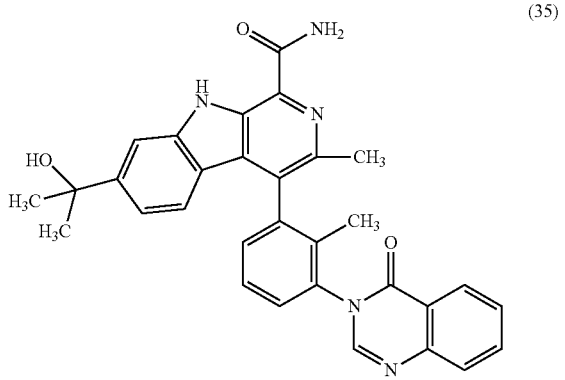 [SMILES: Cc1nc(C(N)=O)c2[nH]c3cc(C(C)(C)O)ccc3c2c1-c1cccc(-n2cnc3ccccc3c2=O)c1C]

(35)

Comparative Example 35 was disclosed in WO 2011/159857 as Example 38 and was prepared according to the procedure described therein.

BIOLOGICAL ASSAYS

Human Recombinant Btk Enzyme Assay

To V-bottom 384-well plates were added test compounds, human recombinant Btk (1 nM, INVITROGEN® Corporation), fluoresceinated peptide (1.5 µM), ATP (20 µM), and assay buffer (20 mM HEPES pH 7.4, 10 mM $MgCl_2$, 0.015% Brij 35 surfactant and 4 mM DTT in 1.6% DMSO), with a final volume of 30 µL. After incubating at room temperature for 60 min, the reaction was terminated by adding 45 µL of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and no inhibitor controls for 0% inhibition. Dose response curves were generated to determine the concentration required for inhibiting 50% of kinase activity ($IC_{50}$). Compounds were dissolved at 10 mM in DMSO and evaluated at eleven concentrations.

Ramos FLIPR Assay

Ramos RA1 B cells (ATCC CRL-1596) at a density of $2\times10^6$ cells/mL in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, #640177) and incubated at room temperature in the dark for 1 hour. Dye-loaded cells were pelleted (Beckmann GS-CKR, 1200 rpm, room temperature, 5 min) and resuspended at room temperature in RPMI minus phenol red with 50 mM HEPES and 10% FBS to a density of $1\times10^6$ cells/mL. 150 µL aliquots (150,000/well) were plated into 96 well poly-D-lysine coated assay plates (BD 35 4640) and briefly centrifuged (Beckmann GS-CKR 800 rpm, 5 min, without brake). Next, 50 µL compound dilutions in 0.4% DMSO/RPMI minus phenol red+50 mM HEPES+10% FBS were added to the wells and the plate was incubated at room temperature in the dark for 1 hour. The assay plate was briefly centrifuged as above prior to measuring calcium levels.

Using the FLIPR1 (Molecular Devices), cells were stimulated by adding goat anti-human IgM (Invitrogen AHI0601) to 2.5 µg/mL. Changes in intracellular calcium concentrations were measured for 180 seconds and percent inhibition was determined relative to peak calcium levels seen in the presence of stimulation only.

Jak2 Tyrosine Kinase Assay

Compounds with activity against Jak2 tyrosine kinase have been observed to cause thrombocytopenia, anemia and neutropenia in human patients in clinical trials (see for example, see Pardanani, A., *Leukemia*, 26:1449 (2012)). Jak2 signaling occurs thru EPO and TPO, which control erythrocyte and platelet proliferation, respectively. Thus, inhibition of Jak2 tyrosine kinase can potentially lead to side-effects in the clinic. Btk inhibitors with improved selectivity over Jak2 tyrosine kinase are desired in order to minimize off target side-effects related to the inhibition of Jak2 tyrosine kinase.

The assays were performed in V-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM beta-glycerolphosphate, 0.015% Brij 35 surfactant and 4 mM DTT). The reaction was initiated by the combination of Jak2 tyrosine kinase with substrates and test compounds. The reaction mixture was incubated at room temperature for 60 minutes and terminated by adding 45 µL of 35 mM EDTA to each sample. The reaction mixture was analyzed on the Caliper LABCHIP® 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; Jak2 fluorescent peptide, 1.5 µM; Jak2, 1 nM; and DMSO, 1.6%. Dose response curves were generated to determine the concentration required inhibiting 50% of kinase activity ($IC_{50}$). Compounds were dissolved at 10 mM in DMSO and evaluated at eleven concentrations, each in duplicate. $IC_{50}$ values were derived by non-linear regression analysis.

Whole Blood Assays of BCR-Stimulated CD69 Expression on B Cells

The efficacy of Btk inhibitor compounds in suppressing CD69 expression on B cells human in whole blood assays is useful for predicting efficacious doses in the clinic and minimizing potential side-effects. Btk inhibitor compounds having higher activity in the whole blood CD69 expression assay are expected to require lower doses than compounds having lower activity, and are expected to cause fewer unwanted side-effects. (Uetrecht, *Chem. Res. Toxicol.*, 12, 387-395 (1999); Nakayama, *Drug Metabolism and Disposition*, 37(9):1970-1977 (2009); Sakatis, *Chem. Res. Toxicol.* (2012)).

To measure BCR-stimulated B cells, ACD-A human whole blood was treated with various concentrations of test compound and stimulated with 30 μg/mL AffiniPure F(ab')2 fragment goat anti human IgM (Jackson 109-006-1299— endotoxin cleared) and 10 ng/mL human IL-4 (Peprotech 200-04) for 18 h at 37° C. with agitation. The cells were blocked with human gamma globulin (Jackson 009-000-002) and stained with FITC-conjugated mouse anti-human CD20 (BD Pharmingen 555622) and PE-conjugated mouse anti-human CD69 monoclonal antibody (BD Pharmingen 555531), lysed and fixed, then washed. The amount of CD69 expression was quantitated by the median fluorescence intensity (MFI) after gating on the CD20-positive B cell population as measured by FACS analysis.

In the whole blood assay of BCR-Stimulated CD69 expression on B cells, increased efficacy of a Btk inhibitor compound is indicated by a lower CD69 $IC_{50}$ value.

TABLE 3

| Example | Btk $IC_{50}$ value (nM) | Jak2 $IC_{50}$ value (nM) | Ratio of Jak2/Btk $IC_{50}$ values | CD69 $IC_{50}$ values (nM) |
|---|---|---|---|---|
| 1 | 1.5 | 1200 | 800 | 140 |
| 2 | 2.4 | 850 | 350 | 200 |
| 3 | 2.3 | 1200 | 520 | 190 |
| 4 | 4.4 | 2000 | 450 | 190 |
| 5 | 0.9 | 1200 | 1300 | 180 |
| 6 | 5.3 | 1800 | 340 | 150 |
| 7 | 1.7 | 1300 | 760 | 220 |
| 8 | 5.8 | 2200 | 380 | 160 |
| 9 | 2.2 | 1000 | 450 | 210 |
| 10 | 1.4 | 1100 | 790 | 120 |
| 11 | 0.63 | 1000 | 1600 | 140 |
| 12 | 0.52 | 980 | 1900 | 140 |
| 13 | 0.94 | 1300 | 1400 | 120 |
| 14 | 1.0 | 1100 | 1100 | 78 |
| 15 | 0.41 | 1000 | 2400 | 59 |
| 16 | 2.1 | 2200 | 1000 | 220 |
| 17 | 1.7 | 1900 | 1100 | 110 |
| 18 | 2.3 | 740 | 320 | 130 |
| 19 | 1.6 | 1900 | 1200 | 140 |
| 20 | 1.6 | 570 | 360 | 130 |
| 21 | 0.93 | 960 | 1000 | 75 |
| 22 | 1.7 | 880 | 520 | 91 |
| 23 | 1.2 | 1000 | 830 | 79 |
| 24 | 0.59 | >2000 | >3400 | 160 |
| 25 | 0.70 | 4600 | 6600 | 69 |
| 26 | 0.84 | >2000 | >2400 | 200 |
| 27 | 1.2 | >2000 | >1700 | 98 |
| 28 | 1.5 | 800 | 530 | 87 |
| 29 | 1.5 | 470 | 310 | 56 |
| 30 | 1.2 | 430 | 360 | 130 |
| 31 | 0.54 | 79 | 150 | 60 |
| 32 | 2.3 | 740 | 320 | 130 |
| 33 | 0.4 | 226 | 540 | 250 |
| Comparative Ex. 34 | 2.6 | 240 | 92 | 650 |
| Comparative Ex. 35 | 6.9 | 200 | 29 | — |

The compounds of the present invention, as exemplified by Examples 1 to 33, have been compared to Comparative Examples 34 and 35, disclosed in U.S. Pat. No. 8,084,620 and WO 2011/159857, respectively, and have been found to be advantageous. The compounds of the present invention have the surprising advantage of the combination of Btk inhibition activity and improved kinase selectivity of Btk inhibition activity over Jak2 inhibition activity. As shown in Table 3, in the reported tests, Examples 1 to 33 show the surprising advantage of the combination of efficacy of Btk inhibition activity and improved kinase selectivity of Btk inhibition activity over Jak2 inhibition activity, as characterized by the ratio of Jak2/Btk $IC_{50}$ values. Increased selectivity for Btk kinase over Jak2 kinase is indicated by a larger value for the ratio of the Jak2/Btk $IC_{50}$ values. Examples 1 to 33 had Btk $IC_{50}$ values of less than 6 nM and ratios of Jak2/Btk $IC_{50}$ values of 150 and greater. In contrast, Comparative Examples 34 and 35 had Btk $IC_{50}$ values of 2.6 and 6.9 nM and ratios of Jak2/Btk $IC_{50}$ values of 92 and 29, respectively.

Additionally, the compounds of the present invention, as exemplified by Examples 1 to 33, also have improved potency in the whole blood BCR-stimulated CD69 expression assay, compared to Comparative Example 34. As shown in Table 3, in the reported tests, Examples 1 to 33 show the surprising advantage of the combination of efficacy of Btk inhibition activity, improved kinase selectivity of Btk inhibition activity over Jak2 inhibition activity, and improved potency in the whole blood BCR-stimulated CD69 expression assay. Examples 1 to 33 had Btk $IC_{50}$ values of less than 6 nM, ratios of Jak2/Btk $IC_{50}$ values of 150 and greater, and CD69 $IC_{50}$ values of 250 nM and less. In contrast, Comparative Example 34 had a Btk $IC_{50}$ value of 2.6 nM, a ratio of Jak2/Btk $IC_{50}$ value of 92, and a CD69 $IC_{50}$ values of 650 nM.

TABLE 4

Unit Cell Parameters of Crystal Forms of Example 3 Determined by Single Crystal X-Ray Diffractometry

| Form | a (Å) | b (Å) | c (Å) | α (°) | β (°) | γ (°) | Volume | Space Group | Molecules/ asymmetric unit (Z') | Density, calc. (g/cm³) | Temp |
|---|---|---|---|---|---|---|---|---|---|---|---|
| SA-1 | 10.9201 | 11.5031 | 23.7434 | 90 | 99.2590 | 90 | 2943.7 | $P2_1$ | 2 | 1.355 | RT |
| SB-2 | 11.5337 | 11.7474 | 23.2486 | 90 | 90.6120 | 90 | 3149.8 | $P2_1$ | 2 | 1.340 | 203 K |
| SE-2 | 11.1799 | 11.9237 | 22.9237 | 90 | 91.2000 | 90 | 3059.2 | $P2_1$ | 2 | 1.315 | 203 K |
| SC-3 | 14.4552 | 11.8207 | 18.8382 | 90 | 93.829 | 90 | 3211.7 | $P2_1$ | 2 | 1.296 | 203 K |

TABLE 4-continued

Unit Cell Parameters of Crystal Forms of Example 3 Determined by Single Crystal X-Ray Diffractometry

| Form | a (Å) | b (Å) | c (Å) | α (°) | β (°) | γ (°) | Volume | Space Group | Molecules/ asymmetric unit (Z') | Density, calc. (g/cm$^3$) | Temp |
|---|---|---|---|---|---|---|---|---|---|---|---|
| SD-3 | 14.5877 | 11.8964 | 19.2500 | 90 | 91.506 | 90 | 3339.5 | P2$_1$ | 2 | 1.346 | 203 K |
| M2-4 | 11.1815 | 17.3429 | 31.6262 | 90 | 90 | 90 | 6132.9 | P2$_1$2$_1$2$_1$ | 2 | 1.331 | 203 K |
| AN-5 | 12.9874 | 11.4967 | 20.3900 | 90 | 105.829 | 90 | 2929.0 | P2$_1$ | 2 | 1.342 | 203 K |
| H1-6 | 10.5755 | 11.5986 | 22.3697 | 90 | 90 | 90 | 2743.9 | P2$_1$2$_1$2$_1$ | 1 | 1.376 | RT |
| E-7 | 9.5968 | 14.2611 | 21.6404 | 90 | 90 | 90 | 2961.7 | P2$_1$2$_1$2$_1$ | 1 | 1.338 | RT |
| SE-8 | 11.4019 | 11.4019 | 45.6578 | 90 | 90 | 90 | 5935.7 | P4$_1$2$_1$2 | 1 | 1.376 | 203 K |

RT = room temperature

TABLE 5

Fractional Atomic Coordinates for the SA-1 Form of Example 3 at Room Temperature

| Atom | X | Y | Z | Atom | X | Y | Z |
|---|---|---|---|---|---|---|---|
| O1 | 0.8236 | 0.1800 | 0.1919 | H29 | -0.0892 | 0.5178 | -0.0396 |
| O2 | 0.5888 | 0.2021 | 0.2235 | C30 | 0.4451 | 0.4402 | -0.3342 |
| O3 | 0.0324 | 0.6009 | -0.1143 | C31 | 0.1424 | 0.7099 | -0.0355 |
| O4 | 0.3464 | 0.2872 | -0.1889 | C32 | -0.0483 | 0.5902 | -0.0287 |
| O5 | 0.6503 | 0.0186 | -0.1841 | O6 | 0.1448 | 0.2717 | 0.6878 |
| N1 | 0.3384 | 0.3498 | 0.0906 | O7 | -0.1602 | 0.5390 | 0.6823 |
| N2 | 0.4907 | 0.1462 | -0.1900 | O8 | 0.4711 | -0.0301 | 0.6158 |
| N3 | 0.3883 | 0.2541 | 0.2099 | O9 | -0.0937 | 0.3580 | 0.2766 |
| N4 | 0.6273 | 0.1447 | -0.2577 | N5 | 0.1593 | 0.2113 | 0.4097 |
| F1 | 0.6959 | 0.2533 | -0.3567 | N6 | 0.0028 | 0.4150 | 0.6901 |
| C1 | 0.5683 | 0.2426 | -0.2839 | N7 | 0.1054 | 0.3034 | 0.2900 |
| C2 | 0.2055 | 0.4787 | 0.0211 | N8 | 0.0263 | 0.2618 | 0.7584 |
| C3 | 0.2782 | 0.3807 | 0.0370 | C33 | -0.1302 | 0.4102 | 0.7610 |
| C4 | 0.1522 | 0.4914 | -0.0355 | C34 | 0.2952 | 0.0867 | 0.4801 |
| C5 | 0.4001 | 0.2459 | 0.0866 | C35 | 0.1443 | 0.5924 | 0.5604 |
| C6 | 0.3005 | 0.2956 | -0.0029 | C36 | 0.0955 | 0.3131 | 0.4131 |
| C7 | 0.3472 | -0.0311 | -0.0613 | C37 | 0.0210 | 0.4335 | 0.5882 |
| C8 | 0.4725 | 0.2953 | -0.2608 | C38 | 0.1129 | 0.3509 | 0.4712 |
| C9 | 0.3804 | 0.2097 | 0.0294 | C39 | 0.0733 | 0.4932 | 0.5467 |
| C10 | 0.2458 | 0.3101 | -0.0597 | C40 | 0.2509 | 0.2545 | 0.5596 |
| C11 | 0.6007 | 0.2942 | -0.3326 | C41 | 0.0505 | 0.4740 | 0.6440 |
| C12 | 0.4714 | 0.1258 | -0.0888 | C42 | 0.1953 | 0.2667 | 0.5030 |
| C13 | 0.5939 | 0.0977 | -0.2090 | C43 | 0.2194 | 0.1812 | 0.4637 |
| C14 | 0.4200 | 0.0666 | -0.0460 | C44 | 0.0544 | 0.4511 | 0.4859 |
| C15 | 0.4444 | 0.0844 | -0.1444 | C45 | 0.3499 | 0.0750 | 0.5368 |
| C16 | 0.4878 | 0.2148 | 0.1912 | C46 | -0.1007 | 0.4603 | 0.7087 |
| C17 | 0.5309 | 0.0834 | 0.1128 | C47 | -0.0217 | 0.5117 | 0.4432 |
| C18 | 0.5149 | 0.0478 | 0.0566 | C48 | 0.1692 | 0.6319 | 0.6159 |
| C19 | 0.7264 | 0.0827 | -0.2808 | C49 | 0.0218 | 0.3764 | 0.3704 |
| C20 | 0.4391 | 0.1079 | 0.0138 | C50 | 0.0065 | 0.3453 | 0.3086 |
| C21 | 0.3233 | -0.0708 | -0.1167 | C51 | 0.3261 | 0.1601 | 0.5753 |
| C22 | 0.1725 | 0.4055 | -0.0755 | C52 | -0.0378 | 0.4751 | 0.3865 |
| C23 | 0.4737 | 0.1818 | 0.1303 | C53 | 0.3755 | -0.1406 | 0.5350 |
| C24 | 0.5401 | 0.3901 | -0.3569 | C54 | 0.1236 | 0.5709 | 0.6583 |
| C25 | 0.4288 | 0.2466 | -0.2113 | C55 | -0.0619 | 0.3305 | 0.5743 |
| C26 | 0.0708 | 0.5973 | -0.0536 | C56 | 0.4363 | -0.0274 | 0.5548 |
| C27 | 0.3714 | -0.0122 | -0.1586 | C57 | 0.0635 | 0.3127 | 0.7111 |
| C28 | 0.5534 | 0.2298 | -0.0749 | C58 | -0.0637 | 0.3141 | 0.7856 |
| C29 | 0.4119 | 0.3943 | -0.2853 | C59 | -0.1804 | 0.3287 | 0.8630 |
| C61 | 0.5601 | -0.0082 | 0.5338 | C60 | 0.0852 | 0.1502 | 0.7767 |
| C62 | -0.0939 | 0.2755 | 0.8375 | H30 | 0.4092 | -0.0406 | 0.6307 |
| C63 | -0.2462 | 0.4231 | 0.8384 | H31 | 0.1615 | 0.1723 | 0.3790 |
| C64 | -0.2213 | 0.4645 | 0.7866 | H32 | 0.1011 | 0.2842 | 0.2547 |
| F2 | -0.0324 | 0.1855 | 0.8656 | H33 | 0.1740 | 0.2955 | 0.3131 |
| O10 | 0.1182 | 0.2705 | 0.1683 | H34 | 0.3092 | 0.0313 | 0.4533 |
| C65 | 0.0654 | 0.3781 | 0.1484 | H35 | 0.1753 | 0.6326 | 0.5318 |
| O11 | -0.3278 | 0.3788 | 0.3082 | H36 | 0.2375 | 0.3097 | 0.5865 |
| O12 | 0.3739 | 0.3014 | 0.3316 | H37 | -0.0629 | 0.5779 | 0.4527 |
| C66 | 0.4261 | 0.1981 | 0.3502 | H38 | 0.2162 | 0.6987 | 0.6247 |
| H1 | 0.8619 | 0.2308 | 0.2148 | H39 | 0.3626 | 0.1527 | 0.6133 |
| H2 | 0.7472 | 0.1765 | 0.1967 | H40 | -0.0892 | 0.5174 | 0.3589 |
| H3 | 0.0906 | 0.6220 | -0.1297 | H41 | 0.4328 | -0.2032 | 0.5455 |
| H4 | 0.3374 | 0.3887 | 0.1214 | H42 | 0.3516 | -0.1390 | 0.4944 |
| H5 | 0.3920 | 0.2718 | 0.2454 | H43 | 0.3032 | -0.1519 | 0.5527 |
| H6 | 0.3196 | 0.2621 | 0.1867 | H44 | 0.1419 | 0.5950 | 0.6960 |
| H7 | 0.1928 | 0.5343 | 0.0481 | H45 | -0.0631 | 0.3087 | 0.5352 |
| H8 | 0.3136 | -0.0708 | -0.0333 | H46 | -0.1445 | 0.3499 | 0.5801 |
| H9 | 0.2588 | 0.2552 | -0.0870 | H47 | -0.0314 | 0.2667 | 0.5987 |
| H10 | 0.5821 | 0.0399 | 0.1400 | H48 | -0.1960 | 0.3012 | 0.8980 |
| H11 | 0.5562 | -0.0184 | 0.0471 | H49 | 0.1472 | 0.1622 | 0.8098 |
| H12 | 0.6961 | 0.0583 | -0.3191 | H50 | 0.1235 | 0.1184 | 0.7465 |
| H13 | 0.7516 | 0.0158 | -0.2576 | H51 | 0.0235 | 0.0971 | 0.7859 |
| H14 | 0.7962 | 0.1336 | -0.2806 | H52 | 0.5928 | 0.0666 | 0.5464 |
| H15 | 0.2748 | -0.1368 | -0.1257 | H53 | 0.5474 | -0.0113 | 0.4930 |
| H16 | 0.1354 | 0.4138 | -0.1134 | H54 | 0.6177 | -0.0677 | 0.5491 |
| H17 | 0.5637 | 0.4220 | -0.3895 | H55 | -0.3061 | 0.4584 | 0.8563 |
| H18 | 0.3548 | -0.0376 | -0.1962 | H56 | -0.2649 | 0.5278 | 0.7690 |
| H19 | 0.6113 | 0.2344 | -0.1012 | H57 | 0.0729 | 0.2173 | 0.1548 |
| H20 | 0.5978 | 0.2227 | -0.0368 | H58 | 0.0660 | 0.3846 | 0.1082 |
| H21 | 0.5035 | 0.2989 | -0.0779 | H59 | 0.1128 | 0.4405 | 0.1680 |
| H22 | 0.3497 | 0.4290 | -0.2687 | H60 | -0.0185 | 0.3821 | 0.1556 |
| H23 | 0.4036 | 0.5045 | -0.3517 | H61 | -0.2515 | 0.3826 | 0.3034 |
| H24 | 0.2186 | 0.7106 | -0.0509 | H62 | -0.3662 | 0.3282 | 0.2853 |
| H25 | 0.1608 | 0.7135 | 0.0054 | H63 | 0.4084 | 0.3542 | 0.3511 |
| H26 | 0.0930 | 0.7757 | -0.0497 | H64 | 0.3774 | 0.1355 | 0.3316 |
| H27 | -0.1018 | 0.6535 | -0.0430 | H65 | 0.4290 | 0.1920 | 0.3906 |
| H28 | -0.0295 | 0.5949 | 0.0121 | H66 | 0.5088 | 0.1939 | 0.3414 |

TABLE 6

Fractional Atomic Coordinates for the SB-2 Form of Example 3 at 203K

| Atom | X | Y | Z | Atom | X | Y | Z |
|---|---|---|---|---|---|---|---|
| N1 | 0.1020 | 0.3433 | 0.6995 | H33 | 0.3069 | 0.0707 | 0.0797 |
| N2 | 0.1451 | 0.2098 | 0.7726 | N6 | 0.0906 | 0.5778 | -0.1977 |
| C1 | 0.1521 | 0.0990 | 0.4257 | N7 | 0.1038 | 0.3597 | 0.2184 |
| N3 | 0.0666 | 0.1387 | 0.3886 | N8 | 0.1832 | 0.4417 | 0.3028 |
| O1 | -0.0810 | 0.2000 | 0.3000 | O5 | 0.1472 | 0.1787 | 0.1924 |
| O2 | -0.0617 | 0.4513 | 0.7014 | O6 | 0.2653 | 0.4991 | -0.1831 |
| O3 | 0.3455 | -0.1959 | 0.4102 | O7 | 0.0530 | 0.5367 | 0.2460 |
| O4 | 0.2578 | 0.2270 | 0.6922 | O8 | 0.4604 | -0.0547 | 0.0595 |
| N4 | -0.2237 | 0.3230 | 0.3182 | F2 | 0.3424 | 0.4176 | 0.3974 |
| F1 | 0.0929 | 0.1320 | 0.8861 | C33 | 0.1488 | 0.3750 | -0.0188 |
| C2 | 0.0515 | 0.2481 | 0.8039 | C34 | 0.1851 | 0.4059 | -0.0748 |
| C3 | 0.0278 | 0.2425 | 0.4073 | C35 | 0.1325 | 0.4955 | -0.1052 |
| C4 | 0.1352 | 0.3947 | 0.6451 | C36 | 0.2185 | 0.2768 | -0.0021 |
| C5 | 0.0876 | 0.2715 | 0.4588 | C37 | 0.0109 | 0.5268 | -0.0219 |
| C6 | -0.0583 | 0.3127 | 0.3831 | C38 | 0.2931 | 0.2545 | -0.0484 |
| C7 | 0.1161 | 0.4086 | 0.5430 | C39 | 0.1671 | 0.5246 | -0.1644 |
| C8 | -0.0236 | 0.3302 | 0.7808 | C40 | 0.0613 | 0.4372 | 0.0086 |
| C9 | 0.1733 | 0.2583 | 0.7207 | C41 | 0.3037 | 0.1183 | 0.0472 |
| C10 | 0.0002 | 0.3801 | 0.7252 | C42 | 0.2346 | 0.2494 | 0.2775 |
| C11 | -0.0792 | 0.4148 | 0.4109 | C43 | 0.0446 | 0.5543 | -0.0770 |
| C12 | 0.0235 | 0.2092 | 0.8599 | C44 | -0.1499 | 0.3417 | 0.1204 |
| C13 | 0.1685 | 0.1791 | 0.4702 | C45 | 0.0317 | 0.3707 | 0.1668 |
| C14 | -0.0210 | 0.4457 | 0.4609 | C46 | 0.1598 | 0.2563 | 0.2269 |
| C15 | -0.1217 | 0.2756 | 0.3314 | C47 | 0.0836 | 0.4073 | 0.1161 |
| C16 | 0.0848 | 0.3536 | 0.5942 | C48 | 0.0150 | 0.4051 | 0.0659 |
| C17 | 0.2155 | -0.0010 | 0.4222 | C49 | 0.2951 | 0.1485 | 0.2878 |

TABLE 6-continued

Fractional Atomic Coordinates for the SB-2 Form of Example 3 at 203K

| Atom | X | Y | Z | Atom | X | Y | Z |
|---|---|---|---|---|---|---|---|
| C18 | 0.2117 | 0.4840 | 0.6463 | C50 | 0.2252 | 0.2048 | 0.0453 |
| C19 | 0.2403 | 0.5377 | 0.5954 | C51 | 0.1092 | 0.4518 | 0.2562 |
| C20 | −0.1198 | 0.3713 | 0.8123 | C52 | −0.1004 | 0.3730 | 0.0688 |
| C21 | 0.1925 | 0.4993 | 0.5443 | C53 | 0.3741 | 0.1670 | −0.0469 |
| C22 | 0.2525 | 0.1567 | 0.5119 | C54 | 0.3862 | 0.2340 | 0.3696 |
| C23 | 0.3707 | −0.1318 | 0.4616 | C55 | −0.0831 | 0.3399 | 0.1697 |
| C24 | 0.2991 | −0.0225 | 0.4636 | C56 | 0.2060 | 0.4509 | 0.1168 |
| C25 | 0.0011 | 0.2555 | 0.5954 | C57 | 0.3254 | 0.3308 | 0.3601 |
| C26 | 0.3168 | 0.0564 | 0.5080 | C58 | 0.2470 | 0.3432 | 0.3137 |
| C27 | 0.0614 | 0.3739 | 0.4866 | C59 | 0.3800 | 0.0980 | 0.0016 |
| C28 | 0.2163 | 0.1107 | 0.7897 | C60 | 0.3714 | 0.1406 | 0.3341 |
| C29 | −0.0681 | 0.2470 | 0.8893 | C61 | 0.4712 | 0.0047 | 0.0064 |
| C30 | −0.1424 | 0.3305 | 0.8659 | C62 | 0.1864 | 0.5408 | 0.3416 |
| C31 | 0.3385 | −0.2087 | 0.5112 | C63 | 0.5902 | 0.0588 | 0.0044 |
| C32 | 0.4991 | −0.1042 | 0.4629 | C64 | 0.4594 | −0.0801 | −0.0416 |
| N5 | 0.2714 | 0.3332 | −0.0921 | O9 | 0.6592 | 0.2259 | 0.2172 |
| C65 | 0.5405 | 0.2502 | 0.2111 | O10 | 0.4998 | 0.0747 | 0.1606 |
| C66 | 0.5222 | 0.3739 | 0.2138 | H34 | 0.0070 | 0.6146 | −0.0961 |
| C67 | 0.4872 | 0.1973 | 0.1604 | H35 | −0.2287 | 0.3217 | 0.1218 |
| O11 | 0.4252 | 0.3177 | 0.8040 | H36 | 0.2841 | 0.0856 | 0.2632 |
| O12 | 0.4975 | 0.3152 | 0.6851 | H37 | 0.1750 | 0.2162 | 0.0765 |
| C68 | 0.5426 | 0.3068 | 0.7874 | H38 | −0.1460 | 0.3725 | 0.0352 |
| C69 | 0.5644 | 0.3351 | 0.7301 | H39 | 0.4239 | 0.1549 | −0.0780 |
| C70 | 0.5898 | 0.1924 | 0.8075 | H40 | 0.4390 | 0.2302 | 0.4007 |
| O13 | 0.3709 | 0.0244 | 0.6545 | H41 | −0.1155 | 0.3181 | 0.2050 |
| H1 | 0.0414 | 0.1032 | 0.3581 | H42 | 0.2590 | 0.3881 | 0.1233 |
| H2 | 0.3817 | −0.1684 | 0.3828 | H43 | 0.2151 | 0.5064 | 0.1476 |
| H3 | −0.2618 | 0.3012 | 0.2876 | H44 | 0.2227 | 0.4866 | 0.0802 |
| H4 | −0.2521 | 0.3759 | 0.3402 | H45 | 0.4125 | 0.0728 | 0.3413 |
| H5 | −0.1347 | 0.4650 | 0.3953 | H46 | 0.1296 | 0.5966 | 0.3288 |
| H6 | −0.0372 | 0.5164 | 0.4780 | H47 | 0.2631 | 0.5747 | 0.3411 |
| H7 | 0.2017 | −0.0531 | 0.3922 | H48 | 0.1687 | 0.5167 | 0.3803 |
| H8 | 0.2441 | 0.5086 | 0.6814 | H49 | 0.6017 | 0.1062 | 0.0382 |
| H9 | 0.2918 | 0.5997 | 0.5956 | H50 | 0.5959 | 0.1053 | −0.0299 |
| H10 | −0.1682 | 0.4274 | 0.7960 | H51 | 0.6489 | −0.0003 | 0.0036 |
| H11 | 0.2123 | 0.5355 | 0.5097 | H52 | 0.5198 | −0.1372 | −0.0379 |
| H12 | 0.2658 | 0.2082 | 0.5422 | H53 | 0.4668 | −0.0414 | −0.0782 |
| H13 | 0.0401 | 0.1886 | 0.6106 | H54 | 0.3842 | −0.1166 | −0.0398 |
| H14 | −0.0267 | 0.2400 | 0.5566 | H55 | 0.6689 | 0.1560 | 0.2173 |
| H15 | −0.0639 | 0.2745 | 0.6197 | H56 | 0.5679 | 0.0577 | 0.1687 |
| H16 | 0.3739 | 0.0412 | 0.5361 | H57 | 0.5018 | 0.2173 | 0.2452 |
| H17 | 0.2617 | 0.0856 | 0.7572 | H58 | 0.5503 | 0.4027 | 0.2503 |
| H18 | 0.1660 | 0.0492 | 0.8019 | H59 | 0.4401 | 0.3902 | 0.2096 |
| H19 | 0.2678 | 0.1320 | 0.8211 | H60 | 0.5642 | 0.4102 | 0.1828 |
| H20 | −0.0830 | 0.2173 | 0.9261 | H61 | 0.4046 | 0.2166 | 0.1590 |
| H21 | −0.2062 | 0.3574 | 0.8867 | H62 | 0.5232 | 0.2282 | 0.1258 |
| H22 | 0.2567 | −0.2276 | 0.5084 | H63 | 0.3998 | 0.3805 | 0.7933 |
| H23 | 0.3538 | −0.1698 | 0.5473 | H64 | 0.4554 | 0.2594 | 0.6917 |
| H24 | 0.3842 | −0.2779 | 0.5096 | H65 | 0.5852 | 0.3644 | 0.8105 |
| H25 | 0.5434 | −0.1737 | 0.4578 | H66 | 0.5784 | 0.4173 | 0.7298 |
| H26 | 0.5195 | −0.0700 | 0.4996 | H67 | 0.6391 | 0.2994 | 0.7211 |
| H27 | 0.5167 | −0.0513 | 0.4321 | H68 | 0.5471 | 0.1674 | 0.8410 |
| H28 | 0.3067 | 0.3359 | −0.1249 | H69 | 0.6712 | 0.2002 | 0.8176 |
| H29 | 0.1084 | 0.5953 | −0.2328 | H70 | 0.5810 | 0.1369 | 0.7769 |
| H30 | 0.0225 | 0.5951 | −0.1844 | H71 | 0.3368 | 0.0852 | 0.6659 |
| H31 | 0.4940 | −0.0185 | 0.0854 | H72 | 0.4340 | 0.0425 | 0.6372 |
| H32 | −0.0480 | 0.5697 | −0.0045 | — | — | — | — |

TABLE 7

Fractional Atomic Coordinates for the SE-2 Form of Example 3 at 203 K

| Atom | X | Y | Z | Atom | X | Y | Z |
|---|---|---|---|---|---|---|---|
| N1 | 0.2690 | 0.3492 | −0.0891 | F1 | 0.3514 | 0.4413 | 0.4010 |
| C1 | 0.1409 | 0.3867 | −0.0160 | F2 | 0.0923 | 0.1460 | 0.8866 |
| C2 | 0.2150 | 0.2946 | 0.0017 | N5 | 0.0597 | 0.1574 | 0.3867 |
| C3 | −0.0030 | 0.5370 | −0.0211 | N6 | −0.2480 | 0.3343 | 0.3203 |
| C4 | 0.1782 | 0.4192 | −0.0720 | N7 | 0.1121 | 0.3629 | 0.7002 |
| C5 | 0.0480 | 0.4486 | 0.0102 | N8 | 0.1541 | 0.2292 | 0.7742 |
| C6 | 0.2943 | 0.2735 | −0.0443 | O5 | 0.3335 | −0.1808 | 0.4063 |
| C7 | 0.1273 | 0.5093 | −0.1029 | O6 | −0.1023 | 0.2149 | 0.3000 |
| C8 | 0.0357 | 0.5670 | −0.0761 | O7 | −0.0549 | 0.4703 | 0.7013 |
| C9 | 0.3179 | 0.1482 | 0.0555 | O8 | 0.2741 | 0.2492 | 0.6957 |
| C10 | 0.3830 | 0.1938 | −0.0416 | C33 | 0.0207 | 0.2604 | 0.4056 |
| C11 | 0.2290 | 0.2281 | 0.0516 | C34 | 0.1493 | 0.1188 | 0.4237 |
| C12 | 0.3959 | 0.1303 | 0.0090 | C35 | 0.0870 | 0.2890 | 0.4570 |
| C13 | 0.4980 | 0.0463 | 0.0143 | C36 | −0.0687 | 0.3291 | 0.3821 |
| O1 | 0.5032 | 0.0008 | 0.0728 | C37 | −0.0872 | 0.4313 | 0.4096 |
| C14 | 0.6182 | 0.1082 | 0.0074 | C38 | −0.0219 | 0.4623 | 0.4599 |
| C15 | 0.4818 | −0.0461 | −0.0301 | C39 | 0.0627 | 0.3909 | 0.4852 |
| C16 | 0.1734 | 0.5410 | −0.1606 | C40 | 0.2573 | 0.1731 | 0.5105 |
| C17 | 0.0709 | 0.4218 | 0.1197 | C41 | 0.2117 | 0.0177 | 0.4206 |
| C18 | 0.0001 | 0.4178 | 0.0679 | C42 | 0.1686 | 0.1974 | 0.4682 |
| C19 | 0.0173 | 0.3856 | 0.1709 | C43 | 0.2972 | −0.0053 | 0.4623 |
| C20 | −0.1192 | 0.3851 | 0.0707 | C44 | 0.3189 | 0.0738 | 0.5066 |
| C21 | −0.1701 | 0.3544 | 0.1228 | C45 | 0.3672 | −0.1156 | 0.4603 |
| C22 | 0.1955 | 0.4681 | 0.1209 | C46 | 0.3343 | −0.1831 | 0.5129 |
| C23 | −0.1009 | 0.3536 | 0.1733 | C47 | 0.4991 | −0.0954 | 0.4605 |
| N2 | 0.1014 | 0.5947 | −0.1968 | C48 | −0.1409 | 0.2899 | 0.3313 |
| O2 | 0.2802 | 0.5205 | −0.1728 | C49 | 0.1457 | 0.4127 | 0.6450 |
| N3 | 0.0935 | 0.3757 | 0.2230 | C50 | 0.0935 | 0.3708 | 0.5937 |
| N4 | 0.1820 | 0.4622 | 0.3063 | C51 | 0.1985 | 0.5167 | 0.5425 |
| C24 | 0.1004 | 0.4683 | 0.2597 | C52 | 0.1215 | 0.4256 | 0.5414 |
| C25 | 0.2392 | 0.2734 | 0.2804 | C53 | 0.2234 | 0.5023 | 0.6459 |
| C26 | 0.1552 | 0.2765 | 0.2299 | C54 | 0.2494 | 0.5552 | 0.5943 |
| C27 | 0.3069 | 0.1771 | 0.2886 | C55 | 0.0102 | 0.2721 | 0.5958 |
| C28 | 0.2503 | 0.3665 | 0.3170 | C56 | 0.1861 | 0.2775 | 0.7223 |
| C29 | 0.4041 | 0.2624 | 0.3710 | C57 | 0.0544 | 0.2641 | 0.8045 |
| C30 | 0.3352 | 0.3559 | 0.3624 | C58 | −0.0212 | 0.3473 | 0.7807 |
| C31 | 0.3902 | 0.1720 | 0.3344 | C59 | 0.0070 | 0.3983 | 0.7252 |
| C32 | 0.1900 | 0.5626 | 0.3432 | C60 | 0.0238 | 0.2235 | 0.8587 |
| O3 | 0.0382 | 0.5511 | 0.2507 | C61 | −0.1203 | 0.3859 | 0.8101 |
| O4 | 0.1433 | 0.2003 | 0.1959 | C62 | −0.0733 | 0.2600 | 0.8877 |
| C63 | −0.1479 | 0.3414 | 0.86397 | H31 | 0.3937 | −0.1903 | 0.3863 |
| C64 | 0.2274 | 0.1319 | 0.7926 | H32 | −0.1449 | 0.4808 | 0.3941 |
| O9 | 0.6211 | 0.2207 | 0.2230 | H33 | −0.0356 | 0.5328 | 0.4768 |
| C65 | 0.5282 | 0.2668 | 0.1881 | H34 | 0.2742 | 0.2237 | 0.5410 |
| C66 | 0.5093 | 0.3861 | 0.2061 | H35 | 0.1952 | −0.0336 | 0.3904 |
| O10 | 0.3868 | 0.0457 | 0.6545 | H36 | 0.3787 | 0.0581 | 0.5348 |
| O11 | 0.5123 | 0.3562 | 0.6907 | H37 | 0.3623 | −0.2596 | 0.5084 |
| C67 | 0.5352 | 0.3390 | 0.7931 | H38 | 0.2480 | −0.1831 | 0.5166 |
| C68 | 0.5476 | 0.3657 | 0.7410 | H39 | 0.3713 | −0.1504 | 0.5475 |
| O12 | 0.4994 | 0.3218 | 0.8483 | H40 | 0.5239 | −0.0604 | 0.4969 |
| H1 | 0.3045 | 0.3516 | −0.1225 | H41 | 0.5187 | −0.0464 | 0.4284 |
| H2 | −0.0655 | 0.5780 | −0.0044 | H42 | 0.5406 | −0.1663 | 0.4562 |
| H3 | −0.0011 | 0.6276 | −0.0956 | H43 | 0.2166 | 0.5531 | 0.5075 |
| H4 | 0.3266 | 0.1051 | 0.0896 | H44 | 0.2583 | 0.5271 | 0.6813 |
| H5 | 0.4339 | 0.1824 | −0.0732 | H45 | 0.3015 | 0.6171 | 0.5942 |
| H6 | 0.1770 | 0.2381 | 0.0829 | H46 | 0.0552 | 0.2052 | 0.6061 |
| H7 | 0.5636 | −0.0392 | 0.0768 | H47 | −0.0283 | 0.2619 | 0.5579 |
| H8 | 0.6254 | 0.1670 | 0.0365 | H48 | −0.0502 | 0.2855 | 0.6248 |
| H9 | 0.6211 | 0.1411 | −0.0312 | H49 | −0.1687 | 0.4424 | 0.7935 |
| H10 | 0.6837 | 0.0555 | 0.0125 | H50 | −0.0900 | 0.2296 | 0.9244 |
| H11 | 0.5497 | −0.0966 | −0.0277 | H51 | −0.2158 | 0.3658 | 0.8839 |
| H12 | 0.4762 | −0.0137 | −0.0688 | H52 | 0.2811 | 0.1118 | 0.7616 |
| H13 | 0.4091 | −0.0872 | −0.0223 | H53 | 0.1755 | 0.0689 | 0.8008 |
| H14 | −0.1663 | 0.3840 | 0.0363 | H54 | 0.2738 | 0.1511 | 0.8273 |
| H15 | −0.2514 | 0.3341 | 0.1238 | H55 | 0.6455 | 0.1622 | 0.2076 |
| H16 | 0.2522 | 0.4074 | 0.1268 | H56 | 0.4546 | 0.2238 | 0.1931 |
| H17 | 0.2041 | 0.5218 | 0.1524 | H57 | 0.5496 | 0.2637 | 0.1470 |
| H18 | 0.2110 | 0.5049 | 0.0841 | H58 | 0.4941 | 0.3890 | 0.2475 |
| H19 | −0.1339 | 0.3316 | 0.2088 | H59 | 0.4412 | 0.4168 | 0.1846 |
| H20 | 0.1273 | 0.6172 | −0.2303 | H60 | 0.5803 | 0.4296 | 0.1978 |
| H21 | 0.0277 | 0.6079 | −0.1873 | H61 | 0.4585 | 0.0608 | 0.6441 |
| H22 | 0.2966 | 0.1156 | 0.2634 | H62 | 0.3532 | 0.1059 | 0.6667 |
| H23 | 0.4610 | 0.2601 | 0.4016 | H63 | 0.4440 | 0.3268 | 0.6901 |
| H24 | 0.4365 | 0.1070 | 0.3404 | H64 | 0.6397 | 0.3409 | 0.7359 |
| H25 | 0.1572 | 0.5463 | 0.3811 | H65 | 0.5425 | 0.4558 | 0.7453 |
| H26 | 0.1448 | 0.6232 | 0.3249 | H66 | 0.6027 | 0.3805 | 0.8196 |
| H27 | 0.2732 | 0.5848 | 0.3479 | H67 | 0.4475 | 0.3641 | 0.8070 |
| H28 | 0.0321 | 0.1221 | 0.3561 | H68 | 0.5447 | 0.2493 | 0.7977 |
| H29 | −0.2911 | 0.3104 | 0.2909 | H69 | 0.5039 | 0.3782 | 0.8676 |
| H30 | −0.2750 | 0.3873 | 0.3425 | — | — | — | — |

TABLE 8

Fractional Atomic Coordinates for the SC-3 Form of Example 3 at 203 K

| Atom | X | Y | Z | Atom | X | Y | Z |
|---|---|---|---|---|---|---|---|
| N1 | 0.1570 | 0.4213 | 0.1942 | H31 | 0.8388 | 0.3944 | 1.0532 |
| N2 | −0.0315 | 0.2317 | 0.6493 | N5 | 0.2102 | 0.5634 | 0.9042 |
| N3 | 0.1903 | 0.4273 | 0.3190 | N6 | 0.0593 | 0.5573 | 0.9433 |
| N4 | −0.2863 | 0.4242 | 0.6606 | N7 | 0.6971 | 0.3629 | 0.9849 |
| O1 | 0.0906 | 0.5505 | 0.2631 | O5 | 0.7930 | 0.5301 | 1.1812 |
| O2 | −0.1967 | 0.2858 | 0.7084 | O6 | 0.1619 | 0.6931 | 0.9830 |
| O3 | 0.1916 | −0.0998 | 0.6914 | O7 | 0.6951 | 0.1102 | 0.7641 |
| O4 | 0.2912 | 0.3088 | 0.3759 | O8 | 0.2650 | 0.4290 | 0.8319 |
| F1 | 0.1868 | 0.3082 | 0.0627 | N8 | 0.8455 | 0.4206 | 1.0964 |
| C1 | 0.0225 | 0.3653 | 0.5762 | F2 | −0.1174 | 0.4467 | 0.9306 |
| C2 | 0.0168 | 0.4667 | 0.5376 | C33 | 0.1441 | 0.6086 | 0.9460 |
| C3 | −0.0520 | 0.3337 | 0.6179 | C34 | 0.5868 | 0.4989 | 0.9715 |
| C4 | 0.1428 | 0.4718 | 0.2587 | C35 | 0.6504 | 0.2448 | 0.8780 |
| C5 | 0.2164 | 0.3292 | 0.1899 | C36 | 0.5710 | 0.4167 | 0.9142 |
| C6 | −0.1313 | 0.4018 | 0.6225 | C37 | 0.5080 | 0.4060 | 0.8554 |
| C7 | 0.2640 | 0.2867 | 0.2506 | C38 | 0.7036 | 0.5260 | 1.0714 |
| C8 | 0.1745 | 0.4839 | 0.3863 | C39 | 0.6570 | 0.6256 | 1.0860 |
| C9 | −0.0606 | 0.5343 | 0.5434 | C40 | 0.0419 | 0.4580 | 0.9038 |
| C10 | −0.1324 | 0.5027 | 0.5846 | C41 | 0.5416 | 0.6001 | 0.9882 |
| C11 | 0.1774 | 0.2547 | 0.5587 | C42 | 0.2994 | 0.6226 | 0.9038 |
| C12 | 0.2520 | 0.3394 | 0.3195 | C43 | 0.6416 | 0.3354 | 0.9250 |
| C13 | 0.0540 | 0.1946 | 0.6299 | C44 | 0.3059 | 0.7128 | 0.8585 |
| C14 | 0.1046 | 0.4447 | 0.4266 | C45 | 0.1117 | 0.4091 | 0.8666 |
| C15 | 0.1006 | 0.0953 | 0.6492 | C46 | 0.4640 | 0.7342 | 0.9012 |
| C16 | 0.1865 | 0.0756 | 0.6231 | C47 | 0.5177 | 0.3168 | 0.8092 |
| C17 | 0.2236 | 0.1560 | 0.5784 | C48 | 0.3607 | 0.4829 | 0.9962 |
| C18 | 0.3225 | 0.1931 | 0.2478 | C49 | 0.3897 | 0.7698 | 0.8577 |
| C19 | −0.2066 | 0.3654 | 0.6673 | C50 | 0.4577 | 0.6388 | 0.9454 |
| C20 | 0.2307 | 0.5743 | 0.4063 | C51 | 0.5794 | 0.6627 | 1.0460 |
| C21 | 0.0449 | 0.3462 | 0.4013 | C52 | 0.2015 | 0.4632 | 0.8646 |
| C22 | 0.1469 | 0.5952 | 0.5101 | C53 | 0.3728 | 0.5827 | 0.9479 |
| C23 | 0.0911 | 0.5015 | 0.4906 | C54 | 0.5886 | 0.2366 | 0.8194 |
| C24 | 0.0904 | 0.2761 | 0.5848 | C55 | 0.5985 | 0.1372 | 0.7680 |
| C25 | 0.2297 | 0.2717 | 0.1249 | C56 | 0.7845 | 0.4917 | 1.1194 |
| C26 | 0.2401 | −0.0335 | 0.6421 | C57 | 0.5557 | 0.0311 | 0.7987 |
| C27 | 0.2159 | 0.6310 | 0.4687 | C58 | 0.0973 | 0.3077 | 0.8283 |
| C28 | 0.2850 | 0.1805 | 0.1224 | C59 | 0.5559 | 0.1598 | 0.6932 |
| C29 | 0.3313 | 0.1391 | 0.1829 | C60 | −0.0120 | 0.6151 | 0.9827 |
| C30 | 0.3371 | −0.0081 | 0.6733 | C61 | −0.0587 | 0.3033 | 0.8590 |
| C31 | 0.2432 | −0.1074 | 0.5760 | C62 | −0.0437 | 0.4022 | 0.8984 |
| C32 | 0.1099 | 0.4735 | 0.1320 | C63 | 0.0122 | 0.2563 | 0.8247 |
| O9 | 0.0354 | 0.7400 | 0.8156 | C64 | 0.6671 | 0.4628 | 1.0129 |
| C65 | 0.0216 | 0.6686 | 0.7680 | H32 | 0.6976 | 0.1909 | 0.8862 |
| C66 | −0.0656 | 0.6040 | 0.7608 | H33 | 0.4597 | 0.4586 | 0.8472 |
| C67 | 0.0918 | 0.6435 | 0.7156 | H34 | 0.6795 | 0.6699 | 1.1249 |
| O10 | 0.4880 | 0.5365 | 0.6404 | H35 | 0.2546 | 0.7353 | 0.8286 |
| C68 | 0.4148 | 0.4904 | 0.6227 | H36 | 0.5202 | 0.7742 | 0.9014 |
| C69 | 0.3315 | 0.4914 | 0.6617 | H37 | 0.4752 | 0.3096 | 0.7694 |
| C70 | 0.4115 | 0.4153 | 0.5579 | H38 | 0.3054 | 0.4936 | 1.0219 |
| O11 | 0.6355 | 0.6043 | 0.5633 | H39 | 0.4144 | 0.4767 | 1.0297 |
| O12 | 0.2797 | 0.2536 | 0.7414 | H40 | 0.3546 | 0.4143 | 0.9679 |
| H1 | −0.0669 | 0.1956 | 0.6772 | H41 | 0.3956 | 0.8325 | 0.8276 |
| H2 | −0.3322 | 0.4059 | 0.6859 | H42 | 0.5514 | 0.7312 | 1.0578 |
| H3 | −0.2919 | 0.4807 | 0.6310 | H43 | 0.5614 | −0.0316 | 0.7661 |
| H4 | 0.1973 | −0.0701 | 0.7314 | H44 | 0.4907 | 0.0448 | 0.8054 |
| H5 | −0.0646 | 0.6034 | 0.5188 | H45 | 0.5878 | 0.0129 | 0.8441 |
| H6 | −0.1836 | 0.5513 | 0.5868 | H46 | 0.1463 | 0.2752 | 0.8050 |
| H7 | 0.2038 | 0.3068 | 0.5282 | H47 | 0.5848 | 0.2261 | 0.6737 |
| H8 | 0.0743 | 0.0426 | 0.6792 | H48 | 0.4898 | 0.1730 | 0.6950 |
| H9 | 0.2821 | 0.1424 | 0.5612 | H49 | 0.5659 | 0.0948 | 0.6632 |
| H10 | 0.3556 | 0.1666 | 0.2891 | H50 | 0.0148 | 0.6815 | 1.0063 |
| H11 | 0.2785 | 0.5969 | 0.3779 | H51 | −0.0346 | 0.5639 | 1.0179 |
| H12 | 0.0219 | 0.3588 | 0.3525 | H52 | −0.1175 | 0.6738 | 0.9497 |
| H13 | −0.0070 | 0.3392 | 0.4311 | H53 | −0.1175 | 0.2691 | 0.8559 |
| H14 | 0.0815 | 0.2773 | 0.4042 | H54 | 0.0027 | 0.1887 | 0.7989 |
| H15 | 0.1369 | 0.6342 | 0.5524 | H55 | −0.0992 | 0.6139 | 0.8033 |
| H16 | 0.2528 | 0.6936 | 0.4826 | H56 | −0.0519 | 0.5245 | 0.7545 |
| H17 | 0.2920 | 0.1448 | 0.0784 | H57 | −0.1033 | 0.6314 | 0.7197 |
| H18 | 0.3689 | 0.0745 | 0.1805 | H58 | 0.1290 | 0.7103 | 0.7087 |
| H19 | 0.3338 | 0.0421 | 0.7138 | H59 | 0.0605 | 0.6212 | 0.6706 |
| H20 | 0.3723 | 0.0280 | 0.6375 | H60 | 0.1316 | 0.5822 | 0.6594 |
| H21 | 0.3674 | −0.0781 | 0.6885 | H61 | 0.3302 | 0.4245 | 0.6914 |
| H22 | 0.2723 | −0.1792 | 0.5889 | H62 | 0.2774 | 0.4920 | 0.6283 |
| H23 | 0.2788 | −0.0695 | 0.5412 | H63 | 0.3313 | 0.5585 | 0.6913 |
| H24 | 0.1806 | −0.1207 | 0.5559 | H64 | 0.4545 | 0.4436 | 0.5247 |
| H25 | 0.0724 | 0.5362 | 0.1468 | H65 | 0.3492 | 0.4154 | 0.5353 |
| H26 | 0.0704 | 0.4181 | 0.1070 | H66 | 0.4287 | 0.3389 | 0.5720 |
| H27 | 0.1555 | 0.5011 | 0.1007 | H67 | 0.5897 | 0.5822 | 0.5867 |
| H28 | 0.7439 | 0.3233 | 1.0024 | H68 | 0.6577 | 0.6661 | 0.5815 |
| H29 | 0.7221 | 0.1653 | 0.7476 | H69 | 0.2607 | 0.1931 | 0.7610 |
| H30 | 0.8928 | 0.3998 | 1.1244 | H70 | 0.2753 | 0.3098 | 0.7699 |

TABLE 9

Fractional Atomic Coordinates for the SD-3 Form of Example 3 at 203 K

| Atom | X | Y | Z | Atom | X | Y | Z |
|---|---|---|---|---|---|---|---|
| N1 | −0.0198 | 0.1841 | 0.6526 | H39 | 0.5091 | 0.1296 | 0.7031 |
| C1 | 0.0649 | 0.1518 | 0.6275 | C37 | 0.5141 | 0.3529 | 0.8608 |
| C2 | 0.1155 | 0.0553 | 0.6439 | C38 | 0.5767 | 0.3683 | 0.9162 |
| C3 | 0.1988 | 0.0403 | 0.6124 | C39 | 0.5876 | 0.4510 | 0.9710 |
| C4 | 0.2291 | 0.1216 | 0.5658 | C40 | 0.5389 | 0.5484 | 0.9893 |
| C5 | 0.1785 | 0.2172 | 0.5490 | C41 | 0.5729 | 0.6123 | 1.0451 |
| C6 | 0.0943 | 0.2331 | 0.5800 | C42 | 0.6507 | 0.5804 | 1.0822 |
| C7 | 0.0227 | 0.3172 | 0.5753 | C43 | 0.7007 | 0.4848 | 1.0665 |
| C8 | 0.0103 | 0.4154 | 0.5359 | C44 | 0.6684 | 0.4205 | 1.0092 |
| C9 | −0.0684 | 0.4791 | 0.5459 | C45 | 0.6099 | 0.0869 | 0.7755 |
| C10 | −0.1341 | 0.4455 | 0.5930 | O5 | 0.7045 | 0.0545 | 0.7726 |
| C11 | −0.1258 | 0.3474 | 0.6318 | C46 | 0.5610 | −0.0147 | 0.8052 |
| C12 | −0.0459 | 0.2826 | 0.6223 | C47 | 0.5736 | 0.1104 | 0.7019 |
| C13 | 0.2563 | −0.0642 | 0.6258 | C48 | 0.7841 | 0.4475 | 1.1068 |
| O1 | 0.2137 | −0.1294 | 0.6803 | O6 | 0.8348 | 0.3739 | 1.0850 |
| C14 | 0.2572 | −0.1377 | 0.5619 | N6 | 0.8009 | 0.4968 | 1.1686 |
| C15 | 0.3529 | −0.0333 | 0.6508 | C49 | 0.4556 | 0.5857 | 0.9502 |
| C16 | −0.1945 | 0.3094 | 0.6830 | C50 | 0.3721 | 0.5266 | 0.9541 |
| O2 | −0.1818 | 0.2255 | 0.7187 | C51 | 0.2977 | 0.5689 | 0.9157 |
| N2 | −0.2704 | 0.3724 | 0.6902 | C52 | 0.3032 | 0.6637 | 0.8746 |
| C17 | 0.0802 | 0.4535 | 0.4854 | C53 | 0.3855 | 0.7216 | 0.8718 |
| C18 | 0.0906 | 0.3957 | 0.4215 | C54 | 0.4606 | 0.6827 | 0.9098 |
| C19 | 0.1577 | 0.4370 | 0.3780 | C55 | 0.3620 | 0.4248 | 0.9988 |
| C20 | 0.2001 | 0.5839 | 0.4566 | N7 | 0.2092 | 0.5129 | 0.9187 |
| C21 | 0.2127 | 0.5281 | 0.3946 | C56 | 0.1439 | 0.5646 | 0.9613 |
| C22 | 0.1334 | 0.5461 | 0.5016 | N8 | 0.0559 | 0.5258 | 0.9558 |
| C23 | 0.0321 | 0.2976 | 0.4013 | C57 | 0.0317 | 0.4338 | 0.9143 |
| N3 | 0.1714 | 0.3822 | 0.3110 | C58 | −0.0595 | 0.3969 | 0.9029 |
| C24 | 0.1220 | 0.4251 | 0.2538 | C59 | −0.0805 | 0.3043 | 0.8644 |
| N4 | 0.1390 | 0.3807 | 0.1900 | C60 | −0.0124 | 0.2436 | 0.8338 |
| C25 | 0.2019 | 0.2947 | 0.1812 | C61 | 0.0782 | 0.2781 | 0.8404 |
| C26 | 0.2190 | 0.2429 | 0.1168 | C62 | 0.0999 | 0.3739 | 0.8799 |
| C27 | 0.2780 | 0.1563 | 0.1099 | C63 | 0.1938 | 0.4164 | 0.8800 |
| C28 | 0.3260 | 0.1144 | 0.1673 | O7 | 0.2558 | 0.3752 | 0.8471 |
| C29 | 0.3129 | 0.1632 | 0.2314 | O8 | 0.1670 | 0.6400 | 1.0005 |
| C30 | 0.2511 | 0.2525 | 0.2388 | C64 | −0.0123 | 0.5867 | 0.9965 |
| C31 | 0.2370 | 0.2991 | 0.3072 | F2 | −0.1297 | 0.4555 | 0.9291 |
| O3 | 0.2776 | 0.2680 | 0.3603 | O9 | −0.0315 | 0.6352 | 0.8142 |
| O4 | 0.0646 | 0.4983 | 0.2621 | C65 | 0.0467 | 0.6974 | 0.7957 |
| C32 | 0.0891 | 0.4341 | 0.1312 | C66 | 0.1015 | 0.6235 | 0.7479 |
| F1 | 0.1750 | 0.2791 | 0.0583 | C67 | 0.0324 | 0.5369 | 0.7208 |
| N5 | 0.7040 | 0.3249 | 0.9806 | C68 | −0.0545 | 0.5713 | 0.7529 |
| C33 | 0.6498 | 0.2923 | 0.9241 | O10 | 0.3335 | 0.6673 | 0.6781 |
| C34 | 0.6618 | 0.2025 | 0.8794 | C69 | 0.4290 | 0.6547 | 0.6901 |
| C35 | 0.5996 | 0.1879 | 0.8240 | C70 | 0.4507 | 0.5461 | 0.7165 |
| C36 | 0.5262 | 0.2635 | 0.8159 | C71 | 0.3638 | 0.4820 | 0.7010 |
| C73 | 0.4496 | 0.4500 | 0.4861 | C72 | 0.3053 | 0.5567 | 0.6543 |
| O11 | 0.5228 | 0.4477 | 0.5332 | H40 | 0.5814 | 0.0441 | 0.6734 |
| C74 | 0.4039 | 0.3419 | 0.4916 | H41 | 0.8483 | 0.4767 | 1.1939 |
| C75 | 0.4679 | 0.2645 | 0.5269 | H42 | 0.7643 | 0.5489 | 1.1832 |
| C76 | 0.5347 | 0.3365 | 0.5613 | H43 | 0.2516 | 0.6888 | 0.8487 |
| O12 | 0.2870 | 0.1954 | 0.7523 | H44 | 0.3902 | 0.7866 | 0.8443 |
| O13 | 0.3474 | 0.0553 | 0.3973 | H45 | 0.5162 | 0.7225 | 0.9085 |
| H1 | −0.0511 | 0.1471 | 0.6828 | H46 | 0.3150 | 0.4382 | 1.0324 |
| H2 | 0.0937 | 0.0021 | 0.6756 | H47 | 0.4198 | 0.4092 | 1.0229 |
| H3 | 0.2860 | 0.1111 | 0.5450 | H48 | 0.3448 | 0.3610 | 0.9699 |
| H4 | 0.2007 | 0.2701 | 0.5173 | H49 | −0.1420 | 0.2817 | 0.8586 |
| H5 | −0.0773 | 0.5459 | 0.5205 | H50 | −0.0273 | 0.1784 | 0.8083 |
| H6 | −0.1860 | 0.4910 | 0.5988 | H51 | 0.1247 | 0.2376 | 0.8186 |
| H7 | 0.2210 | −0.1974 | 0.6727 | H52 | 0.0188 | 0.6398 | 1.0272 |
| H8 | 0.2925 | −0.2052 | 0.5718 | H53 | −0.0466 | 0.5335 | 1.0238 |

TABLE 9-continued

Fractional Atomic Coordinates for the SD-3 Form of Example 3 at 203 K

| Atom | X | Y | Z | Atom | X | Y | Z |
|---|---|---|---|---|---|---|---|
| H9  | 0.2847  | −0.0969 | 0.5241 | H54 | −0.0541 | 0.6268 | 0.9652 |
| H10 | 0.1948  | −0.1583 | 0.5485 | H55 | 0.0835  | 0.7171 | 0.8372 |
| H11 | 0.3500  | 0.0056  | 0.6949 | H56 | 0.0283  | 0.7670 | 0.7719 |
| H12 | 0.3808  | 0.0155  | 0.6168 | H57 | 0.1524  | 0.5871 | 0.7733 |
| H13 | 0.3893  | −0.1010 | 0.6563 | H58 | 0.1262  | 0.6675 | 0.7096 |
| H14 | −0.3110 | 0.3535  | 0.7204 | H59 | 0.0268  | 0.5392 | 0.6700 |
| H15 | −0.2788 | 0.4320  | 0.6645 | H60 | 0.0502  | 0.4609 | 0.7354 |
| H16 | 0.2363  | 0.6468  | 0.4684 | H61 | −0.0912 | 0.6170 | 0.7203 |
| H17 | 0.2582  | 0.5518  | 0.3642 | H62 | −0.0903 | 0.5048 | 0.7651 |
| H18 | 0.1247  | 0.5843  | 0.5437 | H63 | 0.4506  | 0.7117 | 0.7235 |
| H19 | −0.0080 | 0.3181  | 0.3622 | H64 | 0.4609  | 0.6666 | 0.6466 |
| H20 | −0.0047 | 0.2756  | 0.4402 | H65 | 0.4647  | 0.5485 | 0.7666 |
| H21 | 0.0709  | 0.2352  | 0.3881 | H66 | 0.5027  | 0.5131 | 0.6926 |
| H22 | 0.2865  | 0.1243  | 0.0659 | H67 | 0.3321  | 0.4653 | 0.7440 |
| H23 | 0.3667  | 0.0538  | 0.1628 | H68 | 0.3774  | 0.4111 | 0.6775 |
| H24 | 0.3458  | 0.1364  | 0.2706 | H69 | 0.3190  | 0.5453 | 0.6052 |
| H25 | 0.0511  | 0.4944  | 0.1483 | H70 | 0.2398  | 0.5441 | 0.6612 |
| H26 | 0.0507  | 0.3786  | 0.1076 | H71 | 0.4713  | 0.4612 | 0.4387 |
| H27 | 0.1327  | 0.4644  | 0.0989 | H72 | 0.4075  | 0.5113 | 0.4970 |
| H28 | 0.7532  | 0.2902  | 0.9956 | H73 | 0.3868  | 0.3132 | 0.4454 |
| H29 | 0.7110  | 0.1524  | 0.8863 | H74 | 0.3480  | 0.3497 | 0.5185 |
| H30 | 0.4839  | 0.2530  | 0.7788 | H75 | 0.4362  | 0.2180 | 0.5608 |
| H31 | 0.4645  | 0.4025  | 0.8541 | H76 | 0.4974  | 0.2152 | 0.4933 |
| H32 | 0.5421  | 0.6785  | 1.0576 | H77 | 0.5254  | 0.3370 | 0.6115 |
| H33 | 0.6708  | 0.6254  | 1.1197 | H78 | 0.5969  | 0.3093 | 0.5530 |
| H34 | 0.7350  | 0.1077  | 0.7576 | H79 | 0.2609  | 0.2108 | 0.7129 |
| H35 | 0.5709  | −0.0795 | 0.7758 | H80 | 0.2777  | 0.2494 | 0.7810 |
| H36 | 0.4958  | 0.0007  | 0.8071 | H81 | 0.3954  | 0.0411 | 0.4226 |
| H37 | 0.5851  | −0.0301 | 0.8517 | H82 | 0.3403  | 0.1269 | 0.3936 |
| H38 | 0.6074  | 0.1726  | 0.6823 | —   | —       | —      | —      |

TABLE 10

Fractional Atomic Coordinates for the M2-4 Form of Example 3 at 203 K

| Atom | X | Y | Z | Atom | X | Y | Z |
|---|---|---|---|---|---|---|---|
| N1  | 0.5372 | 0.4291  | 0.1019  | C32 | 0.9325 | −0.0002 | 0.1354  |
| N2  | 0.5729 | 0.5600  | 0.0850  | N5  | 0.4286 | −0.0679 | 0.1199  |
| N3  | 0.6996 | 0.0893  | −0.0280 | N6  | 0.5674 | −0.1011 | 0.0667  |
| N4  | 0.5416 | 0.1538  | −0.1474 | N7  | 0.4644 | 0.1942  | 0.3210  |
| O1  | 0.6733 | 0.3589  | 0.1382  | N8  | 0.7855 | 0.1073  | 0.3824  |
| O2  | 0.4046 | 0.4982  | 0.0630  | O5  | 0.0087 | 0.3111  | 0.2331  |
| O3  | 0.6342 | 0.0545  | −0.1153 | O6  | 0.2677 | 0.0059  | 0.1067  |
| O4  | 1.0378 | 0.0176  | 0.0699  | O7  | 0.6582 | 0.2053  | 0.3727  |
| F1  | 0.7255 | 0.6914  | 0.0979  | O8  | 0.5853 | −0.1473 | 0.1332  |
| C1  | 0.5589 | 0.1621  | 0.0046  | F2  | 0.6201 | −0.0991 | −0.0223 |
| C2  | 0.6463 | 0.1387  | 0.0356  | C33 | 0.1846 | 0.2541  | 0.2669  |
| C3  | 0.7323 | 0.0946  | 0.0139  | C34 | 0.5188 | 0.1246  | 0.3138  |
| C4  | 0.6422 | 0.4216  | 0.1244  | C35 | 0.4896 | 0.0118  | 0.2693  |
| C5  | 0.5320 | 0.1444  | −0.0718 | C36 | 0.2813 | 0.2601  | 0.2944  |
| C6  | 0.4303 | 0.2531  | 0.0462  | C37 | 0.3916 | −0.0268 | 0.0484  |
| C7  | 0.5955 | 0.1301  | −0.0344 | C38 | 0.4965 | −0.0642 | 0.0361  |
| C8  | 0.8337 | 0.0653  | 0.0339  | C39 | 0.3975 | −0.0728 | 0.1644  |
| C9  | 0.3932 | 0.2216  | −0.0303 | C40 | 0.4262 | −0.0334 | 0.2359  |
| C10 | 0.8501 | 0.0815  | 0.0766  | C41 | 0.6548 | 0.0200  | 0.3192  |
| C11 | 0.4690 | 0.3595  | 0.0923  | C42 | 0.4566 | −0.0253 | 0.1931  |
| C12 | 0.4288 | 0.1889  | −0.0685 | C43 | 0.3635 | 0.2005  | 0.2959  |
| C13 | 0.4935 | 0.3219  | 0.0544  | C44 | 0.3174 | 0.0094  | 0.0191  |
| C14 | 0.4983 | 0.4971  | 0.0822  | C45 | 0.3554 | −0.0278 | 0.0930  |
| C15 | 0.3461 | 0.2264  | 0.0749  | C46 | 0.6216 | 0.0934  | 0.3325  |
| C16 | 0.7623 | 0.1235  | 0.0988  | C47 | 0.3524 | 0.1339  | 0.2711  |
| C17 | 0.4586 | 0.2101  | 0.0065  | C48 | 0.5217 | −0.0634 | −0.0072 |
| C18 | 0.3857 | 0.3326  | 0.1209  | C49 | 0.3406 | −0.0863 | 0.2481  |
| C19 | 0.3236 | 0.2655  | 0.1119  | C50 | 0.5909 | −0.0201 | 0.2887  |
| C20 | 0.7526 | 0.6232  | 0.1152  | C51 | 0.3456 | 0.0090  | −0.0228 |
| C21 | 0.5738 | 0.1130  | −0.1130 | C52 | 0.5310 | −0.1085 | 0.1074  |
| C22 | 0.6768 | 0.5593  | 0.1095  | C53 | 0.4526 | 0.0844  | 0.2826  |
| C23 | 0.7134 | 0.4916  | 0.1297  | C54 | 0.4490 | −0.0283 | −0.0361 |
| C24 | 0.6617 | 0.1520  | 0.0790  | C55 | 0.2568 | 0.1284  | 0.2432  |
| C25 | 0.8171 | 0.4875  | 0.1533  | C56 | 0.6899 | 0.1387  | 0.3640  |
| C26 | 0.9628 | 0.0558  | 0.0999  | C57 | 0.1745 | 0.1888  | 0.2411  |
| C27 | 0.5853 | 0.3524  | 0.0242  | C58 | 0.3125 | −0.1258 | 0.1764  |

TABLE 10-continued

Fractional Atomic Coordinates for the M2-4 Form of Example 3 at 203 K

| Atom | X | Y | Z | Atom | X | Y | Z |
|---|---|---|---|---|---|---|---|
| C28 | 0.8546 | 0.6191  | 0.1387  | C59 | 0.0875  | 0.3163  | 0.2685  |
| C29 | 0.8880 | 0.5516  | 0.1582  | C60 | 0.2825  | −0.1321 | 0.2190  |
| C30 | 1.0293 | 0.1252  | 0.1175  | C61 | 0.5506  | 0.0308  | 0.1786  |
| C31 | 0.5394 | 0.6268  | 0.0584  | C62 | 0.0172  | 0.3085  | 0.3092  |
| C63 | 0.1406 | 0.3971  | 0.2645  | H31 | −0.0321 | 0.2713  | 0.2351  |
| C64 | 0.6840 | −0.1358 | 0.0557  | H32 | 0.2906  | 0.3038  | 0.3116  |
| O9  | 0.6489 | 0.2289  | 0.1856  | H33 | 0.7226  | −0.0033 | 0.3313  |
| C65 | 0.5443 | 0.2369  | 0.2097  | H34 | 0.2474  | 0.0343  | 0.0283  |
| O10 | 0.8593 | 0.1883  | 0.2209  | H35 | 0.3215  | −0.0911 | 0.2769  |
| C66 | 0.8410 | 0.1261  | 0.2471  | H36 | 0.6160  | −0.0698 | 0.2808  |
| O11 | 0.7082 | 0.3027  | 0.4362  | H37 | 0.2956  | 0.0337  | −0.0425 |
| C67 | 0.6814 | 0.2742  | 0.4743  | H38 | 0.4689  | −0.0294 | −0.0650 |
| O12 | 0.9373 | 0.2494  | 0.4177  | H39 | 0.2477  | 0.0847  | 0.2259  |
| C68 | 0.9929 | 0.3124  | 0.4391  | H40 | 0.1104  | 0.1855  | 0.2219  |
| H1  | 0.7386 | 0.0640  | −0.0473 | H41 | 0.2752  | −0.1572 | 0.1562  |
| H2  | 0.5640 | 0.1387  | −0.1724 | H42 | 0.2234  | −0.1672 | 0.2278  |
| H3  | 0.4985 | 0.1952  | −0.1446 | H43 | 0.6220  | 0.0028  | 0.1703  |
| H4  | 1.1052 | 0.0112  | 0.0803  | H44 | 0.5699  | 0.0659  | 0.2015  |
| H5  | 0.8895 | 0.0353  | 0.0189  | H45 | 0.5207  | 0.0599  | 0.1546  |
| H6  | 0.3236 | 0.2520  | −0.0294 | H46 | −0.0431 | 0.3487  | 0.3106  |
| H7  | 0.3819 | 0.1972  | −0.0927 | H47 | 0.0710  | 0.3134  | 0.3331  |
| H8  | 0.3038 | 0.1808  | 0.0689  | H48 | −0.0214 | 0.2584  | 0.3101  |
| H9  | 0.7727 | 0.1323  | 0.1279  | H49 | 0.1799  | 0.4022  | 0.2373  |
| H10 | 0.3714 | 0.3595  | 0.1462  | H50 | 0.1983  | 0.4053  | 0.2869  |
| H11 | 0.2662 | 0.2468  | 0.1310  | H51 | 0.0772  | 0.4351  | 0.2667  |
| H12 | 0.6043 | 0.1799  | 0.0944  | H52 | 0.7256  | −0.1503 | 0.0814  |
| H13 | 0.8394 | 0.4407  | 0.1661  | H53 | 0.7317  | −0.0987 | 0.0401  |
| H14 | 0.5698 | 0.4065  | 0.0187  | H54 | 0.6712  | −0.1812 | 0.0384  |
| H15 | 0.5812 | 0.3238  | −0.0021 | H55 | 0.6553  | 0.2663  | 0.1693  |
| H16 | 0.6644 | 0.3467  | 0.0364  | H56 | 0.5545  | 0.2109  | 0.2366  |
| H17 | 0.9028 | 0.6632  | 0.1416  | H57 | 0.4775  | 0.2142  | 0.1947  |
| H18 | 0.9582 | 0.5494  | 0.1745  | H58 | 0.5286  | 0.2912  | 0.2146  |
| H19 | 1.1035 | 0.1082  | 0.1305  | H59 | 0.7953  | 0.2007  | 0.2095  |
| H20 | 0.9801 | 0.1507  | 0.1385  | H60 | 0.9150  | 0.0973  | 0.2499  |
| H21 | 1.0471 | 0.1609  | 0.0948  | H61 | 0.7798  | 0.0930  | 0.2350  |
| H22 | 0.4734 | 0.6127  | 0.0400  | H62 | 0.8152  | 0.1440  | 0.2746  |
| H23 | 0.6076 | 0.6420  | 0.0413  | H63 | 0.6689  | 0.2796  | 0.4178  |
| H24 | 0.5157 | 0.6695  | 0.0763  | H64 | 0.7099  | 0.3093  | 0.4960  |
| H25 | 0.8947 | −0.0457 | 0.1237  | H65 | 0.7195  | 0.2244  | 0.4778  |
| H26 | 0.8782 | 0.0245  | 0.1551  | H66 | 0.5953  | 0.2684  | 0.4768  |
| H27 | 1.0052 | −0.0149 | 0.1500  | H67 | 0.8638  | 0.2544  | 0.4197  |
| H28 | 0.4895 | 0.2290  | 0.3387  | H68 | 0.9414  | 0.3299  | 0.4619  |
| H29 | 0.8263 | 0.1335  | 0.4008  | H69 | 1.0060  | 0.3543  | 0.4193  |
| H30 | 0.8068 | 0.0604  | 0.3760  | H70 | 1.0691  | 0.2959  | 0.4506  |

TABLE 11

Fractional Atomic Coordinates for the AN-5 Form of Example 3 at 203 K

| Atom | X | Y | Z | Atom | X | Y | Z |
|---|---|---|---|---|---|---|---|
| N1  | 0.9924  | 0.6814 | 0.0947 | C29 | 0.4287  | 0.2860 | 0.2241  |
| C1  | 1.0444  | 0.8258 | 0.1951 | C30 | 0.2467  | 0.5974 | 0.7121  |
| C2  | 1.0161  | 0.7433 | 0.1389 | C31 | −0.1039 | 0.0566 | 0.5110  |
| N2  | 0.2704  | 0.1624 | 0.4096 | C32 | 0.3565  | 0.2030 | 0.1964  |
| N3  | −0.0856 | 0.3512 | 0.6256 | C33 | 0.4392  | 0.3250 | 0.2896  |
| N4  | 0.3894  | 0.3101 | 0.3969 | C34 | 0.4583  | 0.4081 | 0.4282  |
| N5  | −0.3954 | 0.1970 | 0.5396 | F1  | 0.5134  | 0.4072 | 0.3147  |
| O1  | −0.2963 | 0.3045 | 0.6238 | N6  | 0.2289  | 0.5532 | 0.0900  |
| O2  | 0.1787  | 0.0573 | 0.3196 | N7  | 0.5870  | 0.3648 | −0.1210 |
| O3  | 0.3553  | 0.5578 | 0.7487 | N8  | 0.2074  | 0.5299 | 0.1999  |
| O4  | 0.3596  | 0.2732 | 0.4995 | O5  | 0.3183  | 0.6700 | 0.1776  |
| C3  | 0.3036  | 0.1895 | 0.2999 | O6  | 0.1487  | 0.1663 | −0.2511 |
| C4  | 0.2207  | 0.1026 | 0.4556 | O7  | 0.1375  | 0.4413 | 0.0027  |
| C5  | 0.0214  | 0.3845 | 0.6351 | O35 | 0.6077  | 0.4649 | −0.0814 |
| C6  | 0.1428  | −0.0166 | 0.5477 | C36 | 0.3230  | 0.2303 | −0.1785 |
| C7  | 0.1268  | 0.1400 | 0.4661 | C37 | 0.2557  | 0.1306 | −0.2138 |
| C8  | 0.0878  | 0.0774 | 0.5149 | C38 | 0.3687  | 0.5793 | 0.0337  |
| C9  | 0.2336  | 0.4103 | 0.6439 | C39 | 0.1457  | 0.4328 | 0.1807  |
| C10 | 0.3783  | 0.2770 | 0.3299 | C40 | 0.4083  | 0.6392 | −0.0146 |
| C11 | 0.3417  | 0.2516 | 0.4390 | C41 | 0.2664  | 0.3150 | −0.1487 |
| C12 | 0.0763  | 0.4797 | 0.6715 | C42 | 0.1202  | 0.3970 | 0.1125  |
| C13 | 0.0710  | 0.2412 | 0.4289 | C43 | 0.4283  | 0.2447 | −0.1714 |

TABLE 11-continued

Fractional Atomic Coordinates for the AN-5 Form of Example 3 at 203 K

| Atom | X | Y | Z | Atom | X | Y | Z |
|---|---|---|---|---|---|---|---|
| C14 | 0.0696 | 0.3046 | 0.6030 | C44 | 0.3527 | 0.7332 | −0.0501 |
| C15 | −0.0111 | 0.2197 | 0.5704 | C45 | 0.4300 | 0.4229 | −0.1029 |
| C16 | 0.2697 | 0.6789 | 0.6598 | C46 | 0.5103 | 0.5026 | −0.0711 |
| C17 | −0.2038 | 0.1910 | 0.5624 | C47 | 0.4308 | 0.4781 | 0.0734 |
| C18 | 0.1798 | 0.3155 | 0.6093 | C48 | 0.7037 | 0.5215 | −0.0556 |
| C19 | 0.2459 | 0.1309 | 0.3417 | C49 | 0.1023 | 0.3670 | 0.2238 |
| C20 | −0.1068 | 0.2516 | 0.5868 | C50 | 0.2162 | 0.7098 | 0.0072 |
| C21 | −0.0097 | 0.1194 | 0.5318 | C51 | 0.6074 | 0.6611 | −0.0035 |
| C22 | 0.1846 | 0.4911 | 0.6758 | C52 | 0.2327 | 0.0386 | −0.1643 |
| C23 | 0.2767 | 0.0071 | 0.4870 | C53 | 0.0612 | 0.2994 | 0.0903 |
| C24 | 0.2368 | −0.0556 | 0.5365 | C54 | 0.3045 | 0.0704 | −0.2675 |
| C25 | −0.3011 | 0.2350 | 0.5771 | C55 | 0.4819 | 0.3364 | −0.1343 |
| C26 | 0.2975 | 0.1513 | 0.2349 | C56 | 0.5106 | 0.6026 | −0.0292 |
| C27 | 0.1973 | 0.6564 | 0.7593 | C57 | 0.7010 | 0.6216 | −0.0164 |
| C28 | −0.1980 | 0.0929 | 0.5244 | C58 | 0.2553 | 0.7676 | −0.0395 |
| C59 | 0.3212 | 0.4044 | −0.1104 | H24 | −0.2605 | 0.0489 | 0.5069 |
| C60 | 0.0456 | 0.2675 | 0.2020 | H25 | 0.4722 | 0.3176 | 0.1985 |
| C61 | 0.2545 | 0.5879 | 0.1583 | H26 | −0.1042 | −0.0131 | 0.4870 |
| C62 | 0.2729 | 0.6182 | 0.0426 | H27 | 0.3467 | 0.1807 | 0.1508 |
| C63 | 0.1595 | 0.4650 | 0.0629 | H28 | 0.5324 | 0.3890 | 0.4318 |
| C64 | 0.0194 | 0.2342 | 0.1342 | H29 | 0.4499 | 0.4229 | 0.4733 |
| C65 | 0.2320 | 0.5767 | 0.2708 | H30 | 0.4380 | 0.4770 | 0.4002 |
| F2 | 0.1269 | 0.3898 | 0.2910 | H31 | 0.6344 | 0.3260 | −0.1352 |
| C66 | 0.8052 | 0.4782 | −0.0676 | H32 | 0.1523 | 0.2136 | −0.2812 |
| O8 | 0.8000 | 0.4141 | −0.1178 | H33 | 0.1921 | 0.3084 | −0.1556 |
| N9 | 0.8982 | 0.5101 | −0.0263 | H34 | 0.4653 | 0.1918 | −0.1920 |
| N10 | −0.4881 | 0.0375 | 0.4096 | H35 | 0.3808 | 0.7741 | −0.0813 |
| C67 | −0.5475 | −0.0890 | 0.2994 | H36 | 0.4027 | 0.4056 | 0.0513 |
| C68 | −0.5145 | −0.0213 | 0.3629 | H37 | 0.4236 | 0.4788 | 0.1196 |
| H1 | 0.9974 | 0.8929 | 0.1843 | H38 | 0.5057 | 0.4852 | 0.0746 |
| H2 | 1.1180 | 0.8506 | 0.2021 | H39 | 0.1510 | 0.7326 | 0.0150 |
| H3 | 1.0364 | 0.7890 | 0.2362 | H40 | 0.6092 | 0.7284 | 0.0229 |
| H4 | −0.1316 | 0.3880 | 0.6419 | H41 | 0.1960 | 0.0751 | −0.1342 |
| H5 | −0.4539 | 0.2212 | 0.5481 | H42 | 0.2997 | 0.0054 | −0.1376 |
| H6 | −0.3985 | 0.1480 | 0.5067 | H43 | 0.1880 | −0.0224 | −0.1902 |
| H7 | 0.3557 | 0.5357 | 0.7875 | H44 | 0.0488 | 0.2761 | 0.0447 |
| H8 | 0.1152 | −0.0565 | 0.5794 | H45 | 0.2533 | 0.0152 | −0.2940 |
| H9 | 0.3062 | 0.4204 | 0.6458 | H46 | 0.3696 | 0.0300 | −0.2441 |
| H10 | 0.0412 | 0.5340 | 0.6923 | H47 | 0.3205 | 0.1288 | −0.2976 |
| H11 | 0.1218 | 0.3039 | 0.4311 | H48 | 0.7648 | 0.6631 | 0.0017 |
| H12 | 0.0156 | 0.2664 | 0.4494 | H49 | 0.2168 | 0.8300 | −0.0643 |
| H13 | 0.0389 | 0.2202 | 0.3817 | H50 | 0.2843 | 0.4550 | −0.0885 |
| H14 | 0.3070 | 0.7471 | 0.6825 | H51 | 0.0239 | 0.2208 | 0.2336 |
| H15 | 0.2029 | 0.7025 | 0.6279 | H52 | −0.0250 | 0.1698 | 0.1184 |
| H16 | 0.3140 | 0.6397 | 0.6354 | H53 | 0.2810 | 0.6418 | 0.2753 |
| H17 | 0.2159 | 0.2594 | 0.5904 | H54 | 0.2647 | 0.5161 | 0.3029 |
| H18 | 0.3396 | −0.0171 | 0.4765 | H55 | 0.1663 | 0.6025 | 0.2801 |
| H19 | 0.2735 | −0.1202 | 0.5600 | H56 | 0.9575 | 0.4863 | −0.0338 |
| H20 | 0.2522 | 0.0887 | 0.2165 | H57 | 0.9001 | 0.5548 | 0.0085 |
| H21 | 0.2471 | 0.7127 | 0.7859 | H58 | −0.6241 | −0.0805 | 0.2796 |
| H22 | 0.1791 | 0.5998 | 0.7895 | H59 | −0.5305 | −0.1704 | 0.3092 |
| H23 | 0.1329 | 0.6961 | 0.7337 | H60 | −0.5100 | −0.0607 | 0.2675 |

TABLE 12

Fractional Atomic Coordinates for the H1-6 Form of Example 3 at Room Temperature

| Atom | X | Y | Z | Atom | X | Y | Z |
|---|---|---|---|---|---|---|---|
| N1 | 0.6135 | 0.3022 | 0.1291 | C31 | −0.0330 | 0.1910 | 0.5041 |
| C1 | 0.4861 | 0.2699 | 0.1329 | O3 | 0.2583 | 0.6097 | 0.4356 |
| C2 | 0.5140 | 0.4378 | 0.1846 | O4 | 0.0757 | 0.3581 | 0.3067 |
| C3 | 0.6315 | 0.4018 | 0.1603 | C32 | 0.1334 | 0.5294 | 0.5329 |
| C4 | 0.2928 | 0.3371 | 0.1767 | F1 | 0.0468 | 0.3260 | 0.5710 |
| C5 | 0.7320 | 0.5647 | 0.2046 | O5 | 0.0547 | 0.2775 | 0.0276 |
| C6 | 0.5076 | 0.5372 | 0.2202 | H1 | 0.6712 | 0.2650 | 0.1101 |
| C7 | 0.7432 | 0.4642 | 0.1716 | H2 | 0.2472 | 0.3892 | 0.1998 |
| C8 | 0.6172 | 0.5979 | 0.2282 | H3 | 0.8030 | 0.6105 | 0.2108 |
| C9 | 0.2279 | 0.0573 | 0.0899 | H4 | 0.6141 | 0.6650 | 0.2510 |
| C10 | 0.2980 | 0.1613 | 0.1160 | H5 | 0.4721 | 0.1244 | 0.0847 |
| C11 | 0.4263 | 0.1768 | 0.1076 | H6 | 0.1480 | 0.2331 | 0.1574 |
| C12 | 0.4222 | 0.3523 | 0.1670 | H7 | 0.0768 | 0.1355 | 0.0730 |
| C13 | 0.2343 | 0.2429 | 0.1511 | H8 | 0.2225 | −0.0310 | 0.0119 |
| O1 | 0.0939 | 0.0773 | 0.0920 | H9 | 0.3587 | 0.0122 | 0.0281 |
| C14 | 0.8643 | 0.4211 | 0.1477 | H10 | 0.2580 | 0.0991 | 0.0032 |
| C15 | 0.2706 | 0.0322 | 0.0277 | H11 | 0.2049 | −0.0285 | 0.1687 |
| C16 | 0.2430 | −0.0453 | 0.1308 | H12 | 0.3313 | −0.0611 | 0.1363 |
| O2 | 0.8692 | 0.3628 | 0.1024 | H13 | 0.2025 | −0.1111 | 0.1134 |
| N2 | 0.9694 | 0.4487 | 0.1781 | H14 | 1.0421 | 0.4253 | 0.1657 |
| C17 | 0.1540 | 0.6355 | 0.2977 | H15 | 0.9643 | 0.4898 | 0.2101 |
| C18 | 0.3384 | 0.5117 | 0.2978 | H16 | 0.0771 | 0.6566 | 0.3146 |
| C19 | 0.2228 | 0.5440 | 0.3210 | H17 | 0.4163 | 0.4214 | 0.3666 |
| C20 | 0.4078 | 0.4106 | 0.3243 | H18 | 0.4902 | 0.4048 | 0.3066 |
| C21 | 0.3158 | 0.6634 | 0.2252 | H19 | 0.3612 | 0.3411 | 0.3167 |
| C22 | 0.3847 | 0.5718 | 0.2479 | H20 | 0.3480 | 0.7048 | 0.1931 |
| C23 | 0.2007 | 0.6947 | 0.2493 | H21 | 0.1550 | 0.7554 | 0.2328 |
| N3 | 0.1708 | 0.4804 | 0.3708 | H22 | −0.0158 | 0.1842 | 0.3610 |
| C24 | 0.1923 | 0.5250 | 0.4285 | H23 | −0.0940 | 0.0839 | 0.4407 |
| N4 | 0.1385 | 0.4665 | 0.4747 | H24 | −0.0618 | 0.1478 | 0.5364 |
| C25 | 0.0982 | 0.3838 | 0.3581 | H25 | 0.1867 | 0.4912 | 0.5615 |
| C26 | 0.0546 | 0.3187 | 0.4093 | H26 | 0.0479 | 0.5303 | 0.5474 |
| C27 | −0.0062 | 0.2128 | 0.3995 | H27 | 0.1623 | 0.6071 | 0.5273 |
| C28 | 0.0269 | 0.2925 | 0.5133 | H28 | 0.0015 | 0.3180 | 0.0477 |
| C29 | 0.0754 | 0.3609 | 0.4673 | H29 | 0.0981 | 0.3219 | 0.0046 |
| C30 | −0.0507 | 0.1524 | 0.4471 | — | — | — | — |

TABLE 13

Fractional Atomic Coordinates for the E-7 Form of Example 3 at Room Temperature

| Atom | X | Y | Z | Atom | X | Y | Z |
|---|---|---|---|---|---|---|---|
| O1 | 0.6824 | 0.3544 | −0.0493 | O4 | 0.6263 | 0.4869 | 0.1391 |
| N1 | 0.4205 | −0.0993 | 0.0594 | F1 | 0.3561 | 0.6987 | 0.0032 |
| C1 | 0.5324 | 0.0321 | 0.0919 | O5 | 0.5820 | 0.2157 | −0.2431 |
| C2 | 0.5663 | 0.0175 | 0.0275 | C33 | 0.8341 | 0.1921 | −0.2520 |
| C3 | 0.5679 | 0.1009 | 0.1351 | C34 | 0.7180 | 0.2426 | −0.2245 |
| C4 | 0.4436 | −0.0426 | 0.1097 | H1 | 0.3690 | −0.1486 | 0.0592 |
| C5 | 0.5164 | 0.0920 | 0.1944 | H2 | 0.5391 | 0.1372 | 0.2236 |
| C6 | 0.4996 | −0.0984 | −0.0510 | H3 | 0.4497 | −0.1516 | −0.0622 |
| C7 | 0.3931 | −0.0524 | 0.1701 | H4 | 0.6981 | 0.1165 | −0.0051 |
| C8 | 0.6483 | 0.0631 | −0.0159 | H5 | 0.3995 | 0.0145 | 0.2520 |
| C9 | 0.4317 | 0.0177 | 0.2115 | H6 | 0.7110 | 0.0591 | −0.1039 |
| C10 | 0.4935 | −0.0646 | 0.0087 | H7 | 0.6082 | −0.2139 | −0.1504 |
| C11 | 0.5823 | −0.0841 | −0.1616 | H8 | 0.7912 | −0.1056 | −0.1717 |
| C12 | 0.6552 | 0.0284 | −0.0752 | H9 | 0.7449 | −0.0051 | −0.1927 |
| C13 | 0.5815 | −0.0516 | −0.0940 | H10 | 0.7148 | −0.0919 | −0.2351 |
| O2 | 0.5447 | −0.1820 | −0.1647 | H11 | 0.4638 | −0.0550 | −0.2376 |
| C14 | 0.3048 | −0.1336 | 0.1871 | H12 | 0.4842 | 0.0326 | −0.1948 |
| C15 | 0.7209 | −0.0704 | −0.1931 | H13 | 0.3794 | −0.0467 | −0.1758 |
| C16 | 0.4669 | −0.0337 | −0.1955 | H14 | 0.2148 | −0.1898 | 0.2567 |
| O3 | 0.2688 | −0.1909 | 0.1469 | H15 | 0.2921 | −0.1026 | 0.2729 |
| N2 | 0.2660 | −0.1431 | 0.2459 | H16 | 0.8965 | 0.3781 | 0.0762 |
| C17 | 0.6970 | 0.3338 | 0.0749 | H17 | 0.9840 | 0.2455 | 0.1237 |
| C18 | 0.6598 | 0.1816 | 0.1177 | H18 | 0.8374 | 0.1249 | 0.1501 |
| C19 | 0.6044 | 0.2621 | 0.0886 | H19 | 0.4180 | 0.3287 | 0.0884 |
| C20 | 0.8376 | 0.3289 | 0.0869 | H20 | 0.4033 | 0.2194 | 0.0921 |
| C21 | 0.8893 | 0.2501 | 0.1151 | H21 | 0.4415 | 0.2674 | 0.0292 |
| C22 | 0.8013 | 0.1777 | 0.1306 | H22 | 0.5777 | 0.4563 | −0.1337 |
| C23 | 0.4533 | 0.2701 | 0.0732 | H23 | 0.3388 | 0.6831 | −0.1114 |
| N3 | 0.6426 | 0.4177 | 0.0452 | H24 | 0.4452 | 0.5759 | −0.1760 |
| N4 | 0.5461 | 0.5682 | 0.0566 | H25 | 0.4493 | 0.6677 | 0.1067 |
| C24 | 0.6057 | 0.4911 | 0.0838 | H26 | 0.5777 | 0.7063 | 0.0699 |
| C25 | 0.6371 | 0.4197 | −0.0189 | H27 | 0.6008 | 0.6468 | 0.1300 |
| C26 | 0.5645 | 0.5001 | −0.0452 | H28 | 0.5538 | 0.2519 | −0.2697 |
| C27 | 0.5108 | 0.5688 | −0.0062 | H29 | 0.8006 | 0.1353 | −0.2706 |
| C28 | 0.5396 | 0.5022 | −0.1083 | H30 | 0.9012 | 0.1771 | −0.2206 |
| C29 | 0.3972 | 0.6374 | −0.0950 | H31 | 0.8772 | 0.2306 | −0.2830 |
| C30 | 0.4217 | 0.6349 | −0.0335 | H32 | 0.7242 | 0.2357 | −0.1800 |
| C31 | 0.4584 | 0.5725 | −0.1335 | H33 | 0.7295 | 0.3087 | −0.2337 |
| C32 | 0.5432 | 0.6548 | 0.0941 | — | — | — | — |

TABLE 14

Fractional Atomic Coordinates for the SE-8 Form of Example 3 at 203 K

| Atom | X | Y | Z | Atom | X | Y | Z |
|---|---|---|---|---|---|---|---|
| C1 | 0.6880 | 0.4895 | 0.0251 | F1 | 0.8275 | 0.6234 | 0.0070 |
| C2 | 0.7552 | 0.5380 | 0.0028 | O5 | 0.7464 | 0.6231 | 0.2276 |
| C3 | 0.7467 | 0.4943 | −0.0255 | C33 | 0.6902 | 0.5401 | 0.2462 |
| C4 | 0.6708 | 0.4021 | −0.0316 | C34 | 0.7150 | 0.5706 | 0.2775 |
| C5 | 0.6035 | 0.3535 | −0.0093 | O6 | 0.6752 | 0.7322 | 0.1413 |
| C6 | 0.6121 | 0.3972 | 0.0191 | H1 | 0.7921 | 0.5273 | −0.0406 |
| C7 | 0.3643 | 0.2900 | 0.1269 | H2 | 0.6650 | 0.3726 | −0.0507 |
| C8 | 0.4170 | 0.3504 | 0.1039 | H3 | 0.5522 | 0.2911 | −0.0133 |
| C9 | 0.5266 | 0.3158 | 0.0938 | H4 | 0.6573 | 0.1972 | 0.0996 |
| C10 | 0.5832 | 0.2207 | 0.1065 | H5 | 0.5688 | 0.0960 | 0.1380 |
| C11 | 0.5306 | 0.1603 | 0.1294 | H6 | 0.3854 | 0.1541 | 0.1551 |
| C12 | 0.4210 | 0.1950 | 0.1396 | H7 | −0.0332 | 0.2640 | 0.1374 |
| C13 | 0.1300 | 0.4652 | 0.1674 | H8 | 0.1482 | 0.1999 | 0.1202 |
| C14 | 0.0286 | 0.4043 | 0.1600 | H9 | 0.4867 | 0.4668 | 0.1548 |
| C15 | 0.0354 | 0.3052 | 0.1424 | H10 | 0.5825 | 0.6252 | 0.1764 |
| C16 | 0.1436 | 0.2669 | 0.1321 | H11 | 0.2732 | 0.7447 | 0.2073 |
| C17 | 0.2450 | 0.3278 | 0.1395 | H12 | 0.0862 | 0.6034 | 0.1927 |
| C18 | 0.2382 | 0.4269 | 0.1571 | H13 | 0.6506 | 0.7546 | 0.2134 |
| C19 | 0.3228 | 0.5112 | 0.1682 | H14 | 0.5057 | 0.9864 | 0.1989 |
| C20 | 0.4437 | 0.5229 | 0.1654 | H15 | 0.3763 | 0.9376 | 0.1959 |
| C21 | 0.5007 | 0.6173 | 0.1783 | H16 | 0.4691 | 0.9135 | 0.1708 |
| C22 | 0.4371 | 0.7002 | 0.1939 | H17 | 0.4861 | 0.7392 | 0.2492 |
| C23 | 0.3163 | 0.6886 | 0.1967 | H18 | 0.3970 | 0.8441 | 0.2444 |
| C24 | 0.2591 | 0.5942 | 0.1838 | H19 | 0.5323 | 0.8703 | 0.2489 |
| N1 | 0.5788 | 0.3772 | 0.0703 | H20 | −0.2559 | 0.4447 | 0.1644 |
| C25 | 0.6524 | 0.4709 | 0.0765 | H21 | −0.1866 | 0.3825 | 0.1410 |
| N2 | 0.6947 | 0.5340 | 0.0536 | H22 | 0.3953 | 0.5254 | 0.0939 |
| C26 | 0.5487 | 0.3391 | 0.0424 | H23 | 0.2744 | 0.4594 | 0.0983 |
| N3 | 0.1422 | 0.5653 | 0.1839 | H24 | 0.3468 | 0.4413 | 0.0690 |
| C27 | 0.4954 | 0.8081 | 0.2072 | H25 | 0.7654 | 0.6513 | 0.0825 |
| O1 | 0.6204 | 0.8022 | 0.2018 | H26 | 0.7185 | 0.7116 | 0.0535 |
| C28 | −0.0859 | 0.4524 | 0.1712 | H27 | 0.8383 | 0.6413 | 0.0531 |
| C29 | 0.4582 | 0.9219 | 0.1918 | H28 | 0.7944 | 0.5848 | 0.2177 |
| C30 | 0.4759 | 0.8162 | 0.2405 | H29 | 0.7195 | 0.4611 | 0.2419 |
| N4 | −0.1888 | 0.4229 | 0.1571 | H30 | 0.6054 | 0.5410 | 0.2426 |
| O2 | −0.0947 | 0.5096 | 0.1939 | H31 | 0.7976 | 0.5861 | 0.2800 |
| C31 | 0.3525 | 0.4536 | 0.0900 | H32 | 0.6917 | 0.5056 | 0.2900 |
| O3 | 0.4758 | 0.2620 | 0.0383 | H33 | 0.6700 | 0.6399 | 0.2829 |
| O4 | 0.6661 | 0.4992 | 0.1019 | H34 | 0.6529 | 0.7372 | 0.1591 |
| C32 | 0.7600 | 0.6443 | 0.0614 | H35 | 0.6645 | 0.6624 | 0.1349 |

What is claimed is:

1. A compound of Formula (I):

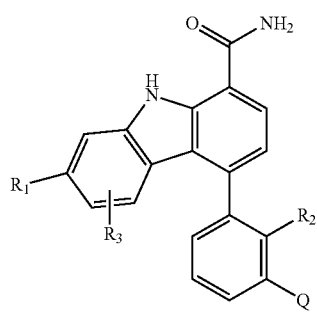

(I)

or a salt thereof, wherein:
Q is:

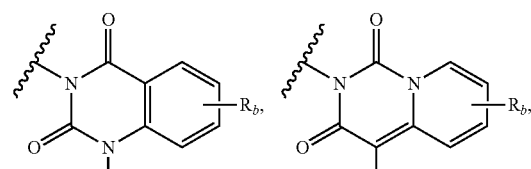

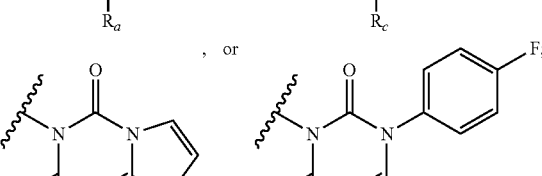

$R_1$ is —C(CH$_3$)$_2$OH, —NHC(=O)C(CH$_3$)$_3$, —N(CH$_3$)$_2$, or —CH$_2$R$_d$;
$R_2$ is Cl or —CH$_3$;
$R_3$ is H, F, or —CH$_3$;
$R_a$ is H or —CH$_3$;
$R_b$ is H, F, Cl, or —OCH$_3$;
$R_c$ is H or F; and
$R_d$ is —OH, —OCH$_3$, —NHC(=O)CH$_3$, or

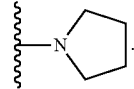

2. The compound according to claim 1 or a salt thereof, wherein:
Q is:

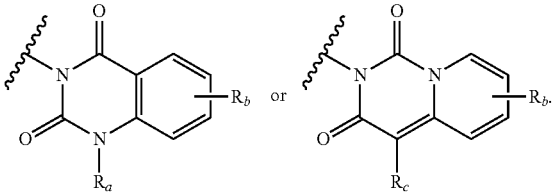

3. The compound according to claim 1 or a salt thereof, wherein:
$R_a$ is —CH$_3$;
$R_b$ is F, Cl, or —OCH$_3$; and
$R_c$ is F.

4. The compound according to claim 1 or a salt thereof, wherein:
$R_2$ is —CH$_3$.

5. The compound according to claim 1 wherein:
Q is:

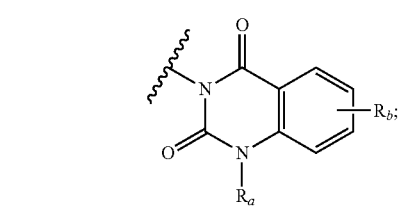

and
$R_1$ is C(CH$_3$)$_2$OH.

6. The compound according to claim 1 or a salt thereof, wherein:

Q is:

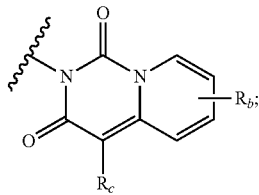

R$_2$ is —CH$_3$; and
R$_3$ is H.

7. The compound according to claim 1 wherein said compound is selected from: 4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (1 and 2); 4-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (3); 4-(3-(S)-(8-fluoro-1-methyl (d$_3$)-2,4-dioxo-1,2-dihydroquinazoline-3(4H)-yl)-2-methylphenyl)-7-(2-hydroxypropan-2-yl)-9H-carbazole-1-carboxamide (4); 4-(2-chloro-3-(8-fluoro-1-methyl-2,4-dioxo-1,2-dihydroquinazolin-3(4H)-yl)phenyl)-7-(2-hydroxypropan-2-yl)-9H-carbazole-1-carboxamide (5); 4-(2-chloro-3-(1-methyl-2,4-dioxo-1,2-dihydroquinazolin-3(4H)-yl)phenyl)-7-(2-hydroxypropan-2-yl)-9H-carbazole-1-carboxamide (6); 7-(2-hydroxypropan-2-yl)-4-(3-(8-methoxy-1-methyl-2,4-dioxo-1,2-dihydroquinazolin-3(4H)-yl)-2-methylphenyl)-9H-carbazole-1-carboxamide (7); 4-(3-(6-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (8); 4-(3-(3-(4-fluorophenyl)-2,6-dioxo-2,3-dihydropyrimidin-1(6H)-yl)-2-methylphenyl)-7-(2-hydroxypropan-2-yl)-9H-carbazole-1-carboxamide (9); 7-(2-hydroxypropan-2-yl)-4-(3-(7-methoxy-1,3-dioxo-1H-pyrido[1,2-c]pyrimidin-2(3H)-yl)-2-methylphenyl)-9H-carbazole-1-carboxamide (10); 7-(2-hydroxypropan-2-yl)-4-(3-(6-methoxy-1,3-dioxo-1H-pyrido[1,2-c]pyrimidin-2(3H)-yl)-2-methylphenyl)-9H-carbazole-1-carboxamide (11); 7-(2-hydroxypropan-2-yl)-4-(3-(5-methoxy-1,3-dioxo-1H-pyrido[1,2-c]pyrimidin-2(3H)-yl)-2-methylphenyl)-9H-carbazole-1-carboxamide (12); 4-(3-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (13); 4-(3-(R)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (14); 4-(3-(S)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (15); 4-(3-(5-chloro-1,3-dioxo-1H-pyrido[1,2-c]pyrimidin-2(3H)-yl)-2-methylphenyl)-7-pivalamido-9H-carbazole-1-carboxamide (16); 4-(3-(5-chloro-1,3-dioxo-1H-pyrido[1,2-c]pyrimidin-2(3H)-yl)-2-methylphenyl)-7-(methoxymethyl)-9H-carbazole-1-carboxamide (17); 4-(3-(5-fluoro-1,3-dioxo-1H-pyrido[1,2-c]pyrimidin-2(3H)-yl)-2-methylphenyl)-7-(methoxymethyl)-9H-carbazole-1-carboxamide (18); 4-(3-(4-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (19); 4-(3-(5,7-dioxo-5H-thiazolo[3,2-c]pyrimidin-6(7H)-yl)-2-methylphenyl)-7-(2-hydroxypropan-2-yl)-9H-carbazole-1-carboxamide (20); 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (21); 4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (22 and 23); 4-(3-(S)-(8-fluoro-1-methyl-2,4-dioxo-1,2-dihydroquinazolin-3(4H)-yl)-2-methylphenyl)-7-(2-hydroxypropan-2-yl)-5-methyl-9H-carbazole-1-carboxamide (24); 4-(3-(8-fluoro-1-methyl-2,4-dioxo-1,2-dihydroquinazolin-3(4H)-yl)-2-methylphenyl)-7-(2-hydroxypropan-2-yl)-5-methyl-9H-carbazole-1-carboxamide (25); 4-(3-(S)-(8-fluoro-1-methyl-2,4-dioxo-1,2-dihydroquinazolin-3(4H)-yl)-2-methylphenyl)-7-(2-hydroxypropan-2-yl)-8-methyl-9H-carbazole-1-carboxamide (26); 4-(3-(S)-(8-fluoro-1-methyl(d$_3$)-2,4-dioxo-1,2-dihydroquinazolin-3(4H)-yl)-2-methylphenyl)-7-(2-hydroxypropan-2-yl)-5-methyl-9H-carbazole-1-carboxamide (27); 4-(3-(5-fluoro-1,3-dioxo-1H-pyrido[1,2-c]pyrimidin-2(3H)-yl)-2-methylphenyl)-7-(hydroxymethyl)-9H-carbazole-1-carboxamide (28); 7-(dimethylamino)-4-(3-(5-fluoro-1,3-dioxo-1H-pyrido[1,2-c]pyrimidin-2(3H)-yl)-2-methylphenyl)-9H-carbazole-1-carboxamide (29); 7-(acetamidomethyl)-4-(3-(5-fluoro-1,3-dioxo-1H-pyrido[1,2-c]pyrimidin-2(3H)-yl)-2-methylphenyl)-9H-carbazole-1-carboxamide (30); 4-(3-(5-chloro-1,3-dioxo-1H-pyrido[1,2-c]pyrimidin-2(3H)-yl)-2-methylphenyl)-7-(pyrrolidin-1-ylmethyl)-9H-carbazole-1-carboxamide (31); 4-(3-(5-fluoro-1,3-dioxo-1H-pyrido[1,2-c]pyrimidin-2(3H)-yl)-2-methylphenyl)-7-(methoxymethyl)-9H-carbazole-1-carboxamide (32); 8-fluoro-4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (33); and salts thereof.

8. A pharmaceutical composition comprising a compound according to claim 1 or a pharmaceutically-acceptable salt thereof; and a pharmaceutically acceptable carrier.

9. A method of treating an autoimmune disease or a chronic inflammatory disease, comprising administering to a mammalian patient a compound according to claim 1 or a pharmaceutically acceptable salt thereof, wherein said autoimmune disease or chronic inflammatory disease is selected from multiple sclerosis, inflammatory bowel disease, and rheumatoid arthritis.

* * * * *

UNITED STATES PATENT AND TRADEMARK OFFICE
CERTIFICATE OF CORRECTION

PATENT NO. : 9,714,234 B2
APPLICATION NO. : 14/392355
DATED : July 25, 2017
INVENTOR(S) : Soo Sung Ko et al.

It is certified that error appears in the above-identified patent and that said Letters Patent is hereby corrected as shown below:

On the Title Page

Column 2 (Abstract), Lines 2-3, Delete "—C(CH$_3$)2OH, —NHC(=0)C(CH$_3$)$_3$," and insert -- —C(CH$_3$)$_2$OH, —NHC(=O)C(CH$_3$)$_3$, --, therefor.

Column 2 (Abstract), Line 3, Delete "—N(CH3)2," and insert -- —N(CH$_3$)$_2$, --, therefor.

Column 2 (Abstract), Line 3, Delete "Cl" and insert -- Cl --, therefor.

Column 2 (Abstract), Line 4, Delete "Cl," and insert -- Cl, --, therefor.

Column 2 (Abstract), Line 5, Delete "—OCH3" and insert -- —OCH$_3$; --, therefor.

Column 2 (Abstract), Lines 5-6, Delete "—OCH3, —NHC(=0)CH3," and insert -- —OCH$_3$, —NHC(=O)CH$_3$, --, therefor.

Column 2 (Abstract), Line 6, Delete "fORMULA (III)," and insert -- Formula (III). --, therefor.

In the Claims

In Claim 7, Line 19, delete "3 (4H)" and insert -- 3(4H) --, therefor.

In Claim 7, Line 22, delete "3 (4H)" and insert -- 3(4H) --, therefor.

In Claim 7, Line 24, delete "methyl (d$_3$)" and insert -- methyl(d$_3$) --, therefor.

In Claim 7, Line 24, delete "3 (4H)" and insert -- 3(4H) --, therefor.

In Claim 7, Line 25, delete "carb azole" and insert -- carbazole --, therefor.

Signed and Sealed this
Sixteenth Day of April, 2019

Andrei Iancu
*Director of the United States Patent and Trademark Office*

In Claim 7, Line 27, delete "3 (4H)" and insert -- 3(4H) --, therefor.

In Claim 7, Lines 29-30, delete "3 (4H)" and insert -- 3(4H) --, therefor.

In Claim 7, Line 30, delete "carb azole" and insert -- carbazole --, therefor.

In Claim 7, Line 36, delete "carb azole" and insert -- carbazole --, therefor.

In Claim 7, Line 45, delete "[1,2-c] pyrimidin" and insert -- [1,2-c]pyrimidin --, therefor.

In Claim 7, Lines 7-8, delete "[1,2-c] pyrimidin" and insert -- [1,2-c]pyrimidin --, therefor.

In Claim 7, Lines 32-33, delete "[1,2-c] pyrimidin" and insert -- [1,2-c]pyrimidin --, therefor.